US007897737B2

(12) United States Patent
Wu et al.

(10) Patent No.: US 7,897,737 B2
(45) Date of Patent: Mar. 1, 2011

(54) 3'-OH UNBLOCKED, NUCLEOTIDES AND NUCLEOSIDES, BASE MODIFIED WITH PHOTOCLEAVABLE, TERMINATING GROUPS AND METHODS FOR THEIR USE IN DNA SEQUENCING

(75) Inventors: Weidong Wu, Houston, TX (US);
Vladislav A. Litosh, Cypress, TX (US);
Brian P. Stupi, Houston, TX (US);
Michael L. Metzker, Houston, TX (US)

(73) Assignee: LaserGen, Inc., Houston, TX (US)

( * ) Notice: Subject to any disclaimer, the term of this patent is extended or adjusted under 35 U.S.C. 154(b) by 496 days.

(21) Appl. No.: 11/567,189

(22) Filed: Dec. 5, 2006

(65) Prior Publication Data
US 2008/0132692 A1 Jun. 5, 2008

(51) Int. Cl.
C07H 19/00 (2006.01)
C07H 21/00 (2006.01)
C07H 19/04 (2006.01)
C07H 19/20 (2006.01)

(52) U.S. Cl. .................. 536/22.1; 536/25.32; 536/26.1; 536/26.2

(58) Field of Classification Search ........................ None
See application file for complete search history.

(56) References Cited

U.S. PATENT DOCUMENTS

| 4,318,846 A * | 3/1982 | Khanna et al. ............ 530/391.5 |
| 4,439,356 A | 3/1984 | Khanna et al. ............... 530/350 |
| 4,657,897 A | 4/1987 | Bristol et al. .................. 514/47 |
| 4,704,381 A | 11/1987 | Schaumann et al. ........... 514/46 |
| 5,151,507 A | 9/1992 | Hobbs, Jr. et al. .......... 536/26.7 |
| 5,188,934 A | 2/1993 | Menchen et al. ................ 435/6 |
| 5,614,386 A | 3/1997 | Metzker et al. ............. 435/91.1 |
| 5,684,142 A | 11/1997 | Mishra et al. ............... 536/22.1 |
| 5,728,529 A | 3/1998 | Metzker et al. ................. 435/6 |
| 5,763,594 A | 6/1998 | Hiatt et al. .................. 536/25.3 |
| 5,773,423 A | 6/1998 | Jacobson et al. ............... 514/45 |
| 5,808,045 A | 9/1998 | Hiatt et al. ............... 536/26.26 |
| 5,861,287 A | 1/1999 | Metzker et al. ............. 435/91.1 |
| 5,872,244 A | 2/1999 | Hiatt et al. ............... 536/26.26 |
| 5,994,063 A | 11/1999 | Metzker et al. ................. 435/6 |
| 6,214,987 B1 | 4/2001 | Hiatt et al. ............... 536/26.26 |
| 6,664,079 B2 | 12/2003 | Ju et al. .................... 435/91.91 |
| 6,762,048 B2 | 7/2004 | Williams .................. 435/287.1 |
| 6,818,395 B1 | 11/2004 | Quake et al. .................... 435/6 |
| 6,833,246 B2 | 12/2004 | Balasubramanian ........... 435/6 |
| 6,869,764 B2 | 3/2005 | Williams et al. ................. 435/6 |
| 6,995,841 B2 | 2/2006 | Scott et al. .................. 356/318 |
| 7,125,660 B2 | 10/2006 | Stanton et al. .................. 435/4 |
| 7,355,036 B2 | 4/2008 | Guimil et al. .............. 536/25.3 |
| 7,476,734 B2 | 1/2009 | Liu |
| 2003/0180769 A1 | 9/2003 | Metzker ........................ 435/6 |
| 2004/0014096 A1* | 1/2004 | Anderson et al. ............... 435/6 |
| 2005/0048601 A1 | 3/2005 | Dellinger et al. ........... 435/68.1 |
| 2005/0049407 A1 | 3/2005 | Dellinger et al. ........... 536/17.4 |
| 2005/0049411 A1 | 3/2005 | Dellinger et al. ........... 536/25.3 |
| 2008/0131952 A1 | 6/2008 | Wu et al. ......................... 435/6 |
| 2009/0081686 A1 | 3/2009 | Wu et al. .................... 536/25.3 |

FOREIGN PATENT DOCUMENTS

| EP | 0 272 007 | 6/1988 |
| EP | 0 866 071 | 9/1998 |
| WO | WO91/05060 | 4/1991 |
| WO | WO97/000967 | 1/1997 |
| WO | WO 97/00967 | 1/1997 |
| WO | WO 03/021212 | 3/2003 |
| WO | WO 2004/018497 | * 3/2004 |
| WO | WO2004/058791 | 7/2004 |

OTHER PUBLICATIONS

Seo et al., Photocleavable fluorescent nucleotides for DNA sequencing on a chip constructed by site-specific coupling chemistry, pp. 5488-5493_PNAS_ Apr. 13, 2004_ vol. 101_No. 15.*
Adzamli et al., "Development of phosphonate derivatives of gadolinium chelates for NMR imaging of calcified soft tissues," *J. Med. Chem.*, 32(1):139-144, 1989.
Bartholomew and Broom, "One-step chemical synthesis of ribonucleosides bearing a photolabile ether protecting group," *J. Chem. Soc. Chem. Commun.*, 38, 1975.
Berlier et al. "Quantitative comparison of long-wavelength alexa fluor dyes to cy dyes: fluorescence of the dyes and their bioconjugates," *The Journal of Histochemistry & Cytochemistry*, 51(12):1699-1712, 2003.
Brandis, "Dye structure affects *Taq* DNA polymerase terminator selectivity," *Nucleic Acids Research*, 27(8):1912-1918, 1999.
Chaulk and MacMillan, "Caged RNA: photo-control of a ribozyme reaction," *Nucleic Acids Res.*, 26:3173-3178, 1998.
Dewey et al., "New uridine derivatives for systematic evolution of RNA ligands by exponential enrichment," *J. Am. Chem. Soc.*, 117:8474-8475, 1995.

(Continued)

*Primary Examiner*—Mark Staples
(74) *Attorney, Agent, or Firm*—Fulbright & Jaworski LLP

(57) ABSTRACT

Provided are novel nucleotides, nucleoside, and their derivatives described herein, that can be used in DNA sequencing technology and other types of DNA analysis. In one embodiment, the nucleotide or nucleoside with an unprotected 3'-OH group is derivatized at the nucleobase to include a fluorescent dye attached via a linker to a photocleavable terminating group. The photocleavable-fluorescent group is designed to terminate DNA synthesis as well as be cleaved so that DNA oligomers can be sequenced efficiently in a parallel format. The design of such rapidly cleavable fluorescent groups on nucleotides and nucleosides can enhance the speed and accuracy of sequencing of large oligomers of DNA in parallel, to allow rapid whole genome sequencing, and the identification of polymorphisms and other valuable genetic information, as well as allowing further manipulation and analysis of nucleic acid molecules in their native state following cleavage of the fluorescent group.

28 Claims, No Drawings

OTHER PUBLICATIONS

Gardner and Jack, "Acyclic and dideoxy terminator preferences denote divergent sugar recognition by archaaeon and *Taq* DNA polymerases," *Nucleic Acids Research*, 30(2):605-613, 2002.

Gardner and Jack, "Determinants of nucleotide sugar recognition in an archaeon DNA polymerase," *Nucleic Acids Research*, 27(12):2545-2553, 1999.

Gebeyehu et al., "Novel biotinylated nucleotide—analogs for labeling and colorimetric detection of DNA," *Nucleic Acids Research*, 15(11):4513-4534, 1987.

Gibbs, "Identification of mutations leading to the Lesch-Nyhan syndrome by automated direct DNA sequencing of in vitro amplified cDNA," *Proc. Natl. Acad. Sci. USA*, 86:1919-1923, 1989.

Gommers-Ampt and Borst, "Hypermodified bases in DNA," *FASEB J.*, 9(11):1034-1042, 1995.

Hampton et al., "Species- or isozyme-specific enzyme inhibitors. 4. Design of a two-site inhibitor of adenylate kinase with isozyme selectivity," *J. Med. Chem.*, 25:638-644, 1982.

International Search Report issued in International Application No. PCT/US07/86559, mailed Aug. 21, 2008.

Ju et al., "Fluorescence energy transfer dye-labeled primers for DNA sequencing and analysis," *Proc. Natl. Acad. Sci USA*, 92:4347-4351, 1995.

Kahl and Greenberg, "Introducing structural diversity in oligonucleotides via photolabile, convertible C5-substituted nucleotides," *Journal of the American Chemical Society*, 121(4):597-604, 1999.

Kong et al., "Characterization of a DNA polymerase from the hyperthermophile archaea *Thermococcus litoralis*," *The Journal of Biological Chemistry*, 268(3):1965-1975, 1993.

Kornher and Livak, "Mutation detection using nucleotide analogs that alter electrophoretic mobility," *Nucleic Acids Research*, 17(19):7779-7784, 1989.

Kulikowski et al., "Structure-activity relationships and conformational features of antiherpetic pyrimidine and purine analogues. A review," *Pharmacy World & Science*, 16(2):127-138, 1994.

Lee et al., "New energy transfer dyes for DNA sequencing," *Nucleic Acids Research*, 25(14):2816-2822, 1997.

Lewis et al., "Color-blind fluorescence detection for four-color DNA sequencing," *PNAS*, 102(15):5346-5351, 2005.

Malecki et al., "Mutations in NEUROD1 are associated with the development of type 2 diabetes mellitus," *Nature Genetics*, 23:323-328, 1999.

McMinn and Greenberg, "Novel solid phase synthesis supports for the preparation of oligonucleotides containing 3'-alkyl amines," *Tetrahedron*, 52(11):3827-3840, 1996.

Metzker et al., "Electrophoretically uniform fluorescent dyes for automated DNA sequencing," *Science*, 271:1420-1422, 1996.

Metzker et al., "Elimination of residual natural nucleotides from 3'-O-modified-dNTP syntheses by enzymatic mop-up," *BioTechniques*, 25:814-817, 1998.

Metzker et al., "Emerging technologies in DNA sequencing," *Genome Research*, 15:1767-1776, 2005.

Metzker et al., "Termination of DNA synthesis by novel 3'-modified-deoxyribonucleoside 5'-triphosphates," *Nucleic Acids Res.*, 22:4259-4267, 1994.

Molecular Probes™ invitrogen detection technologies, "Alexa Fluor® Dyes—Simply the Best and Brightest, Fluorescent dyes and conjugates," 2005.

Office Action issued in U.S. Appl. No. 11/567,193, mailed Nov. 24, 2008.

Office Action issued in U.S. Appl. No. 11/567,193, mailed Sep. 26, 2008.

Ohtsuka et al., "Studies on transfer ribonucleic acids and related compounds. IX. Ribooligonucleotide synthesis using a photosensitive o-nitrobenzyl protection at the 2'-hydroxyl group," *Nucleic Acids Res.*, 1:1351-1357, 1974.

Panchuk-Voloshina et al., "Alexa dyes, a series of new fluorescent dyes that yield exceptionally bright, photostable conjugates," *The Journal of Histochemistry & Cytochemistry*, 47(9):1179-1188, 1999.

Pease et al., "Light-generated oligonucleotide arrays for rapid DNA sequence analysis," *Proc. Natl. Acad. Sci. USA*, 91:5022-5026, 1994.

Perler et al., "Intervening sequences in an Archaea DNA polymerase gene," *Proc. Natl. Acad. Sci. USA*, 89:5577-5581, 1992.

Perler et al., "Thermostable DNA polymerases," *Adv. Protein Chem.*, 48:377-435, 1996.

Pillai et al., "Photoremovable protecting groups in organic synthesis," *Synthesis*, 1-26, 1980.

Reeve and Fuller, "A novel thermostable polymerase for DNA sequencing," *Nature*, 376:796-797, 1995.

Response filed in U.S. Appl. No. 11/567,193, submitted Feb. 24, 2009.

Response filed in U.S. Appl. No. 11/567,193, submitted Oct. 27, 2008.

Sachidanadam et al., "A map of human genome sequence variation containing 1.42 million single nucleotide polymorphisms," *Nature*, 409(6822):928-933, 2001.

Sanger et al., "DNA sequencing with chain-terminating inhibitors," *Proc. Natl. Acad. Sci. USA* 74:5463-5467, 1977.

Southworth et al., "Cloning of thermostable DNA polymerases from hyperthermophilic marine Archaea with emphasis on *Thermococcus* sp. 9° N-7 and mutations affecting 3'-5' exonuclease activity," *Proc. Natl. Acad. Sci. USA*, 93:5281-5285, 1996.

Tabor and Richardson, "A single residue in DNA polymerases of the *Escherichia coli* DNA polymerase I family is critical for distinguishing between deoxy- and dideoxyribonucleotides," *Proc. Natl. Acad. Sci. USA*, 92:6339-6343, 1995.

Vander Horn et al., "Thermo Sequenase™ DNA polymerase and *T. acidophilum* pyrophosphatase: new thermo-stable enzymes for DNA sequencing," *Bio Techniques*, 22:758-765, 1997.

Welch and Burgess, "Synthesis of fluorescent, photolabile 3'-O-protected nucleoside triphosphates for the base addition sequencing scheme," *Nucleosides & Nucleotides*, 18(2):197-201, 1999.

Welch et al., "Synthesis of nucleosides designed for combinatorial DNA sequencing," *Chem. Eur. J.*, 5(3):951-960, 1999.

Wu et al., "Termination of DNA synthesis by $N^6$-alkylated, not 3'-O-alkylated, photocleavable 2'-deoxyadenosine triphosphates," *Nucleic Acids Research*, 35(19):6339-6349, 2007.

Yamashita et al., "Studies on antitumor agents. IX. Synthesis of 3'-O-benzyl-2'-deoxy-5-trifluoromethyluridine," *Chem Pharm. Bull.*, 37(9):2287-2292, 1989.

Li et al., "A photocleavable fluorescent nucleotide for DNA sequencing and analysis," *PNAS*, 100(2):414-419, 2003.

Office Action issued in U.S. Appl. No. 12/268,876, mailed Mar. 5, 2009.

Office Communication, issued in U.S. Appl. No. 11/567,193, dated Mar. 26, 2010.

Corrigenda for Welch et al., "Synthesis of nucleosides designed for combinatorial DNA sequencing," *Chem. Eur. J.*, 11:7145, 2005.

Erratum for Welch and Burgess, "Synthesis of fluorescent, photolabile 3'-O-protected nucleoside triphosphates for the base addition sequencing scheme," *Nucleosides, Nucleotides, and Nucleic Acids*, 25:119, 2006.

Office Action issued in U.S. Appl. No. 11/567,193, mailed Jun. 22, 2009.

Office Action issued in U.S. Appl. No. 12/268,876, mailed Jun. 25, 2009.

Response submitted in U.S. Appl. No. 11/567,193, filed Sep. 22, 2009.

Response submitted in U.S. Appl. No. 12/268,876, filed Apr. 6, 2009.

U.S. Appl. No. 12/483,080, entitled "Nucleotides and nucleosides and methods for their use in DNA sequencing," by Vladislav A. Litosh et al., filed Jun. 11, 2009.

Agbanyo el al., "5'-S-(2-aminoethyl)-N6-(4-nitrobenzyl)-5'-thioadenosine (SAENTA), a novel ligand with high affinity for polypeptides associated with nucleoside transport. Partial purification of the nitrobenzylthioinosine-binding protein of pig erythrocytes by affinity chromatography," *Biochem. J.*, 270:605-614, 1990.

Bodepudi el al., "Synthesis of 2'-deoxy-7,8-dihydro-8-oxoguanosine and 2'-deoxy-7,8-dihydro-8-oxoadenosine and their incorporation into oligomeric DNA," *Chem. Res. Toxicol.*, 5:608-617, 1992.

Bressi et al., "Adenosine analogues as inhibitors of *Trypanosoma brucei* phosphoglycerate kinase: Elucidation of a novel binding mode for a 2-amino-$N^6$ substituted andenosine," *J. Med. Chem.*, 43;4135-4250, 2000.

Chaves des Neves and Pais, "Identification of a spathe regreening factor in *Zantedeschia aethiopicia*," *Biochemical and Biophysical Research Communications*, 95(4):1387-1392, 1980.

Cho et al., "$^{15}$N nuclear magnetic resonance studies on the tautomerism of 8-hydroxy-2'-deoxyguanosine, 8-hydroxyguanosine, and other C8-substituted guanine nucleosides," *Chem. Res. Toxicol.*, 3:445-452, 1990.

Cho et al., "Correlation between NMR spectral parameters of nucleosides and its implication to the conformation about the glycosyl bond," *Biochemical and Biophysical Research Communications*, 180(1):273-278, 1991.

Dressman et al., "Transforming single DNA molecules into fluorescent magnetic particles for detection and enumeration of genetic variations," *Proc. Natl. Acad. Sci. USA*, 100:8817-8822, 2003.

Dutta et al., "Synthesis and biological activities of some N6-(nitro- and—aminobenzyl)adenosines," *Journal of Medicinal Chemistry*, 18(8):780-783, 1975.

Friest et al., "Valyl-tRNA, Isoleucyl-tRNA and Tyrosyl-tRNA synthetase from Baker's Yeast," *Eur. J. Biochem.*, 66:493-497, 1976.

Gao et al., "Structural determinants of A3 adenosine receptor activation: Nucleoside ligands at the agonist/antagonist boundary," *J. Med. Chem.*, 45:4471-4484, 2002.

Golisade et al., "Anti-malarial activity of $N^6$-substituted Adenosine derivatives. Part 1.," *Bioorganic & Medicinal Chemistry*, 10:769-777, 2002.

Harris et al., "Single-molecule DNA sequencing of a viral genome," *Science*, 320:106-109, 2008.

Hashizume et al., "Synthesis and cytokinin activity of alpha-anomeric $N^6$-benzyladenosine," *Agric. Biol. Chem.*, 49(1):225-227, 1985.

Henderson et al., "4,4'-Dimethoxytrityl and 4,4',4"-trimethoxytrityl as protecting tropus for amino functions; selectivity for primary amino groups and application in $^{15}$N-labeling, *J. Chem. Soc. Perkin Trans.*, 1:3407-3413, 1997.

Hermanns et al., "Synthesis of 8-[18O]hydroxy-2'-deoxyguanosine," *Journal of Labelled Compounds and Radiopharmaceuticals*, 36(2):191-197, 1993.

Hobarnter and Silverman, "Modulation of RNA tertiary folding by incorporation of caged nucleotides," *Angew. Chem. Int. Ed.*, 44:7305-7309, 2005.

Holmes and Robins, "Purine nucleosides. IX. The synthesis of 9-beta-D-Ribofuranysyl uric acid and other related 8-substituted purine ribonucleosides," *Journal of the American Chemical Society*, 87:8:1772-176, 1965.

Honda et al., "New type of prefabricated fully protected ribonucleotide monomer unites as useful synthetic intermediates in rapid oligoribonucleotide synthesis," *Chemistry Letters*, pp. 15-18, 1982.

International Human Genome Sequencing Consortium., "Initial sequencing and analysis of the human genome," *Nature*, 409:860-921, 2001.

Jacobson et al., "Methancarba analogues of purine nucleosides as potent and selective adenosine receptor agonists," *J. Med. Chem.*, 43:2196-2203, 2000.

Ju et al., "Four-color DNA sequencing by synthesis using cleavable fluorescent nucleotide reversible terminators," *Proc. Natl. Acad. Sci. USA*, 103:19635-40, 2006.

Kim et al., "2-Substitution of N6-benzyladenosine-5'-uronamides enhances selectivity for A3 adenosine receptors," *J. Med. Chem.*, 37:3614-3621, 1994.

Kobayashi et al., "A microfluidic device for conducting gas-liquid-solid hydrogenation reactions," *Science*, 304:1305-1308, 2004.

Levy et al., "The diploid genome sequence of an individual human," *PLoS Biol.*, 5:e254, 2007.

Lin et al., "8-substituted guanosine and 2'-Deoxyguanosine derivatives as potential inducers of the differentiation of friend erythroleukemia cells," *J. Med. Chem.*, 28:1194-1198, 1985.

Liu et al., "A molecular gate which controls unnatural ATP analogue recognition by the tyrosine kinase v-Src," *Bioorganic & Medicinal Chemistry*, 6:1219-1226, 1998.

Moore and Koreeda, "Application of the change in partition coefficient with pH to the structure determination of alkyl substituted guanosines," *Biochemical and Biophysical Research Communications*, 73(2):459-464, 1976.

Mounetou et al.,"O6-(alkyl/aralkyl)guanosine and 2'-deoxyguanosine derivatives: synthesis and ability to enhance chloroethylnitrosourea antitumor action," *J. Med. Chem.*, 40:2902-2909, 1997.

Mounteou et al., "Synthesis of three no-carrier-added $O^6$-4-[$^{125}$I] iodobenzylguanosine derivatives, new reagents for the assay of O6-alkylguanine-DNA alkyltransferase activity," *Journal of Labelled Compounds and Radiopharmaceuticals*, 36(12):1216-1225, 1995.

Nampalli et al., Efficient synthesis of 8-Oxo-dGTP: A mutagnic nucleotide, *Bioorganic & Medicinal Chemistry Letters*, 10:1677-1679, 2000.

Office Communication, issued in New Zealand Patent Application No. 577303, dated Jul. 28, 2010.

Office Communication, issued in U.S. Appl. No. 12/268,876, dated Jun. 17, 2010.

Office Communication, issued in U.S. Appl. No. 11/567,193, dated Jun. 15, 2010.

Office Communication, issued in U.S. Appl. No. 12/268,876, dated Jul. 12, 2010.

Office Communication, issued in U.S. Appl. No. 11/567,193, dated Jul. 14, 2010.

Response to Office Communication, issued in U.S. Appl. No. 12/268,876, dated Nov. 24, 2009.

Response to Office Communication, issued in U.S. Appl. No. 12/268,876, dated Apr. 6, 2010.

Response to Office Communication, issued in U.S. Appl. No. 11/567,193, dated May 26, 2010.

Response to Office Communication, issued in U.S. Appl. No. 11/567,193, dated Dec. 22, 2009.

Robins and Trip, "Sugar-modified N 6 -(3-methyl-2-butenyl)adenosine derivatives, N 6 -benzyl analogs, and cytokinin-related nucleosides containing sulfur or formycin," 12(12):2179-2187, 1973.

Schold et al., "Treatment of human brain tumor xenografts with O6-benzyl-2'-deoxyguanosine and BCNU," *Cancer Research*, 56:2076-2081, 1996.

Sebat et al., "Large-scale copy number polymorphism in the human genome," *Science*, 305:525-528, 2004.

Seio et al., "Synthesis and properties of new nucleotide analogues processing squaramide moieties as new phosphate isosters," *Eur. J. Org. Chem.*, 5163-5170, 2005.

Seo et al., "Four-color DNA sequencing by synthesis on a chip using photocleavable fluorescent nucleotides," *PNAS*, 102(17):5926-5931, 2005.

Shankar et al.,"O6-3-[125I]iodobenzy1-2'-deoxyguanosine ([125I]IBdG): synthesis and evaluation of its usefulness as an agent for quantification of alkylguanine-DNA alkyltransferase (AGT)," *Bioorganic & Medicinal Chemistry*, 13:3889-3898, 2005.

Shapiro and Shiuey, "Reactions of cytidine with 7-bromomethylbenz[a]anthracene, benzyl bromide, and p-methoxybenzyl bromide. Ratio of Amino to 3 substitution,"*J. Org. Chem.*, 41(9): 1597-1600, 1976.

Sierzchala et al., "Solid-phase oligodeoxynucleotide synthesis: A two-step cycle using peroxy anion deprotection," *J. Am. Chem. Soc.*, 125:13427-13441, 2003.

Stranger et al., "Relative impact of nucleotide and copy number variation on gene expression phenotypes," *Science*, 315:848-853, 2007.

Terrashima et al., "Substrate specificity of human $O^6$-methylguanine-DNA methyltransferase for $O^6$-benzylguanine derivatives in oligodeoxynucleotides," *Chem. Res. Toxicol.*, 10:1234-1239, 1997.

van Tilburg et al., "$N^6$,5'-disubstituted adenosine derivatives as partial agonists for the human adenosine $A_3$ receptor," *J. Med. Chem.*, 42:1393-1400, 1999.

Yu et al., "Synthesis of 3,7,8-$^{15}N_3$-$N^1$-(beta-D-*erythro*-pentofuranosyl)-5-guanidinohydantoin," *Journal of Labelled Compounds and Radiopharmaceuticals*, 46:1269-1277, 2003.

* cited by examiner

3'-OH UNBLOCKED, NUCLEOTIDES AND NUCLEOSIDES, BASE MODIFIED WITH PHOTOCLEAVABLE, TERMINATING GROUPS AND METHODS FOR THEIR USE IN DNA SEQUENCING

This invention was made with government support under grant number R01 HG003573-01 awarded by the NHGRI (National Human Genome Research Institute), which is one of the institutes of the NIH. The government has certain rights in this invention.

FIELD OF INVENTION

The present invention relates generally to compounds and methods for DNA sequencing and other types of DNA analysis. More particularly, the invention relates to nucleotides and nucleosides labeled with photocleavable groups and methods for their use in DNA sequencing and analysis.

BACKGROUND

Methods for rapidly sequencing DNA have become needed for analyzing diseases and mutations in the population and developing therapies. The most commonly observed form of human sequence variation is single nucleotide polymorphisms (SNPs), which occur in approximately 1-in-300 to 1-in-1000 base pairs of genomic sequence. Building upon the complete sequence of the human genome, efforts are underway to identify the underlying genetic link to common diseases by SNP mapping or direct association. Technology developments focused on rapid, high-throughput, and low cost DNA sequencing would facilitate the understanding and use of genetic information, such as SNPs, in applied medicine.

In general, 10%-to-15% of SNPs will affect protein function by altering specific amino acid residues, will affect the proper processing of genes by changing splicing mechanisms, or will affect the normal level of expression of the gene or protein by varying regulatory mechanisms. It is envisioned that the identification of informative SNPs will lead to more accurate diagnosis of inherited disease, better prognosis of risk susceptibilities, or identity of sporadic mutations in tissue. One application of an individual's SNP profile would be to significantly delay the onset or progression of disease with prophylactic drug therapies. Moreover, an SNP profile of drug metabolizing genes could be used to prescribe a specific drug regimen to provide safer and more efficacious results. To accomplish these ambitious goals, genome sequencing will move into the resequencing phase with the potential of partial sequencing of a large majority of the population, which would involve sequencing specific regions or single base pairs in parallel, which are distributed throughout the human genome to obtain the SNP profile for a given complex disease.

Sequence variations underlying most common diseases are likely to involve multiple SNPs, which are dispersed throughout associated genes and exist in low frequency. Thus, DNA sequencing technologies that employ strategies for de novo sequencing are more likely to detect and/or discover these rare, widely dispersed variants than technologies targeting only known SNPs.

Traditionally, DNA sequencing has been accomplished by the "Sanger" or "dideoxy" method, which involves the chain termination of DNA synthesis by the incorporation of 2',3'-dideoxynucleotides (ddNTPs) using DNA polymerase (Sanger, F., Nicklen, S., and Coulson, A. R. (1977) DNA sequencing with chain-terminating inhibitors. *Proc. Natl. Acad. Sci. USA* 74, 5463-5467). The reaction also includes the natural 2'-deoxynucleotides (dNTPs), which extend the DNA chain by DNA synthesis. Balanced appropriately, competition between chain extension and chain termination results in the generation of a set of nested DNA fragments, which are uniformly distributed over thousands of bases and differ in size as base pair increments. Electrophoresis is used to resolve the nested DNA fragments by their respective size. The ratio of dNTP/ddNTP in the sequencing reaction determines the frequency of chain termination, and hence the distribution of lengths of terminated chains. The fragments are then detected via the prior attachment of four different fluorophores to the four bases of DNA (i.e., A, C, G, and T), which fluoresce their respective colors when irradiated with a suitable laser source. Currently, Sanger sequencing has been the most widely used method for discovery of SNPs by direct PCR sequencing (Gibbs, R. A., Nguyen, P.-N., McBride, L. J., Koepf, S. M., and Caskey, C. T. (1989) Identification of mutations leading to the Lesch-Nyhan syndrome by automated direct DNA sequencing of in vitro amplified cDNA. *Proc. Natl. Acad. Sci. USA* 86, 1919-1923) or genomic sequencing (Hunkapiller, T., Kaiser, R. J., Koop, B. F., and Hood, L. (1991) Large-scale and automated DNA sequencing Determination. *Science* 254, 59-67; International Human Genome Sequencing Consortium. Initial sequencing and analysis of the human genome. (2001) *Nature* 409, 860-921).

Another promising sequencing approach is cyclic reversible termination (CRT), which is a cyclic method of detecting the synchronistic, single base additions of multiple templates. This approach differentiates itself from the Sanger method (Metzker, M. L. (2005) *Genome Res.* 15, 1767-1776) in that it can be performed without the need for gel electrophoresis, a major bottleneck in advancing this field. Like Sanger sequencing, however, longer read-lengths translates into fewer sequencing assays needed to cover the entire genome.

It has remained difficult to accomplish the goal of long CRT reads because reversible terminators typically act as poor substrates with commercially available DNA polymerases. Reversible terminators are structured with a 3'-O-blocking group and a nucleobase attached fluorescent dye via a linking group. Both blocking and dye groups require removal prior to subsequent base additions. These nucleotide modifications are not well tolerated by DNA polymerases, which can be mutated by numerous strategies to improve enzymatic performance. Upon deprotection, the nucleobase linker group is left behind, accumulating sequentially in the growing DNA duplex with subsequent CRT cycles. It is believed that poor enzyme kinetics and a sequentially modified DNA duplex limit longer read-lengths. The present invention describes novel, reversible nucleotide structures that require a single attachment of both terminating and fluorescent dye moieties, improving enzyme kinetics as well as deprotection efficiencies. These reversible terminators are incorporated efficiently by a number of commercially available DNA polymerases, with the deprotection step transforming the growing DNA duplex into its natural state.

DNA sequencing read-lengths of CRT technologies are governed by the overall efficiency of each nucleotide addition cycle. For example, if one considers the end-point of 50% of the original starting material as having an acceptable signal-to-noise ratio, the following equation can be applied to estimate the effect of the cycle's efficiency on read-length: $(RL)^{C_{\it eff}}=0.5$, where RL is the read-length in bases and $C_{\it eff}$ is the overall cycle efficiency. In other words, a read-length of 7 bases could be achieved with an overall cycle efficiency of 90%, 70 bases could be achieved with a cycle efficiency of 99% and 700 bases with a cycle efficiency of 99.9%. To achieve the goal of sequencing large stretches, the method must provide very high cycle efficiency or the recovery may fall below acceptable signal to noise ratios. Reversible terminators that exhibit higher incorporation and deprotection efficiencies will achieve higher cycle efficiencies, and thus longer read-lengths.

For CRT terminators to function properly, the protecting group must be efficiently cleaved under mild conditions. The removal of a protecting group generally involves either treatment with strong acid or base, catalytic or chemical reduction, or a combination of these methods. These conditions may be reactive to the DNA polymerase, nucleotides, oligonucleotide-primed template, or the solid support creating undesirable outcomes. The use of photochemical protecting groups is an attractive alternative to rigorous chemical treatment and can be employed in a non-invasive manner.

A number of photoremovable protecting groups including 2-nitrobenzyl, benzyloxycarbonyl, 3-nitrophenyl, phenacyl, 3,5-dimethoxybenzoinyl, 2,4-dinitrobenzenesulphenyl, and their respective derivatives have been used for the syntheses of peptides, polysaccharides, and nucleotides (Pillai, V. N. R. (1980) Photoremovable Protecting Groups in Organic Synthesis. *Synthesis*, 1-26). Of these, the light sensitive 2-nitrobenzyl protecting group has been successfully applied to the 2'-OH of ribonucleosides for diribonucleoside synthesis (Ohtsuka, E., Tanaka, S., and Ikehara, M. (1974) Studies on transfer ribonucleic acids and related compounds. IX(1) Ribooligonucleotide synthesis using a photosensitive o-nitrobenzyl protection at the 2'-hydroxyl group. *Nucleic Acids Res.* 1, 1351-1357), the 2'-OH of ribophosphoramidites in automated ribozyme synthesis (Chaulk, S. G., and MacMillan, A. M. (1998) Caged RNA: photo-control of a ribozyme. *Nucleic Acids Res.* 26, 3173-3178), the 3'-OH of phosphoramidites for oligonucleotide synthesis in the Affymetrix chemistry (Pease, A. C., Solas, D., Sullivan, E. J., Cronin, M. T., Holmes, C. P., and Fodor, S. P. A. (1994) Light-generated oligonucleotide arrays for rapid DNA sequence analysis. *Proc. Natl. Acad. Sci. USA* 91, 5022-5026), and to the 3'-OH group for DNA sequencing applications (Metzker, M. L., Raghavachari, R., Richards, S., Jacutin, S. E., Civitello, A., Burgess, K., and Gibbs, R. A. (1994) Termination of DNA synthesis by novel 3'-modified deoxyribonucleoside triphosphates. *Nucleic Acids Res.* 22, 4259-4267). Under deprotection conditions (ultraviolet light >300 nm), the 2-nitrobenzyl group can be efficiently cleaved without affecting either the pyrimidine or purine bases (Pease, A. C., Solas, D., Sullivan, E. J., Cronin, M. T., Holmes, C. P., and Fodor, S. P. A. (1994) Light-generated oligonucleotide arrays for rapid DNA sequence analysis. *Proc. Natl. Acad. Sci. USA* 91, 5022-5026) and (Bartholomew, D. G., and Broom, A. D. (1975) One-step Chemical Synthesis of Ribonucleosides bearing a Photolabile Ether Protecting Group. *J. Chem. Soc. Chem. Commun.*, 38).

The need for developing new sequencing technologies has never been greater than today with applications spanning diverse research sectors including comparative genomics and evolution, forensics, epidemiology, and applied medicine for diagnostics and therapeutics. Current sequencing technologies are too expensive, labor intensive, and time consuming for broad application in human sequence variation studies. Genome center cost is calculated on the basis of dollars per 1,000 $Q_{20}$ bases and can be generally divided into the categories of instrumentation, personnel, reagents and materials, and overhead expenses. Currently, these centers are operating at less than one dollar per 1,000 $Q_{20}$ bases with at least 50% of the cost resulting from DNA sequencing instrumentation alone. Developments in novel detection methods, miniaturization in instrumentation, microfluidic separation technologies, and an increase in the number of assays per run will most likely have the biggest impact on reducing cost.

It is therefore an object of the invention to provide novel compounds that are useful in efficient sequencing of genomic information in high throughput sequencing reactions.

It is another object of the invention to provide novel reagents and combinations of reagents that can efficiently and affordably provide genomic information.

It is yet another object of the invention to provide libraries and arrays of reagents for diagnostic methods and for developing targeted therapeutics for individuals.

SUMMARY

Provided are nucleoside compounds as well as phosphates and salts thereof, that can be used in DNA sequencing technology. The compounds are optionally in the form of ribonucleoside triphosphate (NTP) and deoxyribonucleoside triphosphate (dNTP) compounds. The nucleotide and nucleoside compounds include a photocleavable group lableled with a fluorescent dye. The nucleotide and nucleoside compounds containing photocleavable protecting groups are designed to terminate DNA synthesis and then be cleave efficiently, so that nucleic acid oligomers can be sequenced rapidly in a parallel format. The presence of such cleavable groups lableled with fluorescent dyes on the nucleotide and nucleoside compounds can enhance the speed and accuracy of sequencing of large oligomers of DNA in parallel, to allow, for example, rapid whole genome sequencing, and the identification of polymorphisms and other valuable genetic information.

A variety of nucleotide and nucleoside compounds, containing the nucleobases adenine, cytosine, guanine, thymine, uracil, or naturally occurring derivatives thereof, are provided that include cleavable groups and/or which can be derivatized to include a detectable label such as a dye.

In one embodiment the base of the nucleoside covalently attached with a 2-nitrobenzyl group, and the alpha carbon position of the 2-nitrobenzyl group is optionally substituted with one alkyl or aryl group as described herein. The 2-nitrobenzyl group can be functionalized to enhance the termination properties as well as the light catalyzed deprotection rate. The termination properties of the 2-nitrobenzyl and alpha carbon substituted 2-nitrobenzyl group attached to the nucleobase occur even when the 3'-OH group on the ribose sugar is unblocked. These 3'-OH unblocked terminators are well-tolerated by a number of commercially available DNA polymerases, representing a key advantage over 3'-O-blocked terminators. The alpha carbon substituted 2-nitrobenzyl group also can be derivatized to include a selected fluorescent dye.

In one embodiment the base of the nucleoside is covalently attached with a 2-nitrobenzyl group, and the 2-nitrobenzyl group is optionally substituted with one or more of an electron donating and electron withdrawing group as described herein. The 2-nitrobenzyl group can be functionalized to enhance the light catalyzed deprotection rate. The 2-nitrobenzyl group also can be derivatized to include a detectable fluorescent dye.

In particular, methods for DNA sequencing are provided using combinations of the four nucleoside triphosphate compounds, modified with 2-nitrobenzyl groups, and derivatives described herein and labeled with distinct fluorescent dyes, which could be used for identifying the incorporated bases to reveal the underlying DNA sequence.

DETAILED DESCRIPTION

Provided are nucleotide and nucleoside compounds as well as salts, esters and phosphates thereof, that can be used in rapid DNA sequencing technology. The compounds are optionally in the form of ribonucleoside triphosphates (NTPs) and deoxyribonucleoside triphosphates (dNTP). The nucleotide and nucleoside compounds in one embodiment includes a photocleavable group labeled with a fluorescent dye. The nucleotide and nucleoside compounds include photoremovable protecting groups that are designed to terminate DNA synthesis as well as cleave rapidly, so that these monomers can be used for rapid sequencing in a parallel format. The presence of such rapidly cleavable groups labeled with fluorescent dyes on the nucleotide and nucleoside compounds can enhance the speed and accuracy of sequencing of large oligomers of DNA in parallel, to allow, for example, rapid whole genome sequencing, and the identification of polymorphisms and other valuable genetic information.

A variety of nucleotide and nucleoside compounds, containing the nucleobases adenine, cytosine, guanine, thymine, uracil, or naturally occurring derivatives thereof, are provided that include cleavable groups and/or which can be derivatized to include a detectable label such as a dye.

In one embodiment, the nucleobases adenine, cytosine, guanine, thymine, uracil, or naturally occurring derivatives thereof, can be covalently attached to a photoremovable protecting group such as a 2-nitrobenzyl group. The 2-nitrobenzyl group can be derivatized to enhance its termination of DNA synthesis as well as deprotection rate, thus increasing its usefulness in DNA sequencing. The photoremovable protecting group, such as the 2-nitrobenzyl group, also can be derivatized with a fluorescent dye by covalent linkage to the photoremovable protecting group.

I. Advantages of Compounds for Sequencing

Nucleotide and nucleoside compounds are provided which are useful in DNA sequencing technology. Cyclic reversible termination (CRT) is a cyclic method of detecting the synchronous, single base additions of multiple templates. This approach differentiates itself from the Sanger method in that it can be performed without the need for gel electrophoresis and highly-parallel format, which are major bottlenecks in advancing this field. Like Sanger sequencing, however, longer read-lengths translates into fewer sequencing assays needed to cover the entire genome.

The CRT cycle comprises three steps, incorporation, imaging, and deprotection. For this procedure, cycle efficiency, cycle time, and sensitivity are important factors. The cycle efficiency is the product of deprotection and incorporation efficiencies and determines the CRT read-length. The CRT cycle time is the sum of incorporation, imaging, and deprotection times. For rapid CRT for whole genome sequencing, the nucleotide and nucleoside compounds as disclosed herein may be used, which can exhibit fast and efficient deprotection properties. These compounds can be labeled with fluorescent dyes, attached directly to the 2-nitrobenzyl, providing fluorescent, reversible terminators with similar deprotection properties.

The read-length of CRT technologies are governed by the overall efficiency of each nucleotide addition cycle, product of deprotection and incorporation efficiencies. For example, if one considers the end-point of 50% of the original starting material as having an acceptable signal-to-noise ratio, the following equation can be applied to estimate the effect of the cycle's efficiency on read-length:

$$(RL)^{Ceff} = 0.5$$

where RL is the read-length in bases and Ceff is the overall cycle efficiency. In other words, a read-length of 7 bases could be achieved with an overall cycle efficiency of 90%, 70 bases could be achieved with a cycle efficiency of 99% and 700 bases with a cycle efficiency of 99.9%. The efficiency of incorporation of compounds according to the invention may range from about 70% to about 100% of the incorporation of the analogous native nucleoside. Preferably, the efficiency of incorporation will range from about 85% to about 100%. Photocleavage efficiencies will preferably range from about 85% to about 100%. Further, termination of nucleic acid extension will range from about 90% to about 100% upon incorporation of compounds according to the invention. Nucleotide and nucleoside compounds in one embodiment have a cycle efficiency of at least 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%.

When applied to genomic DNA, the compounds can be used in CRT to read directly from genomic DNA. Fragmented genomic DNA can be hybridized to a high-density oligonucleotide chip containing priming sites that span selected chromosomes. Each priming sequence is separated by the estimated read-length of the CRT method. Between base additions, a fluorescent imager can simultaneously image the entire high-density chip, marking significant improvements in speed and sensitivity. The fluorophore, which is attached to the 2-nitrobenzyl group or its derivatives described herein, is removed by UV irradiation releasing the 2-nitrobenzyl group for the next round of base addition. After approximately 500 CRT cycles, the complete and contiguous genome sequence information can then be compared to the reference human genome to determine the extent and type of sequence variation in an individual's sample.

II. Compounds

A variety of nucleosides and compounds as well as their mono, di and triphosphates are provided. The compounds are useful for DNA sequencing technology. In one embodiment, the nucleotide and nucleoside compounds include a photocleavable terminating group labeled with a fluorescent dye that can be detected and efficiently cleaved in CRT reactions. The nucleotide and nucleoside compounds can be converted into their respective natural nucleoside monophosphates for subsequent rounds of DNA polymerase reactions.

In a particular embodiment, a nucleotide and nucleoside compounds are provided comprising a deoxyribose or ribose sugar and a base, wherein the base is covalently linked to a photocleavable terminating, 2-nitrobenzyl group. The 2-nitrobenzyl group can be substituted with groups that increase termination of DNA synthesis as well as the rate of deprotection. In addition, the 2-nitrobenzyl group can be detectable by attaching a reporter group, such as a dye. The dye may be optionally linked to 2-nitrobenzyl group by a bifunctional linker. Compounds according to the invention may be represented by the following formula:

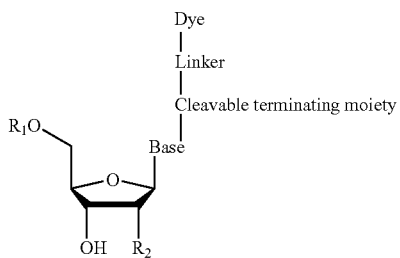

wherein $R_1$ is H, monophosphate, diphosphate or triphosphate, $R_2$ is H or OH, base is cytosine, uracil, thymine, adenine, or guanine, or naturally occurring derivatives thereof, cleavable terminating moiety is a group imparting polymerase termination properties to the compound, linker is a bifunctional group, and dye is a fluorophore.

Compounds according to the invention can be designed as fluorescent, photolabile reversible terminators useful in DNA synthesis sequencing. The compounds can be optimized reversible terminators, modified to have fast and efficient deprotection behavior and good fluorescent properties in aqueous solutions. In one embodiment, a compound is provided having a structure of formulas I-VII:

formula I

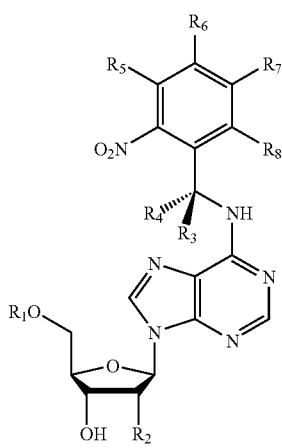

formula II

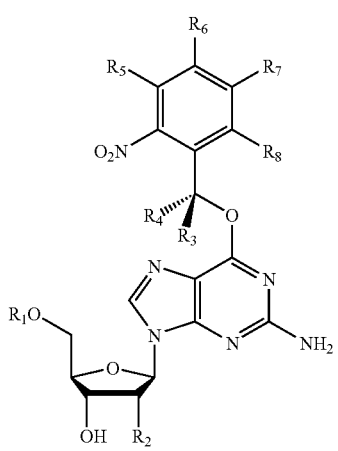

formula III

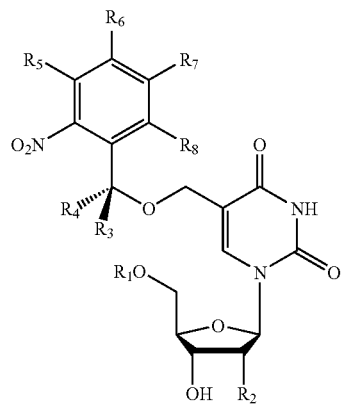

formula IV

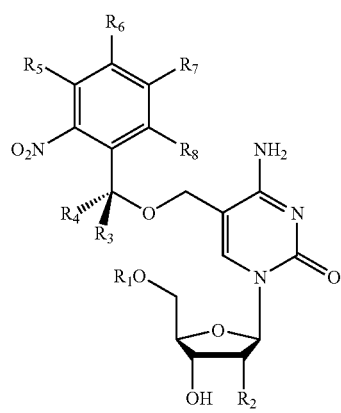

formula V

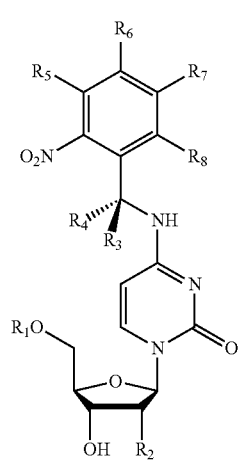

-continued formula VI

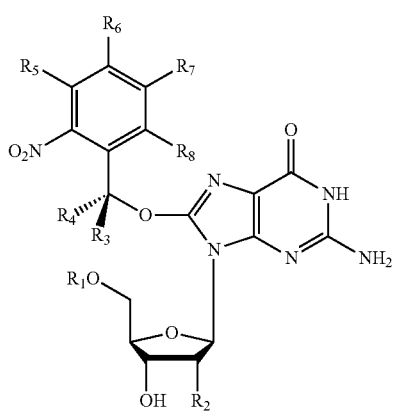

or formula VII

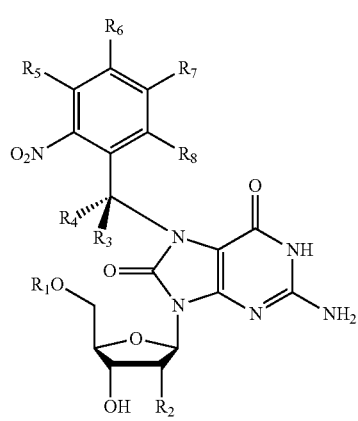

wherein $R_1$=H, monophosphate, diphosphate or triphosphate, $R_2$=H or OH, $R_3$ and $R_4$ are each independently selected from the group of H, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group such as a phenyl, naphthyl, or pyridine ring, with the proviso that at least one of $R_3$ and $R_4$ is H, $R_5$, $R_6$, $R_7$, and $R_8$ are each independently selected from the group H, $OCH_3$, $NO_2$, CN, a halide, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl an aromatic group such as a phenyl, naphthyl, or pyridine ring, and/or a linker group of the general structure:

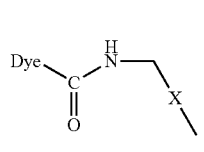
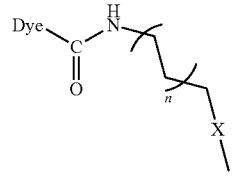
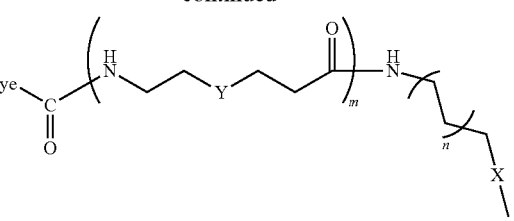

$X$=$CH_2$, CH=CH, C≡C, O, S, or NH, Y=$CH_2$, O, or NH, n=an integer from 0-12; m=an integer from 0-12, and Dye=a fluorophore, or pharmaceutically acceptable salt or ester thereof or enantiomer, racemic mixture, or stereoisomer thereof.

In a particular embodiment, in the compounds provided herein comprising a derivatized 2-nitrophenyl ring, such as the compounds of formulas I-VII, the rate of deprotection and removal of the 2-nitrophenyl group during DNA sequencing can be enhanced by including an electron donating group at the 4-position or an electron withdrawing group at the 5-position of the 2-nitrophenyl ring.

In a preferred embodiment, $R_3$ and $R_4$ are selected from the group consisting of, but not limited to, —$CH_3$, —$CH_2CH_3$, —$CH_2CH_2CH_3$, isopropyl, tert-butyl, phenyl, 2-nitrophenyl, and 2,6-dinitrophenyl. Alternatively, $R_3$ and $R_4$ are selected from the group consisting of, but not limited to, alkyl and aromatic groups optionally containing at least one heteroatom in the alkyl or aromatic groups, and further wherein the aromatic group may optionally be an aryl such as phenyl or polycyclic such as a naphthyl group. In certain embodiments, $R_5$, $R_6$, $R_7$, and $R_8$ are selected from an aromatic group consisting of aryl and polycyclic groups.

Alternatively, photocleavable terminating moieties may have the following general structures:

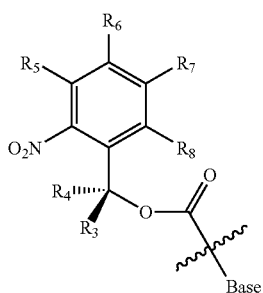
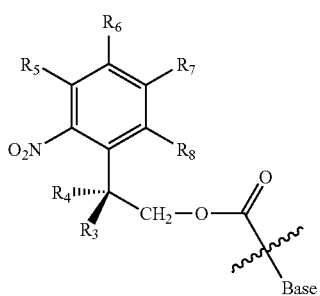

For example, compounds with such photocleavable terminating moieties could have the following structures:

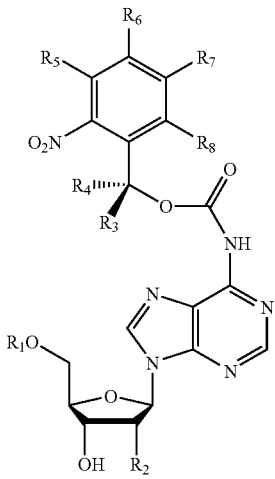

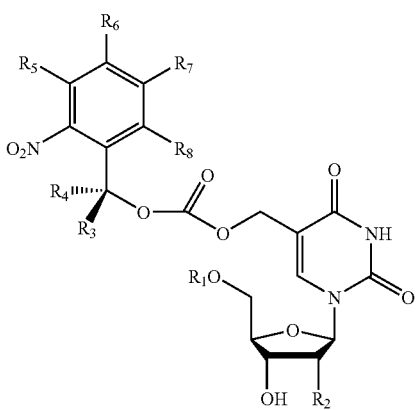

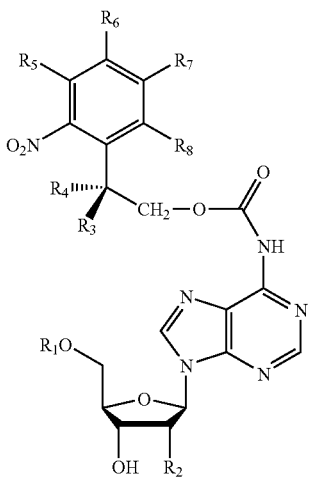

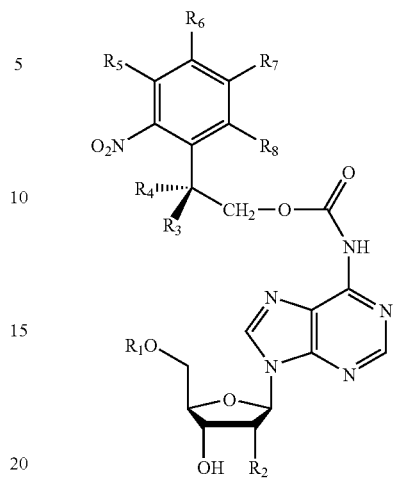

A compound according to claim 1, wherein the cleavable terminating moiety is attached to the base through a linkage selected from the group consisting of benzyl amine, benzyl ether, carbamate, carbonate, 2-(o-nitrophenyl)ethyl carbamate, and 2-(o-nitrophenyl)ethyl carbonate. Such embodiments are within the scope of the current invention.

Fluorescent dyes are not particularly limited. For example, the flurophore may be seclected from the group consisting of, but not limited to, BODIPY, fluoroscein, rhodamine, coumarin, xanthene, cyanine, pyrene, phthalocyanine, phycobiliprotein, ALEXA FLUOR® (e.g., ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700 or ALEXA FLUOR® 750),squariane dye, combinations resulting in energy transfer dyes, and derivatives thereof.

Preferred embodiments include but are not limited to the following compounds:

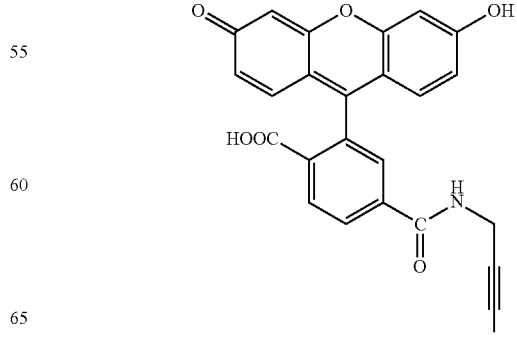

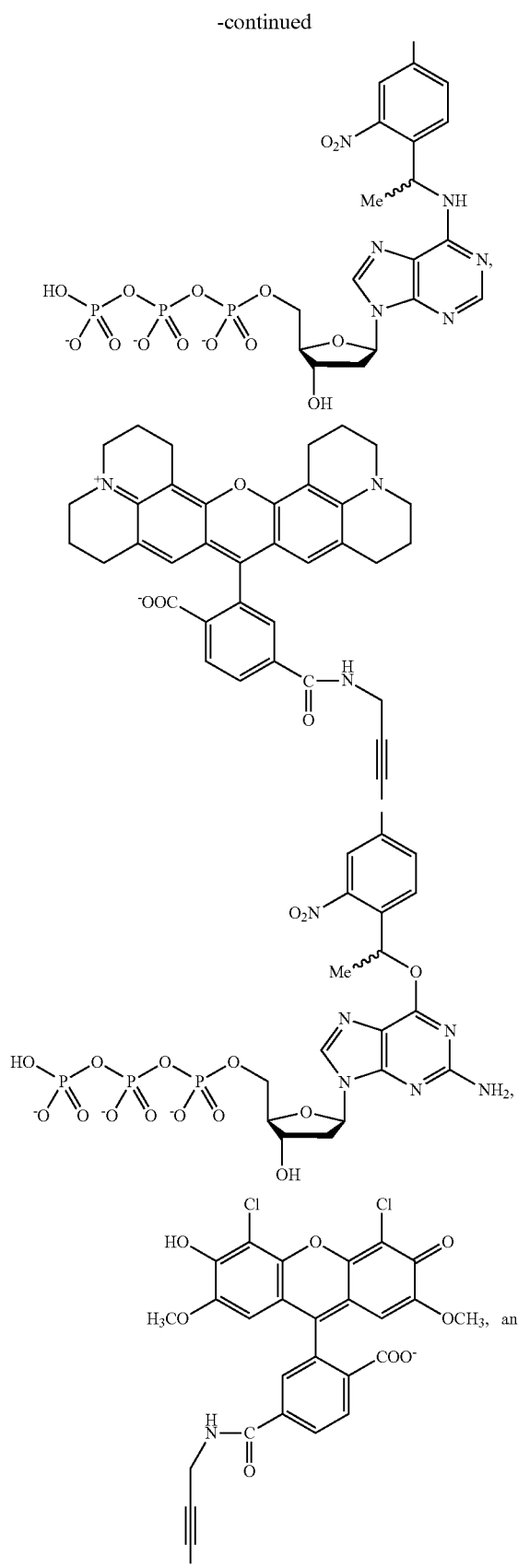

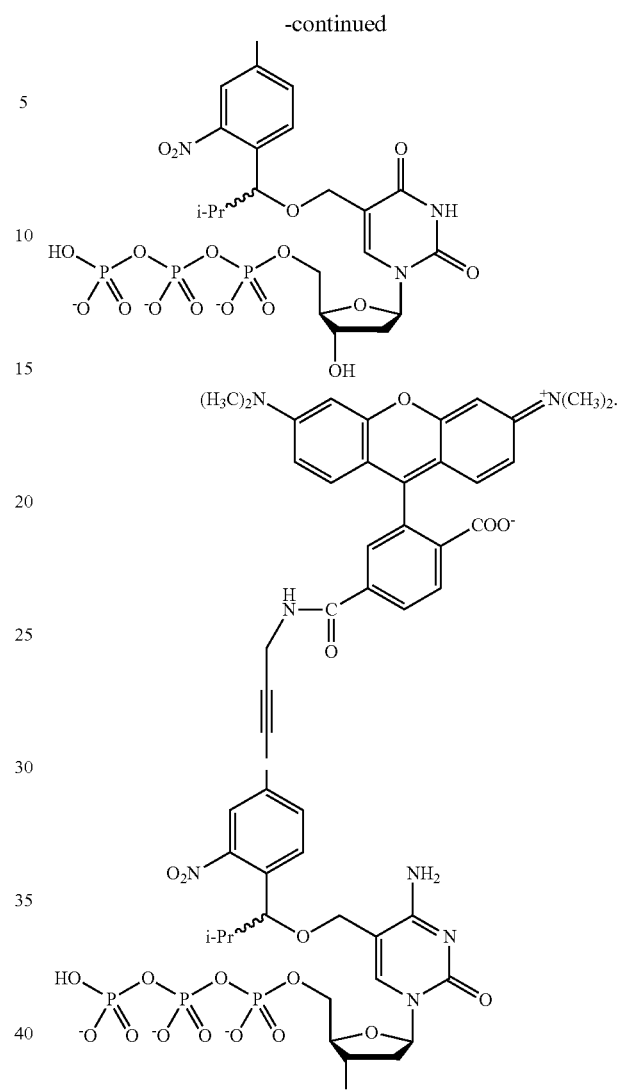

III. Synthesis of Compounds

The compounds disclosed herein can be synthesized generally as disclosed herein, and using methods available in the art. For example, the following general scheme represents the synthesis of an adenosine compound:

General Scheme for synthesis of an Adenosine N6-modified compound

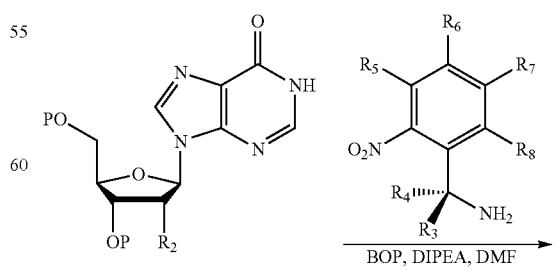

P denotes a suitable protecting group
$R_2$ = H or OH group with a suitable protecting group -continued

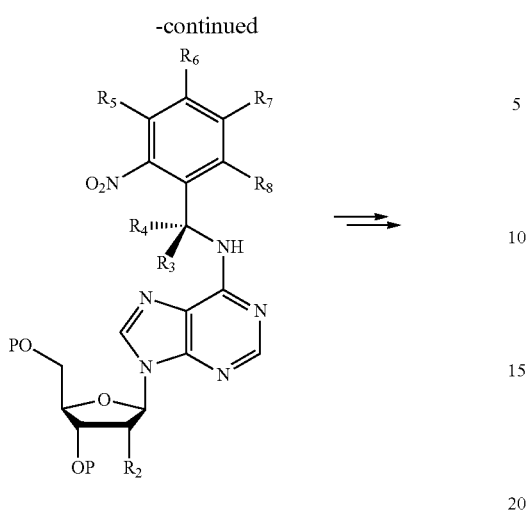

$R_1$ to $R_8$ has the same definition as defined for the general structure

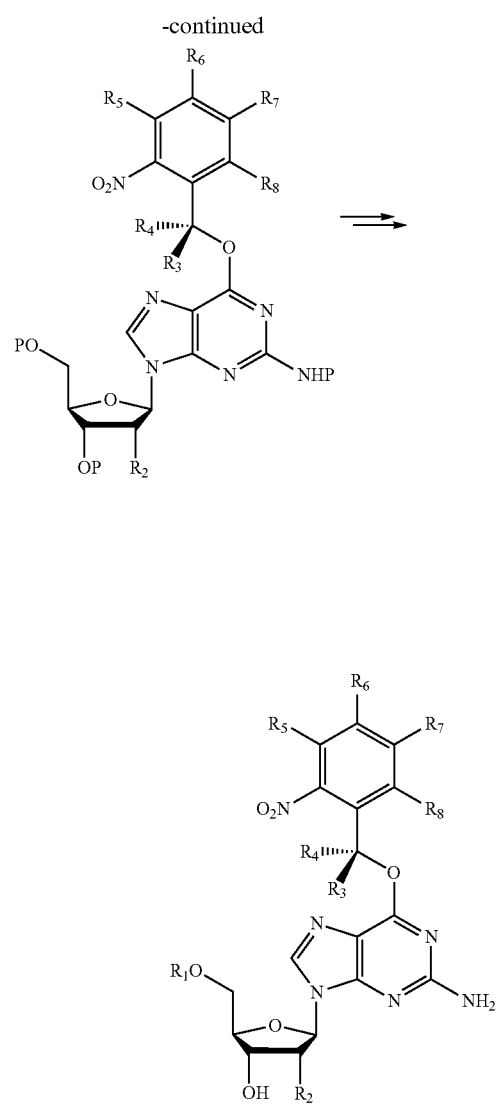

$R_1$ to $R_8$ has the same definition as defined for the general structure

General Scheme for synthesis Guanosine O6-modified compounds

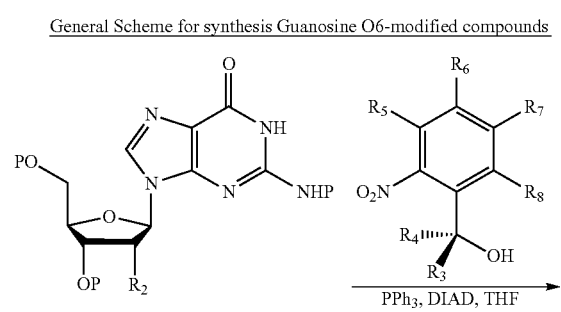

P denotes a suitable protecting group
$R_2$ = H or OH group with a suitable protecting group General Scheme for synthesis Guanosine 8-Oxo-modified compounds P denotes a suitable protecting group
$R_2$ = H or OH group with a suitable protecting group -continued

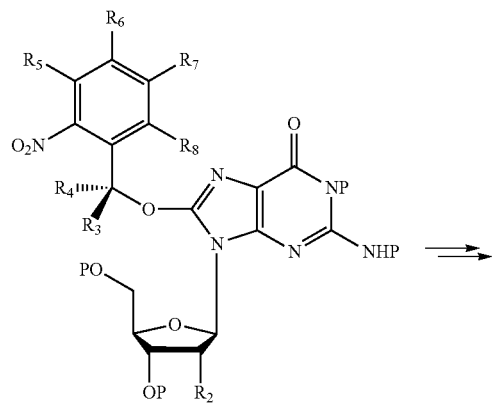

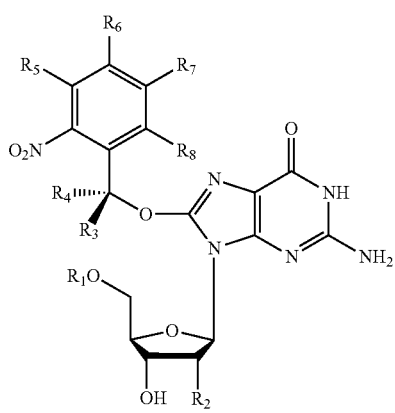

R₁ to R₈ has the same definition as
defined for the general structure

General Scheme for synthesis Uridine 5-HOMe-modified compounds

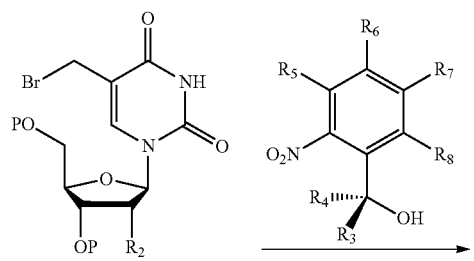

P denotes a suitable protecting group
R₂ = H or OH group with a suitable protecting group

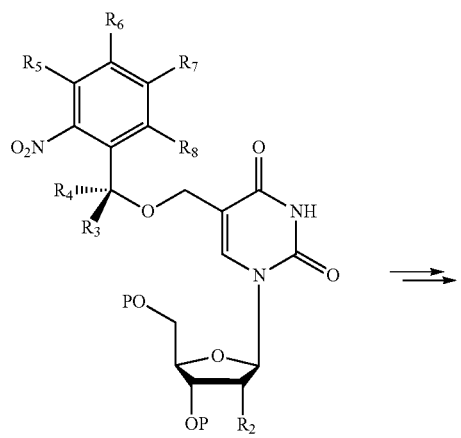

-continued

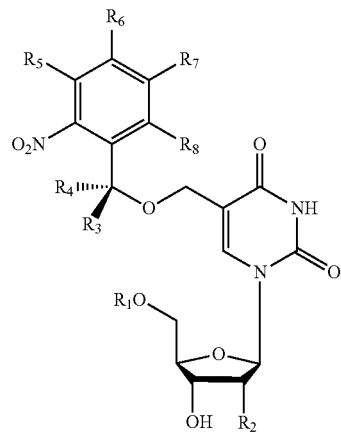

R₁ to R₈ has the same definition as
defined for the general structure

General Scheme for synthesis Cytidine 5-HOMe-modified compounds

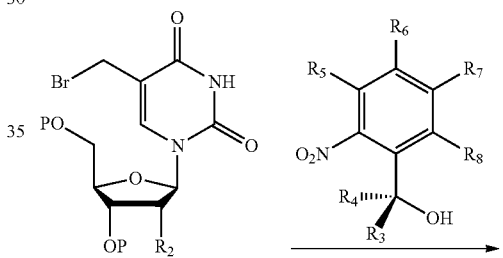

P denotes a suitable protecting group
R₂ = H or OH group with a suitable protecting group

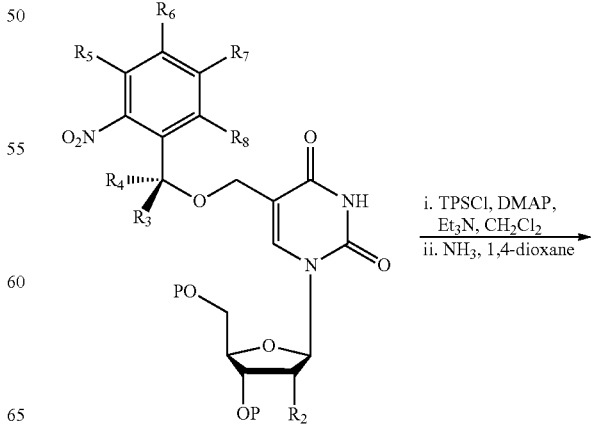

i. TPSCl, DMAP,
Et₃N, CH₂Cl₂
ii. NH₃, 1,4-dioxane

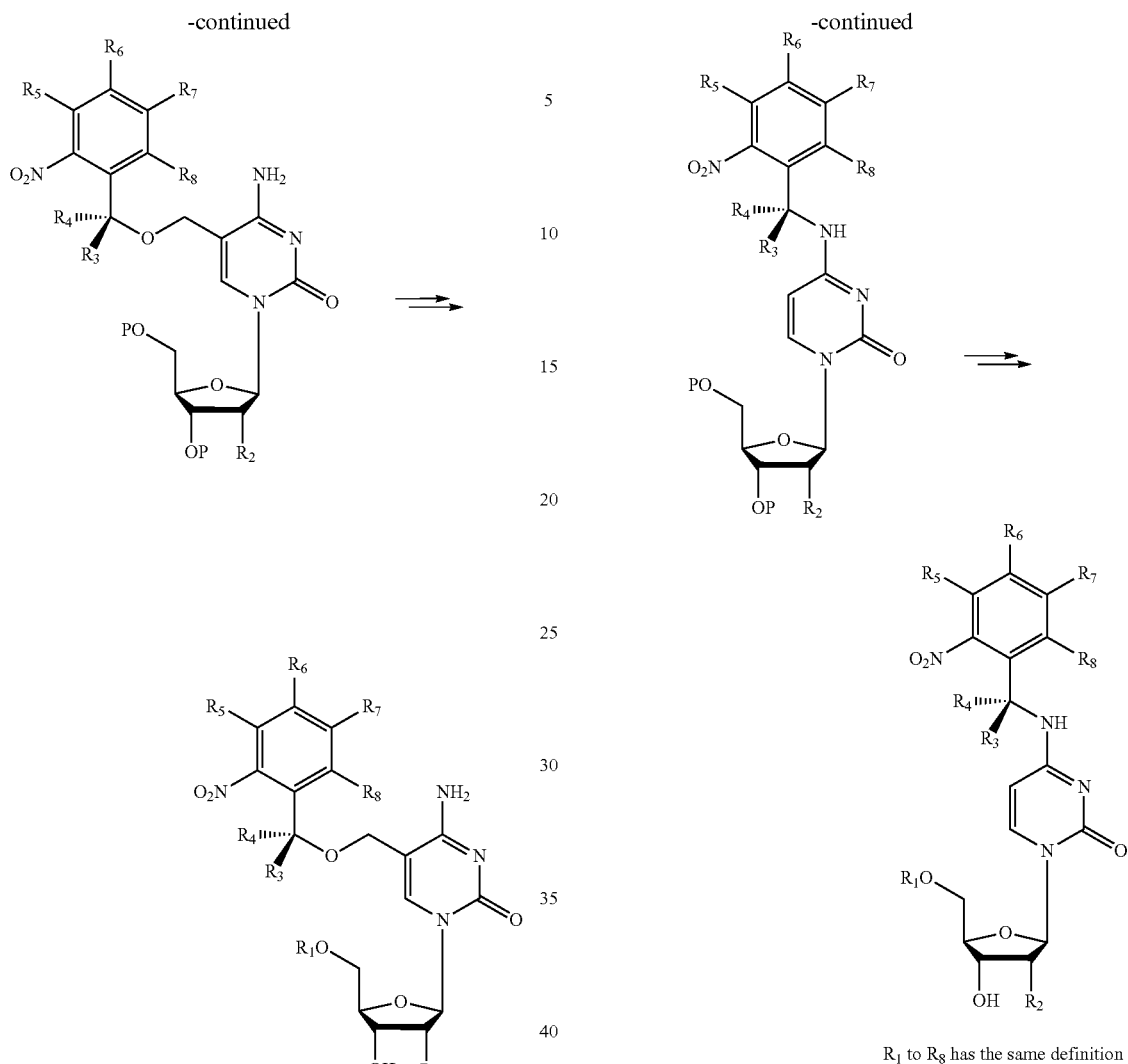

$R_1$ to $R_8$ has the same definition as defined for the general structure

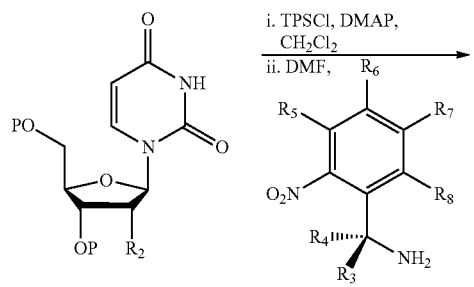

P denotes a suitable protecting group
$R_2$ = H or OH group with a suitable protecting group Additional details are provided in the Examples section.

IV. Methods of Use of Compounds According to the Invention

The nucleoside compounds disclosed herein can be used in for a variety of purposes in DNA sequencing technology. Polymerases used in conjunction with the compounds according to the invention may be native polymerases or modified polymerases. Polymerases include without limitation Taq DNA polymerase, Klenow(-exo-) DNA polymerase, Bst DNA polymerase, VENT® (exo-) DNA polymerase (DNA polymerase A cloned from *Thermococcus litoralis* and containing the D141A and E143A mutations), Pfu(-exo-) DNA polymerase, and DEEPVENT™ (exo-) DNA polymerase (DNA polymerase A, cloned from the *Pyrococcus* species GB-D, and containing the D141A and E143A mutations). Modified polymerases include without limitation AMPLITAQ® DNA polymerase, FS (Taq DNA polymerase that contains the G46D and F667Y mutations), THERMOSEQUENASE™ DNA polymerase (Taq DNA polymerase that contains the F667Y mutation), THERMOSEQUENASE™ II DNA polymerase (blend of THERMOSEQUENASE™ DNA polymerase and *T. acidophilum* pyrophosphatase), THERMI- NATOR™ DNA polymerase (DNA polymerase A, cloned from the *Thermococcus* species 9° N-7 and containing the D141A, E143A and A485L mutations), THERMINATOR™ II DNA polymerase (THERMINATOR™ DNA polymerase that contains the additional Y409V mutation), and VENT® (exo-) A488L DNA polymerase (VENT® (exo-) DNA polymerase that contains the A488L mutation). Preferably, compounds according to the invention are incorporated at levels equal to or near the incorporation levels of naturally-occurring nucleotides, thus resulting in no bias against the compounds according to the invention. Even more preferably, compounds according to the invention are compatible with commercially-available polymerases.

In one embodiment, the compounds can be used in cyclic reversible termination (CRT), which is a cyclic method of detecting the synchronous, single base additions of multiple templates. Longer read-lengths translate into fewer sequencing assays needed to cover the entire genome. A method of synthesizing a nucleic acid comprises the following steps: attaching the 5'-end of a primer to a solid surface; hybridizing a target nucleic acid to the primer attached to the solid surface; adding one or more compounds according to the formula

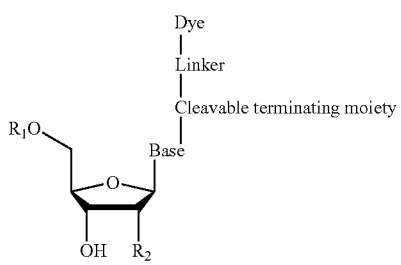

wherein $R_1$ is H, monophosphate, diphosphate or triphosphate, $R_2$ is H or OH, base is cytosine, uracil, thymine, adenine, or guanine, or naturally occurring derivatives thereof, cleavable terminating moiety is a group imparting polymerase termination properties to the compound, linker is a bifunctional group, and dye is a fluorophore; adding DNA polymerase to the hybridized primer/target nucleic acid complex to incorporate the compound of the previous step into the growing primer strand, wherein the incorporated compound terminates the polymerase reaction at an efficiency of between about 90% to about 100%; washing the solid surface to remove unincorporated components; detecting the incorporated fluorophore, wherein the detector is optionally a pulsed multiline excitation detector for imaging fluorescent dyes; optionally adding one or more chemical compounds to permanently cap unextended primers; exposing the solid support to a light source to remove the photocleavable moiety resulting in an extended primer with naturally-occurring components; washing the solid surface to remove the cleaved protecting group; and repeating the above steps in a cyclic fashion.

In another embodiment, compounds according to the invention can be used in a method of determining the sequence of a nucleic acid molecule comprising the steps of adding a target nucleic acid molecule to a sequencing apparatus, adding one or more compounds according to the invention to the sequencing apparatus, adding a polymerase enzyme and optionally naturally-occurring nucleic acid components to the sequencing apparatus, performing a polymerase reaction to incorporate at least one of the compounds of the previous step into a growing nucleic acid strand, and analyzing the result of the polymerase reaction for incorporation of at least one compound according to the invention. The steps can be performed in any order and in any number of iterations. Preferably, the incorporation step is followed by termination of strand growth at a rate of from about 90% to about 100%. In another embodiment, the incorporation of the inventive compound occurs at about 70% to about 100% of the rate of incorporation of a native substrate of the analogous base, such that no significant bias occurs. For example, the incorporation rate may occur at about 85% to about 100% of the normal rate for the corresponding nucleotide base. An important embodiment includes the step of exposing the nucleic acid molecule resulting from incorporation of a modified nucleotide to a UV or light source to remove a photocleavable terminating moiety from the nucleic acid. Preferably, the efficiency of the photocleavage step is about 85% to about 100% from exposure to the UV or light source.

Methods according to the invention can be practiced individually or in combination. For example, the method of sequencing a nucleic acid molecule can be practiced in part as a method of incorporating a non-naturally occurring component into a nucleic acid molecule, or a separate method of converting a non-naturally occurring component in a nucleic acid molecule into a naturally-occurring component following incorporation of a compound according to the invention.

In one embodiment, methods according to the invention include the aspect of terminating nucleic acid synthesis following incorporation of an unprotected 3'-OH nucleotide. Advantageously, an unprotected 3'-OH nucleotide can be incorporated by polymerases at a higher level, resulting in lower levels of modified nucleotide present in the polymerase reaction and lower bias compared to natural nucleotides. Therefore, a preferred embodiment includes a method of terminating nucleic acid synthesis comprising the step of placing a 3'-OH unprotected nucleotide or nucleoside in the environment of a polymerase and allowing incorporation of the 3'-OH unprotected nucleotide or nucleoside into a nucleic acid molecule, wherein the 3'-OH unprotected nucleotide or nucleoside is a compound according to the following formula:

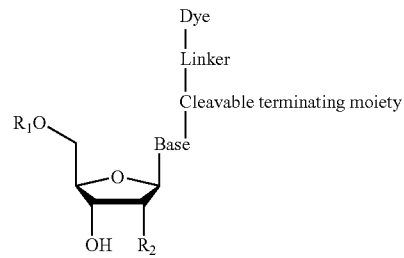

wherein $R_1$ is H, monophosphate, diphosphate or triphosphate, $R_2$ is H or OH, base is cytosine, uracil, thymine, adenine, or guanine, or naturally occurring derivatives thereof, cleavable terminating moiety is a group imparting polymerase termination properties to the compound, linker is a bifunctional group, and dye is a fluorophore. Preferrably, the method has an efficiency of termination upon incorporation of the 3'-OH unprotected nucleotide or nucleoside ranging from about 90% to about 100%. Alternatively, the method may have an efficiency of incorporation of the 3'-OH unprotected nucleotide or nucleoside ranges from about 70% to about 100% compared to the efficiency of incorporation of a naturally-occurring nucleotide or nucleoside with the same base.

The nucleotide and nucleoside compounds can be used in CRT to read directly from genomic DNA. Fragmented genomic DNA can be hybridized to a high-density oligonucleotide chip containing priming sites that span selected chromosomes. Each priming sequence is separated by the estimated read-length of the CRT method. Between base additions, a fluorescent imager, such as a Pulsed Multiline Excitation (PME) detector, can simultaneously image the entire high-density chip, marking significant improvements in speed and sensitivity. The fluorophore, which is attached to the cleavable terminating group on the base, is removed by UV irradiation transforming the modified nucleotide into its natural from for the next round of base addition. After approximately 500 CRT cycles, the completed and contiguous genome sequence information can then be compared to the reference human genome to determine the extent and type of sequence variation in an individual's sample. Methods for cyclic reversible termination have been developed in the art and can be used, as described, e.g., in WO 2003/021212, the disclosure of which is incorporated herein by reference.

In one embodiment, a method for sequencing a nucleic acid by detecting the identity of a nucleotide analogue after the nucleotide analogue is incorporated into a growing strand of DNA in a polymerase reaction is used, which comprises the following steps:
(a) attaching the 5' end of a nucleic acid to a solid surface;
(b) attaching a primer to the nucleic acid attached to the solid surface;
(c) adding a polymerase and one or more different nucleoside triphosphate compounds to the nucleic acid wherein the nucleoside triphosphate compound incorporates and then terminates the polymerase reaction and wherein each nucleoside triphosphate compound comprises a base selected from the group consisting of adenine, guanine, cytosine, thymine, and uracil, and their analogues and a photocleavable terminating group attached to the base, the photocleavable group comprising a detectable label, and a deoxyribose or ribose sugar;
(d) optionally washing the solid surface to remove unincorporated nucleotide analogues;
(e) detecting and thereby identifying the detectable label, such as a fluorescent dye or reporter molecule, attached to the terminated nucleoside triphosphate, e.g. with PME;
(f) optionally adding one or more chemical compounds to permanently cap any unreacted —OH group on the primer attached to the nucleic acid or on a primer extension strand formed by adding one or more nucleotides to the primer;
(g) exposing the solid surface to a light source to remove the photocleavable protecting group containing the unique label or reporter molecule, wherein the remaining incorporated nucleoside monophosphate unit resembles a natural, native, or unmodified nucleic acid molecule;
(h) washing the solid surface to remove the cleaved protecting group; and
(i) repeating steps (c) through (h) for determining the sequence of identified incorporated nucleotide analogs into the growing primer strand.

PME Detector

In one embodiment, a pulsed-multiline excitation ("PME") for color-blind fluorescence detection can be used as described in US 2003/0058440 published Mar. 27, 2003, or WO 2003/021212, published Mar. 13, 2003. This technology provides fluorescence detection with application for high-throughput identification of informative SNPs, for more accurate diagnosis of inherited disease, better prognosis of risk susceptibilities, or identification of sporadic mutations. The PME technology has two main advantages that significantly increase fluorescence sensitivity: (1) optimal excitation of all fluorophores in the genomic assay and (2) "color-blind" detection, which collects considerably more light than standard wavelength resolved detection. This technology differs significantly from DNA sequencing instrumentation which features single source excitation and color dispersion for DNA sequence identification. The technology can be used in clinical diagnostics, forensics, and general sequencing methodologies and will have the capability, flexibility, and portability of targeted sequence variation assays for a large majority of the population.

In one embodiment, an apparatus and method for use in high-throughput DNA sequence identification is used. A pulse-multiline excitation apparatus for analyzing a sample containing one or more fluorescent species is used, comprising: one or more lasers configured to emit two or more excitation lines, each excitation line having a different wavelength; a timing circuit coupled to the one or more lasers and configured to generate the two or more excitation lines sequentially according to a timing program to produce time-correlated fluorescence emission signals from the sample; a non-dispersive detector positioned to collect the time-correlated fluorescence emission signals emanating from the sample; and an analyzer coupled to the detector and configured to associate the time-correlated fluorescence emission signals with the timing program to identify constituents of the sample.

The detector and the analyzer may be integral. In one embodiment, the two or more excitation lines intersect at the sample, or the two or more excitation lines may be configured so that they do not intersect in the sample. The two or more excitation lines may be coaxial.

In one embodiment, the apparatus may further comprise an assembly of one or more prisms in operative relation with the one or more lasers and configured to render radiation of the two or more excitation lines substantially colinear and/or coaxial.

The apparatus may have a plurality of excitation lines, for example 1, 2, 3, 4, 5, 6, 7, 8, 9, 10, 11, 12, 13, 14, 15, 16 or more excitation lines having 1, 2, 3, 4, 5, 6, 7, 8, 9, 10, 11, 12, 13, 14, 15, 16 or more excitation wavelengths, respectively. The sample may be comprised a plurality of vessels such as capillaries, for example in 1, 2, 3, 4, 5, 6, 7, 8, 9, 10, 11, 12, 13, 14, 15, 16, up to 20, up to 24, up to 28, up to 36, up to 48, up to 64, up to 96, up to 384 or more capillaries. A sheath flow cuvette may be used.

The timing program may comprise a delay between the firing of each laser of between about 10 fs and about 5 s, between about 1 ms and about 100 ms, or between about 50 ps and about 500 ps. One or more of the excitation lines is pulsed. The pulsed excitation line may be controlled by TTL logic or by mechanical or electronic means. In one embodiment, the apparatus may generate a sequence of discrete excitation lines that are time-correlated with the fluorescence emission signals from the sample.

The lasers may independently comprise a diode laser, a semiconductor laser, a gas laser, such as an argon ion, krypton, or helium-neon laser, a diode laser, a solid-state laser such as a Neodymium laser which will include an ion-gain medium, such as YAG and yttrium vanadate ($YVO_4$), or a diode pumped solid state laser. Other devices, which produce light at one or more discrete excitation wavelengths, may also be used in place of the laser. The laser may further comprise a Raman shifter in operable relation with at least one laser beam. In one embodiment of the invention, the excitation wavelength provided by each laser is optically matched to the absorption wavelength of each fluorophore.

The detector may comprise a charged couple device, a photomultiplier tube, a silicon avalanche photodiode or a silicon PIN detector. The footprint of the device is preferably small, such as less than 4 ft×4 ft×2 ft, less than 1 ft×1 ft×2 ft, and could be made as small as 1 in×3 in×6 in.

Another aspect comprises a method of identifying sample components comprising: (a) preparing a sample comprising sample components, a first dye and a second dye; (b) placing the sample in the beam path of a first excitation line and a second excitation line; (c) sequentially firing the first excitation line and the second excitation line; (d) collecting fluorescence signals from the samples as a function of time; and (e) sorting the fluorescence by each excitation line's on-time window, wherein the sample components are identified. It is an aspect of the invention that the fluorescence signals are collected from discrete time periods in which no excitation line is incident on the sample, the time periods occurring between the firing of the two excitation lines. This technique is known as "looking in the dark." Yet another aspect is that the absorption maximum of the first dye substantially corresponds to the excitation wavelength of the first excitation line. The absorption maximum of the second dye may also substantially corresponds to the excitation wavelength of the second excitation line. In yet another aspect there is a third and fourth dye and a third and fourth excitation line, wherein the absorption maxima of the third and fourth dyes substantially correspond to the excitation wavelengths of the third and four excitation lines, respectively. Similarly, there may be 5, 6, 7, 8, 9, 10, 11, 12, 13, 14, 15, 16 or more dyes wherein the absorption maxima of the dyes substantially corresponds to excitation wavelengths of a 5th, 6th, 7th, 8th, 9th, 10th, 11 th, 12th, 13th, 14th, or more excitation lines, respectively. The dyes may be a zanthene, fluorescein, rhodamine, BODIPY, cyanine, coumarin, pyrene, phthalocyanine, phycobiliprotein, ALEXA FLUOR® (e.g., ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700 or ALEXA FLUOR® 750), squariane dyes, or some other suitable dye.

In one embodiment, sample components enable the determination of SNPs. The method may be for the high-throughput identification of informative SNPs. The SNPs may be obtained directly from genomic DNA material, from PCR amplified material, or from cloned DNA material and may be assayed using a single nucleotide primer extension method. The single nucleotide primer extension method may comprise using single unlabeled dNTPs, single labeled dNTPs, single 3'-modified dNTPs, single base-modified 2'-dNTPs, single alpha-thio-dNTPs or single labeled 2', 3'dideoxynucleotides. The mini-sequencing method may comprise using single unlabeled dNTPs, single labeled dNTPs, single 3'-modified dNTPs, single base-modified 2'-dNTPs, single alpha-thio-dNTPs or single labeled 2', 3'-dideoxynucleotides. The SNPs may be obtained directly from genomic DNA material, from PCR amplified material, or from cloned DNA materials.

Also envisioned are methods for detecting nucleic acids. Nucleic acids may be detected in situ or in various gels, blots, and similar methods for detecting nucleic acids, such as disclosed in U.S. Pat. No. 7,125,660, which is incorporated herein by reference.

EXAMPLES

Example 1 dA Compounds

Synthesis of 3'-O-(2-nitrobenzyl)-2'-deoxyadenosine triphosphate (WW1p108)

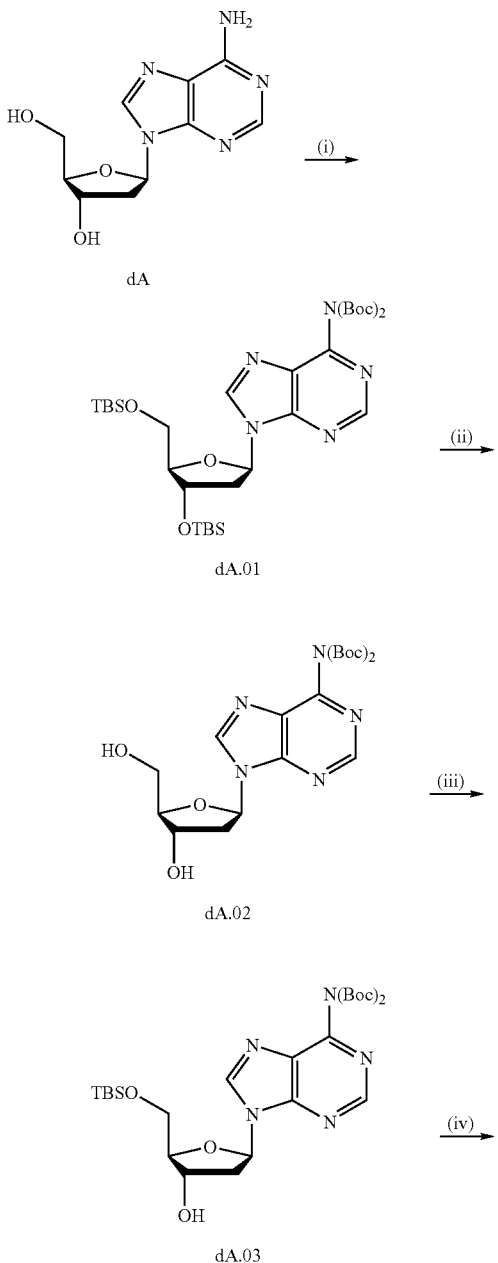

-continued

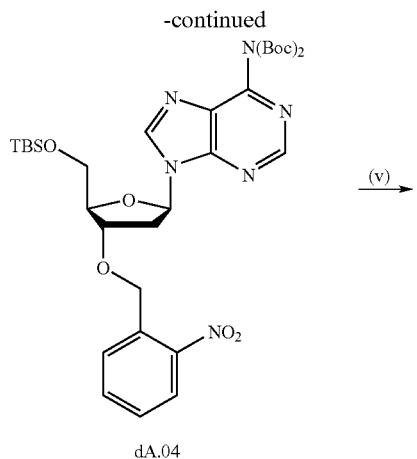

dA.04

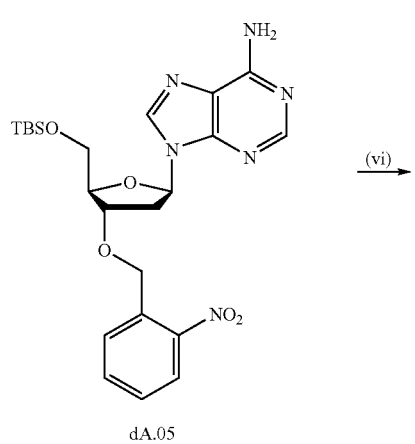

dA.05

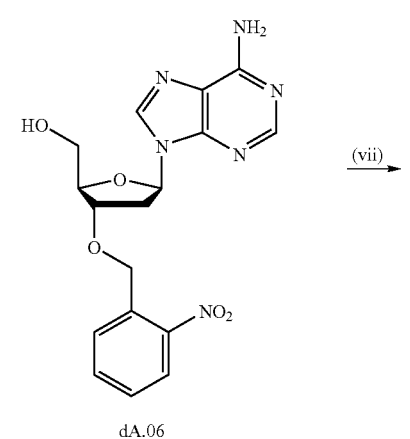

dA.06

-continued

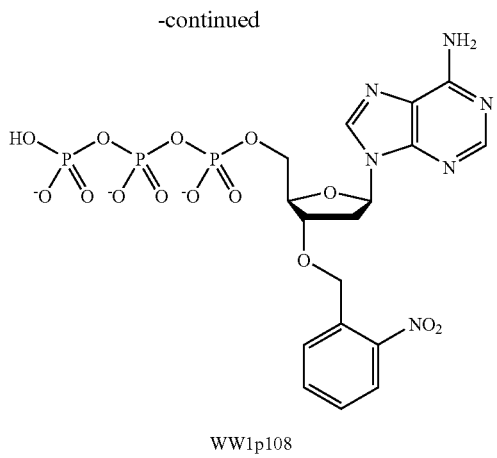

WW1p108

Scheme. Synthesis of 3'-O-(2-nitrobenzyl)-2'-deoxyadenosine-5'-triphosphate. (i) TBSCl, imidazole, DMF, room temperature, overnight; Boc$_2$O, DMAP, DMF, room temperature, overnight, 83%; (ii) n-Bu$_4$NF, THF, 0° C., then gradually warmed to room temperature, 96%; (iii) TBSCl, imidazole, DMF, 83%; (iv) n-Bu$_4$NOH, NaI, NaOH, CH$_2$Cl$_2$/H$_2$O, 2-nitrobenzyl bromide, room temperature, 91%; (v) SiO$_2$, high vacuum, 70-80° C., 24 hours, 91%; (vi) n-Bu$_4$NF, THF, 0° C., then gradually warmed to room temperature, 23%; (vii) POCl$_3$, (MeO)$_3$PO, minus 20° C.; (n-Bu$_3$NH)$_2$ H$_2$P$_2$O$_7$, n-Bu$_3$N, DMF; 1 M HNEt$_3$HCO$_3$, 31%.

$N^6,N^6$-Bis-tert-butyloxycarbonyl-3',5'-O-bis-tert-butyldimethylsilyl-2'-deoxyadenosine (dA.01)

Compound dA.01 was synthesized according to the procedure described by Furrer and Giese[1]. A solution of 2'-deoxyadenosine dA (2.5 g, 10 mmol), imidazole (4.5 g, 66 mmol), and TBSCl (4.82 g, 32 mmol) in anhydrous DMF (25 mL) was stirred at room temperature overnight. Methanol (20 mL) was added, and the mixture was stirred for 20 minutes and then concentrated in vacuo. The residue was dissolved in anhydrous DMF (15 mL) followed by the addition of DMAP (3.66 g, 30 mmol) and Boc$_2$O (6.55 g, 30 mmol). The reaction was stirred at room temperature overnight and then concentrated in vacuo. The residue was dissolved in CH$_2$Cl$_2$ (100 mL) and washed twice with saturated NH$_4$Cl solution (50 mL each). The combined aqueous layer was extracted with CH$_2$Cl$_2$ (50 mL). The combined organic layer was then dried over Na$_2$SO$_4$, concentrated in vacuo, and purified by silica gel column chromatography to give $N^6,N^6$-bis-tert-butyloxycarbonyl-3',5'-O-bis-tert-butyldimethylsilyl-2'-deoxyadenosine dA.01 (5.66 g, 83%) as a white foam.

[1] Furrer, E. and Giese, B. (2003) On the distance-independent hole transfer over long (A•T)$_n$-sequences in DNA. Helvetica Chimica Acta, 86, 3623-3632.

$N^6,N^6$-Bis-tert-butyloxycarbonyl-2'-deoxyadenosine (dA.02)

A solution of Bu$_4$NF (7.85 g, 30 mmol) in THF (30 mL) was added to a solution of compound dA.01 (6.78 g, 10 mmol) in THF (30 mL) at 0° C. The reaction mixture was gradually warmed to room temperature, stirred for two hours, and then concentrated in vacuo. The residue was dissolved in CH$_2$Cl$_2$ (100 mL) and washed twice with saturated NH$_4$Cl solution (100 mL each). The organic layer was then dried over Na$_2$SO$_4$, concentrated in vacuo, and purified by silica gel column chromatography to yield $N^6,N^6$-bis-tert-butyloxycarbonyl-2'-deoxyadenosine dA.02 (4.34 g, 96%) as a white foam.

$^1$H NMR (400 MHz, CDCl$_3$): δ 8.84 (s, 1 H, H-8), 8.20 (s, 1 H, H-2), 6.41 (dd, 1 H, J=5.6 Hz and 9.2 Hz, H-1'), 4.77 (d, 1 H, H-4'), 4.21 (s, 1 H, H-3'), 3.98 (dd, 1 H, H-5'a), 3.80 (m, 1 H, H-5'b), 3.00 (m, 1 H, H-2'a), 2.36 (m, 1 H, H-2'b), 1.47 (s, 18 H, (CH$_3$)$_3$CO).

$N^6,N^6$-Bis-tert-butyloxycarbonyl-5'-O-tert-butyldimethylsilyl-2'-deoxyadenosine (dA.03)

A solution of TBSCl (1.88 g, 12.5 mmol) in anhydrous DMF (5 mL) was added to a solution of compound dA.02 (4.34 g, 9.6 mmol) and imidazole (1.3 g, 19.2 mmol) in anhydrous DMF (20 mL) at 0° C. The mixture was gradually warmed to room temperature and stirred for two days. Water (50 mL) was added, and the mixture was extracted three times with ethyl acetate (40 mL each). The combined organic layer was washed with saturated NH$_4$Cl solution (50 mL), dried over Na$_2$SO$_4$, and purified by silica gel column chromatography to yield $N^6,N^6$-bis-tert-butyloxycarbonyl-5'-O-tert-butyl-dimethylsilyl-2'-deoxyadenosine dA.03 (4.68 g, 83%) as a white foam.

$^1$H NMR (400 MHz, CDCl$_3$): δ 8.84 (s, 1 H, H-8), 8.42 (s, 1 H, H-2), 6.57 (t, 1 H, J=6.4 Hz, H-1'), 4.69 (m, 1 H, H-4'), 4.10 (m, 1 H, H-3'), 3.89 (m, 2 H, H-5'a and H-5'b), 2.70 (m, 1 H, H-2'a), 2.58 (m, 1 H, H-2'b), 1.44 (s, 18 H, (CH$_3$)$_3$CO), 0.91 (s, 9 H, (CH$_3$)$_3$CSi), 0.10 (s, 6 H, (CH$_3$)$_2$Si).

$N^6,N^6$-Bis-tert-butyloxycarbonyl-5'-O-tert-butyldimethylsilyl-3'-O-(2-nitrobenzyl)-2'-deoxyadenosine (dA.04)

A solution of compound dA.03 (1.13 g, 2 mmol) in CH$_2$Cl$_2$ (3 mL) was mixed with a solution of n-Bu$_4$NOH (0.94 mL, 4 mmol, 55% aqueous solution) and NaI (20 mg, catalytic amount) in NaOH (1 M; 3 mL). To the mixture, a solution of 2-nitrobenzyl bromide (1.3 g, 6 mmol) in CH$_2$Cl$_2$ (2 mL) was added dropwise, and the reaction mixture was stirred at room temperature for two hours in the dark. The organic layer was separated, and the aqueous layer was extracted twice with CH$_2$Cl$_2$ (10 mL each). The combined organic layer was dried over Na$_2$SO$_4$, concentrated in vacuo, and purified by silica gel column chromatography to yield $N^6,N^6$-bis-tert-butyloxycarbonyl-5'-O-tert-butyldimethylsilyl-3'-O-(2-nitrobenzyl)-2'-deoxyadenosine dA.04 (1.28 g, 91%) as a white foam.

$^1$H NMR (400 MHz, CDCl$_3$): δ 8.85 (s, 1 H, H-8), 8.43 (s, 1 H, H-2), 8.10 (dd, 1 H, Ph-H), 7.81 (d, 1 H, Ph-H), 7.70 (t, 1 H, Ph-H), 7.51 (t, 1 H, Ph-H), 6.57 (t, 1 H, J=6.8 Hz, H-1'), 4.98 (dd, 2 H, PhCH$_2$), 4.45 (m, 1 H, H-4'), 4.33 (m, 1 H, H-3'), 3.90 (m, 2 H, H-5'a and H-5'b), 2.73 (m, 2 H, H-2'a and H-2'b), 1.46 (s, 18 H, (CH$_3$)$_3$CO), 0.91 (s, 9 H, (CH$_3$)$_3$CSi), 0.11 (s, 6 H, (CH$_3$)$_2$Si);

ToF-MS (ESI): For the molecular ion C$_{33}$H$_{49}$N$_6$O$_9$Si [M+H]$^+$, the calculated mass was 701.3330, and the observed mass was 701.3317.

5'-O-tert-Butyldimethylsilyl-3'-O-(2-nitrobenzyl)-2'-deoxyadenosine (dA.05)

Silica gel 60 (10 g, 100-200 mesh, activated by heating to 70-80° C. under reduced pressure for 24 hours) was added to a solution of compound dA.04 (1.28 g, 1.8 mmol) in CH$_2$Cl$_2$ (50 mL), and the mixture was evaporated in vacuo to dryness. The residue obtained was heated to 70-80° C. for two days under reduced pressure, washed three times with methanol (50 mL each), and filtered using a buchi funnel. The combined filtrate was concentrated in vacuo and purified by silica gel column chromatography to yield 5'-O-tert-butyldimethylsilyl-3'-O-(2-nitrobenzyl)-2'-deoxyadenosine dA.05 (0.83 g, 91%) as a white foam.

$^1$H NMR (400 MHz, CDCl$_3$): δ 8.34 (s, 1 H, H-8), 8.15 (s, 1 H, H-2), 8.09 (d, 1 H, Ph-H), 7.81 (d, 1 H, Ph-H), 7.67 (t, 1 H, Ph-H), 7.47 (t, 1 H, Ph-H), 6.50 (t, 1 H, J=6.8 Hz, H-1'), 6.03 (bs, 2 H, 6-NH$_2$), 4.96 (dd, 2 H, PhCH$_2$), 4.43 (m, 1 H, H-4'), 4.30 (m, 1 H, H-3'), 3.88 (m, 2 H, H-5'a and H-5'b), 2.71 (m, 2 H, H-2'a and H-2'b), 0.91 (s, 9 H, (CH$_3$)$_3$CSi), 0.10 (s, 6 H, (CH$_3$)$_2$Si);

ToF-MS (ESI): For the molecular ion C$_{23}$H$_{33}$N$_6$O$_5$Si [M+H]$^+$, the calculated mass was 501.2282, and the observed mass was 501.1702.

3'-O-(2-Nitrobenzyl)-2'-deoxyadenosine (dA.06)

A solution of n-Bu$_4$NF (314 mg, 1.2 mmol) in THF (1.2 mL) was added to a solution of compound dA.05 (400 mg, 0.8 mmol) in THF (3 mL) at 0° C. The reaction mixture was gradually warmed to room temperature and stirred for four hours. Methanol (10 mL) was added to dissolve the precipitate formed during the reaction, followed by the addition of silica gel 60 (1.5 g). The mixture was evaporated in vacuo to dryness, and the residue was purified by silica gel column chromatography to yield 3'-O-(2-nitrobenzyl)-2'-deoxyadenosine dA.06 (72 mg, 23%) as a white foam.

$^1$H NMR (400 MHz, DMSO-d$_6$): δ 8.35 (s, 1 H, H-8), 8.13 (s, 1 H, H-2), 8.06 (d, 1 H, Ph-H), 7.79 (m, 2 H, Ph-H), 7.60 (m, 1 H, Ph-H), 7.34 (bs, 2 H, 6-NH$_2$, D$_2$O exchangeable), 6.33 (dd, 1 H, J=4.8 and 6.8 Hz, H-1'), 5.40 (t, 1 H, D$_2$O exchangeable, 5'-OH)), 4.92 (s, 2 H, PhCH$_2$), 4.36 (m, 1 H, H-4'), 4.12 (m, 1 H, H-3'), 3.59 (m, 2 H, H-5'a and H-5'b), 2.85 (m, 1 H, H-2'a), 2.54 (m, 1 H, H-2'b);

ToF-MS (ESI): For the molecular ion C$_{17}$H$_{19}$N$_6$O$_5$ [M+H]$^+$, the calculated mass was 387.1417, and the observed mass was 387.1350.

3'-O-(2-Nitrobenzyl)-2'-deoxyadenosine-5'-triphosphate (WW1p108)

POCl$_3$ (26 μL, 0.24 mmol) was added to a solution of compound dA.06 (72 mg, 0.18 mmol) in trimethylphosphate (1 mL), and maintained at minus 20-30° C. for 2.5 hours. A solution of bis-tri-n-butylammonium pyrophosphate (427 mg, 0.9 mmol) and tri-n-butylamine (0.2 mL) in anhydrous DMF (2 mL) was added. After five minutes of stirring, triethylammonium bicarbonate buffer (1 M, pH 7.5; 10 mL) was added. The reaction was stirred at room temperature for one hour and then lyophilized to dryness. The residue was dissolved in water (10 mL), filtered, and purified by anion exchange chromatography using a Q Sepharose FF column (2.5×20 cm) with a linear gradient of NH$_4$HCO$_3$ (50 mM to 500 mM in 300 minutes) at a flow rate of 4.5 mL/min. The fractions containing triphosphate were combined and lyophilized to give 3'-O-(2-nitrobenzyl)-2'-deoxyadenosine-5'-triphosphate WW1p108 (38 mg, 31%) as a white fluffy solid.

$^1$H NMR (400 MHz, D$_2$O): δ 8.50 (s, 1 H, H-8), 8.24 (s, 1 H, H-2), 8.10 (d, 1 H, Ph-H), 7.78 (d, 1 H, Ph-H), 7.62 (m, 1 H, Ph-H), 6.50 (dd, 1 H, J=6.8 and 8 Hz, H-1'), 5.03 (dd, 2 H, Ph-CH$_2$), 4.65 (m, 1 H, H-4'), 4.53 (m, 1 H, H-3'), 4.22 (m, 2 H, H-5'a and H-5'b), 2.80 (m, 2 H, H-2'a and H-2'b);

$^{31}$P NMR (162 MHz, D$_2$O): δ -5.54 (d, J=19.4 Hz), -10.85 (d, J=19.4 Hz), -21.31 (t, J=19.4 Hz);

ToF-MS (ESI): For the molecular ion C$_{17}$H$_{21}$N$_6$O$_{14}$P$_3$Na [M+Na]$^+$, the calculated mass was 649.0226, and the observed mass was 649.0212.

The triphosphate was further purified using preparative HPLC without UV detection to give sample free from contamination of the natural nucleotide (e.g., dATP). Determination of the concentration of the triphosphate solution was performed by UV/VIS measurement using the extinction coefficient of $\epsilon_{260}$=20,800.

Synthesis of $N^6$-(2-nitrobenzyl)-2'-deoxyadenosine triphosphate (WW1p129)

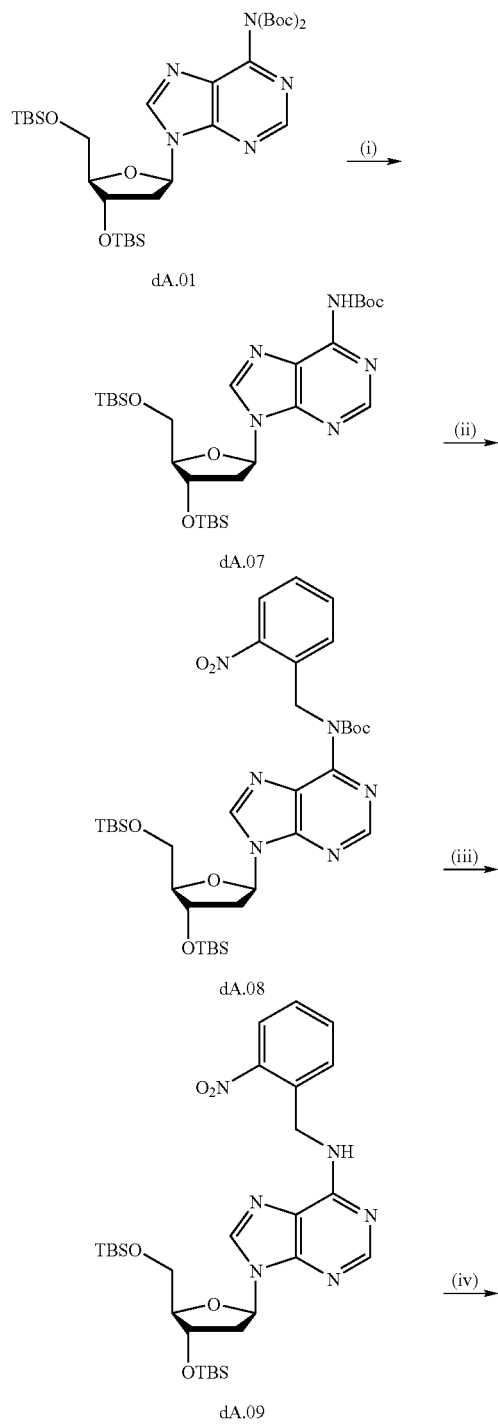

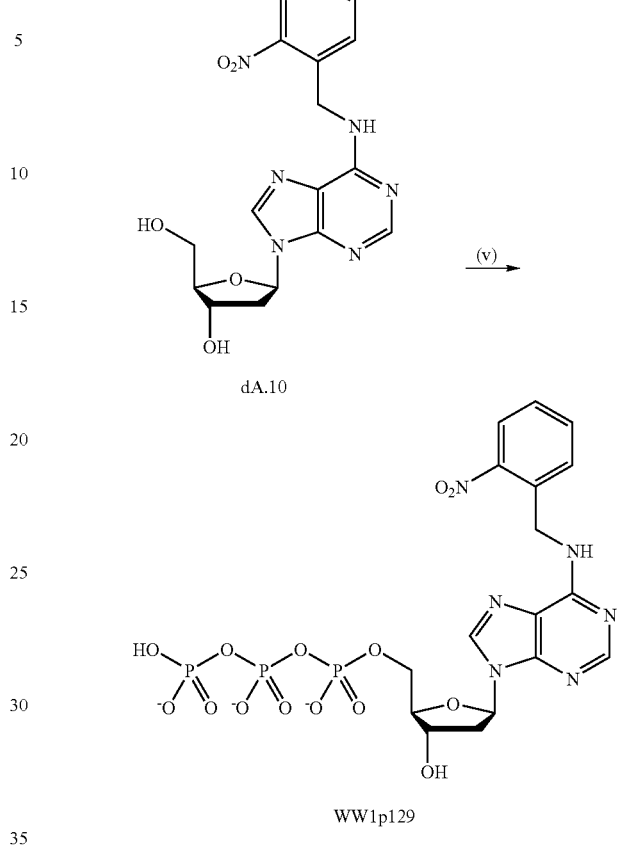

Scheme. Synthesis of $N^6$-(2-nitrobenzyl)-2'-deoxyadenosine-5'-triphosphate. (i) Mg(ClO$_4$)$_2$, THF, 50° C., 68%; (ii) NaH, DMF, 2-nitrobenzyl bromide, 0° C., then gradually warmed to room temperature, 49%; (iii) SiO$_2$, vacuum, 70-80° C., 87%; (iv) n-Bu$_4$NF, THF, 43%; (v) POCl$_3$, (MeO)$_3$PO, minus 20-30° C.; (n-Bu$_3$NH)$_2$H$_2$P$_2$O$_7$, n-Bu$_3$N, DMF; 1 M HNEt$_3$HCO$_3$; 60%.

$N^6$-tert-Butyloxycarbonyl-3',5'-O-bis-tert-butyldimethylsilyl-2'-deoxyadenosine (dA.07)

Mg(ClO$_4$)$_2$ (155 mg, 0.7 mmol) was added to a solution of compound dA.01 (2.36 g, 3.5 mmol) in anhydrous THF (35 mL) and stirred at 50° C. overnight. Solvent was removed in vacuo, and the crude product was purified by silica gel column chromatography to give $N^6$-tert-butyloxycarbonyl-3',5'-O-bis-tert-butyldimethylsilyl-2'-deoxyadenosine dA.07 (1.39 g, 68%) as a yellow foam.

$^1$H NMR (400 MHz, CDCl$_3$): δ 8.74 (s, 1 H, H-8), 8.29 (s, 1 H, H-2), 8.24 (s, 1 H, 6-NHBoc), 6.49 (t, 1 H, J=6.4 Hz, H-1'), 4.60 (m, 1 H, H-4'), 4.02 (m, 1 H, H-3'), 3.86 (dd, 1 H, H-5'a), 3.77 (dd, 1 H, H-5'b), 2.62 (m, 1 H, H-2'a), 2.47 (m, 1 H, H-2'b), 1.54 (s, 9 H, (CH$_3$)$_3$CO), 0.90 (s, 18 H, (CH$_3$)$_3$CSi), 0.08 (2 s, 12 H, (CH$_3$)$_2$Si).

$N^6$-tert-Butyloxycarbonyl-$N^6$-(2-nitrobenzyl)-3',5'-O-bis-tert-butyldimethylsilyl-2'-deoxyadenosine (dA.08)

NaH (5.3 mg, 0.22 mmol, dry) was added to a solution of compound dA.07 (116 mg, 0.2 mmol) in anhydrous DMF (2 mL) at 0° C. and stirred for 30 minutes. A solution of 2-nitrobenzyl bromide (43 mg, 0.2 mmol) in anhydrous DMF (0.5 mL) was added dropwise. The mixture was gradually warmed to room temperature and stirred for two hours. DMF was removed in vacuo, and the residue was dissolved in ethyl acetate (20 mL), washed twice with saturated NH$_4$Cl solution (10 mL each) and once with water (10 mL). The combined aqueous layer was extracted with ethyl acetate (10 mL), and the combined organic layer was dried over Na$_2$SO$_4$, concentrated in vacuo, and purified by silica gel column chromatography to yield N$^6$-tert-butyloxycarbonyl-N$^6$-(2-nitrobenzyl)-3',5'-O-bis-tert-butyldimethylsilyl-2'-deoxyadenosine dA.08 (70 mg, 49%) as a viscous oil.

$^1$H NMR (400 MHz, CDCl$_3$): δ 8.69 (s, 1 H, H-8), 8.38 (s, 1 H, H-2), 8.05 (dd, 1 H, Ph-H), 7.77 (d, 1 H, Ph-H), 7.56 (m, 1 H, Ph-H), 7.40 (m, 1 H, Ph-H), 6.51 (t, 1 H, J=6.4 Hz, H-1'), 5.63 (s, 2 H, Ph-CH$_2$), 4.63 (m, 1 H, H-4'), 4.03 (m, 1 H, H-3'), 3.87 (m, 1 H, H-5'a), 3.78 (m, 1 H, H-5'b), 2.63 (m, 1 H, H-2'a), 2.46 (m, 1 H, H-2'b), 1.40 (s, 9 H, (CH$_3$)$_3$CO), 0.92 (s, 18 H, (CH$_3$)$_3$CSi), 0.10 (2 s, 12 H, (CH$_3$)$_2$Si—);

ToF-MS (ESI): For the molecular ion C$_{34}$H$_{55}$N$_6$O$_7$Si$_2$ [M+H]$^+$, the calculated mass was 715.3671, and the observed mass was 715.3661.

N$^6$-(2-Nitrobenzyl)-3',5'-O-bis-tert-butyldimethylsilyl-2'-deoxyadenosine (dA.09)

Silica gel 60 (3.5 g, 100-200 mesh, activated by heating to 70-80° C. under reduced pressure for 24 hours) was added to a solution of compound dA.08 (325 mg, 0.45 mmol) in CH$_2$Cl$_2$ (20 mL), and the mixture was evaporated in vacuo to dryness. The residue was heated to 70-80° C. under reduced pressure for two days, washed three times with methanol (20 mL each), and filtered using a buchi funnel. The combined filtrate was concentrated in vacuo and purified by silica gel column chromatography to yield N$^6$-(2-nitrobenzyl)-3',5'-O-bis-tert-butyldimethylsilyl-2'-deoxyadenosine dA.09 (238 mg, 86%) as a yellow foam.

$^1$H NMR (400 MHz, CDCl$_3$): δ 8.37 (s, 1 H, H-8), 8.09 (s, 1 H, H-2), 8.07 (d, 1 H, Ph-H), 7.74 (d, 1 H, Ph-H), 7.56 (m, 1 H, Ph-H), 7.42 (m, 1 H, Ph-H), 6.57 (t, 1 H, 6-NH), 6.44 (t, 1 H, J=6.4 Hz, H-1'), 5.19 (bs, 2 H, Ph-CH$_2$), 4.61 (m, 1 H, H-4'), 4.00 (m, 1H, H-3'), 3.86 (dd, 1 H, H-5'a), 3.76 (dd, 1 H, H-5'b), 2.63 (m, 1 H, H-2'a), 2.43 (m, 1 H, H-2'b), 0.91 (s, 18 H, (CH$_3$)$_3$CSi), 0.09 (2 s, 12 H, (CH$_3$)$_2$Si—);

ToF-MS (ESI): For the molecular ion C$_{29}$H$_{47}$N$_6$O$_5$Si$_2$ [M+H]$^+$, the calculated mass was 615.3147, and the observed mass was 615.2288.

N$^6$-(2-Nitrobenzyl)-2'-deoxyadenosine (dA.10)

A solution of n-Bu$_4$NF (216 mg, 0.83 mmol) in THF (1 mL) was added to a solution of compound dA.09 (202 mg, 0.33 mmol) in THF (5 mL) at 0° C. The reaction mixture was gradually warmed to room temperature and stirred for two hours. Silica gel 60 (1 g) was added, and the mixture was evaporated in vacuo to dryness. The residue was purified by silica gel column chromatography to yield N$^6$-(2-nitrobenzyl)-2'-deoxyadenosine dA.10 (55 mg, 43%) as a white foam.

$^1$H NMR (400 MHz, DMSO-d$_6$): δ 8.48 (br s, 1 H, D2O exchangeable, 6-NH), 8.41 (s, 1H, H-8), 8.16 (s, 1 H, H-2), 8.04 (dd, 1 H, Ph-H), 7.66 (d, 1 H, Ph-H), 7.51 (m, 2 H, Ph-H), 6.35 (t, 1 H, J=6.4 Hz, H-1'), 5.32 (d, 1 H, D$_2$O exchangeable, 3'-OH), 5.17 (t, 1 H, D$_2$O exchangeable, 5'-OH), 4.97 (bs, 2 H, Ph-CH$_2$), 4.41 (m, 1 H, H-4'), 3.87 (m, 1 H, H-3'), 3.60 (m, 1 H, H-5'a), 3.52 (m, 1 H, H-5'b), 2.71 (m, 1 H, H-2'a), 2.28 (m, 1 H, H-2'b);

ToF-MS (ESI): For the molecular ion C$_{17}$H$_{19}$N$_6$O$_5$ [M+H]$^+$, the calculated mass was 387.1417, and the observed mass was 387.1186.

N$^6$-(2-Nitrobenzyl)-2'-deoxyadenosine-5'-triphosphate (WW1p129)

POCl$_3$ (19 μL, 0.2 mmol) was added to a solution of compound dA.10 (52 mg, 0.13 mmol) in trimethylphosphate (0.5 mL) and maintained at minus 20-30° C. for 2.5 hours. A solution of bis-tri-n-butylammonium pyrophosphate (308 mg, 0.65 mmol) and tri-n-butylamine (130 μL) in anhydrous DMF (1.3 mL) was added. After five minutes of stirring, triethylammonium bicarbonate buffer (1 M, pH 7.5; 10 mL) was added. The reaction was stirred at room temperature for one hour and then lyophilized to dryness. The residue was dissolved in water (10 mL), filtered, and purified by anion exchange chromatography using a Q Sepharose FF column (2.5×20 cm) with a linear gradient of NH$_4$HCO$_3$ (50 mM to 500 mM in 300 minutes) at a flow rate of 4.5 mL/min. The fractions containing triphosphate were combined and lyophilized to give N$^6$-(2-nitrobenzyl)-2'-deoxyadenosine-5'-triphosphate WW1p129 (53 mg, 60%) as a white fluffy solid.

$^1$H NMR (400 MHz, D$_2$O): δ 8.42 (s, 1 H, H-8), 8.13 (s, 1 H, H-2), 8.09 (d, 1 H, Ph-H), 7.55 (m, 2 H, Ph-H), 7.45 (m, 1 H, Ph-H), 6.46 (t, 1 H, J=6.4 Hz, H-1'), 5.05 (bs, 2 H, Ph-CH$_2$), 4.29 (s, 1 H, H-3'), 4.21 (m, 2 H, H-5'a and H-5'b), 2.78 (m, 1 H, H-2'a), 2.59 (m, 1 H, H-2'b);

$^{31}$P NMR (162 MHz, D$_2$O): δ-5.86 (d, J=16.2 Hz), −10.78 (d, J=16.2 Hz), −19.22 (t, J=16.2 Hz);

ToF-MS (ESI): For the molecular ion C$_{17}$H$_{22}$N$_6$O$_{14}$P$_3$ [M-H]$^-$, the calculated mass was 625.0250, and the observed mass was 625.0231.

The triphosphate was further purified using preparative HPLC without UV detection to give sample free from contamination of the natural nucleotide. Determination of the concentration of the triphosphate solution was performed by UV/VIS measurement using the extinction coefficient of ε$_{260}$=20,800.

Synthesis of N$^6$-(4-methoxy-2-nitrobenzyl)-2'-deoxyadenosine triphosphate (WW2p005)

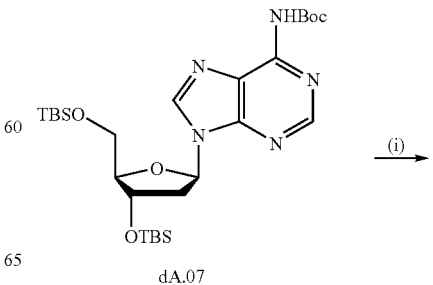

dA.07

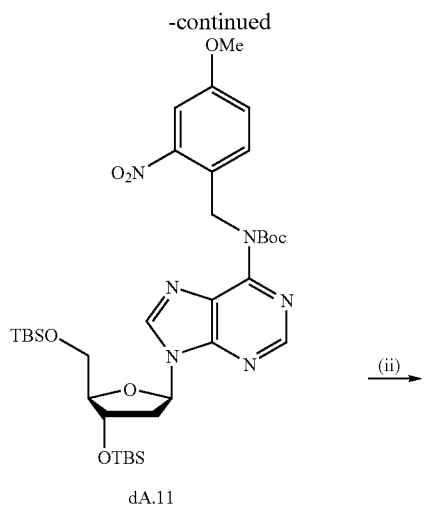

dA.11

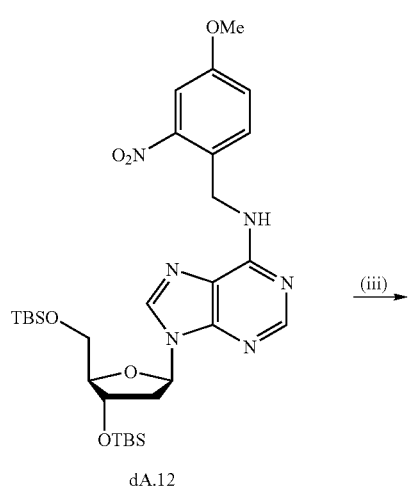

dA.12

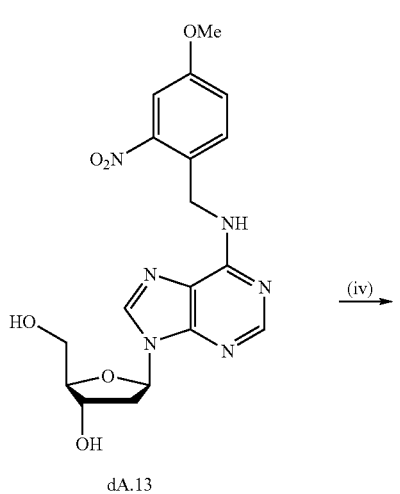

dA.13

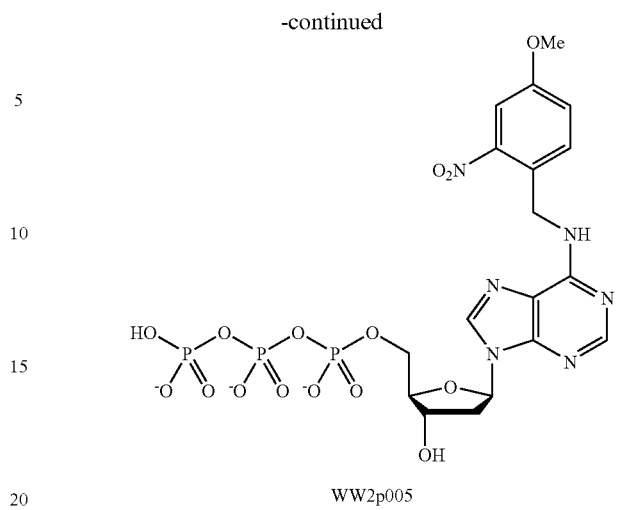

WW2p005

Scheme. Synthesis of $N^6$-(4-methoxy-2-nitrobenzyl)-2'-deoxyadenosine-5'-triphosphate. (i) NaH, DMF, 4-methoxy-2-nitrobenzyl bromide, 0° C., then gradually warmed to room temperature, 64%; (ii) SiO$_2$, high vacuum, 70-80° C., 24 hours, 84%; (iii) n-Bu$_4$NF, THF, 99%; (iv) POCl$_3$, (MeO)$_3$PO, minus 20-30° C.; (n-Bu$_3$NH)$_2$H$_2$P$_2$O$_7$, n-Bu$_3$N, DMF; 1 M HNEt$_3$HCO$_3$; 40%.

$N^6$-tert-Butyloxycarbonyl-$N^6$-(4-methoxy-2-nitrobenzyl)-3',5'-O-bis-tert-butyldimethylsilyl-2'-deoxyadenosine (dA.11)

NaH (26 mg, 1.1 mmol, dry) was added to a solution of compound dA.07 (580 mg, 1.0 mmol) in anhydrous DMF (5 mL) at 0° C. and stirred for 45 minutes. A solution of 4-methoxy-2-nitrobenzyl bromide (260 mg, 1.05 mmol) in anhydrous DMF (1.0 mL) was added dropwise. The mixture was gradually warmed to room temperature and stirred overnight. DMF was removed in vacuo, and the residue was dissolved in ethyl acetate (50 mL) and washed twice with saturated NH$_4$Cl solution (30 mL each). The combined aqueous layer was extracted with ethyl acetate (20 mL), and the combined organic layer was dried over Na$_2$SO$_4$, concentrated in vacuo, and purified by silica gel column chromatography to yield N6-tert-butyloxycarbonyl-$N^6$-(4-methoxy-2-nitrobenzyl)-3',5'-O-bis-tert-butyldimethylsilyl-2'-deoxyadenosine dA.11 (480 mg, 64%) as a viscous oil.

$^1$H NMR (400 MHz, CDCl$_3$): δ 8.68 (s, 1 H, H-8), 8.37 (s, 1 H, H-2), 7.66 (d, 1 H, J=8.7 Hz, Ph-H), 7.55 (d, 1 H, J=2.7 Hz, Ph-H), 7.10 (dd, 1 H, J=2.7 and 8.7 Hz, Ph-H), 6.51 (t, 1 H, J=6.4 Hz, H-1'), 5.55 (s, 2 H, Ph-CH$_2$), 4.63 (m, 1 H, H-4'), 4.03 (m, 1H, H-3'), 3.87 (m, 1 H, H-5'a), 3.84 (s, 3 H, OCH$_3$), 3.78 (m, 1 H, H-5'b), 2.63 (m, 1 H, H-2'a), 2.44 (m, 1 H, H-2'b), 1.41 (s, 9 H, (CH$_3$)$_3$CO), 0.92 (s, 18 H, (CH$_3$)$_3$CSi), 0.10 (2 s, 12 H, (CH$_3$)$_2$Si—);

ToF-MS (ESI): For the molecular ion C$_{35}$H$_{57}$N$_6$O$_8$Si$_2$ [M+H]$^+$, the calculated mass was 745.3776, and the observed mass was 745.3782.

$N^6$-(4-Methoxy-2-nitrobenzyl)-3',5'-O-bis-tert-butyldimethylsilyl-2'-deoxyadenosine (dA.12)

Silica gel 60 (5 g, 100-200 mesh, activated by heating to 70-80° C. under reduced pressure for 24 hours) was added to a solution of compound dA.11 (530 mg, 0.71 mmol) in CH₂Cl₂ (30 mL), and the mixture was evaporated in vacuo to dryness. The residue was heated to 70-80° C. under reduced pressure for two days, washed three times with methanol (20 mL each), and filtered using a buchi funnel. The combined filtrate was concentrated in vacuo and purified by silica gel column chromatography to yield $N^6$-(4-methoxy-2-nitrobenzyl)-3',5'-O-bis-tert-butyldimethylsilyl-2'-deoxyadenosine dA.12 (385 mg, 84%) as a yellow foam.

$^1$H NMR (400 MHz, CDCl₃): δ 8.37 (s, 1 H, H-8), 8.08 (s, 1 H, H-2), 7.66 (d, 1 H, J=8.5 Hz, Ph-H), 7.57 (m, 1 H, J=2.7 Hz Ph-H), 7.09 (dd, 1 H, J=2.7 and 8.7 Hz Ph-H), 6.52 (t, 1 H, 6-NH), 6.43 (t, 1 H, J=6.4 Hz, H-1'), 5.07 (bs, 2 H, Ph-CH₂), 4.60 (m, 1 H, H-4'), 4.00 (m, 1 H, H-3'), 3.87 (m, 1 H, H-5'a), 3.85 (s, 3 H, OCH₃), 3.76 (dd, 1 H, H-5'b), 2.62 (m, 1 H, H-2'a), 2.43 (m, 1 H, H-2'b), 0.91 (s, 18 H, (CH₃)₃CSi), 0.09 (2 s, 12 H, (CH₃)₂Si—);

ToF-MS (ESI): For the molecular ion $C_{30}H_{48}N_6O_6Si_2$ [M+H]⁺, the calculated mass was 645.3252, and the observed mass was 645.3248.

$N^6$-(4-Methoxy-2-nitrobenzyl)-2'-deoxyadenosine (dA.13)

A solution of n-Bu₄NF (353 mg, 1.35 mmol) in THF (2 mL) was added to a solution of compound dA.12 (350 mg, 0.54 mmol) in THF (5 mL) at 0° C. The reaction mixture was gradually warmed to room temperature and stirred for four hours. Silica gel 60 (1.5 g) was added, and the mixture was evaporated in vacuo to dryness. The residue was purified by silica gel column chromatography to yield $N^6$-(4-methoxy-2-nitrobenzyl)-2'-deoxyadenosine dA.13 (225 mg, 99%) as a yellow foam.

$^1$H NMR (400 MHz, DMSO-d₆): δ 8.40 (bs, 1 H, D₂O exchangeable, 6-NH), 8.39 (s, 1H, H-8), 8.15 (s, 1 H, H-2), 7.54 (d, 1 H, J=2.7 Hz, Ph-H), 7.44 (d, 1 H, J=8.2 Hz, Ph-H), 7.24 (d, 1 H, J=2.7 and 8.7 Hz, Ph-H), 6.33 (t, 1 H, J=6.7 Hz, H-1'), 5.32 (d, 1H, D₂O exchangeable, 3'-OH), 5.17 (t, 1 H, D₂O exchangeable, 5'-OH), 4.88 (bs, 2 H, Ph-CH₂), 4.40 (m, 1 H, H-4'), 3.87 (m, 1 H, H-3'), 3.81 (s, 3 H, OCH₃), 3.60 (m, 1 H, H-5'a), 3.52 (m, 1 H, H-5'b), 2.70 (m, 1 H, H-2'a), 2.26 (m, 1 H, H-2'b);

ToF-MS (ESI): For the molecular ion $C_{18}H_{21}N_6O_6$ [M+H]⁺, the calculated mass was 417.1523, and the observed mass was 417.1458.

$N^6$-(4-Methoxy-2-nitrobenzyl)-2'-deoxyadenosine-5'-triphosphate (WW2p005)

POCl₃ (19 μL, 0.2 mmol) was added to a solution of compound dA.13 (42 mg, 0.1 mmol) in trimethylphosphate (0.5 mL) and maintained at minus 20-30° C. for three hours. A solution of bis-tri-n-butylammonium pyrophosphate (237 mg, 0.5 mmol) and tri-n-butylamine (100 μL) in anhydrous DMF (1 mL) was added. After five minutes of stirring, triethylammonium bicarbonate buffer (1 M, pH 7.5; 10 mL) was added. The reaction was stirred at room temperature for one hour and then lyophilized to dryness. The residue was dissolved in water (10 mL), filtered, and purified by anion exchange chromatography using a Q Sepharose FF column (2.5×20 cm) with a linear gradient of NH₄HCO₃ (50 mM to 500 mM in 300 minutes) at a flow rate of 4.5 mL/min. The fractions containing triphosphate were combined and lyophilized to give $N^6$-(4-methoxy-2-nitrobenzyl)-2'-deoxyadenosine-5'-triphosphate WW2p005 (28 mg, 40%) as a white fluffy solid.

$^1$H NMR (400 MHz, D₂O): δ 8.41 (s, 1 H, H-8), 8.17 (s, 1 H, H-2), 7.64 (d, 1 H, J=2.7 Hz, Ph-H), 7.47 (d, 1 H, J=8.7 Hz, Ph-H), 7.15 (d, 1 H, J=2.7 and 8.7 Hz, Ph-H), 6.46 (t, 1 H, J=6.7 Hz, H-1'), 4.97 (bs, 2 H, Ph-CH₂), 4.29 (s, 1 H, H-3'), 4.20 (m, 2 H, H-5'a and H-5'b), 3.84 (s, 3 H, OCH₃), 2.80 (m, 1 H, H-2'a), 2.60 (m, 1 H, H-2'b);

$^{31}$P NMR (162 MHz, D₂O): δ-5.97 (d, J=19.9 Hz), −11.07 (d, J=19.3 Hz), −21.76 (t, J=19.3 Hz);

ToF-MS (ESI): For the molecular ion $C_{18}H_{21}N_6O_{15}P_3Na$ [M-2H+Na]⁻, the calculated mass was 677.0175, and the observed mass was 677.0197.

The triphosphate was further purified using preparative HPLC without UV detection to give sample free from contamination of the natural nucleotide. Determination of the concentration of the triphosphate solution was performed by UV/VIS measurement using the extinction coefficient of $\epsilon_{260}$=20,800.

Synthesis of 6-FAM Labeled $N^6$-[4-(3-amino-1-propyl)-2-nitrobenzyl]-2'-deoxyadenosine triphosphate (WW2p055)

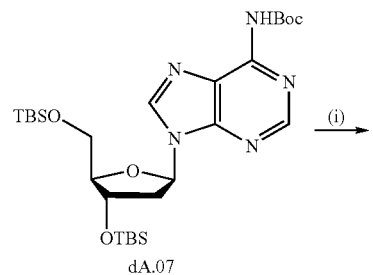

dA.07

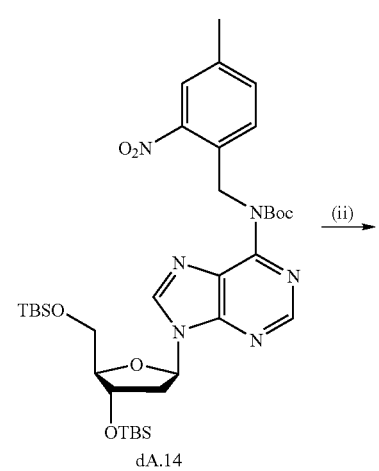

dA.14

39
-continued
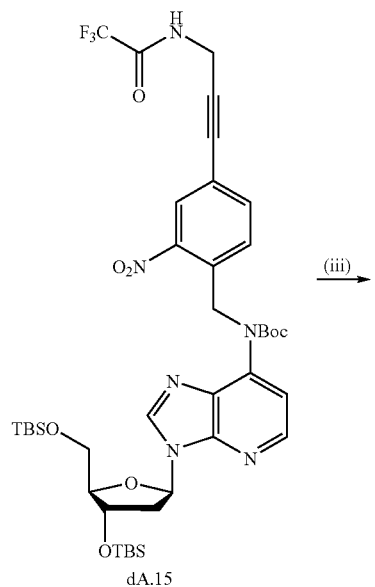
dA.15
(iii) →
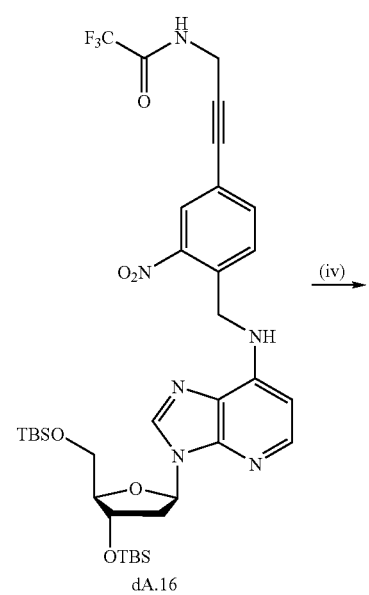
dA.16
(iv) →
40
-continued
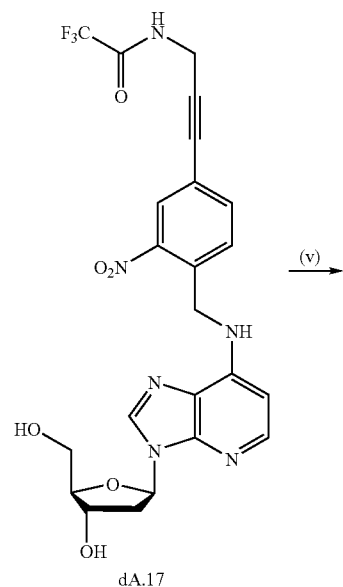
dA.17
(v) →
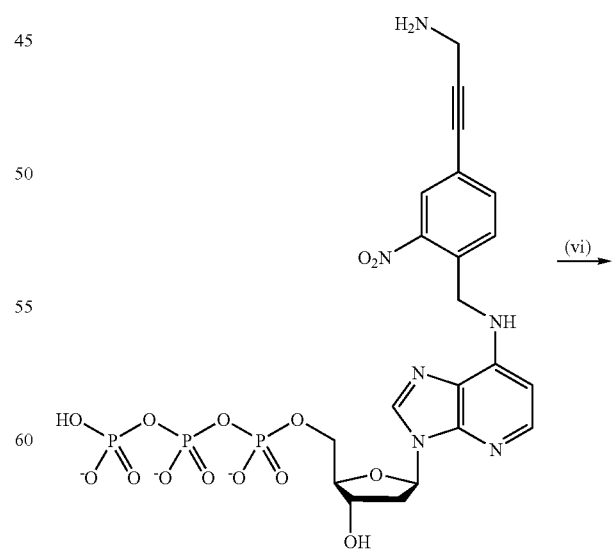
dA.18
(vi) →

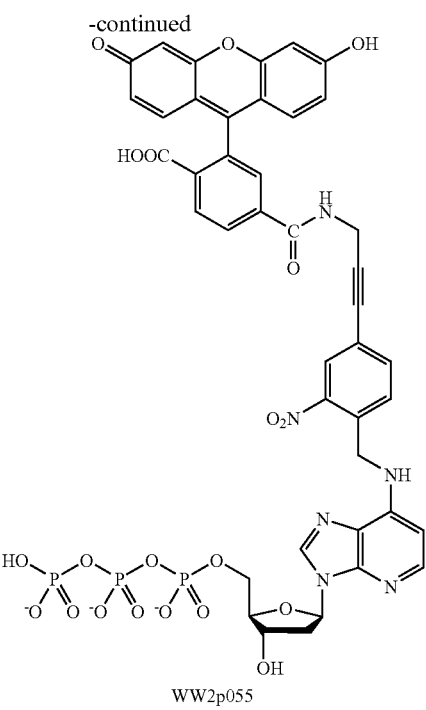

WW2p055

Scheme. Synthesis of 6-FAM labeled N⁶-[4-(3-amino-1-propyl)-2-nitrobenzyl]-2'deoxyadenosine triphosphate. (i) NaH, DMF, 4-iodo-2-nitrobenzyl bromide, 0° C., then gradually warmed to room temperature, 61%; (ii) PdCl$_2$(PPh$_3$)$_2$, CuI, Et$_3$N, THF, reflux, 94%; (iii) SiO$_2$, vacuum, 70-80° C., 82%; (iv) n-Bu$_4$NF, THF, 0° C., then gradually warmed to room temperature, 33%; (v) POCl$_3$, proton sponge, (MeO)$_3$PO, minus 20-30° C., two hours; (n-Bu$_3$NH)$_2$H$_2$P$_2$O$_7$, n-Bu$_3$N, DMF, two minutes; 1 M HNEt$_3$HCO$_3$, one hour; NH$_4$OH, one hour; 72%; (vi) 6-FAM-SE, 0.1 M NaHCO$_3$/NaCO$_3$, pH 9.2.

N⁶-tert-Butyloxycarbonyl-N⁶-(4-iodo-2-nitrobenzyl)-3',5'-O-bis-tert-butyldimethylsilyl-2'-deoxyadenosine (dA.14)

NaH (40 mg, 1.66 mmol, dry) was added to a solution of compound dA.07 (875 mg, 1.51 mmol) in anhydrous DMF (10 mL) at 0° C. and stirred for 45 minutes. A solution of 4-iodo-2-nitrobenzyl bromide (516 mg, 1.51 mmol) in anhydrous DMF (2 mL) was added dropwise. The mixture was gradually warmed to room temperature and stirred for four hours. DMF was removed in vacuo, and the residue was dissolved in ethyl acetate (50 mL), washed with saturated NH$_4$Cl solution (30 mL), and washed twice with water (30 mL each). The combined aqueous layer was extracted with ethyl acetate (20 mL), and the combined organic layer was dried over Na$_2$SO$_4$, concentrated in vacuo, and purified by silica gel column chromatography to yield N⁶-tert-butyloxycarbonyl-N⁶-(4-iodo-2-nitrobenzyl)-3',5'-O-bis-tert-butyldimethylsilyl-2'-deoxyadenosine dA.14 (777 mg, 61%) as a white foam.

$^1$H NMR (400 MHz, CDCl$_3$) δ 8.66 (s, 1 H, H-8), 8.38 (s, 1 H, H-2), 8.34 (d, 1 H, J=1.1 Hz, Ph-H), 7.85 (dd, 1 H, J=1.1 and 8.3 Hz, Ph-H), 7.50 (d, 1 H, J=8.3 Hz, Ph-H), 6.50 (t, 1 H, J=6.3 Hz, H-1'), 5.54 (s, 2 H, Ph-CH$_2$), 4.63 (m, 1 H, H-3'), 4.03 (m, 1 H, H-4'), 3.87 (m, 1 H, H-5'a), 3.78 (m, 1 H, H-5'b), 2.62 (m, 1 H, H-2'a), 2.46 (m, 1 H, H-2'b), 1.41 (s, 9 H, (CH$_3$)$_3$CO), 0.92 (s, 18 H, (CH$_3$)$_3$CSi), 0.10 (2 s, 12 H, (CH$_3$)$_2$Si).

N⁶-tert-Butyloxycarbonyl-N⁶-[4-(3-trifluoroacetamido-1-propynyl)-2-nitrobenzyl]-3',5'-O-bis-tert-butyldimethylsilyl-2'-deoxyadenosine (dA.15)

Under a N$_2$ atmosphere, a mixture of compound dA.14 (730 mg, 0.87 mmol), N-propargyltrifluoroacetamide (183 mg, 1.2 mmol), CuI (33 mg, 0.17 mmol), bis(triphenylphosphine)palladium(II) chloride (61 mg, 0.087 mmol), and Et$_3$N (1.6 mL, 11.57 mmol) in anhydrous THF (7.5 mL) was refluxed for six hours in the dark. The mixture was concentrated in vacuo, and the residue was purified by silica gel column chromatography to yield N⁶-tert-butyloxycarbonyl-N⁶-[4-(3-trifluoroacetamido-1-propynyl)-2-nitrobenzyl]-3',5'-O-bis-tert-butyldimethylsilyl-2'-deoxyadenosine dA.15 (706 mg, 94%) as a yellow foam.

$^1$H NMR (400 MHz, CDCl$_3$): δ 8.67 (s, 1 H, H-8), 8.39 (s, 1 H, H-2), 8.06 (d, 1 H, J=1.5 Hz, Ph-H), 7.73 (d, 1 H, J=8.2 Hz, Ph-H), 7.56 (dd, 1 H, J=1.5 and 8.2 Hz, Ph-H), 7.28 (br s, 1 H, NH), 6.51 (t, 1 H, J=6.4 Hz, H-1'), 5.59 (s, 2 H, Ph-CH$_2$), 4.63 (m, 1 H, H-3'), 4.37 (m, 2 H, CH$_2$), 4.03 (m, 1 H, H-4'), 3.87 (m, 1 H, H-5'a), 3.78 (m, 1 H, H-5'b), 2.63 (m, 1 H, H-2'a), 2.48 (m, 1 H, H-2'b), 1.40 (s, 9 H, (CH$_3$)$_3$CO), 0.92 (s, 18H, (CH$_3$)$_3$CSi), 0.10 (2 s, 12 H, (CH$_3$)$_2$Si—).

N⁶-[4-(3-Trifluoroacetamido-1-propynyl)-2-nitrobenzyl]-3',5'-O-bis-tert-butyldimethylsilyl-2'-deoxyadenosine (dA.16)

Silica gel 60 (3.5 g, 100-200 mesh, activated by heating to 70-80° C. under reduced pressure for 24 hours) was added to a solution of compound dA.15 (507 mg, 0.59 mmol) in CH$_2$Cl$_2$ (30 mL), and the mixture was evaporated in vacuo to dryness. The residue was heated to 70-80° C. under reduced pressure for 42 hours, washed three times with methanol (20 mL each), and filtered using a buchi funnel. The combined filtrate was concentrated in vacuo and purified by silica gel column chromatography to yield N⁶-[4-(3-trifluoroacetamido-1-propynyl)-2-nitrobenzyl]-3',5'-O-bis-tert-butyldimethyl-silyl-2'-deoxyadenosine dA.16 (366 mg, 82%) as a yellow foam.

$^1$H NMR (400 MHz, CDCl$_3$): δ 8.35 (s, 1 H, H-8), 8.12 (s, 1 H, H-2), 8.05 (d, 1 H, J=1.3 Hz, Ph-H), 7.66 (d, 1 H, J=8.0 Hz, Ph-H), 7.48 (dd, 1 H, J=1.3 and 8.0 Hz, Ph-H), 7.20 (bs, 1 H, NH), 6.54 (t, 1 H, NH), 6.44 (t, 1 H, J=6.4 Hz, H-1'), 5.16 (bs, 2 H, Ph-CH$_2$), 4.61 (m, 1 H, H-4'), 4.39 (d, 2 H, CH$_2$), 4.00 (m, 1 H, H-3'), 3.87 (m, 1 H, H-5'a), 3.78 (m, 1 H, H-5'b), 2.62 (m, 1 H, H-2'a), 2.44 (m, 1 H, H-2'b), 1.40 (s, 9 H, (CH$_3$)$_3$CO), 0.91 (s, 18 H, (CH$_3$)$_3$CSi), 0.09 (2 s, 12 H, (CH$_3$)$_2$Si—).

N⁶-[4-(3-Trifluoroacetamido-1-propynyl)-2-nitrobenzyl]-2'-deoxyadenosine (dA.17)

A solution of n-Bu$_4$NF (282 mg, 1.08 mmol) in THF (2 mL) was added to a solution of compound dA.16 (330 mg, 0.43 mmol) in THF (5 mL) at 0° C. The reaction mixture was gradually warmed to room temperature and stirred for two hours. Methanol (5 mL) and silica gel 60 (2 g) were added, and the mixture was evaporated in vacuo to dryness. The residue was purified by silica gel column chromatography to yield N⁶-[4-(3-trifluoroacetamido-1-propynyl)-2-nitrobenzyl]-2'-deoxyadenosine dA.17 (75 mg, 33%) as a white foam.

$^1$H NMR (400 MHz, DMSO-d$_6$): δ 10.08 (t, 1 H, D$_2$O exchangeable, NH), 8.50 (br s, 1H, D$_2$O exchangeable, NH), 8.42 (s, 1 H, H-8), 8.16 (s, 1 H, H-2), 8.06 (d, 1 H, J=1.6 Hz, Ph-H), 7.71 (dd, 1 H, J=1.6 and 8.1 Hz, Ph-H), 7.51 (m, 1 H, Ph-H), 6.35 (t, 1 H, J=6.4 Hz, H-1'), 5.30 (d, 1 H, D$_2$O exchangeable, 3'-OH), 5.13 (br s, 1 H, D$_2$O exchangeable, 5'-OH), 4.96 (br s, 2 H, Ph-CH$_2$), 4.41 (m, 1 H, H-4'), 4.29 (d, 2 H, CH$_2$), 3.87 (m, 1 H, H-3'), 3.60 (m, 1 H, H-5'a), 3.51 (m, 1 H, H-5'b), 2.72 (m, 1 H, H-2'a), 2.27 (m, 1 H, H-2'b).

N$^6$-[4-(3-Amino-1-propyl)-2-nitrobenzyl]-2'-deoxy-adenosine-5'-triphosphate (dA.18)

POCl$_3$ (8.5 µL, 0.09 mmol) was added to a solution of compound dA.17 (32 mg, 0.06 mmol) and proton sponge (19 mg, 0.09 mmol) in trimethylphosphate (0.5 mL) and maintained at minus 20-30° C. for two hours. A solution of bis-tri-n-butylammonium pyrophosphate (142 mg, 0.3 mmol) and tri-n-butylamine (60 µL) in anhydrous DMF (0.6 mL) was added. After two minutes of stirring, triethylammonium bicarbonate buffer (1 M, pH 7.5; 5 mL) was added. The reaction was stirred for one hour at room temperature, followed by the dropwise addition of concentrated ammonium hydroxide (10 mL, 27%) at 0° C. The mixture was stirred for an additional hour at room temperature and then lyophilized to dryness. The residue obtained was dissolved in water (10 mL), filtered, and purified by anion exchange chromatography using a Q Sepharose FF column (2.5×20 cm) with a linear gradient of NH$_4$HCO$_3$ (50 mM to 500 mM in 300 minutes) at a flow rate of 4.5 mL/min. The fractions containing triphosphate were combined and lyophilized to give triphosphate dA.18 (31 mg, 72%) as a white fluffy solid.

$^1$H NMR (400 MHz, D$_2$O): δ 8.47 (s, 1 H, H-8), 8.23 (s, 1 H, Ph-H), 8.20 (s, 1 H, H-2), 7.65 (d, 1 H, J=8.2 Hz, Ph-H), 7.57 (d, 1 H, J=8.2 Hz, Ph-H), 6.52 (t, 1 H, J=6.8 Hz, H-1'), 5.14 (br s, 2 H, Ph-CH$_2$), 4.31 (s, 1 H, H-4'), 4.21 (m, 2 H, H-5'a and H-5'b), 3.60 (s, 2 H, CH$_2$), 2.82 (m, 1 H, H-2'a), 2.62 (m, 1 H, H-2'b);

$^{31}$P NMR (162 MHz, D$_2$O): δ-5.43 (d, J=15.4 Hz), −10.46 (d, J=15.6 Hz), −18.85 (t, J=15.6 Hz);

ToF-MS (ESI): For the molecular ion C$_{20}$H$_{23}$N$_7$O$_{14}$P$_3$ [M-H]$^-$, the calculated mass was 678.0516, and the observed mass was 678.0857.

6-FAM Labeled N$^6$-[4-(3-Amino-1-propyl)-2-nitrobenzyl]-2'-deoxyadenosine-5'-triphosphate (WW2p055)

A solution of 6-FAM-SE (6.7 mg, 0.014 mmol) in anhydrous DMSO (70 µL) was added to a solution of triphosphate dA.18 (4.4 µmol) in Na$_2$CO$_3$/NaHCO$_3$ buffer (0.1 M, pH 9.2; 3 mL) and incubated at room temperature for one hour. The reaction was purified by reverse-phase HPLC using a Perkin Elmer OD-300 C$_{18}$ column (4.6×250 mm) to yield the 6-FAM labeled triphosphate WW2p055 (2.6 mg, 49%). Mobile phase: A, 100 mM triethylammonium acetate (TEAA) in water (pH 7.0); B, 100 mM TEAA in water/CH$_3$CN (30:70). Elution was performed with a linear gradient of 5-20% B for 20 minutes and then 20-90% B for 20 minutes. The concentration of WW2p055 was estimated by adsorption spectroscopy using the extinction coefficient of the 6-FAM dye (i.e., 68,000 at 494 nm).

$^{31}$P NMR (162 MHz, D$_2$O): δ-5.87 (d, J=19.8 Hz), −11.01 (d, J=19.1 Hz), −21.76 (t, J=19.8 Hz);

ToF-MS (ESI): For the molecular ion C$_{41}$H$_{35}$N$_7$O$_{20}$P$_3$ [M+H]$^+$, the calculated mass was 1038.1150, and the observed mass was 1138.1281.

Synthesis of 5(6)-SFX labeled N$^6$-[4-(3-amino-1-propyl)-2-nitrobenzyl]-2'deoxy-adenosine triphosphate (WW2p052)

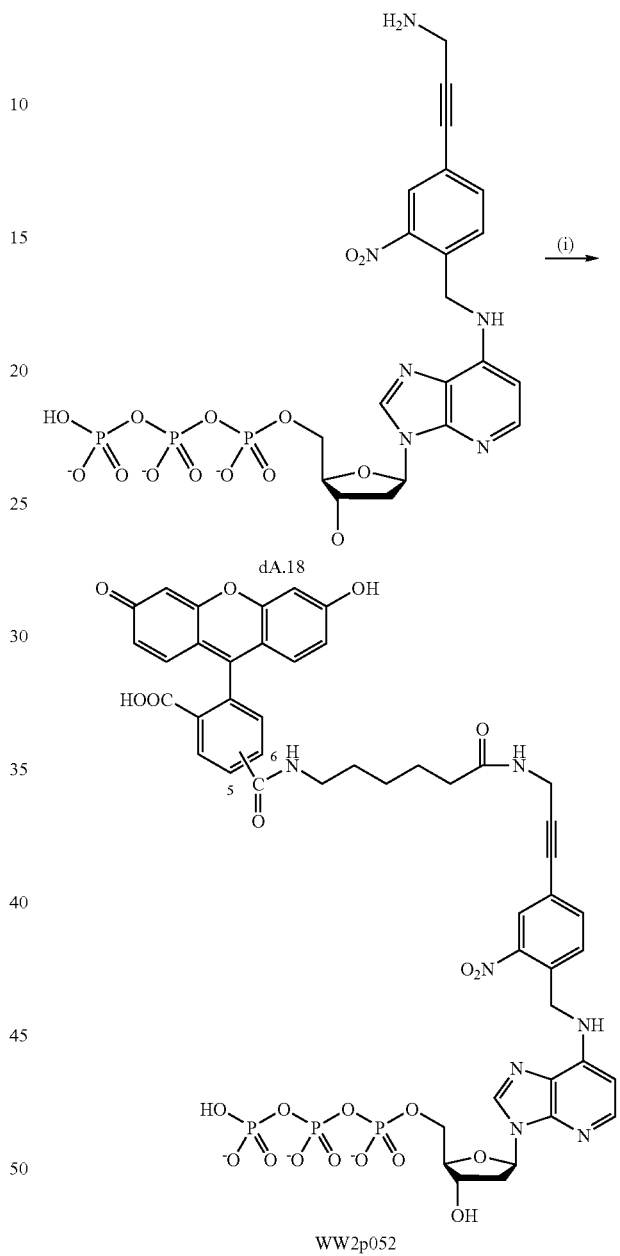

Scheme. Synthesis of 5(6)-SFX labeled N$^6$-[4-(3-amino-1-propyl)-2-nitrobenzyl]-2'-deoxyadenosine triphosphate. (i) 5(6)-SFX, 0.1 M NaHCO$_3$/NaCO$_3$, pH 9.2.

5(6)-SFX labeled N$^6$-[4-(3-Amino-1-propyl)-2-nitrobenzyl]-2'-deoxyadenosine-5'-triphosphate (WW2p052)

A solution of 5(6)-SFX (1.5 mg, 2.55 µmol) in anhydrous DMSO (30 µL) was added to a solution of triphosphate dA.18 (0.54 µmol) in Na$_2$CO$_3$/NaHCO$_3$ buffer (0.1 M, pH 9.2; 0.8 mL) and incubated at room temperature for one hour. The reaction was purified by reverse-phase HPLC using a Perkin Elmer OD-300 $C_{18}$ column (4.6×250 mm) to yield the 5(6)-SFX labeled triphosphate WW2p052. Mobile phase: A, 100 mM triethylammonium acetate (TEAA) in water (pH 7.0); B, 100 mM TEAA in water/$CH_3CN$ (30:70). Elution was performed with a linear gradient of 5-20% B for 20 minutes and then 20-90% B for 20 minutes. The concentration of WW2p052 was estimated by adsorption spectroscopy using the extinction coefficient of the 6-FAM dye (i.e., 68,000 at 494 nm).

Synthesis of $N^6$-[1-(2-nitrophenyl)ethyl]-2'-deoxyadenosine triphosphate (WW3p006)

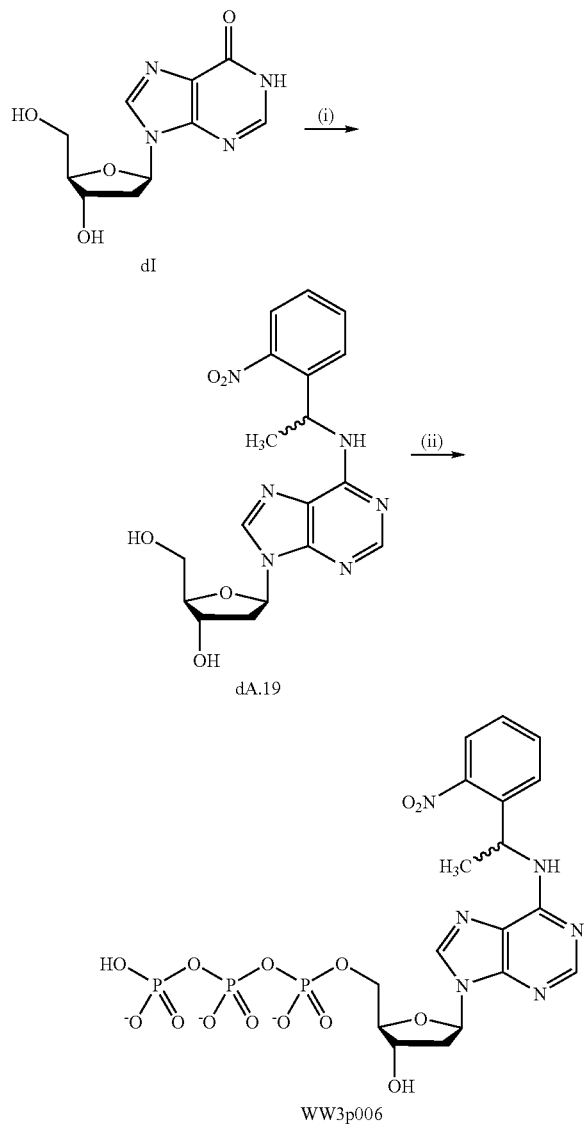

Scheme. Synthesis of $N^6$-[1-(2-nitrophenyl)ethyl]-2'-deoxyadenosine triphosphate (i) 1-(2-nitrophenyl)ethylamine, BOP, DIPEA, DMF, room temperature, overnight, 42%; (ii) $POCl_3$, proton sponge, $(MeO)_3PO$, 0° C., two hours; $(n-Bu_3NH)_2H_2P_2O_7$, $n-Bu_3N$, DMF, five minutes; 1 M $HNEt_3HCO_3$, one hour.

$N^6$-[1-(2-Nitrophenyl)ethyl]-2'-deoxyadenosine (dA.19)

To a suspension of 2'-deoxyinosine (100 mg, 0.4 mmol) and benzotriazol-1-yloxytris(dimethylamino)phosphonium hexafluorophosphate (BOP, 210 mg, 0.48 mmol) in anhydrous DMF (1 mL), N,N-diisopropylethylamine (100 μL, 0.6 mmol) was added followed by the addition of a solution of 1-(2-nitrophenyl)ethylamine (250 mg, 1.51 mmol) in DMF (1 mL). The reaction was stirred at room temperature for 64 hours. Silica gel 60 (1 g, 60-200 mesh) was added, and the mixture was evaporated in vacuo to dryness. The residue was purified by silica gel column chromatography to yield $N^6$-[1-(2-nitrophenyl)ethyl]-2'-deoxyadenosine dA.19 (67 mg, 42%, 1:1 mixture of diastereomers) as a white foam.

$^1$H NMR (400 MHz, DMSO-$d_6$) for diastereomers: δ 8.68 (br s, 1 H, $D_2O$ exchangeable, NH), 8.42 (br s, 1 H, H-8), 8.16 and 8.06 (2 s, 1 H, H-2), 7.88 (m, 2 H, Ph-H), 7.69 (m, 1 H, Ph-H), 7.46 (m, 1 H, Ph-H), 6.34 (m, 1 H, H-1'), 5.79 (m, 1 H, Ph-CH), 5.32 (br s, 1 H, $D_2O$ exchangeable, 3'-OH), 5.16 (br s, 1 H, $D_2O$ exchangeable, 5'-OH), 4.42 (m, 1 H, H-3'), 3.88 (m, 1 H, H-4'), 3.61 (m, 1 H, H-5'a), 3.53 (m, 1 H, H-5'b), 2.71 (m, 2 H, H-2'a), 2.25 (m, 1 H, H-2'b), 1.68 (d, 3 H, J=6.8 Hz, $CH_3$)

$N^6$-[1-(2-Nitrophenyl)ethyl]-2'-deoxyadenosine-5'-triphosphate (WW3p006)

Compound dA.19 (30 mg, 0.075 mmol) and proton sponge (32 mg, 0.15 mmol) were evaporated three times from anhydrous pyridine (2 mL) and dissolved in trimethylphosphate (0.5 mL). $POCl_3$ (10.5 μL, 0.11 mmol) was added, and the mixture was stirred for two hours at 0° C. A solution of bis-tri-n-butylammonium pyrophosphate (178 mg, 0.38 mmol) and tri-n-butylamine (75 μL) in anhydrous DMF (0.75 mL) was added. After five minutes of stirring, triethylammonium bicarbonate buffer (1 M, pH 7.5; 10 mL) was added. The reaction was stirred for one hour at room temperature and then lyophilized to dryness. The residue was dissolved in water (10 mL), filtered, and part of the solution was purified with reverse-phase HPLC using a Perkin Elmer OD-300 $C_{18}$ column (4.6×250 mm) to yield $N^6$-[1-(2-nitrophenyl)ethyl]-2'-deoxyadenosine-5'-triphosphate WW3p006 (1:1 mixture of diastereomers). Mobile phase: A, 100 mM triethylammonium acetate (TEAA) in water (pH 7.0); B, 100 mM TEAA in water/$CH_3CN$ (30:70). Elution was performed with a linear gradient of 5-50% B for 40 minutes and then 50-90% B for 10 minutes.

$^1$H NMR (400 MHz, $D_2O$) for diastereomers: δ 8.47 (s, 1 H, H-8), 8.12 (2 s, 1 H, H-2), 8.02 (d, 1 H, J=8.2 Hz, Ph-H), 7.78 (d, 1 H, J=7.8 Hz, Ph-H), 7.67 (t, 1 H, J=7.6 Hz, Ph-H), 7.49 (t, 1 H, J=8.1 Hz, Ph-H), 6.49 (t, 1 H, J=6.4 Hz, H-1'), 5.89 (bs, 1H, Ph-CH), 4.29 (m, 1 H, H-4'), 4.23-4.15 (m, 2 H, H-5'a and H-5'b), 2.81 (m, 1 H, H-2'a), 2.58 (m, 1 H, H-2'b), 1.74 (d, 3 H, J=6.8 Hz, $CH_3$);

$^{31}$P NMR (162 MHz, $D_2O$) for diastereomers: δ-5.65 (m), −10.52 (d, J=19.6 Hz), −21.32 (m);

ToF-MS (ESI): For the molecular ion $C_{18}H_{21}N_6O_{14}P_3Na$ [M-2H+Na]$^-$, the calculated mass was 661.0226, and the observed mass was 661.0492.

Synthesis of 6-FAM labeled N⁶-{1-[4-(3-amino-1-propynyl)-2-nitrophenyl]ethyl}-2'-deoxyadenosine triphosphate (WW3p015)

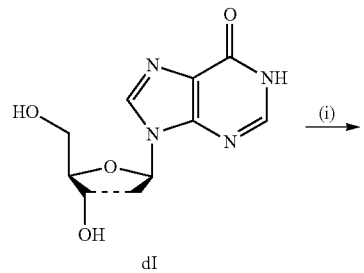
dI

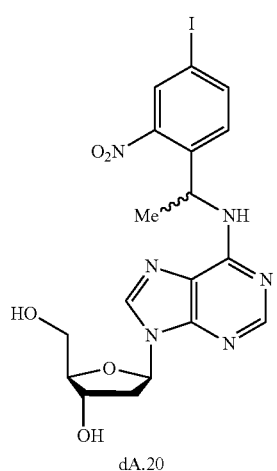
dA.20

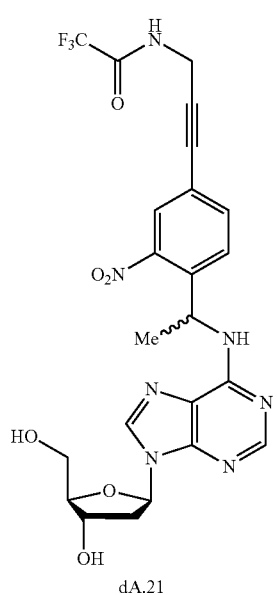
dA.21

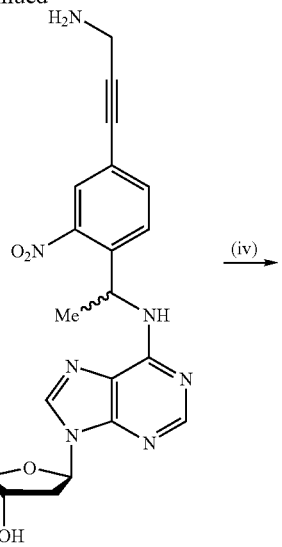

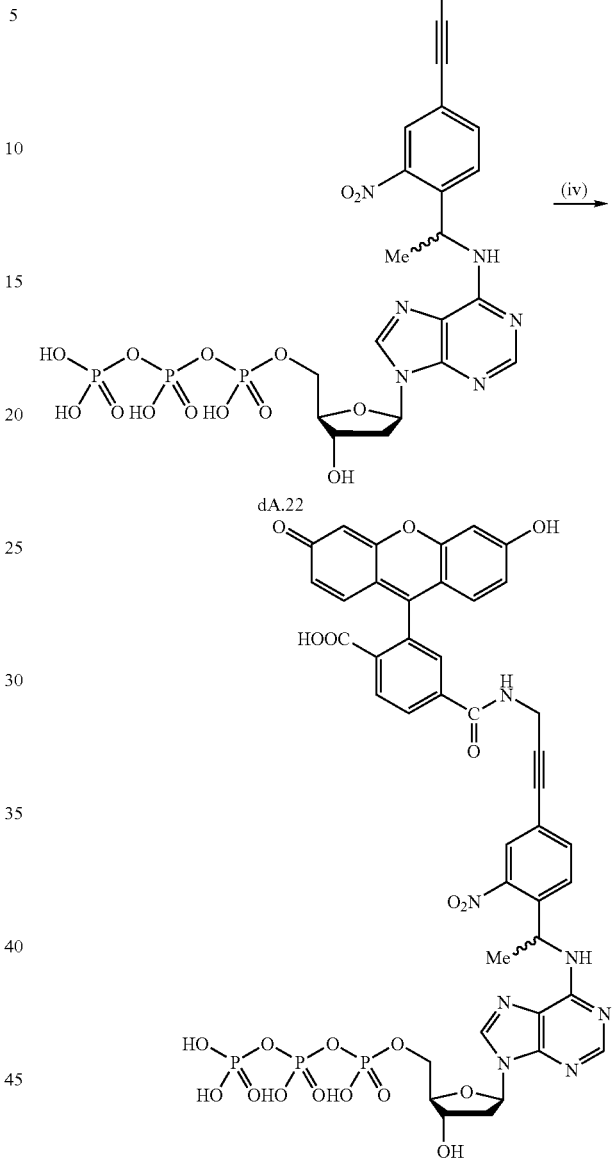

Scheme. Synthesis of 6-FAM labeled $N^6$-{1-[4-(3-amino-1-propynyl)-2-nitrophenyl]ethyl}-2'-deoxyadenosine triphosphate. (i) 1-(4-iodo-2-nitrophenyl)ethylamine, BOP, DIPEA, DMF, room temperature, 65%; (ii) N-propargyltrifluoroacetamide, Pd(PPh$_3$)$_4$(0), CuI, Et$_3$N, anhydrous DMF, 4.5 h, 94%; (iii) POCl$_3$, proton sponge, (MeO)$_3$PO, 0° C., two hours; (n-Bu$_3$NH)$_2$H$_2$P$_2$O$_7$, n-Bu$_3$N, DMF, five minutes; 1 M HNEt$_3$HCO$_3$, one hour; NH$_4$OH, one hour; (iv) 6-FAM-SE, 0.1 M NaHCO$_3$/Na$_2$CO$_3$, pH 9.2, one hour.

$N^6$-[1-(4-Iodo-2-nitrophenyl)ethyl]-2'-deoxyadenosine (dA.20)

To a suspension of 2'-deoxyinosine (150 mg, 0.6 mmol) and benzotriazol-1-yloxytris(dimethylamino)phosphonium hexafluorophosphate (BOP, 379 mg, 0.86 mmol) in anhydrous DMF (1.5 mL), N,N-diisopropylethylamine (186 µL, 1.1 mmol) was added followed by the addition of a solution of 1-(4-iodo-2-nitrophenyl)ethylamine (460 mg, 1.57 mmol) in anhydrous DMF (0.5 mL). The mixture was stirred under nitrogen atmosphere for 48 hours. DMF was removed in vacuo, and the crude product was purified by silica gel column chromatography to yield $N^6$-[1-(4-iodo-2-nitrophenyl)ethyl]-2'-deoxyadenosine dA.20 (204 mg, 65%, 1:1 mixture of diastereomers) as a white foam.

$^1$H NMR (400 MHz, DMSO-$d_6$) for diastereomers: δ 8.72 (br m, 1 H, $D_2O$ exchangeable, NH), 8.42 (br s, 1 H, H-8), 8.20 (s, 1 H, H-2), 8.06 (m, 2 H, Ph-H), 7.65 (m, 1 H, Ph-H), 6.34 (m, 1 H, H-1'), 5.70 (br s, 1 H, PhCH), 5.32 (br s, 1 H, $D_2O$ exchangeable, 3'-OH), 5.15 (br m, 1 H, $D_2O$ exchangeable, 5'-OH), 4.42 (m, 1 H, H-4'), 3.88 (m, 1 H, H-3'), 3.61 (m, 1 H, H-5'a), 3.53 (m, 1 H, H-5'b), 2.71 (m, 1 H, H-2'a), 2.25 (m, 1 H, H-2'b), 1.65 (d, 3 H, J=6.9 Hz, $CH_3$);

$^{13}$C NMR (100 MHz, MeOH-$d_4$) for diastereomers: δ 153.39 (CH), 151.94 (C), 150.65 (C), 143.44 (CH), 141.82 (C), 141.40 (C), 133.77/133.69 (CH), 130.55/130.52 (CH), 121.37 (C), 92.09 (C), 91.87 (C), 89.97 (CH), 87.21 (CH), 73.18/73.15 (CH), 65.78/65.76 ($CH_2$), 47.12 (CH), 41.62 ($CH_2$), 37.14/37.10 ($CH_3$);

ES-MS (ESI): m/e 525 [M-H]$^-$.

$N^6$-{1-[4-(3-Trifluoroacetamido-1-propynyl)-2-nitrophenyl]ethyl}-2'-deoxyadenosine (dA.21)

A solution of compound dA.20 (108 mg, 0.21 mmol), N-propargyltrifluoroacetamide (127 mg, 0.84 mmol), CuI (11 mg, 0.06 mmol), tetrakis(triphenylphosphine)-palladium (0) (33 mg, 0.03 mmol), and $Et_3N$ (80 μL, 0.56 mmol) in anhydrous DMF (1.5 mL) was stirred at room temperature for four and a half hours. The mixture was concentrated in vacuo and purified by silica gel column chromatography to yield $N^6$-{1-[4-(3-trifluoroacetamido-1-propynyl)-2-nitrophenyl]ethyl}-2'-deoxyadenosine dA.21 (106 mg, 94%, 1:1 mixture of diastereomers) as a waxy solid.

$^1$H NMR (400 MHz, DMSO-$d_6$) for diastereomers: δ 10.10 (br m, 1 H, $D_2O$ exchangeable, NH), 8.71 (br m, 1 H, $D_2O$ exchangeable, NH), 8.43 (br s, 1 H, H-8), 8.15 and 8.06 (2 s, 1 H, H-2), 7.93 (s, 1 H, Ph-H), 7.86 (m, 1 H, Ph-H), 7.75 (m, 1 H, Ph-H), 6.35 (br m, 1 H, H-1'), 5.73 (br m, 1 H, Ph-CH), 5.31 (br s, 1 H, $D_2O$ exchangeable, 3'-OH), 5.15 (br m, 1 H, $D_2O$ exchangeable, 5'-OH), 4.40 (m, 1 H, H-4'), 4.31 (d, 2 H, J=5.3 Hz, $CH_2$), 3.88 (m, 1 H, H-3'), 3.62 (m, 1 H, H-5'a), 3.51 (m, 1 H, H-5'b), 2.71 (m, 1 H, H-2'a), 2.25 (m, 1 H, H-2'b), 1.67 (d, 3 H, J=6.8 Hz, $CH_3$);

$^{13}$C NMR (100 MHz, MeOH-$d_4$) for diastereomers: δ 157.85/157.48 (C), 152.26 (CH), 149.50 (C), 140.27 (C), 136.04 (CH), 128.02 (CH), 127.07 (CH), 122.56 (C), 120.25 (C), 117.81 (C), 114.96 (C), 88.85 (CH), 86.08 (CH), 85.81 (C), 80.67 (C), 72.07/72.04 (CH), 62.66/62.63 ($CH_2$), 48.30 (CH), 40.47 ($CH_2$), 29.46 ($CH_2$), 24.26 ($CH_3$);

$N^6$-{1-[4-(3-Amino-1-propynyl)-2-nitrophenyl]ethyl}-2'-deoxyadenosine-5'-triphosphate (dA.22)

Compound dA.21 (44 mg, 0.08 mmol) and proton sponge (34 mg, 0.16 mmol) were evaporated three times from anhydrous pyridine (2 mL) and dissolved in trimethylphosphate (0.5 mL). $POCl_3$ (11 μL, 0.12 mmol) was added, and the mixture was stirred for two hours at 0° C. A solution of bis-tri-n-butylammonium pyrophosphate (190 mg, 0.4 mmol) and tri-n-butylamine (80 μL) in anhydrous DMF (0.8 mL) was added. After five minutes of stirring, triethylammonium bicarbonate buffer (1 M, pH 7.5; 10 mL) was added. The reaction was stirred for one hour at room temperature and then lyophilized to dryness. The residue was dissolved in water (10 mL), filtered, and part of the solution was purified with reverse-phase HPLC using a Perkin Elmer OD-300 $C_{18}$ column (4.6×250 mm) to yield $N^6$-{1-[4-(3-trifluoroacetamido-1-propynyl)-2-nitrophenyl]ethyl}-2'-deoxyadenosine-5'-triphosphate. Mobile phase: A, 100 mM triethylammonium acetate (TEAA) in water (pH 7.0); B, 100 mM TEAA in water/$CH_3CN$ (30:70). HPLC purification was achieved using a linear gradient of 5-50% B for 20 minutes and then 50-90% B for 10 minutes. $N^6$-{1-[4-(3-trifluoroacetamido-1-propynyl)-2-nitrophenyl]ethyl}-2'-deoxyadenosine-5'-triphosphate was then treated with concentrated ammonium hydroxide (1 mL, 27%) at room temperature for one hour to yield $N^6$-{1-[4-(3-amino-1-propynyl)-2-nitrophenyl]ethyl}-2'-deoxyadenosine-5'-triphosphate dA.22 (1:1 mixture of diastereomers).

$^1$H NMR (400 MHz, $D_2O$): δ 8.45 (s, 1 H, H-8), 8.08 (2 s, 1 H, H-2), 7.95 (s, 1 H, Ph-H), 7.65 (m, 1 H, Ph-H), 7.53 (m, 1 H, Ph-H), 6.45 (t, 1 H, J=6.4 Hz, H-1'), 5.80 (br s, 1 H, Ph-CH), 4.28 (s, 1 H, H-4'), 4.18 (m, 2 H, H-5'a and H-5'b), 3.64 (s, 2 H, $CH_2$), 2.78 (m, 1 H, H-2'a), 2.57 (m, 1 H, H-2'b), 1.69 (d, 3 H, J=6.8 Hz, $CH_3$);

$^{31}$P NMR (162 MHz, $D_2O$): δ-5.29 (d, J=20.1 Hz), −10.45 (d, J=19.1 Hz), −21.08 (t, J=19.6 Hz);

ToF-MS (ESI): For the molecular ion $C_{21}H_{25}N_7O_{14}P_3$ [M-H]$^-$, the calculated mass was 692.0672 and the observed mass was 692.0757.

6-FAM Labeled $N^6$-{1-[4-(3-Amino-1-propynyl)-2-nitrophenyl]ethyl}-2'-deoxyadenosine-5'-triphosphate (WW3p015)

A solution of 6-FAM-SE (1.5 mg, 3.15 μmol) in anhydrous DMSO (30 μL) was added to a solution of triphosphate dA.22 (0.34 μmol) in $Na_2CO_3/NaHCO_3$ buffer (0.1 M, pH 9.2; 100 μL) and incubated at room temperature for one hour. The reaction was purified by reverse-phase HPLC using a Perkin Elmer OD-300 $C_{18}$ column (4.6×250 mm) to yield the 6-FAM labeled triphosphate WW3p015. Mobile phase: A, 100 mM triethylammonium acetate (TEAA) in water (pH 7.0); B, 100 mM TEAA in water/$CH_3CN$ (30:70). HPLC purification was achieved using a linear gradient of 5-50% B for 40 minutes and then 50-90% B for 10 minutes. The concentration of WW3p015 was estimated by adsorption spectroscopy using the extinction coefficient of the 6-FAM dye (i.e., 68,000 at 494 nm).

Separation of Diastereoisomers $N^6$-{1-[4-(3-amino-1-propynyl)-2-nitrophenyl]-ethyl}-2'-deoxyadenosine-5'-triphosphate (dA.22 dS1 and dA.22 ds2)

Separation of the two diastereoisomers of dA.22 was performed by reverse-phase HPLC using a Perkin Elmer OD-300 $C_{18}$ column (4.6×250 mm) to yield $N^6$-{(R or S)-1-[4-(3-amino-1-propynyl)-2-nitrophenyl]ethyl}-2'-deoxyadenosine triphosphate dA.22 dS1 (single diastereoisomer, absolute configuration not determined) and $N^6$-{(S or R)-1-[4-(3-amino-1-propynyl)-2-nitrophenyl]ethyl}-2'-deoxyadenosine triphosphate dA.22 dS2 (single diastereoisomer, absolute configuration not determined). Mobile phase: A, 100 mM triethylammonium acetate (TEAA) in water (pH 7.0); B, 100 mM TEAA in water/$CH_3CN$ (30:70). HPLC purification was achieved using a linear gradient of 5-25% B for 50 minutes and then 25-50% B for 30 minutes.

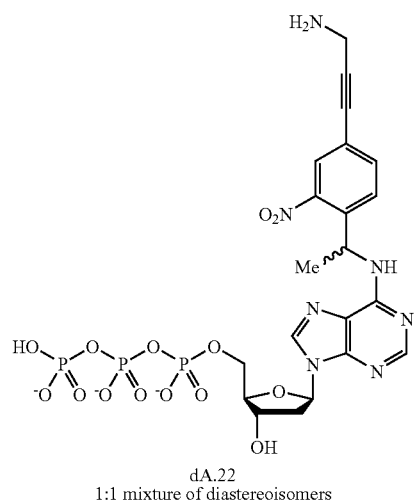

dA.22
1:1 mixture of diastereoisomers

HPLC separation of diastereoisomers →

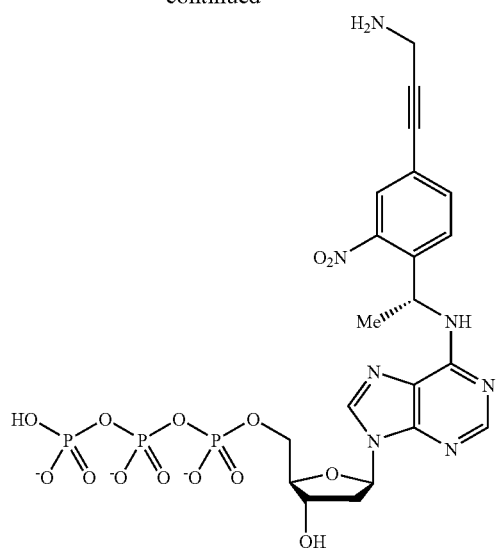

dA.22 ds2
Slow eluting single diastereoisomer,
absolute configuration not determined,
drawing is representative Synthesis of 6-FAM Labeled Single Diastereoisomer N$^6$-{(R or S)-1-[4-(3-amino-1-propynyl)-2-nitrophenyl]ethyl}-2'-deoxyadenosine-5'-triphosphate (WW3p021)

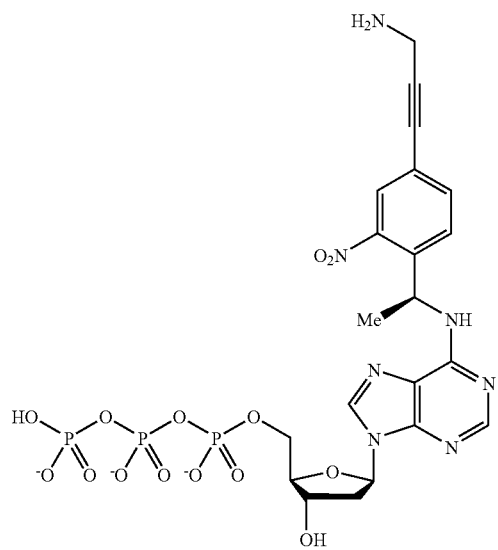

dA.22 ds1
Fast eluting single diastereoisomer,
absolute configuration not determined,
drawing is representative

+

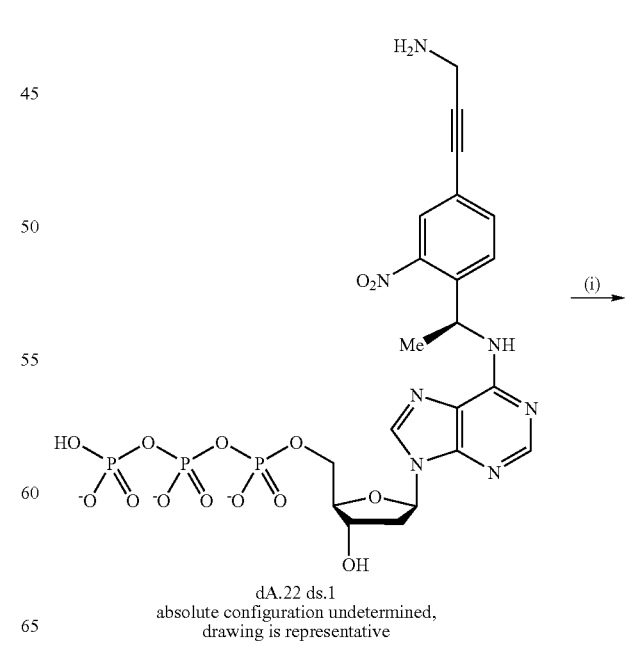

(i) → dA.22 ds.1
absolute configuration undetermined,
drawing is representative

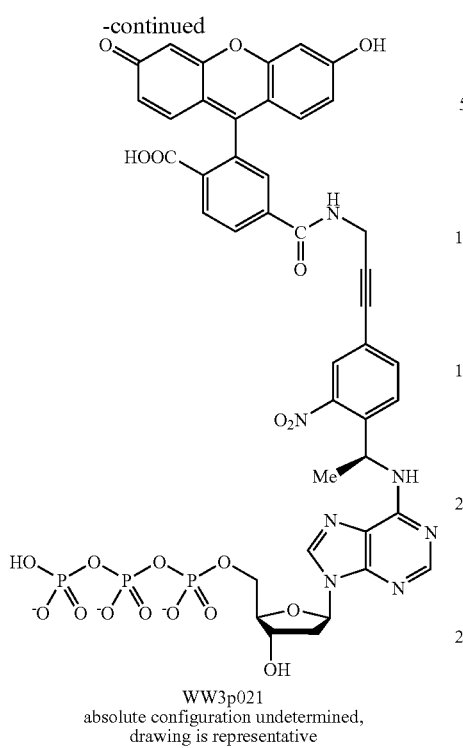

WW3p021
absolute configuration undetermined,
drawing is representative

Scheme. Synthesis of 6-FAM labeled single diastereoisomer N⁶-{(R or S)-1-[4-(3-amino-1-propynyl)-2-nitrophenyl]ethyl}-2'-deoxyadenosine-5'-triphosphate. (i) 6-FAM-SE, 0.1 M NaHCO₃/Na₂CO₃, pH 9.2, one hour.

6-FAM Labeled Single Diastereoisomer N⁶-{(R or S)-1-[4-(3-amino-1-propynyl)-2-nitrophenyl]ethyl}-2'-deoxyadenosine-5'-triphosphate (WW3p021)

A solution of 6-FAM-SE (0.75 mg, 1.57 μmol) in anhydrous DMSO (15 μL) was added to a solution of triphosphate dA.22 ds1 (0.26 μmol, single diastereoisomer, absolute configuration not determined) in Na₂CO₃/NaHCO₃ buffer (0.1 M, pH 9.2; 150 μL) and incubated at room temperature for one hour. The reaction was purified by reverse-phase HPLC using a Perkin Elmer OD-300 C₁₈ column (4.6×250 mm) to yield the 6-FAM labeled single diastereoisomer triphosphate WW3p021. Mobile phase: A, 100 mM triethylammonium acetate (TEAA) in water (pH 7.0); B, 100 mM TEAA in water/CH₃CN (30:70). HPLC purification was achieved using a linear gradient of 5-50% B for 40 minutes and then 50-90% B for 10 minutes. The concentration of WW3p021 was estimated by absorption spectroscopy using the extinction coefficient of the 6-FAM dye (i.e., 68,000 at 494 nm).

Synthesis of 6-FAM Labeled Single Diastereoisomer N⁶-{(R or S)-1-{4-[3-(6-aminocaproyl)amino-1-propynyl]-2-nitrophenyl}ethyl}-2'-deoxyadenosine-5'-triphosphate (WW3p032)

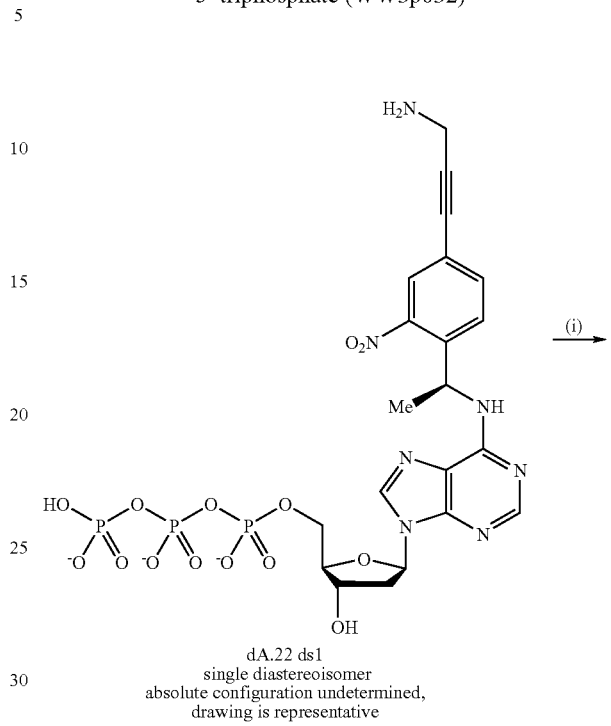

dA.22 ds1
single diastereoisomer
absolute configuration undetermined,
drawing is representative

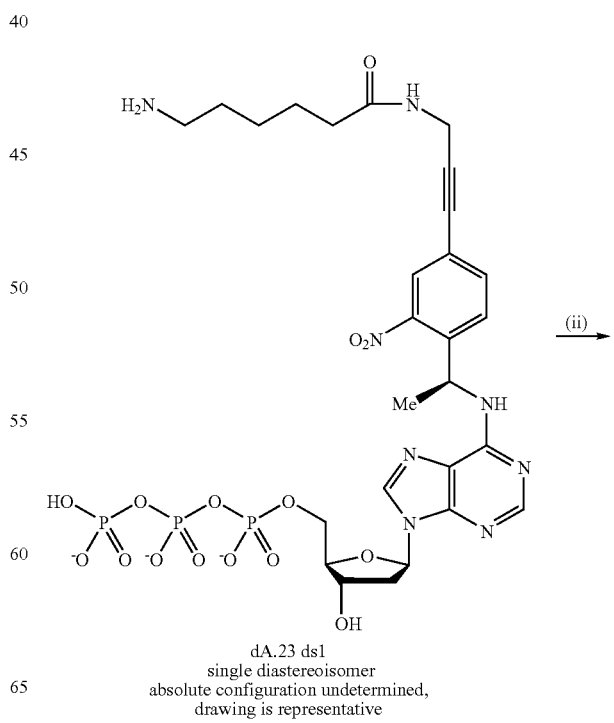

dA.23 ds1
single diastereoisomer
absolute configuration undetermined,
drawing is representative

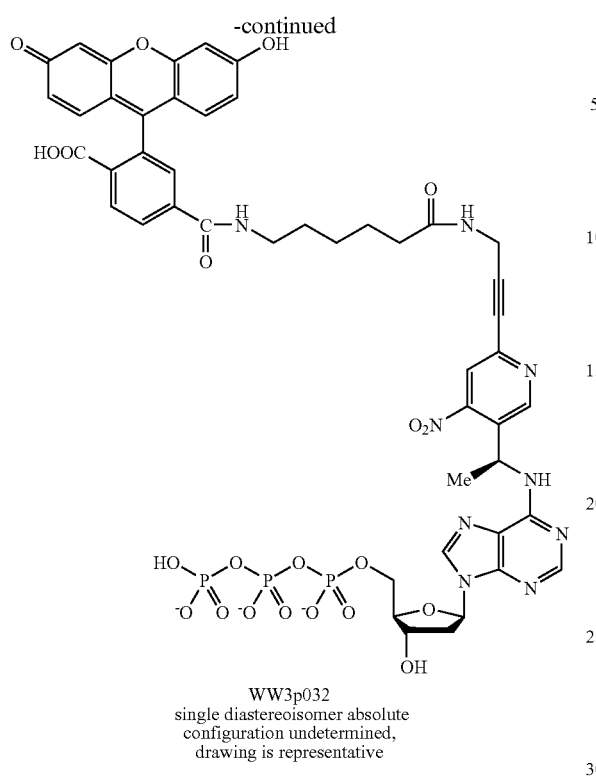

WW3p032
single diastereoisomer absolute
configuration undetermined,
drawing is representative Scheme. Synthesis of 6-FAM labeled single diastereoisomer $N^6$-{(R or S)-1-{4-[3-(6-aminocaproyl)amino-1-propynyl]-2-nitrophenyl}ethyl}-2'-deoxyadenosine triphosphate. (i) 6-N-(trifluoroacetyl)aminocaproic acid N-succinimidyl ester, 0.1 M NaHCO$_3$/Na$_2$CO$_3$, pH 9.2, one hour; NH4OH, one hour; (ii) 6-FAM-SE, 0.1 M NaHCO$_3$/Na$_2$CO$_3$, pH 9.2, one hour.

$N^6$-{(R or S)-1-{4-[3-(6-Aminocaproyl)amino-1-propynyl]-2-nitrophenyl}ethyl}-2'-deoxyadenosine-5'-triphosphate (Single Diastereoisomer dA.23 ds1)

A solution of 6-N-(trifluoroacetyl)aminocaproic acid N-succinimidyl ester (0.5 mg, 1.54 µmol) in anhydrous DMSO (10 µL) was added to a solution of triphosphate dA.22 ds1 (0.25 µmol, single diastereoisomer, absolute configuration not determined) in Na$_2$CO$_3$/NaHCO$_3$ buffer (0.1 M, pH 9.2; 200 µL) and incubated at room temperature for one hour. NH$_4$OH (500 uL, 25% aq) was added and the mixture was incubated at room temperature for another hour. The reaction was purified by reverse-phase HPLC using a Perkin Elmer OD-300 C$_{18}$ column (4.6×250 mm) to yield triphosphate dA.23 ds1 (single diastereoisomer, absolute configuration not determined). Mobile phase: A, 100 mM triethylammonium acetate (TEAA) in water (pH 7.0); B, 100 mM TEAA in water/CH$_3$CN (30:70). HPLC purification was achieved using a linear gradient of 5-50% B for 20 minutes and then 50-90% B for 10 minutes.

Synthesis of 6-FAM Labeled Single Diastereoisomer $N^6$-{(R or S)-1-{4-[3-(6-aminocaproyl)amino-1-propynyl]-2-nitrophenyl}ethyl}-2'-deoxyadenosine-5'-triphosphate (WW3p032)

A solution of 6-FAM-SE (0.5 mg, 1.05 µmol) in anhydrous DMSO (10 µL) was added to a solution of triphosphate dA.23 ds1 (0.196 µmol, single diastereoisomer, absolute configuration not determined) in Na$_2$CO$_3$/NaHCO$_3$ buffer (0.1 M, pH 9.2; 200 µL) and incubated at room temperature for one hour. The reaction was purified by reverse-phase HPLC using a Perkin Elmer OD-300 C$_{18}$ column (4.6×250 mm) to yield the 6-FAM labeled single diastereoisomer triphosphate WW3p032. Mobile phase: A, 100 mM triethylammonium acetate (TEAA) in water (pH 7.0); B, 100 mM TEAA in water/CH$_3$CN (30:70). HPLC purification was achieved using a linear gradient of 5-50% B for 40 minutes and then 50-90% B for 10 minutes. The concentration of WW3p032 was estimated by absorption spectroscopy using the extinction coefficient of the 6-FAM dye (i.e., 68,000 at 494 nm).

Example 2 dT Compounds

Synthesis Of $N^3$-(2-nitrobenzyl)-thymidine-5'-triphosphate (WW1P050)

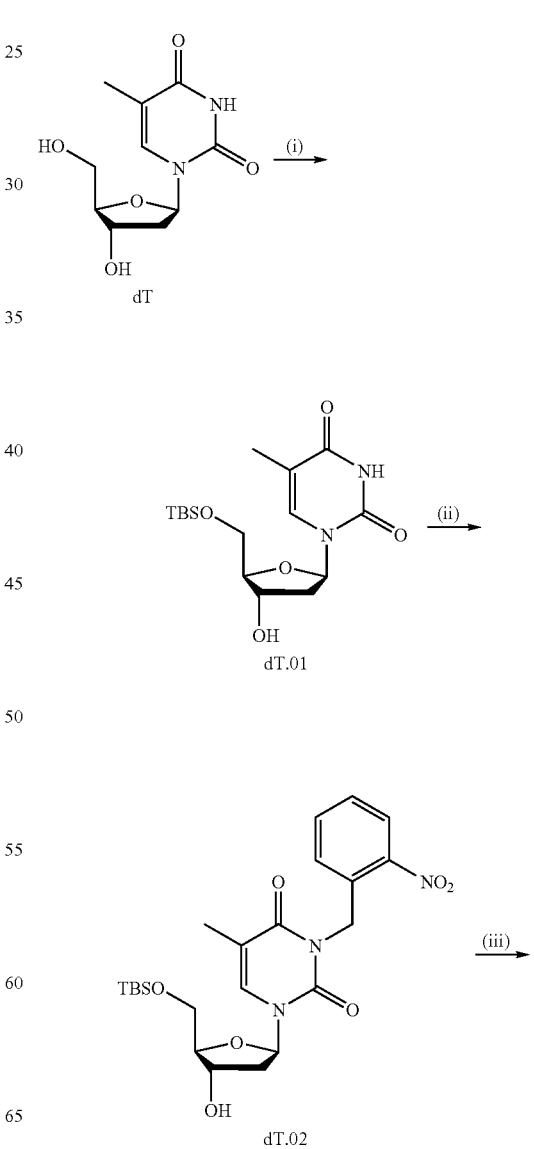

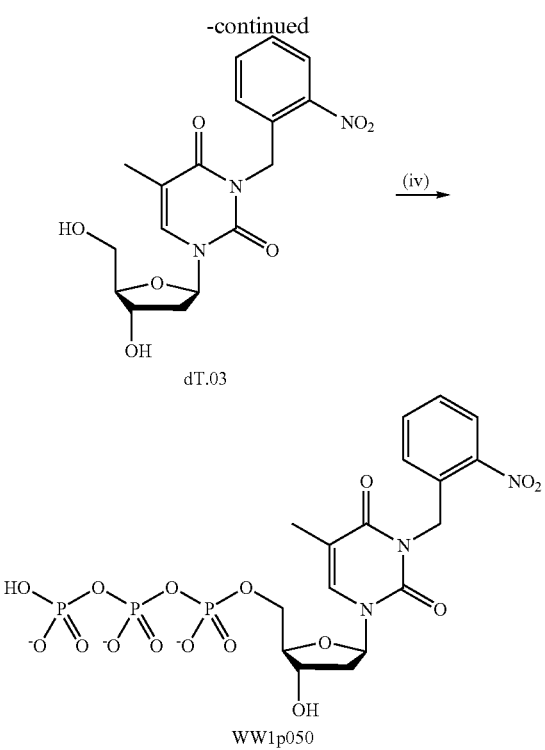

Scheme. Synthesis of N³-(2-nitrobenzyl)-thymidine-5'-triphosphate. (i) TBSCl, imidazole, anhydrous CH₂Cl₂, room temperature, overnight, 58%; (ii) 2-nitrobenzyl bromide, n-Bu₄NOH, NaI, NaOH (1 M), CHCl₃, room temperature, overnight, 37%; (iii) n-Bu₄NF, THF, 25° C., 45 minutes, 80%; (iv) POCl₃, proton sponge, (MeO)₃PO, 0° C., six hours; (n-Bu₃NH)₂H₂P₂O₇, n-Bu₃N, DMF, five minutes; 1 M HNEt₃HCO₃, one hour, 56%.

5'-O-tert-butyldimethylsilyl-thymidine (dT.01)

A solution of thymidine dT (2.85 g, 11.76 mmol), imidiazole (2.44 g, 35.80 mmol) and TBSCl (1.77 g, 11.76 mmol) in anhydrous CH₂Cl₂ (20 mL) was stirred at room temperature overnight under a N₂ atmosphere. The reaction mixture was then concentrated in vacuo to a viscous oil, followed by the addition of ethyl ether (60 mL) and water (60 mL). The organic layer was separated and washed twice with water (20 mL each), and the combined aqueous layer was extracted with ethyl ether (20 mL). The combined organic layer was dried over Na₂SO₄, concentrated in vacuo and purified by silica gel column chromatography to give 5'-O-tert-butyldimethylsilyl-thymidine dT.01 (3.44 g, 82%) as a white solid.

¹H NMR (400 MHz, CDCl₃): δ 9.35 (br s, 1 H, H-3), 7.53 (d, 1 H, J=1.2 Hz, H-6), 6.39 (dd, 1 H, J=8.3, 5.6 Hz, H-1'), 4.45 (m, 1 H, H-4'), 4.07 (m, 1 H, H-3'), 3.87 (m, 2 H, H-5'a and H-5'b), 2.99 (br. s, 1 H, 3'-OH), 2.38 (m, 1 H, H-2'b), 2.09 (m, 1 H, H-2'b), 1.91 (d, 3 H, J=1.2 Hz, 5-Me), 0.92 (s, 9 H, (CH₃)₃CSi), 0.11 (s, 6 H, (CH₃)₂Si).

N³-(2-Nitrobenzyl)-5'-O-tert-butyldimethylsilyl-thymidine (dT.02)

To a vigorously stirred mixture of compound dT.01 (660 mg, 1.85 mmol), tetrabutylammonium hydroxide (0.5 mL), sodium iodide (55 mg) in CHCl₃ (5 mL), and NaOH (1 M; 5 mL), a solution of 2-nitrobenzyl bromide (400 mg, 1.85 mmol) in CHCl₃ (5 mL) was added dropwise and stirred at room temperature overnight. The organic layer was separated, and the aqueous layer was extracted twice with chloroform (5 mL each). The combined organic layer was washed with water (5 mL), brine (5 mL), and dried over Na₂SO₄. The solvent was evaporated in vacuo, and the residue was purified by silica gel column chromatography to yield N³-(2-nitrobenzyl)-5'-O-tert-butyldimethylsilyl-thymidine dT.02 (562 mg, 58%) as a white foam.

¹H NMR (CDCl₃): δ 7.98 (dd, 1 H, J=7.2, 1.2 Hz, Ph-H), 7.60 (d, 1 H, J=1.2 Hz, H-6), 7.49 (dt, 1 H, J=7.6, 1.2 Hz, Ph-H), 7.36 (dt, 1 H, J=8.1, 1.4 Hz, Ph-H), 7.16 (dd, 1 H, J=7.8, 1.1 Hz, Ph-H), 6.31 (dd, 1 H, J=8.2, 5.7 Hz, H-1'), 5.50 (d, 1 H, J=16.2 Hz, PhCH₂), 5.44 (d, 1 H, J=16.2 Hz, PhCH₂), 4.40 (m, 1 H, H-4'), 3.97 (q, 1 H, J=2.4 Hz, H-3'), 3.82 (dq, 2 H, J=11.4, 2.4 Hz, H-5'a and H-5'b), 2.98 (s, 1 H, 3'-OH), 2.29 (m, 1 H, H-2'a), 2.05 (m, 1 H, H-2'b), 1.93 (d, 3 H, J=1.2 Hz, 5-Me), 0.90 (s, 9 H, (CH₃)₃CSi), 0.09 (s, 3 H, (CH₃)Si), 0.08 (s, 3 H, (CH₃)Si).

N³-(2-Nitrobenzyl)-thymidine (dT.03)

A solution of n-Bu₄NF (1.0 M in THF, 1.125 mL, 1.125 mmol) was added dropwise to a solution of compound dT.02 (369 mg, 0.75 mmol) in THF (3.75 mL). The reaction mixture was stirred at room temperature for 45 minutes, concentrated in vacuo, and purified by silica gel column chromatography to yield N³-(2-nitrobenzyl)-thymidine dT.03 (225 mg, 80%) as a white foam.

¹H NMR (CDCl₃): δ 8.01 (dd, 1 H, J=8.2, 1.3 Hz, Ph-H), 7.51 (m, 2 H, H-6 and Ph-H), 7.40 (m, 1 H, Ph-H), 7.21 (dd, 1 H, J=7.8, 0.9 Hz, Ph-H), 6.21 (t, 1 H, J=6.7 Hz, H-1'), 5.49 (dd, 2 H, PhCH₂), 4.53 (m, 1 H, H-4'), 3.97 (m, 1 H, H-3'), 3.78 (m, 2 H, H-5'a and H-5'b), 2.30 (m, 2 H, H-2'a and H-2'b), 1.94 (s, 3 H, 5-CH₃).

N³-(2-Nitrobenzyl)-thymidine-5'-triphosphate (WW1p050)

POCl₃ (30 μL, 0.33 mmol) was added to a solution of compound dT.03 (38 mg, 0.11 mmol) and proton sponge (32 mg, 0.15 mmol) in trimethylphosphate (0.5 mL) at 0° C. and stirred for six hours. A solution of bis-tri-n-butylammonium pyrophosphate (237 mg, 0.5 mmol) and tri-n-butylamine (100 μL) in anhydrous DMF (1 mL) was added. After five minutes of stirring, triethylammonium bicarbonate buffer (1 M, pH 7.5; 10 mL) was added to the solution. The reaction was stirred at room temperature for one hour and then lyophilized to dryness. The residue obtained was dissolved in water (10 mL), filtered, and purified by anion exchange chromatography using a Q Sepharose FF column (2.5×20 cm) with a linear gradient of NH₄HCO₃ (50 mM to 500 mM in 240 minutes) at a flow rate of 4.5 mL/min. The fractions containing triphosphate were combined and lyophilized to give triphosphate N³-(2-nitrobenzyl)-thymidine-5'-triphosphate WW1p050 (38 mg, 56%) as a white fluffy solid.

¹H NMR (400 MHz, D₂O): δ 8.15 (d, 1 H, J=8.2 Hz, Ph-H), 7.82 (s, 1 H, H-6), 7.64 (t, 1 H, J=7.6 Hz, Ph-H), 7.54 (t, 1 H, J=7.6 Hz, Ph-H), 7.24 (d, 1 H, J=7.8 Hz, Ph-H), 6.35 (t, 1 H, J=6.7 Hz, H-1'), 5.47 (s, 2 H, Ph-CH₂), 4.64 (m, 1 H, H-4'), 4.25 (m, 3 H, H-3', H-5'a and H-5'b), 2.40 (m, 2 H, H-2'a and H-2'b), 1.98 (s, 3 H, 5-CH₃);

³¹P NMR (162 MHz, D₂O): δ-6.12 (d, J=15.6 Hz), −11.21 (d, J=15.4 Hz), −19.565 (d, J=15.6 Hz);

ToF-MS (ESI): For the molecular ion C₁₇H₂₀N₃O₁₆P₃Na [M-2H+Na]⁻, the calculated mass was 637.9954, and the observed mass was 637.9802.

Synthesis of 5-(2-nitrobenzyloxymethyl)-2'-deoxyuridine-5'-triphosphate (VL3p03085)

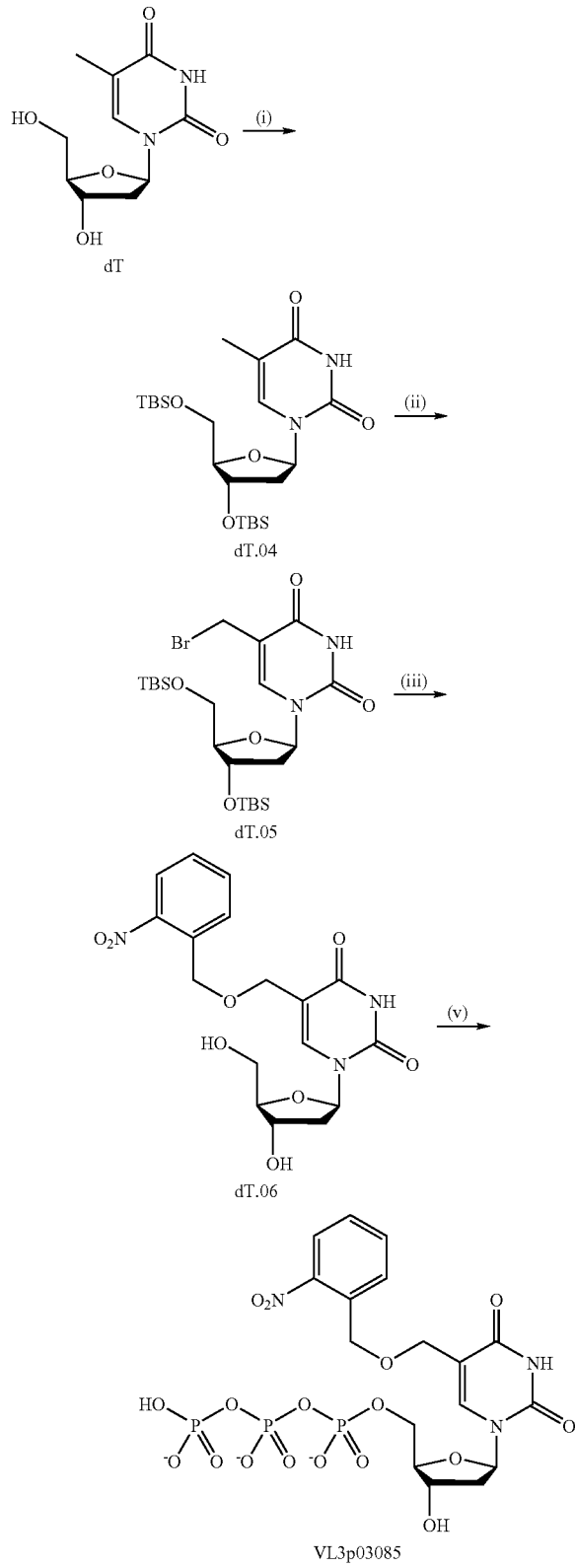

Scheme. Synthesis of 5-(2-nitrobenzyloxymethyl)-2'-deoxyuridine-5'-triphosphate. (i) TBSCl, imidazole, anhydrous DMF, room temperature, overnight, 90%; (ii) NBS, benzoyl peroxide, $CCl_4$, reflux, one hour, 44%; (iii) 2-nitrobenzyl alcohol, 110-115° C., 10 minutes, 35%; (iv) $POCl_3$, proton sponge, $(MeO)_3PO$, 0° C., two hours; $(n-Bu_3NH)_2$ $H_2P_2O_7$, $n-Bu_3N$, DMF; 1 M $HNEt_3HCO_3$, one hour, 22%.

3',5'-O-Bis-tert-butyldimethylsilyl-thymidine (dT.04)

To a solution of thymidine (5.00 g, 20.64 mmol) and imidazole (9.0 g, 132.1 mmol) in anhydrous DMF (11 mL), a solution of TBSCl (9.96 g, 66.05 mmol) in DMF (11 mL) was added dropwise, and the mixture was stirred at room temperature overnight under a $N_2$ atmosphere. After the mixture was diluted with water (100 mL), the formed precipitate was filtered and dissolved in ethyl ether (125 mL). The ether solution was washed twice with water (25 mL each) and once with brine (25 mL), dried over $Na_2SO_4$, and concentrated under reduced pressure to a waxy solid, which was re-crystallized from hexane/ethyl either (10:1) to yield 3',5'-O-bis-tert-butyldimethylsilyl-thymidine dT.04 (10.64 g, 90%).

$^1$H NMR (400 MHz, $CDCl_3$): δ 8.51 (br s, 1 H, H-3), 7.48 (d, 1 H, J=1.2 Hz, H-6), 6.34 (dd, 1 H, J=5.8 and 8.0 Hz, H-1'), 4.41 (m, 1 H, H-3'), 3.93 (m, 2 H, H-4'), 3.87 (dd, 1 H, J=2.6 and 11.4 Hz, H-5'a), 3.76 (dd, 1 H, J=2.6 and 11.4, Hz, H-5'b), 2.17 (m, 1 H, H-2'a), 2.01 (m, 1 H, H-2'b), 1.92 (d, 3 H, J=1.2 Hz, $CH_3$), 0.93 (s, 9 H, $(CH_3)_3CSi$), 0.88 (s, 9 H, $(CH_3)_3CSi$), 0.11 (s, 6 H, $(CH_3)_2Si$), 0.08 (s, 6 H, $(CH_3)_2Si$).

5-Bromomethyl-3',5'-bis-O-tert-butyldimethylsilyl-2'-deoxyuridine (dT.05)

A solution of compound dT.04 (4.63 g, 9.83 mmol), N-bromosuccinimide (3.68 g, 20.68 mmol), and benzoyl peroxide (0.10 g, 75% aqueous solution) in $CCl_4$ (100 mL) was refluxed for one hour. The mixture was filtered and the filtrate was concentrated in vacuo and purified by silica gel column chromatography to yield 5-bromomethyl-3',5'-O-bis-tert-butyldimethylsilyl-2'-deoxyuridine dT.05 (2.40 g, 44%).

$^1$H NMR (400 MHz, $CDCl_3$): δ 9.16 (br s, 1 H, H-3), 7.89 (s, 1 H, H-6), 6.30 (dd, 1 H, J=5.8 and 7.7 Hz, H-1'), 4.41 (m, 1 H, H-3'), 4.29 (d, 1 H, J=10.6 Hz, $CH_2Br$), 4.23 (d, 1 H, J=10.6 Hz, $CH_2Br$), 3.98 (m, 2 H, H-4'), 3.89 (dd, 1 H, J=2.6 and 11.4 Hz, H-5'b), 3.78 (dd, 1 H, J=2.6 and 11.4, Hz, H-5'a), 2.30 (m, 1 H, H-2'a), 2.01 (m, 1 H, H-2'b), 0.95 (s, 9 H, $(CH_3)_3CSi$), 0.91 (s, 9 H, $(CH_3)_3CSi$), 0.15 (s, 6 H, $(CH_3)_2Si$), 0.09 (s, 6 H, $(CH_3)_2Si$).

5-(2-Nitrobenzyloxymethyl)-2'-deoxyuridine (dT.06)

Compound dT.05 (238 mg, 0.43 mmol) and 2-nitrobenzyl alcohol (331 mg, 2.17 mmol) was heated neat at 110-115° C. for 10 minutes under a $N_2$ atmosphere. The mixture was cooled down to room temperature, dissolved in ethyl acetate, and purified by silica gel chromatography to yield 5-(2-nitrobenzyloxymethyl)-2'-deoxyuridine dT.06 (60 mg, 35%).

$^1$H NMR (400 MHz, DMSO-$d_6$): δ 11.41 (br s, 1 H, $D_2O$ exchangeable, NH), 8.05 (d, J=8.0 Hz, 1 H, Ph-H), 7.96 (s, 1 H, H-6), 7.78 (m, 2 H, Ph-H), 7.56 (m, 1 H, Ph-H), 6.17 (t, 1 H, J=6.8 Hz, H-1'), 5.25 (d, 1 H, $D_2O$ exchangeable, 3'-OH), 5.00 (t, 1 H, J=5.0 Hz, $D_2O$ exchangeable, 5'-OH), 4.48 (s, 2 H, $CH_2$), 4.24 (m, 1 H, H-3'), 4.23 (s, 2H, $CH_2$), 3.79 (m, 1 H, H-4'), 3.57 (m, 2 H, H-5'), 2.11 (m, 2 H, H-2');

$^{13}$C NMR (100 MHz, MeOH-$d_4$): δ 163.38 (C), 147.18 (C), 139.53 (CH), 134.80 (C), 133.81 (C), 132.87 (CH), 128.53

(CH), 127.63 (CH), 123.75 (CH), 110.24 (C), 87.16 (CH), 82.83 (CH), 70.41 (CH), 68.26 (CH$_2$), 64.73 (CH$_2$), 61.05 (CH$_2$), 39.58 (CH$_2$);

ToF-MS (ESI): For the molecular ion C$_{17}$H$_{20}$N$_3$O$_8$ [M+H]$^+$, the calculated mass was 394.1250, and the observed mass was 394.1286.

5-(2-Nitrobenzyloxymethyl)-2'-deoxyuridine-5'-triphosphate (VL3p03085)

POCl$_3$ (22 μL, 0.24 mmol) was added to a solution of compound dT.06 (48 mg, 0.12 mmol) and proton sponge (39 mg, 0.18 mmol) in trimethylphosphate (0.5 mL) at 0° C. and stirred for two hours. A solution of bis-tri-n-butylammonium pyrophosphate (285 mg, 0.6 mmol) and tri-n-butylamine (120 μL) in anhydrous DMF (1.2 mL) was added. After two minutes of stirring, triethylammonium bicarbonate buffer (1 M, pH 7.5; 10 mL) was added. The reaction was stirred at room temperature for one hour and then lyophilized to dryness. The residue was dissolved in water (10 mL), filtered, and purified by anion exchange chromatography using a Q Sepharose FF column (2.5×20 cm) with a linear gradient of NH$_4$HCO$_3$ (50 mM to 500 mM in 300 minutes) at a flow rate of 4.5 mL/min. The fractions containing triphosphate were combined and lyophilized to give 5-(2-nitrobenzyloxymethyl)-2'-deoxyuridine-5'-triphosphate VL3p03085 (16 mg, 22%) as a white fluffy solid.

$^1$H NMR (400 MHz, D$_2$O): δ 8.01 (d, J=8.0 Hz, 1 H, Ph-H), 7.78 (s, 1 H, H-6), 7.65 (m, 2 H, Ph-H), 7.52 (m, 1 H, Ph-H), 6.26 (t, J=6.8 Hz, 1 H, H-1'), 4.93 (m, 2 H, CH$_2$), 4.57 (m, 1 H, H-3'), 4.41 (s, 2 H, CH$_2$), 4.21 (m, 3 H, H-4' and H-5'), 2.34 (m, 2 H, H-2');

$^{31}$P NMR (162 Hz, D$_2$O): δ-5.58 (d, J=18.5 Hz), −10.91 (d, J=18.5 Hz), −20.80 (br);

TOF-MS (ESI): For the molecular ion C$_{17}$H$_{21}$N$_3$O$_{17}$P$_3$ [M-H]$^-$, the calculated mass was 632.0084, and the observed mass was 631.9779.

Synthesis of 5-[1-(2-nitrophenyl)ethyloxymethyl]-2'-deoxyuridine-5'-triphosphate (WW2p043)

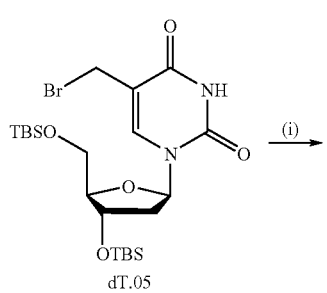

dT.05

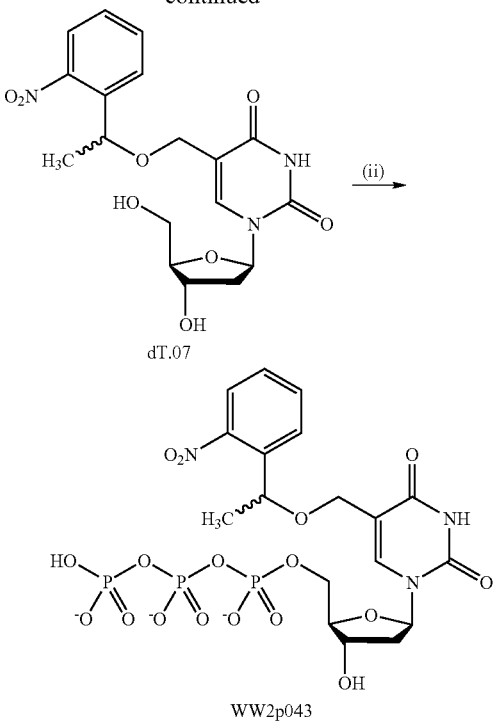

Scheme. Synthesis of 5-[1-(2-nitrophenyl)ethyloxymethyl]-2'-deoxyuridine-5'-triphosphate. (i) 1-(2-nitrophenyl)ethanol (1.25 g, 7.50 mmol), 110-115° C., 10 minutes, 8%; (ii) POCl$_3$, proton sponge, (MeO)$_3$PO, 0° C., three hours; (n-Bu$_3$NH)$_2$H$_2$P$_2$O$_7$, n-Bu$_3$N, DMF; 1 M HNEt$_3$HCO$_3$, one hour, 55%.

5-[1-(2-Nitrophenyl)ethyloxymethyl]-2'-deoxyuridine (dT.07)

Compound dT.05 (0.81 g, 1.5 mmol) and 1-(2-nitrophenyl)ethanol (1.25 g, 7.50 mmol) were heated neat at 110-115° C. for 10 minutes under a N$_2$ atmosphere. The mixture was cooled down to room temperature, dissolved in ethyl acetate, and purified by silica gel chromatography to yield 5-[1-(2-nitrophenyl)ethyloxymethyl]-2'-deoxyuridine dT.07 (48 mg, 8%, 1:1 mixture of diastereomers).

$^1$H NMR (400 MHz, DMSO-d$_6$) for diastereomers: δ 11.36 and 11.35 (2 br s, 1 H, D$_2$O exchangeable, NH), 7.95 (m, 1 H, Ph-H), 7.87 (m, 1 H, Ph-H), 7.76 (m, 2 H, H-6 and Ph-H), 7.54 (m, 1 H, Ph-H), 6.14 (m, 1 H, H-1'), 5.25 (d, 1 H, D$_2$O exchangeable, 3'-OH), 5.00 (m, 2 H, among them 1 H D$_2$O exchangeable, 5'-OH and CH), 4.24 (m, 1 H, H-3'), 3.96 (m, 2 H, CH$_2$), 3.78 (m, 1 H, H-4'), 3.57 (m, 2 H, H-5'), 2.08 (m, 2 H, H-2'), 1.43 (d, J=6.3 Hz, 3 H, CH$_3$);

ToF-MS (ESI): For the molecular ion C$_{18}$H$_{22}$N$_3$O$_8$ [M+H]$^+$, the calculated mass was 408.1407, and the observed mass was 408.1446.

5-[1-(2-Nitrophenyl)ethyloxymethyl]-2'-deoxyuridine-5'-triphosphate (WW2p043)

POCl$_3$ (15 μL, 0.17 mmol) was added to a solution of compound dT.07 (34 mg, 0.08 mmol) and proton sponge (27 mg, 0.12 mmol) in trimethylphosphate (0.5 mL) at 0° C. and stirred for three hours. A solution of tri-n-butylammonium pyrophosphate (197 mg, 0.4 mmol) and tri-n-butylamine (100 μL) in anhydrous DMF (0.8 mL) was added. After five minutes of stirring, triethylammonium bicarbonate buffer (1 M, pH 7.5, 10 mL) was added. The reaction was stirred at room temperature for one hour and then lyophilized to dryness. The residue was dissolved in water (10 mL), filtered, and purified by anion exchange chromatography using a Q Sepharose FF column (2.5×20 cm) with a linear gradient of $NH_4HCO_3$ (50 mM to 500 mM in 300 minutes) at a flow rate of 4.5 mL/min. The fractions containing triphosphate were combined and lyophilized to give 5-[1-(2-nitrophenyl)ethyloxymethyl]-2'-deoxyuridine-5'-triphosphate WW2p043 (32 mg, 55%, 1:1 mixture of diastereomers) as a white fluffy solid.

$^1$H NMR (400 MHz, $D_2O$) for diastereomers: δ 7.93 (m, 1 H, Ph-H), 7.71-7.61 (m, 3H, H-6 and Ph-H), 7.49 (m, 1 H, Ph-H), 6.18 and 6.12 (2 t, J=6.6 Hz, 1 H, H-1'), 5.13 (m, 1 H, CH), 4.53 (m, 1 H, H-3'), 4.39 (m, 1 H, H-4'), 4.20 (m, 4 H, $CH_2$ and H-5'), 2.28 (m, 2 H, H-2'), 1.54 (d, 3 H, J=6.3 Hz, $CH_3$);

$^{31}$P NMR (162 MHz, $D_2O$): δ-7.98 (br), −12.64 (br), −23.33 (br);

ToF-MS (ESI): For the molecular ion $C_{18}H_{24}N_3O_{17}P_3Na$ [M+Na]$^+$, the calculated mass was 670.0216, and the observed mass was 670.0176.

Synthesis of 6-JOE labeled 5-[4-(3-amino-1-propynyl)-2-nitrobenzyloxymethyl]-2'-deoxyuridine-5'-triphosphate (WW2p075)

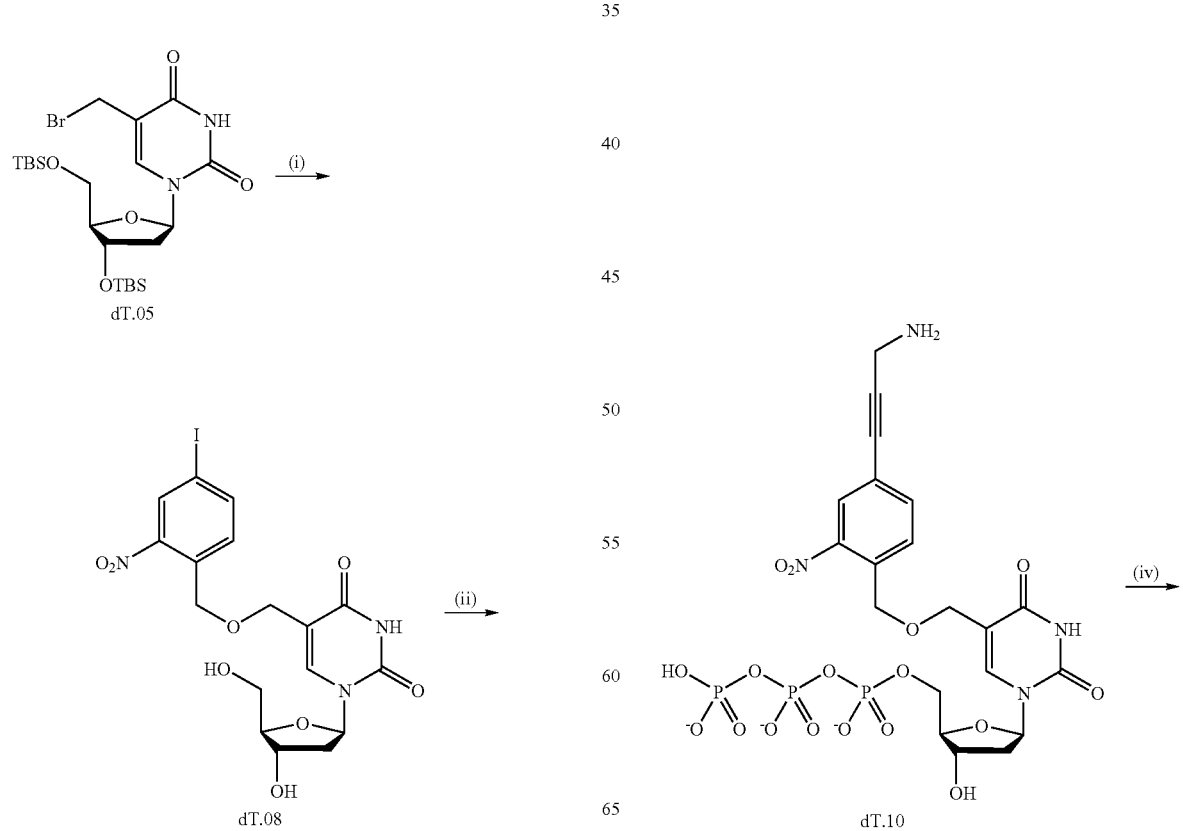

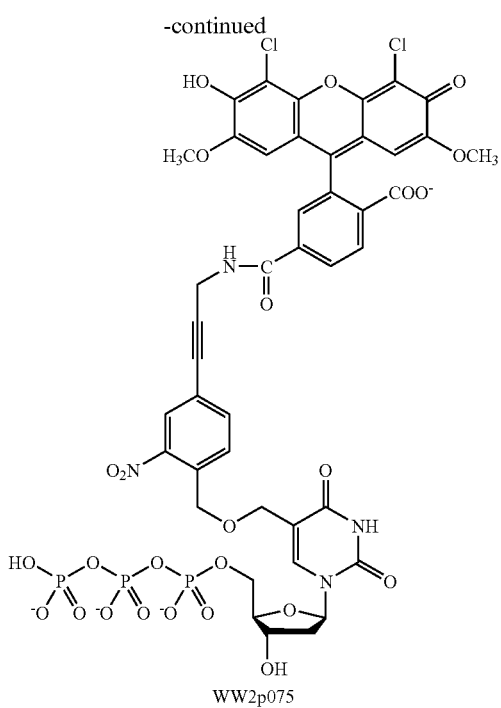

WW2p075

Scheme. Synthesis of 6-JOE labeled 5-[4-(3-amino-1-propynyl)-2-nitrobenzyl-oxymethyl]-2'-deoxyuridine-5'-triphosphate. (i) 4-iodo-2-nitrobenzyl alcohol, neat, 110-115° C., 10 minutes, 10%; (ii) N-propargyltrifluoroacetamide, Pd(PPh$_3$)$_4$ (O), CuI, Et$_3$N, anhydrous DMF, four hours, 50%; (iii) POCl$_3$, proton sponge, (MeO)$_3$PO, 0° C., four hours; (n-Bu$_3$NH)$_2$H$_2$P$_2$O$_7$, n-Bu$_3$N, DMF, five minutes; 1 M HNEt$_3$HCO$_3$, one hour; NH$_4$OH, one hour; 31%; (iv) 6-JOE-SE, 0.1 M Na$_2$CO$_3$/NaHCO$_3$ buffer (pH 9.2), one hour.

5-(4-Iodo-2-nitrobenzyloxymethyl)-2'-deoxyuridine (dT.08)

Compound dT.05 (0.59 g, 1.06 mmol) and 4-iodo-2-nitrobenzyl alcohol (1.09 g, 3.9 mmol) were heated neat at 110-115° C. for 10 minutes under a N$_2$ atmosphere. The mixture was cooled down to room temperature, dissolved in ethyl acetate, and purified by silica gel chromatography to yield 5-(4-iodo-2-nitrobenzyloxymethyl)-2'-deoxyuridine dT.08 (52 mg, 10%) as a low-melting solid.

$^1$H NMR (400 MHz, DMSO-d$_6$): δ 11.42 (s, 1 H, D$_2$O exchangeable, N—H), 8.34 (d, 1 H, J=1.7 Hz, Ph-H), 8.09 (dd, 1 H, J=1.7 and 8.2 Hz, Ph-H), 7.96 (s, 1 H, H-6), 7.56 (d, 1 H, J=8.2, Ph-H), 6.16 (t, 1 H, J=6.8 Hz, H-1'), 5.25 (d, 1 H, D$_2$O exchangeable, 3'-OH), 5.02 (t, 1 H, D$_2$O exchangeable, 5'-OH), 4.77 (s, 2 H, CH$_2$), 4.20 (m, 1 H, H-3'), 4.22 (s, 2 H, CH$_2$), 3.79 (m, 1 H, H-4'), 3.57 (m, 2 H, H-5'), 2.11 (m, 2 H, H-2').

5-[4-(3-Trifluoroacetamido-1-propynyl)-2-nitrobenzyloxymethyl]-2'-deoxyuridine (dT.09)

A solution of compound dT.08 (51 mg, 0.1 mmol), N-propargyltrifluoroacetylamide (45 mg, 0.3 mmol), tetrakis(triphenylphosphine)-palladium(0) (12 mg, 0.01 mmol), CuI (4 mg, 0.02 mmol), and Et$_3$N (28 µL, 0.2 mmol) in anhydrous DMF (1.2 mL) was stirred at room temperature for four hours. The mixture was concentrated in vacuo and purified by silica gel column chromatography to yield 5-[4-(3-trifluoroacetamido-1-propynyl)-2-nitrobenzyloxymethyl]-2'-deoxyuridine dT.09 (27 mg, 50%) as a waxy solid.

$^1$H NMR (400 MHz, DMSO-d$_6$): δ 11.44 (s, 1 H, D$_2$O exchangeable, N3-H), 10.44 (1 H, D$_2$O exchangeable, N—H (COCF$_3$)), 8.06 (s, 1 H, Ph-H), 7.97 (s, 1 H, H-6), 7.79 (s, 2 H, Ph-H), 6.16 (t, J=6.8 Hz, 1 H, H-1'), 5.25 (d, 1 H, D$_2$O exchangeable, 3'-OH), 5.02 (t, 1 H, D$_2$O exchangeable, 5'-OH), 4.83 (s, 2 H, Ph-CH$_2$), 4.30 (s, 2 H, CH$_2$), 4.23 (m, 3H, CH$_2$ and H-3'), 3.79 (m, 1 H, H-4'a), 3.57 (m, 2 H, H-5'), 2.10 (m, 2 H, H-2'a and H-2'b);

ES+ MS (ESI): 543 [M+H]$^+$; ES− MS (ESI): 541 [M+H]$^+$

5-[4-(3-Amino-1-propynyl)-2-nitrobenzyloxymethyl]-2'-deoxyuridine-5'-triphosphate (dT.10)

POCl$_3$ (8 µL, 88 µmol) was added to a solution of compound dT.09 (24 mg, 44 µmol) and proton sponge (14 mg, 66 µmol) in trimethylphosphate (0.5 mL) at 0° C. and stirred for two hours. Additional POCl$_3$ (8 µL, 88 µmol) was added and stirred for another two hours. A solution of bis-tri-n-butylammonium pyrophosphate (104 mg, 0.22 mmol) and tri-n-butylamine (50 µL) in anhydrous DMF (0.5 mL) was added. After five minutes of stirring, triethylammonium bicarbonate buffer (1 M, pH 7.5; 10 mL) was added. The reaction was stirred at room temperature for one hour, followed by the dropwise addition of concentrated ammonium hydroxide (5 mL, 27%) at 0° C. The mixture was stirred for an additional hour at room temperature and then lyophilized to dryness. The residue was dissolved in water (10 mL), filtered, and purified by anion exchange chromatography using a Q Sepharose FF column (2.5×20 cm) with a linear gradient of NH$_4$HCO$_3$ (50 mM to 500 mM in 300 minutes) at a flow rate of 4.5 mL/min. The fractions containing triphosphate were combined and lyophilized to give triphosphate dT.10 (10 mg, 31%) as a white fluffy solid.

$^1$H NMR (400 MHz, D$_2$O): δ 8.10 (d, J=5.1 Hz, 1 H, Ph-H), 7.75 (m, 2 H, H-6 and Ph-H), 7.65 (m, 1 H, J=8.0 Hz, Ph-H), 6.27 (t, J=6.8 Hz, 1 H, H-1'), 4.95 (m, 2 H, CH$_2$), 4.58 (m, 1 H, H-3'), 4.43 (s, 2 H, CH$_2$), 4.22 (m, 3 H, H-4' and H-5'), 3.64 (s, 2 H, CH$_2$), 2.33 (m, 2 H, H-2');

$^{31}$P NMR (162 Hz, D$_2$O): δ-6.51 (d, J=15.0 Hz), −11.56 (d, J=15.6 Hz), −19.82 (t, J=15.0 Hz);

TOF-MS (ESI): For the molecular ion C$_{20}$H$_{23}$N$_4$O$_{17}$P$_3$Na [M-2H+Na]$^-$, the calculated mass was 707.0169, and the observed mass was 707.0321.

6-JOE Labeled 5-[4-(3-Amino-1-propynyl)-2-nitrobenzyloxymethyl]-2'-deoxyuridine-5'-triphosphate (WW2p075)

A solution of 6-JOE-SE (1.25 mg, 2 µmol) in anhydrous DMSO (50 µL) was added to a solution of triphosphate dT.10 (1.4 µmol) in Na$_2$CO$_3$/NaHCO$_3$ buffer (0.1 M, pH 9.2; 0.5 mL) and incubated at room temperature for one hour. The reaction was purified by reverse-phase HPLC using a Perkin Elmer OD-300 C$_{18}$ column (4.6×250 mm) to yield the 6-JOE labeled triphosphate WW2p075. Mobile phase: A, 100 mM triethylammonium acetate (TEAA) in water (pH 7.0); B, 100 mM TEAA in water/CH$_3$CN (30:70). Elution was performed with a linear gradient of 5-38% B for 40 minutes and then 38-90% B for 10 minutes. The concentration of WW2p075 was estimated by adsorption spectroscopy using the extinction coefficient of the 6-JOE dye (i.e., 75,000 at 520 nm).

Synthesis of 6-JOE labeled 5-{1-[4-(3-amino-1-propynyl)-2-nitrophenyl]ethyl-oxymethyl}-2'-deoxyuridine-5'-triphosphate (WW2p113)
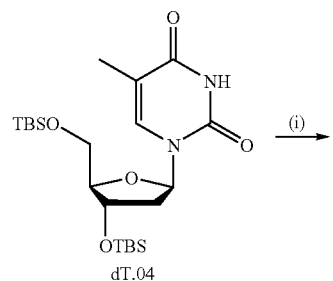
dT.04
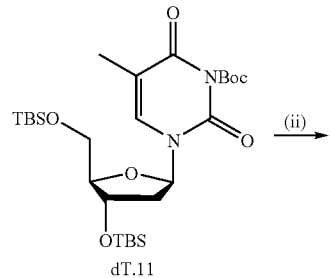
dT.11
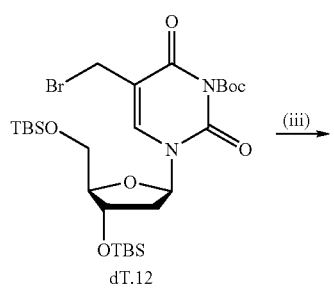
dT.12
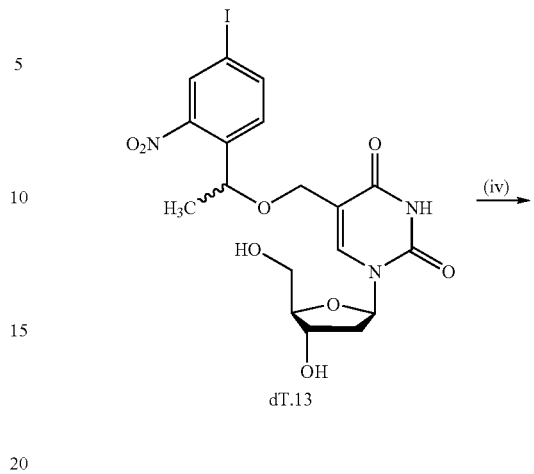
dT.13
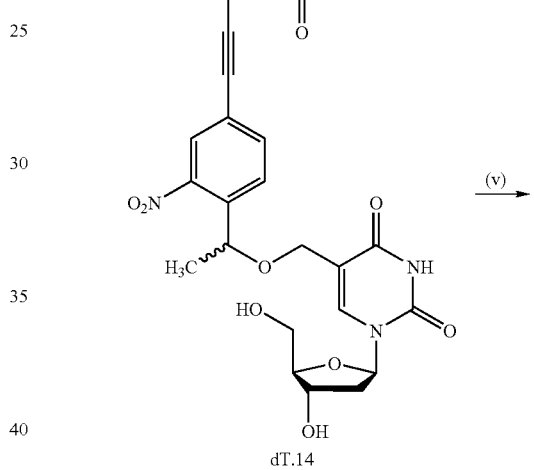
dT.14
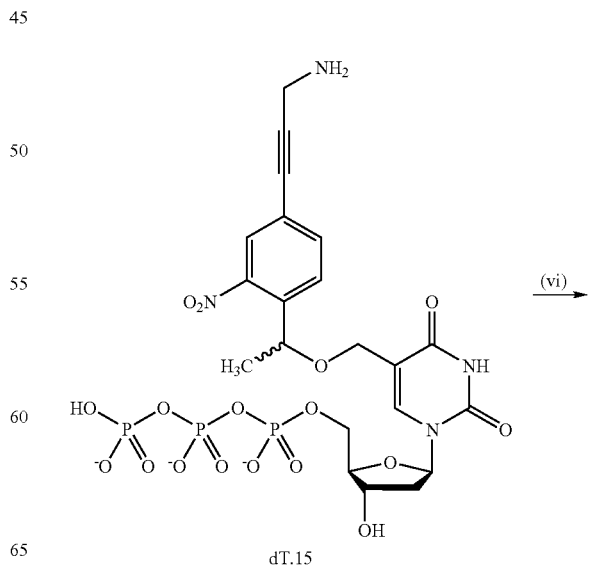
dT.15

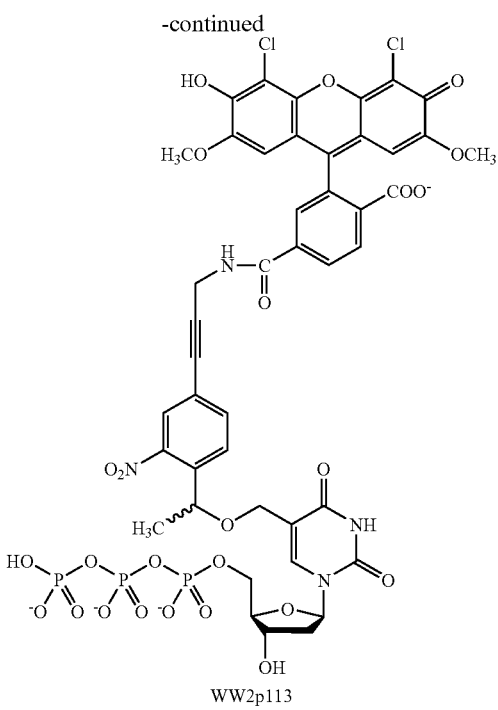

WW2p113

Scheme. Synthesis of 6-JOE labeled 5-{1-[4-(3-Amino-1-propynyl)-2-nitrophenyl]-ethyloxy-methyl}-2'-deoxyuridine-5'-triphosphate. (i) Boc$_2$O, DMAP, anhydrous DMF, room temperature, 16 hours, 78%; (ii) NBS, benzoyl peroxide, CCl$_4$, reflux, one hour, 43%; (iii) 1-(4-iodo-2-nitrophenyl)ethanol, neat, 95° C., 50 minutes, 13%; (iv) N-propargyl-trifluoroacetamide, Pd(PPh$_3$)$_4$ (0), CuI, Et$_3$N, anhydrous DMF, four hours, 76%; (v) POCl$_3$, proton sponge, (MeO)$_3$PO, 0° C.; (n-Bu$_3$NH)$_2$H$_2$P$_2$O$_7$, n-Bu$_3$N, DMF; 1 M HNEt$_3$HCO$_3$, one hour; NH$_4$OH, one hour; 31%; (vi) 6-JOE-SE, 0.1 M Na$_2$CO$_3$/NaHCO$_3$ buffer (pH 9.2), one hour.

$N^3$-tert-Butyloxycarbonyl-3',5'-O-bis-tert-butyldimethylsilyl-thymidine (dT.11)

To a solution of compound dT.04 (2.43 g, 5.15 mmol) and DMAP (1.39 g, 11.34 mmol) in anhydrous DMF (45 mL), a solution of di-tert-butyldicarbonate (2.47 g, 11.34 mmol) in DMF (9 mL) was added dropwise. The mixture was stirred at room temperature for 16 hours under a N$_2$ atmosphere. The mixture was concentrated in vacuo, and the crystalline residue was dissolved in CH$_2$Cl$_2$ (80 mL), washed with saturated NH$_4$Cl solution (10 mL), dried over Na$_2$SO$_4$, and concentrated in vacuo. The residue was purified by silica gel column chromatography to yield $N^3$-tert-butyloxycarbonyl-3',5'-O-bis-tert-butyldimethylsilyl-thymidine dT.11 (2.30 g, 78%) as a white solid.

$^1$H NMR (400 MHz, CDCl$_3$): δ 7.50 (d, 1 H, J=1.1 Hz, H-6), 6.34 (dd, 1 H, J=5.8 and 7.9 Hz, H-1'), 4.42 (m, 1 H, H-3'), 3.95 (m, 2 H, H-4'), 3.87 (dd, 1 H, J=2.5 and 11.4 Hz, H-5'a), 3.76 (dd, 1 H, J=2.5 and 11.4 Hz, H-5'b), 2.17 (m, 1 H, H-2'a), 2.01 (m, 1 H, H-2'b), 1.92 (d, 3 H, J=1.2 Hz, CH$_3$), 1.60 (s, 9 H, (CH$_3$)$_3$COCON), 0.93 (s, 9 H, (CH$_3$)$_3$CSi), 0.88 (s, 9 H, (CH$_3$)$_3$CSi), 0.11 (s, 6 H, (CH$_3$)$_2$Si), 0.08 (s, 6 H, (CH$_3$)$_2$Si).

$N^3$-tert-Butyloxycarbonyl-5-bromomethyl-3',5'-bis-O-tert-butyldimethylsilyl-2'-deoxyuridine (dT.12)

A solution of compound dT.11 (570 mg, 1.00 mmol), N-bromosuccinimide (0.37 g, 2.10 mmol), and benzoyl peroxide (10 mg, 75% aqueous solution) in CCl$_4$ (10 mL) was refluxed for one hour. The mixture was filtered, concentrated in vacuo, and purified by silica gel column chromatography to yield $N^3$-tert-butyloxycarbonyl-5-bromomethyl-3',5'-O-bis-tert-butyldimethylsilyl-2'-deoxyuridine dT.12 (281 mg, 43%) as a waxy solid.

$^1$H NMR (400 MHz, CDCl$_3$): δ 7.89 (s, 1 H, H-6), 6.27 (dd, 1 H, J=5.7 and 7.7 Hz, H-1'), 4.39 (m, 1 H, H-3'), 4.27 (d, 1 H, J=10.6 Hz, CH$_2$Br), 4.20 (d, 1 H, J=10.6 Hz, CH$_2$Br), 3.98 (m, 2 H, H-4'), 3.89 (dd, 1 H, J=2.5 and 11.4, Hz, H-5'b), 3.78 (dd, 1 H, J=2.6 and 11.4 Hz, H-5'a), 2.30 (m, 1 H, H-2'a), 2.04 (m, 1 H, H-2'b), 1.61 (s, 9 H, (CH$_3$)$_3$COCON), 0.95 (s, 9 H, (CH$_3$)$_3$CSi), 0.89 (s, 9 H, (CH$_3$)$_3$CSi), 0.14 (s, 6 H, (CH$_3$)$_2$Si), 0.07 (s, 6 H, (CH$_3$)$_2$Si);

$^{13}$C NMR (100 MHz, CDCl$_3$): δ 159.21 (C), 147.99 (C), 147.32 (C), 138.46 (CH), 111.30 (C), 88.34 (CH), 87.22 (C), 86.00 (CH), 72.28 (CH), 63.04 (CH$_2$), 41.93 (CH$_2$), 27.42 (CH$_3$), 25.99 (CH$_3$), 25.71 (CH$_3$), 25.65 (CH$_3$), 24.91 (CH$_2$), 18.47 (C), 17.97 (C), −3.58 (CH$_3$), −4.65 (CH$_3$), −4.86 (CH$_3$), −5.32 (CH$_3$).

5-[1-(4-Iodo-2-nitrophenyl)ethyloxymethyl]-2'-deoxyuridine (dT.13)

Compound dT.12 (323 mg, 0.50 mmol) and 1-(4-iodo-2-nitrophenyl)ethanol (293 mg, 2.23 mmol) were heated neat at 95-97° C. for 50 minutes under a N$_2$ atmosphere. The mixture was cooled down to room temperature, dissolved in ethyl acetate, and purified by silica gel chromatography to yield 5-[1-(4-iodo-2-nitrophenyl)ethyloxymethyl]-2'-deoxyuridine dT.13 (34 mg, 13%, 1:1 mixture of diastereomers) as a waxy solid.

$^1$H NMR (400 MHz, MeOH-d$_4$) for diastereomers: δ 8.26 (t, 1 H, J=1.7 Hz, H-6), 8.05 (dd, 1 H, J=1.6, 8.3 Hz, Ph-H), 8.02 (d, 1 H, J=10.6 Hz, Ph-H), 7.60 (dd, 1 H, J=1.1, 8.3 Hz, Ph-H), 6.26 (m, 1 H, H-1'), 5.03 (m, 1 H, PhCH), 4.41 (m, 1 H, H-3'), 4.10 (m, 2 H, CH$_2$), 3.94 (m, 1 H, H-4'), 3.80 (m, 1 H, H-5'a), 3.74 (m, 1 H, H-5'b), 2.30 (m, 1 H, H-2'a), 2.20 (m, 1 H, H-2'b), 1.50 (m, 3 H, CH$_3$).

5-{1-[4-(3-Trifluoroacetamido-1-propynyl)-2-nitrophenyl]ethyloxymethyl}-2'-deoxyuridine (dT.14)

A solution of compound dT.13 (52 mg, 0.1 mmol), N-propargyltrifluoroacetylamide (44 mg, 0.29 mmol), tetrakis (triphenylphosphine)-palladium(0) (12 mg, 0.01 mmol), CuI (4 mg, 0.02 mmol), and Et$_3$N (27 μL, 0.2 mmol) in anhydrous DMF (1.5 mL) was stirred at room temperature for four hours. The mixture was concentrated in vacuo and purified by silica gel column chromatography to yield 5-[1-(4-{3-trifluoroacetamido-1-propynyl}-2-nitrophenyl)ethyloxymethyl]-2'-deoxy-uridine dT.14 (41 mg, 76%, 1:1 mixture of diastereomers) as a waxy solid.

$^1$H NMR (400 MHz, DMSO-d$_6$) for diastereomers: δ 11.36, 11.35(2 s, 1 H, D$_2$O exchangeable, NH), 10.11 (t, 1 H, J=5.6 Hz, D$_2$O exchangeable, NH), 7.98 (s, 1 H, H-6), 7.88 (d, 1 H, J=8.1 Hz, Ph-H), 7.78 (m, 2 H, Ph-H), 6.14 (t, J=7.0 Hz, 1 H, H-1'), 5.25 (m, 1 H, D$_2$O exchangeable, 3'-OH), 5.01 (m, 1 H, D$_2$O exchangeable, 5'-OH), 4.98 (m, 1 H, PhCH), 4.33 (m, 2 H, CH$_2$), 4.24 (m, 1 H, H-3'), 4.00 (m, 1 H, H-5'a), 3.94 (m, 1 H, H-5'b), 3.78 (m, 1 H, H-4'), 3.57 (m, 2 H, CH$_2$), 2.08 (m, 2 H, H-2'a and H-2'b), 1.41 (d, J=8.1 Hz, 3 H, CH$_3$);

ES$^+$ MS (ESI): 579 [M+Na]$^+$.

5-{1-[4-(3-Amino-1-propynyl)-2-nitrophenyl]ethyloxymethyl}-2'-deoxyuridine-5'-triphosphate (dT.15)

POCl$_3$ (10 µL, 0.11 mmol) was added to a solution of compound dT.14 (30 mg, 0.054 mmol) and proton sponge (17 mg, 0.08 mmol) in trimethylphosphate (0.5 mL) at 0° C. and stirred for two hours. Additional POCl$_3$ (2.5 µL, 0.03 mmol) was added and stirred for another hour. A solution of bis-tri-n-butylammonium pyrophosphate (128 mg, 0.27 mmol) and tri-n-butylamine (60 µL) in anhydrous DMF (0.54 mL) was added. After five minutes of stirring, triethylammonium bicarbonate buffer (1 M, pH 7.5; 10 mL) was added. The reaction was stirred at room temperature for one hour, followed by the dropwise addition of concentrated ammonium hydroxide (5 mL, 27%) at 0° C. The mixture was stirred at room temperature for an additional hour and then lyophilized to dryness. The residue was dissolved in water (10 mL), filtered, and purified by anion exchange chromatography using a Q Sepharose FF column (2.5×20 cm) with a linear gradient of NH$_4$HCO$_3$ (50 mM to 500 mM in 300 minutes) at a flow rate of 4.5 mL/min. The fractions containing triphosphate were combined and lyophilized to give triphosphate dT.15 (16 mg, 40%, 1:1 mixture of diastereomers) as a white fluffy solid.

$^1$H NMR (400 MHz, D$_2$O) for diastereomers: δ 8.01 (m, 1 H, Ph-H), 7.74-7.55 (m, 3H, H-6 and Ph-H), 6.18 and 6.12 (2 t, J=6.4 Hz, 1 H, H-1'), 5.11 (m, 1 H, PhCH), 4.53 (m, 1 H, H-3'), 4.37 (m, 1 H, H-4'), 4.20 (m, 4 H, CH$_2$ and H-5'), 3.65 (s, 2 H, CH$_2$), 2.35 (m, 1 H, H-2'a), 2.25 (m, 1 H, H-2'b), 1.54 (d, 3 H, J=6.4 Hz, CH$_3$);

$^{31}$P NMR (162 MHz, D$_2$O) for diastereomers: δ-5.87 (d, J=19.8 Hz), −11.18 and −11.30 (2 d, J=19.4 Hz), −21.62 (t, J=19.6 Hz);

ToF-MS (ESI): For the molecular ion C$_{21}$H$_{27}$N$_4$O$_{17}$P$_3$Na [M+Na]$^+$, the calculated mass was 723.0482, and the observed mass was 723.0497.

6-JOE Labeled 5-{1-[4-(3-Amino-1-propynyl)-2-nitrophenyl]ethyloxymethyl}-2'-deoxy-uridine-5'-triphosphate (WW2p113)

A solution of 6-JOE-SE (0.75 mg, 1.2 µmol) in anhydrous DMSO (30 µL) was added to a solution of triphosphate dT.15 (0.56 µmol) in Na$_2$CO$_3$/NaHCO$_3$ buffer (0.1 M, pH 9.2; 200 µL) and incubated at room temperature for one hour. The reaction was purified by reverse-phase HPLC using a Perkin Elmer OD-300 C$_{18}$ column (4.6×250 mm) to yield the 6-JOE labeled triphosphate WW2p113. Mobile phase: A, 100 mM TEAA in water (pH 7.0); B, 100 mM TEAA in water/CH$_3$CN (30:70). Elution was performed with a linear gradient of 5-50% B for 40 minutes and then 50-90% B for 10 minutes. The concentration of WW2p113 was estimated by adsorption spectroscopy using the extinction coefficient of the 6-JOE dye (i.e., 75,000 at 520 nm).

Synthesis of 5-[1-(2-nitrophenyl)-2-(methyl)propyloxymethyl]-2'-deoxyuridine-5'-triphosphate (WW2p148)

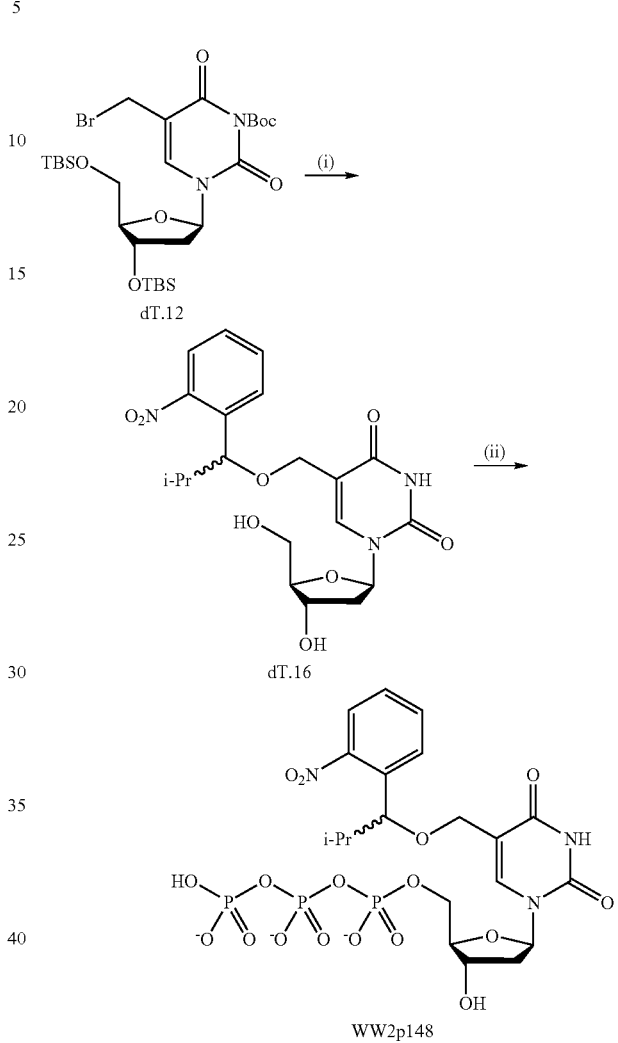

Scheme. Synthesis of 5-[1-(2-nitrophenyl)-2-(methyl)propyloxymethyl]-2'-deoxyuridine-5'-triphosphate. (i) 1-(2-nitrophenyl)-2-methylpropanol, 100-110° C., 35 minutes, 14%; (ii) POCl$_3$, proton sponge, (MeO)$_3$PO, 0° C., three hours; (n-Bu$_3$NH)$_2$H$_2$P$_2$O$_7$, n-Bu$_3$N, DMF; 1 M HNEt$_3$HCO$_3$, one hour.

5-[1-(2-Nitrophenyl)-2-(methyl)propyloxymethyl]-2'-deoxyuridine (dT.16)

Compound dT.12 (0.316 g, 0.486 mmol) and 1-(2-nitrophenyl)-2-methylpropanol (0.706 g, 3.62 mmol) were heated neat at 100-110° C. for 35 minutes under a nitrogen atmosphere. The mixture was cooled down to room temperature, dissolved in ethyl acetate, and purified by silica gel chromatography to yield 5-[1-(2-nitrophenyl)-2-(methyl)propyloxymethyl]-2'-deoxyuridine dT.16 (30 mg, 14%, 1:1 mixture of diastereomers).

$^1$H NMR (400 MHz, DMSO-d$_6$) for diastereomers: δ 11.33 and 11.34 (2 br s, 1 H, D$_2$O exchangeable, NH), 7.95 (m, 1 H, Ph-H), 7.83 (m, 1 H, Ph-H), 7.72 (m, 1 H, Ph-H), 7.68 (m, 1 H, H-6), 7.54 (m, 1 H, Ph-H), 6.14 (m, 1 H, H-1'), 5.26 (d, 1

H, D₂O exchangeable, 3'-OH), 4.97 (m, 1 H, 1 H D₂O exchangeable, 5'-OH), 4.66 (m, 1 H, CH), 4.22 (m, 1 H, H-3'), 3.98 (m, 2 H, CH₂), 3.78 (m, 1 H, H-4'), 3.55 (m, 2 H, H-5'), 2.08 (m, 2 H, H-2'), 1.72 (m, 1 H, CH), 0.85 (m, 3 H, CH₃), 0.80 (m, 3 H, CH₃);

¹³C NMR (100 MHz, CDCl₃) for diastereomers: δ 165.04 (C), 152.20/151.09 (C), 141.19/141.04 (CH), 139.28 (C), 138.05 (C), 134.08 (CH), 130.57/130.51 (CH), 129.60 (CH), 125.25/125.19 (CH), 112.62/112.43 (C), 89.12 (CH)/86.64 (CH), 82.72/82.40 (CH), 72.45 (CH), 65.78/65.61 (CH₂), 63.01 (CH₂), 41.50/41.45 (CH₂), 36.21 (CH), 26.68 (CH), 19.85/19.80 (CH₃), 18.20/18.14 (CH₃);

5-[1-(2-Nitrophenyl)-2-(methyl)propyloxymethyl]-2'-deoxyuridine-5'-triphosphate (WW2p148)

POCl₃ (13 µL, 0.17 mmol) was added to a solution of compound dT.16 (30 mg, 0.07 mmol) and proton sponge (30 mg, 0.14 mmol) in trimethylphosphate (0.5 mL) at 0° C. and stirred for three hours. A solution of tri-n-butylammonium pyrophosphate (166 mg, 0.35 mmol) and tri-n-butylamine (70 µL) in anhydrous DMF (0.7 mL) was added. After five minutes of stirring, triethylammonium bicarbonate buffer (1 M, pH 7.5; 10 mL) was added. The reaction was stirred at room temperature for one hour and then lyophilized to dryness. The residue was dissolved in water (10 mL), filtered, and part of the solution was purified by anion exchange chromatography using a Q Sepharose FF column (2.5×20 cm) with a linear gradient of NH₄HCO₃ (50 mM to 500 mM in 240 minutes) at a flow rate of 4.5 mL/min. The fractions containing triphosphate were combined and lyophilized to give 5-[1-(2-nitrophenyl)-2-(methyl)propyloxymethyl]-2'-deoxyuridine-5'-triphosphate WW2p148 (1:1 mixture of diastereomers) as a white fluffy solid.

¹H NMR (400 MHz, D₂O) for diastereomers: δ 7.93 (m, 1 H, Ph-H), 7.74-7.64 (m, 3 H, H-6 and Ph-H), 7.52 (m, 1 H, Ph-H), 6.19 and 6.13 (2 t, J=6.6 Hz, 1 H, H-1'), 4.55 (m, 1 H, H-3'), 4.40 (m, 1 H, H-4'), 4.21 (m, 4 H, CH₂ and H-5'), 2.38-2.22 (m, 2 H, H-2'), 1.99 (m, 1 H, CH), 1.01 (m, 3 H, CH₃), 0.78 (m, 3 H, CH₃).

³¹P NMR (162 MHz, D₂O) for diastereomers: δ-5.26 (d, J=20.1 Hz), −10.66 and −10.72 (2 d, J=19.6 Hz), −21.17 (t, J=19.6 Hz).

ToF-MS (ESI): For the molecular ion C₂₀H₂₇N₃O₁₇P₃ [M-H]⁻, the calculated mass was 674.0553, and the observed mass was 674.0470.

Synthesis of 6-JOE Labeled 5-{1-[4-(3-amino-1-propynyl)-2-nitrophenyl]-2-(methyl)propyloxymethyl}-2'-deoxyuridine-5'-triphosphate (WW2p150)

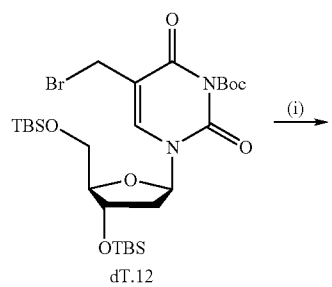
dT.12

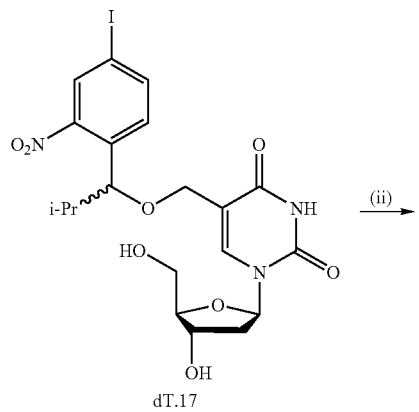
dT.17

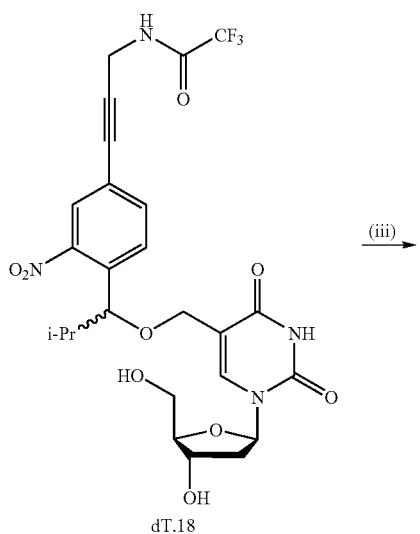
dT.18

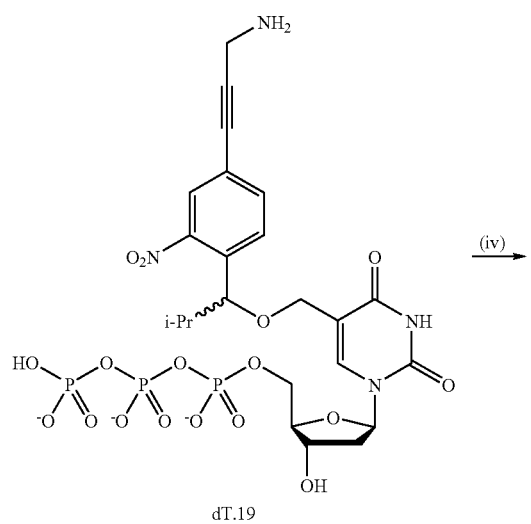
dT.19

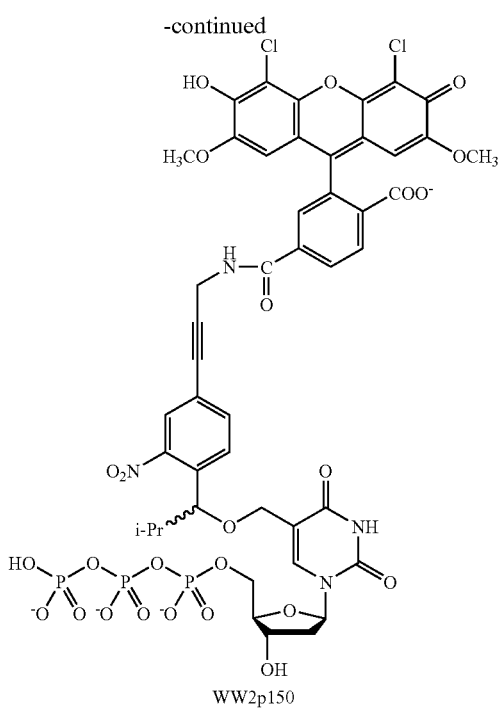

WW2p150

Scheme. Synthesis of 6-JOE labeled 5-{1-[4-(3-Amino-1-propynyl)-2-nitrophenyl]-2-(methyl)propyloxymethyl}-2'-deoxyuridine-5'-triphosphate. (i) 1-(4-iodo-2-nitrophenyl)-2-methylpropanol, neat, 108° C., 45 minutes, 18%; (ii) N-propargyltrifluoroacetamide, Pd(PPh$_3$)$_4$ (O), CuI, Et$_3$N, anhydrous DMF, 4.5 hours, 99%; (iii) POCl$_3$, proton sponge, (MeO)$_3$PO, 0° C., three hours; (n-Bu$_3$NH)$_2$H$_2$P$_2$O$_7$, n-Bu$_3$N, DMF; 1 M HNEt$_3$HCO$_3$, one hour; NH$_4$OH, one hour; (iv) 6-JOE-SE, 0.1 M Na$_2$CO$_3$/NaHCO$_3$ buffer (pH 9.2), one hour.

5-[1-(4-Iodo-2-nitrophenyl)-2-(methyl)propyloxymethyl]-2'-deoxyuridine (dT.17)

Compound dT.12 (400 mg, 0.615 mmol) and 1-(4-iodo-2-nitrophenyl)-2-methylethanol (800 mg, 2.49 mmol) were heated neat at 108° C. for 45 minutes under a nitrogen atmosphere. The mixture was cooled down to room temperature, dissolved in ethyl acetate, and purified by silica gel chromatography to yield 5-[1-(4-iodo-2-nitrophenyl)-2-(methyl) propyloxymethyl]-2'-deoxyuridine dT.17 (64 mg, 18%, 1:1 mixture of diastereomers) as a waxy solid.

$^1$H NMR (400 MHz, MeOH-d$_4$) for diastereomers: δ 8.22 (m, 1 H, H-6), 8.02 (m, 2 H, Ph-H), 7.49 (m, 1 H, Ph-H), 6.22 (m, 1 H, H-1'), 4.69 (m, 1 H, CH), 4.41 (m, 1 H, H-3'), 4.10 (m, 2 H, CH$_2$), 3.92 (m, 1 H, H-4'), 3.75 (m, 2 H, H-5'a), 2.17 (m, 1 H, H-2'a), 2.15 (m, 1 H, H-2'b), 1.90(m, 1 H, CH), 0.92 (m, 3 H, CH$_3$), 0.85 (m, 3 H, CH$_3$);

$^{13}$C NMR (100 MHz, CDCl$_3$) for diastereomers: δ 165.11 (C), 152.16/151.18 (C), 143.12 (CH), 141.44/141.32 (CH), 137.91/137.88 (C), 133.83/133.77 (CH), 132.37/132.33 (CH), 130.80/129.67 (C), 112.40/112.24 (C), 92.75 (C), 89.12 (CH)/86.90 (CH), 82.43/82.18 (CH), 72.39/72.37 (CH), 65.83/65.70 (CH$_2$), 62.96 (CH$_2$), 41.56/41.49 (CH$_2$), 36.01 (CH), 27.83/26.37 (CH), 19.82/19.78 (CH$_3$), 17.91/17.88 (CH$_3$);

5-{1-[4-(3-Trifluoroacetamido-1-propynyl)-2-nitrophenyl]-2-(methyl)]propyloxymethyl}-2'-deoxyuridine (dT.18)

A solution of compound dT.17 (60 mg, 0.107 mmol), N-propargyl-trifluoroacetylamide (48.5 mg, 0.321 mmol), tetrakis(triphenylphosphine)-palladium(0) (12.4 mg, 0.01 mmol), CuI (4 mg, 0.02 mmol), and Et$_3$N (30 μL, 0.214 mmol) in anhydrous DMF (1.5 mL) was stirred at room temperature for 4.5 hours. The mixture was concentrated in vacuo and purified by silica gel column chromatography to yield 5-[1-(4-{3-trifluoroacetamido-1-propynyl}-2-nitrophenyl)-2-(methyl)propyloxymethyl]-2'-deoxyuridine dT.18 (62 mg, 99%, 1:1 mixture of diastereomers) as a waxy solid.

$^1$H NMR (400 MHz, DMSO-d$_6$) for diastereomers: δ 11.36, 11.35(2 s, 1 H, D$_2$O exchangeable, N$^3$—H), 10.11 (t, 1 H, J=5.3 Hz, D$_2$O exchangeable, NHTFA), 7.99 (m, 1 H, H-6), 7.86 (m, 1 H, Ph-H), 7.75 (m, 1 H, Ph-H), 7.65 (m, 1 H, Ph-H), 6.12 (m, 1 H, H-1'), 5.26 (m, 1 H, D$_2$O exchangeable, 3'-OH), 4.97 (m, 1 H, D$_2$O exchangeable, 5'-OH), 4.62 (m, 1 H, CH), 4.31 (m, 2 H, CH$_2$), 4.30 (m, 1 H, H-3'), 3.98 (m, 2 H, CH$_2$), 3.78 (m, 1 H, H-4'), 3.55 (m, 2 H, H-5'a and H-5'b), 2.08 (m, 2 H, H-2'a and H-2'b), 1.77 (m, 1 H, CH), 0.82 (m, 6 H, 2 CH$_3$);

5-{1-[4-(3-Amino-1-propynyl)-2-nitrophenyl]-2-(methyl)propyloxymethyl}-2'-deoxyuridine-5'-triphosphate (dT.19)

POCl$_3$ (8 μL, 0.09 mmol) was added to a solution of compound dT.18 (34 mg, 0.06 mmol) and proton sponge (26 mg, 0.12 mmol) in trimethylphosphate (0.3 mL) at 0° C. and stirred for two hours. Additional POCl$_3$ (4 μL, 0.045 mmol) was added and stirred for another hour. A solution of bis-tri-n-butylammonium pyrophosphate (142 mg, 0.3 mmol) and tri-n-butylamine (60 μL) in anhydrous DMF (0.6 mL) was added. After five minutes of stirring, triethylammonium bicarbonate buffer (1 M, pH 7.5; 10 mL) was added. The reaction was stirred at room temperature for one hour, followed by the dropwise addition of concentrated ammonium hydroxide (5 mL, 27%) at 0° C. The mixture was stirred at room temperature for an additional hour and then lyophilized to dryness. The residue was dissolved in water (10 mL), filtered, and part of the solution was purified by anion exchange chromatography using a Q Sepharose FF column (2.5×20 cm) with a linear gradient of NH$_4$HCO$_3$ (50 mM to 500 mM in 240 minutes) at a flow rate of 4.5 mL/min. The fractions containing triphosphate were combined and lyophilized to give triphosphate dT.19 (1:1 mixture of diastereomers) as a white fluffy solid.

$^1$H NMR (400 MHz, D$_2$O) for diastereomers: δ 8.06 and 8.04 (2 s, 1 H, Ph-H), 7.78 (m, 1 H, Ph-H), 7.69-7.59 (m, 2 H, H-6 and Ph-H), 6.13 (m, 1 H, H-1'), 4.55 (m, 1 H, H-3'), 4.46 and 4.34 (2 d, 2 H, CH$_2$), 4.20 (m, 3 H, H-4' and H-5'), 3.87 and 3.83 (2 s, 2H, CH$_2$), 2.40-2.20 (m, 2 H, H-2'), 1.99 (m, 1 H, CH), 1.02 (m, 3 H, CH$_3$), 0.79 (m, 3 H, CH$_3$);

$^{31}$P NMR (162 MHz, D$_2$O) for diastereomers: δ-5.15 (d, J=19.8 Hz), −10.48 and −10.54 (2 d, J=19.6 Hz), −21.0 (m);

ToF-MS (ESI): For the molecular ion C$_{23}$H$_{30}$N$_4$O$_{17}$P$_3$ [M-H]$^-$, the calculated mass was 727.0819, and the observed mass was 727.0828.

6-JOE Labeled 5-{1-[4-(3-amino-1-propynyl)-2-nitrophenyl]-2-(methyl)propyloxymethyl}-2'-deoxyuridine-5'-triphosphate (WW2p150)

A solution of 6-JOE-SE (0.75 mg, 1.2 µmol) in anhydrous DMSO (30 µL) was added to a solution of triphosphate WW2p145 (0.47 µmol) in Na$_2$CO$_3$/NaHCO$_3$ buffer (0.1 M, pH 9.2; 0.3 mL) and incubated at room temperature for one hour. The reaction was purified by reverse-phase HPLC using a Perkin Elmer OD-300 C$_{18}$ column (4.6×250 mm) to yield the 6-JOE labeled triphosphate WW2p150. Mobile phase: A, 100 mM TEAA in water (pH 7.0); B, 100 mM TEAA in water/CH$_3$CN (30:70). HPLC purification was achieved using a linear gradient of 5-50% B for 40 minutes and then 50-90% B for 10 minutes. The concentration of WW2p150 was estimated by adsorption spectroscopy using the extinction coefficient of the 6-JOE dye (i.e., 75,000 at 520 nm).

Synthesis of 6-JOE Labeled 5-{(R or S)-1-[4-(3-amino-1-propynyl)-2-nitrophenyl]-2-(methyl)propyloxymethyl}-2'-deoxyuridine-5'-triphosphate (WW3p024)

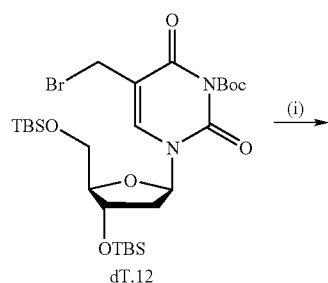
dT.12

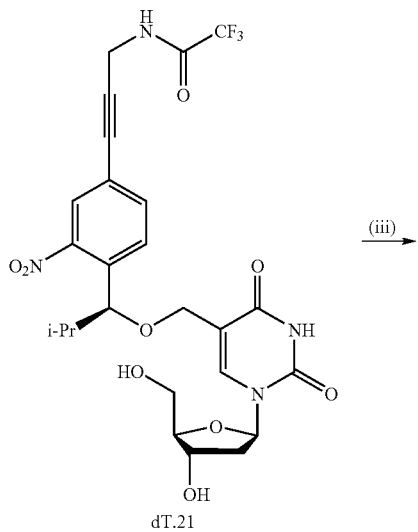
dT.21

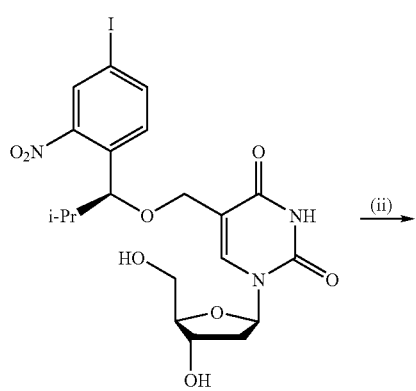
dT.20
absolute configuration not determined, drawing is representative

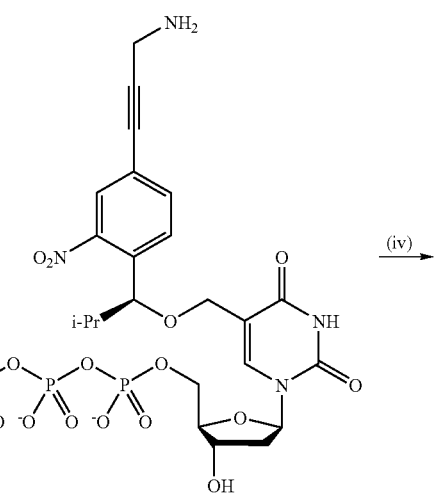
dT.22

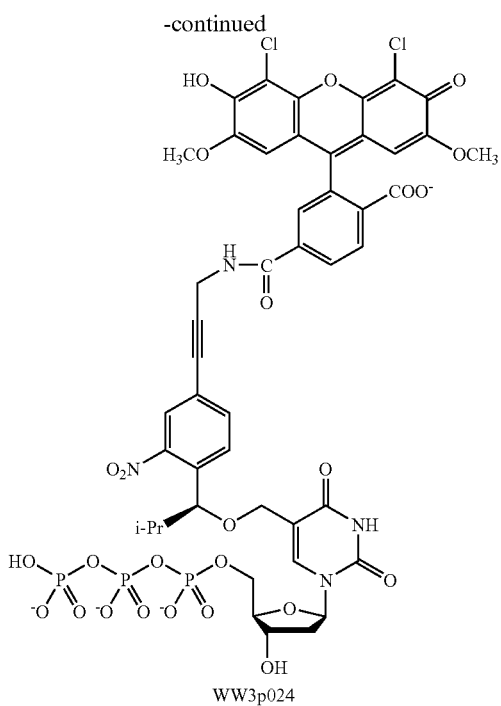

WW3p024

Scheme. Synthesis of 6-JOE labeled 5-{(R or S)-1-[4-(3-Amino-1-propynyl)-2-nitrophenyl]-2-(methyl)propyloxymethyl}-2'-deoxyuridine-5'-triphosphate. (i) (S or R)-1-(4-iodo-2-nitrophenyl)-2-methylpropanol, neat, 108° C., 45 minutes, 20%; (ii) N-propargyltrifluoroacetamide, Pd(PPh$_3$)$_4$ (O), CuI, Et$_3$N, anhydrous DMF, 4.5 hours, 81%; (iii) POCl$_3$, proton sponge, (MeO)$_3$PO, 0° C., two hours; (n-Bu$_3$NH)$_2$ H$_2$P$_2$O$_7$, n-Bu$_3$N, DMF; 1 M HNEt$_3$HCO$_3$, one hour; NH$_4$OH, two hours; (iv) 6-JOE-SE, 0.1 M Na$_2$CO$_3$/NaHCO$_3$ buffer (pH 9.2), one hour.

5-[(R or S)-1-(4-Iodo-2-nitrophenyl)-2-(methyl)propyloxymethyl]-2'-deoxyuridine (dT.20)

Compound dT.12 (143 mg, 0.22 mmol) and enantio-pure (S or R)-1-(4-iodo-2-nitrophenyl)-2-methylpropanol (282 mg, 0.88 mmol, absolute configuration not determined) were heated neat at 108° C. for 45 minutes under a nitrogen atmosphere. The mixture was cooled down to room temperature, dissolved in ethyl acetate, and purified by silica gel chromatography to yield 5-[(R or S)-1-(4-iodo-2-nitrophenyl)-2-(methyl)propyloxymethyl]-2'-deoxyuridine dT.20 (25 mg, 20%, absolute configuration not determined) as a waxy solid.

$^1$H NMR (400 MHz, MeOH-d$_4$) δ 8.22 (d, 1 H, J=1.8 Hz, H-6), 8.01 (m, 2 H, Ph-H), 7.50 (d, 1 H, J=8.3 Hz, Ph-H), 6.25 (t, 1 H, J=7.2 Hz, H-1'), 4.69 (d, 1 H, J=5.8 Hz, PhCH), 4.41 (m, 1 H, H-3'), 4.10 (m, 2 H, CH$_2$), 3.92 (m, 1 H, H-4'), 3.75 (m, 2 H, H-5'a), 2.17 (m, 1 H, H-2'a), 2.15 (m, 1 H, H-2'b), 1.90 (m, 1 H, CH), 0.92 (m, 3 H, CH$_3$), 0.85 (m, 3 H, CH$_3$);

5-{(R or S)-1-[4-(3-Trifluoroacetamido-1-propynyl)-2-nitrophenyl]-2-(methyl)-propyloxymethyl}-2'-deoxyuridine (dT.21)

A solution of compound dT.20 (24 mg, 0.043 mmol), N-propargyl-trifluoroacetylamide (28 mg, 0.186 mmol), tetrakis(triphenylphosphine)-palladium(0) (7.2 mg, 0.006 mmol), CuI (2.4 mg, 0.012 mmol), and Et$_3$N (17 µL, 0.124 mmol) in anhydrous DMF (1.5 mL) was stirred at room temperature for 4.5 hours. The mixture was concentrated in vacuo and purified by silica gel column chromatography to yield 5-{(R or S)-1-[4-(3-trifluoro-acetamido-1-propynyl)-2-nitrophenyl]-2-(methyl)propyloxymethyl]-2'-deoxyuridine dT.21 (19.8 mg, 81%, absolute configuration not determined) as a waxy solid.

$^1$H NMR (400 MHz, MeOH-d$_4$): δ 8.01 (br s, 1 H, H-6), 7.95 (d, 1 H, J=1.2 Hz, Ph-H), 7.72 (m, 2 H, Ph-H), 6.25 (t, 1 H, J=6.7 Hz, H-1'), 4.74 (d, 1 H, J=5.8 Hz, PhCH), 4.38 (m, 1 H, H-3'), 4.34 (s, 2 H, CH$_2$), 4.05 (m, 2 H, CH$_2$), 3.55, 3.93 (m, 1 H, H-4'), 3.77 (m, 2 H, H-5'a and H-5'b), 2.15 (m, 2 H, H-2'a and H-2'b), 1.90 (m, 1 H, CH), 0.92 (m, 6 H, 2×CH$_3$);

5-{(R or S)-1-[4-(3-Amino-1-propynyl)-2-nitrophenyl]-2-(methyl)propyloxymethyl}-2'-deoxyuridine-5'-triphosphate (dT.22)

POCl$_3$ (6 µL, 0.06 mmol) was added to a solution of compound dT.21 (18 mg, 0.03 mmol) and proton sponge (13 mg, 0.06 mmol) in trimethylphosphate (0.3 mL) at 0° C. and stirred for two hours. A solution of bis-tri-n-butylammonium pyrophosphate (73 mg, 0.15 mmol) and tri-n-butylamine (30 µL) in anhydrous DMF (0.3 mL) was added. After five minutes of stirring, triethylammonium bicarbonate buffer (1 M, pH 7.5; 5 mL) was added. The reaction was stirred for one hour at room temperature and then lyophilized to dryness. The residue was dissolved in water (5 mL), filtered, and part of the solution was purified with reverse-phase HPLC using a Perkin Elmer OD-300 C$_{18}$ column (4.6×250 mm) to yield 5-{(R or S)-1-[4-(3-trifluoroacetamido-1-propynyl)-2-nitrophenyl]-2-(methyl)propyloxymethyl}-2'-deoxyuridine-5'triphosphate. Mobile phase: A, 100 mM triethylammonium acetate (TEAA) in water (pH 7.0); B, 100 mM TEAA in water/CH$_3$CN (30:70). HPLC purification was achieved using a linear gradient of 5-50% B for 40 minutes and then 50-90% B for 10 minutes. The purified triphosphate was then treated with concentrated ammonium hydroxide (27%; 0.5 mL) at room temperature for two hours to yield 5-{(R or S)-1-[4-(3-amino-1-propynyl)-2-nitrophenyl]-2-(methyl)-propyloxymethyl}-2'-deoxyuridine-5'-triphosphate (dT.22, absolute configuration not determined).

$^1$H NMR (400 MHz, D$_2$O): δ 8.01 (s, 1 H, Ph-H), 7.76 (d, 1 H, J=6.9 Hz, Ph-H), 7.62 (m, 2 H, H-6 and Ph-H), 6.17 (t, 1 H, J=6.4 Hz, H-1'), 4.55 (m, 1 H, H-3'), 4.39 and 4.29 (2 d, 2 H, J=6.4 Hz, CH$_2$), 4.17 (m, 3 H, H-4' and H-5'), 3.74 (s, 2 H, CH$_2$), 2.28 (m, 2 H, H-2'), 2.00 (m, 1 H, CH), 0.79 (m, 3 H, CH$_3$);

$^{31}$P NMR (162 MHz, D$_2$O): δ-5.40 (d, J=19.4 Hz), -10.75 (d, J=19.4 Hz), -21.23 (t, J=19.4 Hz).

6-JOE Labeled 5-{(R or S)-1-[4-(3-amino-1-propynyl)-2-nitrophenyl]-2-(methyl)-propyloxymethyl}-2'-deoxyuridine-5'-triphosphate (WW3p024)

A solution of 6-JOE-SE (0.625 mg, 1 µmol) in anhydrous DMSO (25 µL) was added to a solution of triphosphate dT.22 (0.31 µmol) in Na$_2$CO$_3$/NaHCO$_3$ buffer (0.1 M, pH 9.2; 180 µL) and incubated at room temperature for one hour. The reaction was purified by reverse-phase HPLC using a Perkin Elmer OD-300 C$_{18}$ column (4.6×250 mm) to yield the 6-JOE labeled triphosphate WW3p024. Mobile phase: A, 100 mM TEAA in water (pH 7.0); B, 100 mM TEAA in water/CH$_3$CN (30:70). HPLC purification was achieved using a linear gradient of 5-50% for 40 minutes and then 50-90% B for 10 minutes. The concentration of WW3p024 was estimated by adsorption spectroscopy using the extinction coefficient of the 6-JOE dye (i.e., 75,000 at 520 nm).

Example 3 dC Compounds

Synthesis of N4-(2-nitrobenzyl)-2'-deoxycytidine-5'-triphosphate (WW2p044)

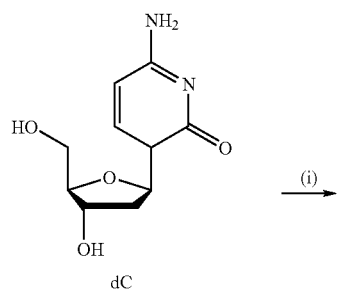
dC

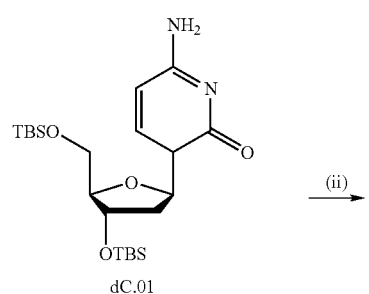
dC.01

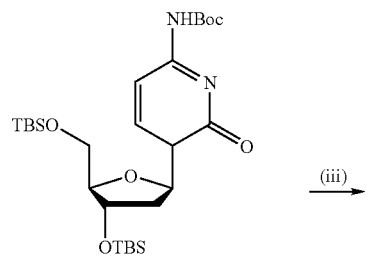
dC.02

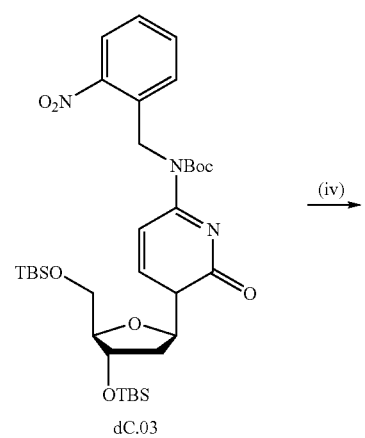
dC.03

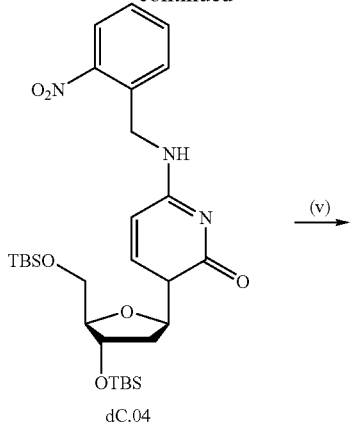
dC.04

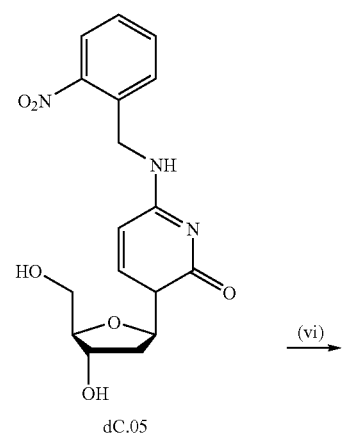
dC.05

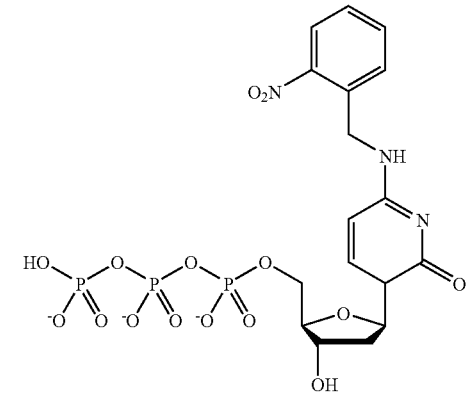
WW2p044

Scheme. Synthesis of $N^4$-(2-nitrobenzyl)-2'-deoxycytidine triphosphate. (i) TBSCl, imidazole, anhydrous DMF, room temperature, overnight, 84%; (ii) Boc$_2$O, DMAP, Et$_3$N, CH$_2$Cl$_2$, room temperature, overnight, 56%; (iii) 2-nitrobenzyl bromide, NaH, anhydrous DMF, 0° C., then gradually warmed to room temperature, overnight, 37%; (iv) SiO$_2$, vacuum, 70-80° C., 48 hours, 79%; (v) n-Bu$_4$NF, THF, 0° C., then gradually warmed to room temperature, two hours, 59%; (vi) POCl$_3$, proton sponge, (MeO)$_3$PO, 0° C., two hours; (n-Bu$_3$NH)$_2$H$_2$P$_2$O$_7$, n-Bu$_3$N, DMF, five minutes; 1 M HNEt$_3$HCO$_3$, one hour, 52%.

3',5'-O-Bis-tert-butyldimethylsilyl-2'-deoxycytidine (dC.01)

2'-deoxycytidine dC (2.85 g, 12.54 mmol), imidiazole (6.49 g, 95.31 mmol), and TBSCl (7.18 g, 47.65 mmol) were added to anhydrous DMF (27 mL) and stirred at room temperature overnight under a $N_2$ atmosphere. Methanol (20 mL) was added, and the mixture was stirred for 30 minutes and then concentrated in vacuo. Ethyl acetate (60 mL) and water (60 mL) were then added. The organic layer was separated and washed twice with water (20 mL), and the combined aqueous layer was extracted with ethyl acetate (20 mL). The combined organic layer was dried with $Na_2SO_4$, concentrated in vacuo, and purified by silica gel chromatography to give 3',5'-O-bis-tert-butyldimethylsilyl-2'-deoxycytidine dC.01 (4.79 g, 84%) as a white foam.

$^1$H NMR (400 MHz, $CDCl_3$): δ 7.95 (d, 1 H, J=7.4 Hz, H-6), 6.26 (t, 1 H, J=5.6 Hz, H-1'), 5.69 (d, 1 H, J=7.4 Hz, H-5), 4.37 (m, 1 H, H-3'), 3.90 (m, 2 H, H-4' and H-5'a), 3.76 (m, 1 H, H-5'b), 2.40 (m, 1 H, H-2'a), 2.08 (m, 1 H, H-2'b), 0.91 (s, 9 H, $(CH_3)_3CSi$), 0.87 (s, 9 H, $(CH_3)_3CSi$), 0.10 (s, 6 H, $(CH_3)_2Si$), 0.05 (s, 6 H, $(CH_3)_2Si$).

$N^4$-tert-Butyloxycarbonyl-3',5'-O-bis-tert-butyldimethylsilyl-2'-deoxycytidine (dC.02)

Under a nitrogen atmosphere, a solution of di-tert-butyldicarbonate (0.34 g, 1.58 mmol) in anhydrous $CH_2Cl_2$ (3 mL) was slowly added to a solution of compound dC.01 (0.5 g, 1.10 mmol), $Et_3N$ (0.15 mL, 1.10 mmol), and DMAP (0.13 g, 1.10 mmol) in anhydrous $CH_2Cl_2$ (5 mL). The mixture was stirred overnight at room temperature, concentrated in vacuo, and purified by silica gel chromatography to yield $N^4$-tert-butyloxycarbonyl-3',5'-O-bis-tert-butyldimethylsilyl-2'-deoxycytidine dC.02 (0.34 g, 56%) as a white foam.

$^1$H NMR (400 MHz, $CDCl_3$): δ 8.30 (d, 1 H, J=7.4 Hz H-6), 7.47 (bs, 1 H, NH), 7.14 (d, 1 H, J=7.4 Hz, H-5), 6.25 (t, 1 H, J=5.6 Hz, H-1'), 4.38 (m, 1 H, H-3'), 3.95 (m, 2H, H-4' and H-5'a), 3.78 (m, 1 H, H-5'), 2.50 (m, 1 H, H-2'a), 2.10 (m, 1 H, H-2'b), 1.51 (s, 9 H, $(CH_3)_3CO$), 0.93 (s, 9 H, $(CH_3)_3CSi$), 0.88 (s, 9 H, $(CH_3)_3CSi$), 0.11 (s, 6 H, $(CH_3)_2Si$), 0.06 (s, 6 H, $(CH_3)_2Si$).

$N^4$-tert-Butyloxycarbonyl-$N^4$-(2-nitrobenzyl)-3',5'-O-bis-tert-butyldimethylsilyl-2'-deoxycytidine (dC.03)

NaH (32 mg, 1.26 mmol, dry) was added to a solution of compound dC.02 (540 mg, 0.97 mmol) in anhydrous DMF (6 mL) at 0° C. and stirred for 30 minutes under a nitrogen atmosphere. A solution of 2-nitrobenzyl bromide (313 mg, 1.45 mmol) in anhydrous DMF (1.5 mL) was added dropwise. The reaction mixture was gradually warmed to room temperature and stirred overnight. Following the addition of ethyl acetate (60 mL), the mixture was washed three times with saturated $NH_4Cl$ solution (40 mL), and the combined aqueous layer was extracted with ethyl acetate (40 mL). The combined organic layer was dried with $Na_2SO_4$, concentrated in vacuo, and purified by silica gel chromatography to yield $N^4$-tert-butyloxycarbonyl-$N^4$-(2-nitrobenzyl)-3',5'-O-bis-tert-butyldimethylsilyl-2'-deoxycytidine dC.03 (250 mg, 37%) as a white foam.

$^1$H NMR (400 MHz, $CDCl_3$): δ 8.29 (d, 1 H, J=7.6 Hz, H-6), 8.05 (d, 1 H, J=8.0 Hz, Ph-H), 7.53 (t, 1 H, J=7.5 Hz, Ph-H), 7.38 (t, 1 H, J=7.6 Hz, Ph-H), 7.28 (m, 2 H, Ph-H and H-5), 6.26 (t, 1 H, J=5.6 Hz, H-1'), 5.60 (q, 2 H, Ph-$CH_2$), 4.41 (m, 1 H, H-3'), 3.96 (m, 2 H, H-4' and H-5'a), 3.80 (m, 1 H, H-5'b), 2.51 (m, 1 H, H-2'a), 2.15 (m, 1H, H-2'b), 1.28 (s, 9 H, $(CH_3)_3CO$), 0.95 (s, 9 H, $(CH_3)_3CSi$), 0.88 (s, 9 H, $(CH_3)_3CSi$), 0.14 (s, 6 H, $(CH_3)_2Si$), 0.07 (s, 6 H, $(CH_3)_2Si$).

$N^4$-(2-Nitrobenzyl)-3',5'-O-bis-tert-butyldimethylsilyl-2'-deoxycytidine (dC.04)

Silica gel 60 (2.5 g, 100-200 mesh, activated by heating to 50-60° C. under reduced pressure for 24 hours) was added to a solution of compound dC.03 (250 mg, 0.36 mmol) in $CH_2Cl_2$ (5 mL), and the mixture was evaporated in vacuo to dryness. The residue was heated to 60-70° C. under reduced pressure for 48 hours, washed three times with MeOH (30 mL), and filtered using a buchi funnel. The combined filtrate was concentrated in vacuo and purified by silica gel chromatography to yield $N^4$-(2-nitrobenzyl)-3',5'-O-bis-tert-butyldimethylsilyl-2'-deoxycytidine dC.04 (0.185 g, 79%) as a white foam.

$^1$H NMR (400 MHz, $CDCl_3$): δ 8.02 (d, 1 H, J=8.0 Hz, Ph-H), 7.92 (d, 1 H, J=7.2 Hz, H-6), 7.79 (d, 1 H, J=7.5 Hz, Ph-H), 7.57 (t, 1 H, J=7.3 Hz, Ph-H), 7.41 (t, 1 H, J=7.5 Hz, Ph-H), 6.38 (bs, 1 H, NH), 6.26 (t, 1 H, J=5.2 Hz, H-1'), 5.68 (d, 1 H, J=7.2 Hz, H-5), 4.92 (m, 2 H, Ph-$CH_2$), 4.36 (m, 1 H, H-3'), 3.88 (m, 2 H, H-4' and H-5'a), 3.75 (m, 1 H, H-5'b), 2.39 (m, 1 H, H-2'a), 2.07 (m, 1 H, H-2'b), 0.91 (s, 9 H, $(CH_3)_3CSi$), 0.87 (s, 9 H, $(CH_3)_3CSi$), 0.09 (s, 6 H, $(CH_3)_2Si$), 0.05 (s, 6 H, $(CH_3)_2Si$).

$N^4$-(2-Nitrobenzyl)-2'-deoxycytidine (dC.05)

A solution of n-$NBu_4F$ (190 mg, 0.73 mmol) in THF (1.4 mL) was added dropwise to a solution of compound dC.04 (170 mg, 0.29 mmol) in THF (3.4 mL) at 0° C. under a nitrogen atmosphere. The reaction mixture was stirred for two hours, concentrated in vacuo, and purified by silica gel chromatography to yield $N^4$-(2-nitrobenzyl)-2'-deoxycytidine dC.05 (62 mg, 59%) as a white foam.

$^1$H NMR (400 MHz, DMSO-$d_6$): δ 8.23 (t, 1 H, $D_2O$ exchangeable, NH), 8.07 (d, 1 H, J=8.0 Hz, Ph-H), 7.83 (d, 1 H, J=7.4 Hz, H-6), 7.74 (t, 1 H, J=7.5 Hz, Ph-H), 7.54 (m, 2 H, Ph-H), 6.13 (t, 1 H, J=6.8 Hz, H-1'), 5.91 (d, 1 H, J=7.4 Hz, H-5), 5.19 (d, 1 H, $D_2O$ exchangeable, 3'-OH), 4.97 (t, 1 H, $D_2O$ exchangeable, 5'-OH), 4.78 (m, 2 H, Ph-$CH_2$), 4.19 (m, 1 H, H-3'), 3.76 (m, 1 H, H-4'), 3.55 (m, 2 H, H-5'a and H-5'b), 2.09 (m, 1 H, H-2'a), 1.93 (m, 1 H, H-2'b);

$^{13}$C NMR (100 MHz, $CD_3OD$): δ 165.71, 158.51, 149.70, 141.75, 135.09, 134.73, 131.30, 129.43, 125.94, 96.75, 88.83, 87.57, 72.03, 62.78, 42.71, 42.00.

$N^4$-(2-Nitrobenzyl)-2'-deoxycytidine-5'-triphosphate (WW2p044)

$POCl_3$ (17 μL, 0.2 mmol) was added to a solution of compound dC.05 (36 mg, 0.1 mmol) and proton sponge (32 mg, 0.15 mmol) in trimethylphosphate (0.5 mL) at 0° C. and stirred for two hours. Additional $POCl_3$ (9 μL, 0.1 mmol) was added and stirred for another hour. A solution of bis-tri-n-butylammonium pyrophosphate (237 mg, 0.5 mmol) and tri-n-butylamine (100 μL) in anhydrous DMF (1 mL) was added. After five minutes of stirring, triethylammonium bicarbonate buffer (1 M, pH 7.5; 10 mL) was added. The reaction was stirred for one hour at room temperature and then lyophilized to dryness. The residue was dissolved in water (10 mL), filtered, and purified by anion exchange chromatography using a Q Sepharose FF column (2.5×20 cm) with a linear gradient of $NH_4HCO_3$ (50 mM to 500 mM in 300 minutes) at a flow rate of 4.5 mL/min. The fractions containing triphosphate were combined and lyophilized to give the triphosphate WW2p044 (34 mg, 52%) as a white fluffy solid.

$^1$H NMR (400 MHz, D$_2$O): δ 8.12 (d, 1 H, J=8.0 Hz, Ph-H), 7.83 (d, 1 H, J=7.6 Hz, H-6), 7.69 (t, 1 H, J=7.6 Hz, Ph-H), 7.60 (d, 1 H, J=7.6 Hz, Ph-H), 7.53 (t, 1 H, J=8.0 and 7.6 Hz, Ph-H), 6.29 (t, 1 H, J=6.8 Hz, H-1'), 6.15 (d, 1 H, J=7.6 Hz, H-5), 4.85 (bs, 2 H, Ph-CH$_2$), 4.58 (m, 1 H, H-3'), 4.21 (m, 3 H, H-4', H-5'a and H-5'b), 2.38 (m, 1 H, H-2'a), 2.28 (m, 1 H, H-2'b);

$^{31}$P NMR (162 MHz, D$_2$O): δ -5.61 (d, J=15.9 Hz), -10.60 (d, J=15.4 Hz), -19.26 (br);

ToF-MS (ESI): For the molecular ion C$_{16}$H$_{21}$N$_4$O$_{15}$P$_3$Na [M+Na]$^+$, the calculated mass was 625.0114, and the observed mass was 624.9993.

Synthesis of N4-[4-(3-amino-1-propynyl)-2-nitrobenzyl]-2'-deoxycytidine-5'-triphosphate and dye labeling (WW2p080)

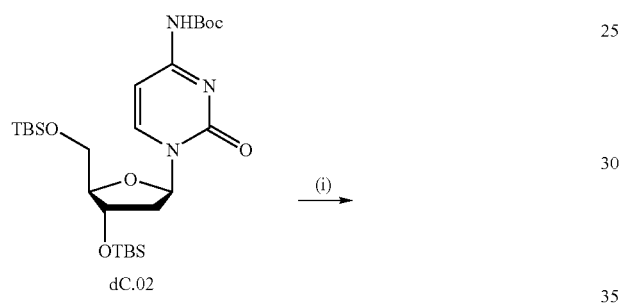
dC.02

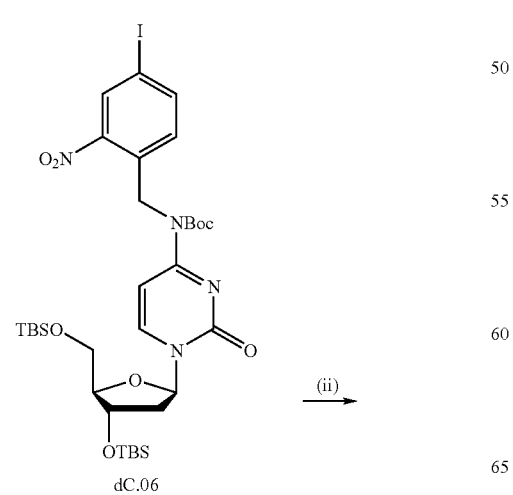
dC.06

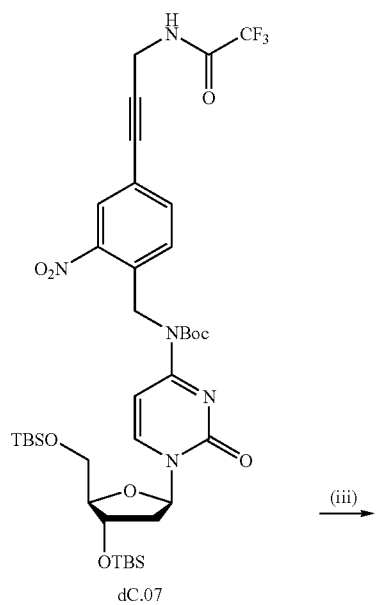
dC.07

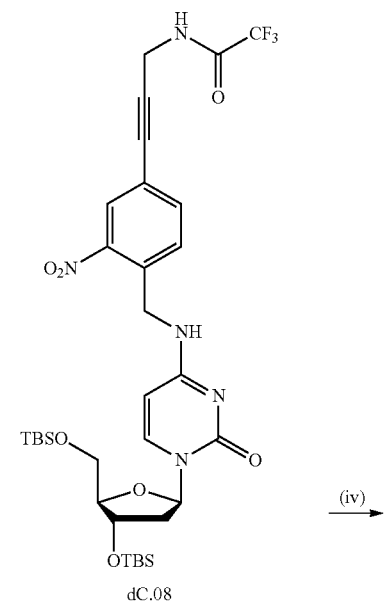
dC.08

87

-continued

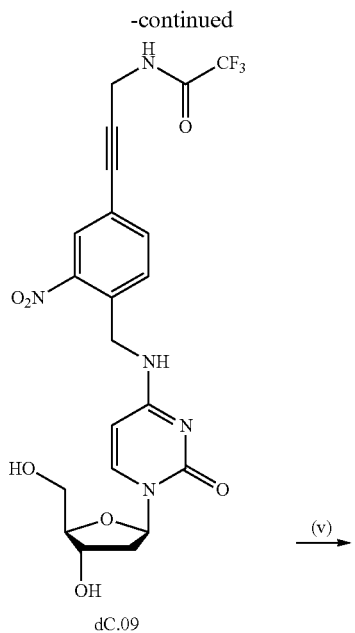

dC.09

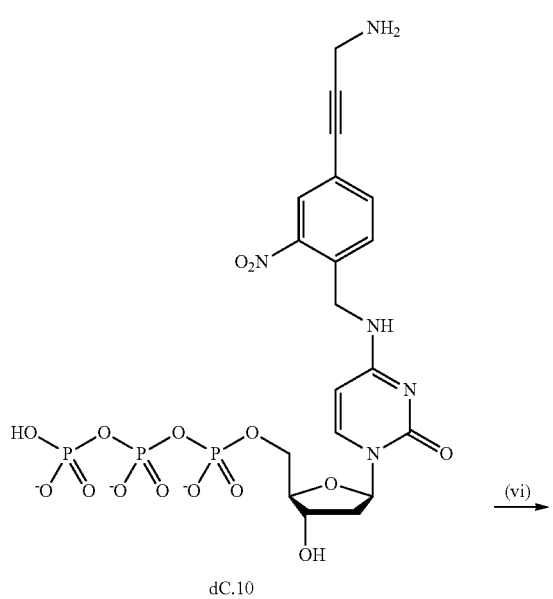

dC.10

88

-continued

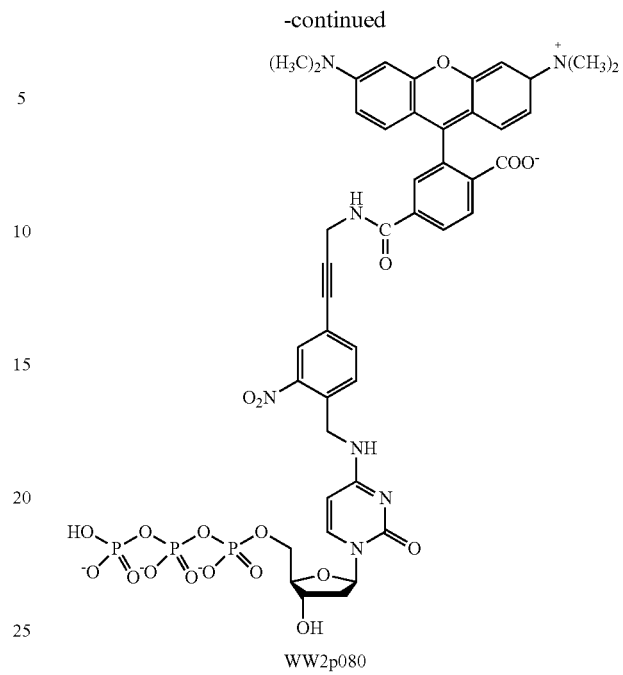

WW2p080

Scheme. Synthesis of 6-TAMRA labeled $N^4$-[4-(3-amino-1-propynyl)-2-nitrobenzyl]-2'-deoxycytidine-5'-triphosphate. (i) 4-iodo-2-nitrobenzyl bromide, n-Bu$_4$NBr, CH$_2$Cl$_2$, 1 M NaOH, room temperature, four hours, 45%; (ii) N-propargyltrifluoroacetamide, PdCl$_2$(PPh$_3$)$_2$, CuI, Et$_3$N, THF, reflux, three hours, 82%; (iii) SiO$_2$, vacuum, 70-80° C., 48 hours, 81%; (iv) n-Bu$_4$NF, THF, 0° C., two hours, then room temperature overnight, 39%; (v) POCl$_3$, proton sponge, (MeO)$_3$PO, 0° C., two hours; (n-Bu$_3$NH)$_2$H$_2$P$_2$O$_7$, n-Bu$_3$N, DMF, five minutes; 1 M HNEt$_3$HCO$_3$, one hour; NH$_4$OH, one hour; 39%; (vi) 6-TAMRA-SE, 0.1 M Na$_2$CO$_3$/NaHCO$_3$ buffer (pH 9.2), one hour.

$N^4$-tert-Butyloxycarbonyl-$N^4$-(4-iodo-2-nitrobenzyl)-3',5'-O-bis-tert-butyldimethylsilyl-2'-deoxycytidine (dC.06)

A solution of 4-iodo-2-nitrobenzyl bromide (461 mg, 1.35 mmol) in CH$_2$Cl$_2$ (4 mL) was added dropwise to a mixture of compound dC.02 (250 mg, 0.45 mmol) and n-Bu$_4$NBr (145 mg, 0.45 mmol) in CH$_2$Cl$_2$ (4 mL) and NaOH (1 M; 4.5 mL). The reaction was stirred vigorously at room temperature for four hours. The organic layer was separated, and the aqueous layer was extracted twice with CH$_2$Cl$_2$ (4 mL each). The combined organic layer was dried with Na$_2$SO$_4$, concentrated in vacuo, and purified by silica gel chromatography to give $N^4$-tert-butyloxycarbonyl-$N^4$-(4-iodo-2-nitrobenzyl)-3',5'-O-bis-tert-butyldimethylsilyl-2'-deoxycytidine dC.06 (167 mg, 45%) as a white foam.

$^1$H NMR (400 MHz, CDCl$_3$): δ 8.37 (d, 1 H, J=1.8 Hz, Ph-H), 8.30 (d, 1 H, J=7.5 Hz, H-6), 7.82 (dd, 1 H, J=1.8 Hz and 8.3 Hz, Ph-H), 7.26 (d, 1 H, J=7.5 Hz, H-5), 6.99 (d, 1 H, J=8.4 Hz, Ph-H), 6.24 (dd, 1 H, J=6.3 and 5.0 Hz, H-1'), 5.52 (q, 2 H, Ph-CH$_2$), 4.41 (m, 1 H, H-3'), 3.96 (m, 2 H, H-4' and H-5'a), 3.80 (m, 1 H, H-5'b), 2.51 (m, 1 H, H-2'a), 2.14 (m, 1 H, H-2'b), 1.34 (s, 9 H, (CH$_3$)$_3$CO), 0.95 (s, 9 H, (CH$_3$)$_3$CSi), 0.89 (s, 9 H, (CH$_3$)$_3$CSi), 0.14 (s, 3 H, (CH$_3$)Si), 0.13 (s, 3 H, (CH$_3$)Si), 0.08 (s, 3 H, (CH$_3$)Si), 0.07 (s, 3 H, (CH$_3$)Si).

$N^4$-tert-Butyloxycarbonyl-$N^4$-[4-(3-trifluoroacetamido-1-propynyl)-2-nitrobenzyl]-3',5'-O-bis-tert-butyldimethylsilyl-2'-deoxycytidine (dC.07)

Under a nitrogen atmosphere, a solution of bis(triphenylphosphine)palladium(II) dichloride (41 mg, 0.058 mmol) in anhydrous THF (3 mL) was quickly added to a mixture of compound dC.06 (315 mg, 0.39 mmol), CuI (15 mg, 0.078 mmol), Et$_3$N (0.73 mL, 5.2 mmol) and N-propargyltrifluoroacetamide (82 mg, 0.54 mmol) in anhydrous THF (7 mL). The reaction mixture was refluxed for two hours, concentrated in vacuo, and purified by silica gel chromatography to yield $N^4$-tert-butyloxycarbonyl-$N^4$-[4-(3-trifluoroacetamido-1-propynyl)-2-nitrobenzyl]-3',5'-O-bis-tert-butyldimethylsilyl-2'-deoxycytidine dC.07 (268 mg, 82%) as a white foam.

$^1$H NMR (400 MHz, CDCl$_3$): δ 8.33 (d, 1 H, J=7.7 Hz, H-6), 8.03 (d, 1 H, J=1.5 Hz, Ph-H), 7.61 (bs, 1 H, NH), 7.50 (dd, 1 H, J=1.5 Hz and 8.2 Hz, Ph-H), 7.32 (d, 1 H, J=7.7 Hz, H-5), 7.18 (d, 1 H, J=8.2 Hz, Ph-H), 6.24 (t, 1 H, J=6.0 Hz, H-1'), 5.56 (q, 2 H, PhCH$_2$), 4.42 (m, 1 H, H-3'), 4.35 (d, 2 H, CH$_2$), 3.97 (m, 2 H, H-5'a and H-4'), 3.80 (m, 1 H, H-5'b), 2.50 (m, 1 H, H-2'a), 2.05 (m, 1 H, H-2'b), 1.31 (s, 9 H, (CH$_3$)$_3$CO), 0.96 (s, 9 H, (CH$_3$)$_3$CSi), 0.89 (s, 9 H, (CH$_3$)$_3$CSi), 0.15 (s, 3 H, (CH$_3$)Si), 0.14 (s, 3 H, (CH$_3$)Si), 0.07 (s, 6 H, (CH$_3$)$_2$Si).

$N^4$-[4-(3-Trifluoroacetamido-1-propynyl)-2-nitrobenzyl]-3',5'-O-bis-tert-butyldimethylsilyl-2'-deoxycytidine (dC.08)

Silica gel 60 (3.1 g, 100-200 mesh, activated by heating to 50-60° C. under reduced pressure for 24 hours) was added to a solution of compound dC.07 (305 mg, 0.36 mmol) in CH$_2$Cl$_2$ (4 mL), and the mixture was evaporated in vacuo to dryness. The residue was heated to 60-70° C. under reduced pressure for 24 hours, washed three times with MeOH (30 mL), and filtered using a buchi funnel. The combined filtrate was concentrated in vacuo and purified by silica gel chromatography to yield $N^4$-[4-(3-trifluoroacetamido-1-propynyl)-2-nitrobenzyl]-3',5'-O-bis-tert-butyldimethylsilyl-2'-deoxycytidine dC.08 (219 mg, 81%) as a white foam.

$^1$H NMR (400 MHz, CDCl$_3$): δ 8.25 (bs, 1 H, N—H), 7.94 (d, 1 H, J=7.4 Hz, H-6), 7.84 (s, 1 H, Ph-H), 7.62 (d, 1 H, J=7.7 Hz, Ph-H), 7.41 (d, 1 H, J=7.8 Hz, Ph-H), 6.25 (m, 2 H, N—H and H-1'), 5.67 (d, 1 H, J=7.3 Hz, H-5'), 4.83 (m, 2 H, Ph-CH$_2$), 4.38 (m, 2 H, CH$_2$ and H-3'), 3.90 (m, 2 H, H-4' and H-5'a), 3.75 (m, 1 H, H-5'b), 2.36 (m, 1 H, H-2'a), 2.05 (m, 1 H, H-2'b), 0.90 (s, 9 H, (CH$_3$)$_3$CSi), 0.87 (s, 9 H, (CH$_3$)$_3$CSi), 0.08 (s, 6H, (CH$_3$)$_2$Si), 0.05 (s, 6 H, (CH$_3$)$_2$Si).

$N^4$-[4-(3-Trifluoroacetamido-1-propynyl)-2-nitrobenzyl]-2'-deoxycytidine (dC.09)

A solution of n-Bu$_4$NF (94 mg, 0.36 mmol) in THF (2.5 mL) was added dropwise to a solution of compound dC.08 (200 mg, 0.27 mmol) in THF (1 mL) at 0° C. under a N$_2$ atmosphere. The reaction mixture was stirred at 0° C. for two hours and then at room temperature overnight, concentrated in vacuo, and purified by silica gel chromatography to yield N-[4-(3-trifluoroacetamido-1-propynyl)-2-nitrobenzyl]-2'-deoxycytidine dC.09 (54 mg, 39%) as a white foam.

$^1$H NMR (400 MHz, (DMSO-d$_6$): δ 10.12 (t, 1 H, N—H), 8.26 (t, 1 H, N—H), 8.08 (s, 1 H, Ph-H), 7.84 (d, 1 H, J=7.5 Hz, H-6), 7.78 (d, 1 H, J=8.1 Hz, Ph-H), 7.50 (d, 1 H, J=8.1 Hz, Ph-H), 6.13 (t, 1 H, J=6.8 Hz, H-1'), 5.91 (d, 1 H, J=7.4 Hz, H-5), 5.20 (d, 1 H, 3'-OH), 5.10 (t, 1 H, 5'-OH), 4.77 (d, 2 H, Ph-CH$_2$), 4.35 (m, 1 H, H-3'), 4.31 (m, 2 H, CH$_2$), 3.80 (m, 1 H, H-4'), 3.55 (m, 2 H, H-5'), 2.10 (m, 1 H, H-2'a), 1.92 (m, 1 H, H-2'b).

$N^4$-[4-(3-Amino-1-propynyl)-2-nitrobenzyl]-2'-deoxycytidine-5'-triphosphate (dC.10)

POCl$_3$ (18 μL, 0.2 mmol) was added to a solution of compound dC.09 (49 mg, 0.1 mmol) and proton sponge (32 mg, 0.15 mmol) in trimethylphosphate (0.5 mL) at 0° C. and stirred for two hours. A solution of bis-tri-n-butylammonium pyrophosphate (237 mg, 0.5 mmol) and tri-n-butylamine (100 uL) in anhydrous DMF (1 mL) was added. After five minutes of stirring, triethylammonium bicarbonate buffer (1 M, pH 7.5; 10 mL) was added. The reaction was stirred for one hour at room temperature, followed by the dropwise addition of concentrated ammonium hydroxide (5 mL, 27%) at 0° C. The mixture was stirred for an additional hour at room temperature and then lyophilized to dryness. The residue was dissolved in water (10 mL), filtered, and purified by anion exchange chromatography using a Q Sepharose FF column (2.5×20 cm) with a linear gradient of NH$_4$HCO$_3$ (50 mM to 500 mM in 300 minutes) at a flow rate of 4.5 mL/min. The fractions containing triphosphate were combined and lyophilized to give the triphosphate dC.10 (28 mg, 39%) as a white fluffy solid.

$^1$H NMR (400 MHz, D$_2$O): δ 8.22 (s, 1 H, Ph-H), 7.88 (d, 1 H, J=7.6 Hz, H-6), 7.74 (d, 1 H, J=8.0 Hz, Ph-H), 7.59 (d, 1 H, J=8.0 Hz, Ph-H), 6.33 (t, 1 H, J=6.8 Hz, H-1'), 6.18 (d, 1 H, J=7.6 Hz, H-5), 4.61 (m, 1 H, H-3'), 4.24 (m, 3 H, H-4', H-5'), 3.63 (s, 2 H, CH$_2$), 2.42 (m, 1 H, H-2'a), 2.29 (m, 1 H, H-2'b);

$^{31}$P NMR (162 MHz, D$_2$O): δ-5.88 (d, J=15.6 Hz), −10.69 (d, J=15.6 Hz), −19.25 (t, J=15.6 Hz);

ToF-MS (ESI): For the molecular ion C$_{19}$H$_{22}$N$_5$O$_{15}$P$_3$Na [M-2H+Na]$^-$, the calculated mass was 676.0223, and the observed mass was 676.0563.

6-TAMRA Labeled $N^4$-[4-(3-Amino-1-propynyl)-2-nitrobenzyl]-2'-deoxycytidine-5'-triphosphate (WW2p080)

A solution of 6-TAMRA-SE (0.75 mg, 1.4 μmol) in anhydrous DMSO (30 μL) was added to a solution of triphosphate dC.10 (1.6 μmol) in Na$_2$CO$_3$/NaHCO$_3$ buffer (0.1 M, pH 9.2; 0.3 mL) and incubated at room temperature for 30 minutes. The reaction was purified with reverse-phase HPLC using a Perkin Elmer OD-300 C$_{18}$ column (4.6×250 mm) to yield the 6-TAMRA labeled triphosphate WW2p080. Mobile phase: A, 100 mM triethylammonium acetate (TEAA) in water (pH 7.0); B, 100 mM TEAA in water/CH$_3$CN (30:70). HPLC purification was achieved a linear gradient of 5-50% B for 40 minutes and then 50-90% B for 10 minutes. The concentration of WW2p080 was estimated by adsorption spectroscopy using the extinction coefficient of the 6-TAMRA dye (i.e., 65,000 at 555 nm).

Synthesis of N4-[1-(2-nitrophenyl)ethyl]-2'-deoxy-cytidine-5'-triphosphate (WW2p115)

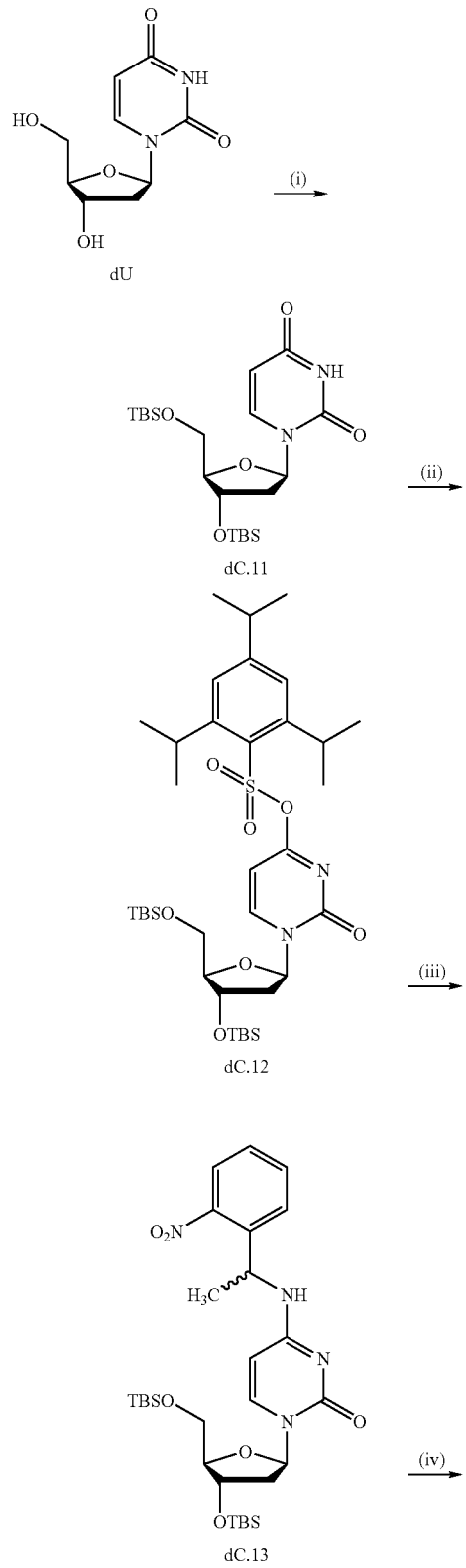

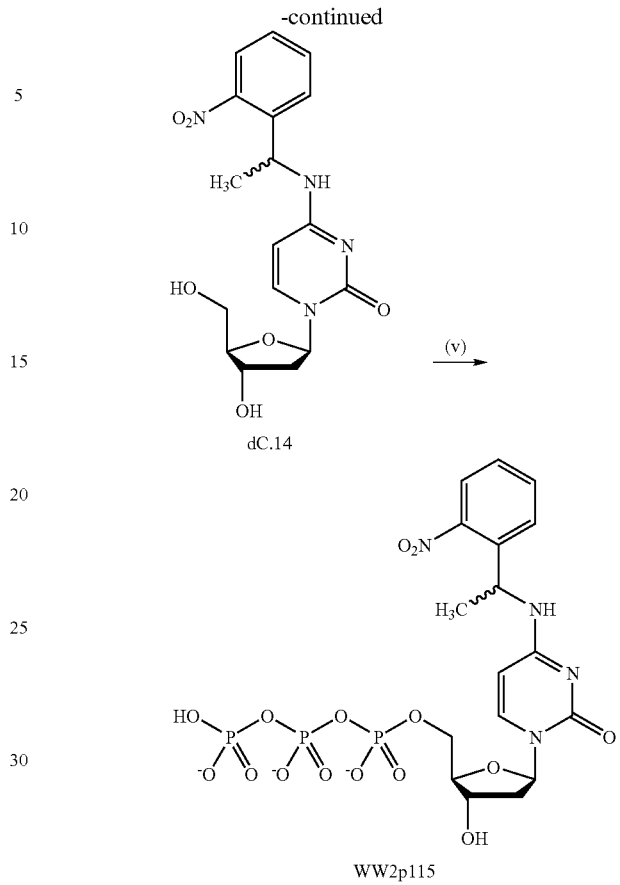

Scheme. Synthesis of N⁴-[1-(2-nitrophenyl)ethyl]-2'-deoxycytidine-5'-triphosphate. (i) TBSCl, imidiazole, DMF, room temperature, three hours, 92%; (ii) TPSCl, DMAP, $CH_2Cl_2$, room temperature, 88%; (iii) 1-(2-nitrophenyl)ethylamine dC.13c, DMF, 90° C., 1.5 hours, 39%; (iv) n-Bu₄NF, THF, 0° C., two hours, then room temperature, one hour, 90%; (v) $POCl_3$, proton sponge, $(MeO)_3PO$, 0° C., two hours; $(n-Bu_3NH)_2H_2P_2O_7$, n-Bu₃N, DMF, five minutes; 1 M $HNEt_3HCO_3$, one hour.

3',5'-O-Bis-tert-butyldimethylsilyl-2'-deoxyuridine (dC.11)

Under a nitrogen atmosphere, a mixture of 2'-deoxyuridine dU (2.5 g, 10.95 mmol), TBSCl (7.26 g, 48.2 mmol) and imidiazole (6.56 g, 96.4 mmol) in anhydrous DMF (25 mL) was stirred at 0° C. for two hours and then warmed to room temperature over one hour. The reaction mixture was concentrated in vacuo and purified by silica gel column chromatography to yield 3',5'-O-bis-tert-butyldimethylsilyl-2'-deoxyuridine dC.11 (4.62 g, 92%) as a white foam.

¹H NMR (400 MHz, $CDCl_3$): δ 9.48 (s, 1 H, NH), 7.80 (d, 1 H, J=8.1 Hz, H-6), 6.19 (t, 1 H, J=6.4 Hz, H-1'), 5.59 (d, 1 H, J=8.1 Hz, H-5), 4.31 (m, 1 H, H-3'), 3.81 (m, 2 H, H-4' and H-5'a), 3.65 (m, 1 H, H-5'b), 2.21 (m, 1 H, H-2'a), 1.97 (m, 1 H, H-2'b), 0.81 (s, 9 H, $(CH_3)_3CSi$), 0.79 (s, 9 H, $(CH_3)_3CSi$), 0.00 (s, 6 H, $(CH_3)_2Si$), −0.02 (2s, 3 H each, $(CH_3)_2Si$).

$O^4$-(2,4,6-Triisopropylbenzenesulfonyl)-3',5'-O-bis-tert-butyldimethylsilyl-2'-deoxyuridine (dC.12)

2,4,6-Triisopropylbenzenesulfonyl chloride (660 mg, 2.19 mmol) was added to a solution of compound dC.11 (500 mg, 1.09 mmol), DMAP (6.7 mg, catalytic amount) and $Et_3N$ (0.62 mL, 4.38 mmol) in anhydrous $CH_2Cl_2$ (6 mL) under a nitrogen atmosphere. The reaction mixture was stirred overnight at room temperature, concentrated in vacuo, and purified by silica gel column chromatography to yield $O^4$-(2,4,6-triisopropylbenzenesulfonyl)-3',5'-O-bis-tert-butyldimethylsilyl-2'-deoxyuridine dC.12 (690 mg, 88%) as a white foam.

$^1$H NMR (400 MHz, $CDCl_3$): δ 8.46 (d, 1 H, J=7.3 Hz, H-6), 7.20 (s, 2 H, Ph-H), 6.08 (dd, 1 H, J=4.3 Hz, H-1'), 6.01 (d, 1 H, J=7.3 Hz, H-5), 4.33 (m, 1 H, H-3'), 4.25 (m, 2 H, CH), 3.94 (m, 2 H, H-4' and H-5'a), 3.76 (m, 1 H, H-5'b), 2.91 (m, 1 H, CH), 2.48 (m, 1 H, H-2'a), 2.12 (m, 1 H, H-2'b), 1.31 (d, 6 H, $CH_3$), 1.26 (dd, 12 H, $CH_3$), 0.91 (s, 9 H, $(CH_3)_3CSi$), 0.86 (s, 9 H, $(CH_3)_3CSi$), 0.10 and 0.09 (2 s, 6 H, $(CH_3)_2Si$), 0.04 (s, 6 H, $(CH_3)_2Si$).

$N^4$-[1-(2-nitrophenyl)ethyl]-3',5'-O-bis-tert-butyldimethylsilyl-2'deoxycytidine (dC.13)

A solution of compound dC.12 (410 mg, 0.56 mmol) and 1-(2-nitrophenyl)ethylamine dC.13c (470 mg, 2.82 mmol) in anhydrous DMF (3 mL) was heated to 90° C. for 1.5 hours and then concentrated in vacuo. The residue was dissolved in $CH_2Cl_2$ (50 mL), washed with saturated $NH_4Cl$ solution (30 mL), with water (30 mL), and with saturated $NaHCO_3$ solution (30 mL). The organic layer was dried with $Na_2SO_4$, filtered, concentrated in vacuo, and purified by silica gel column chromatography to yield $N^4$-[1-(2-nitrophenyl)ethyl]-3',5'-O-bis-tert-butyldimethylsilyl-2' deoxycytidine dC.13 (130 mg, 39%, 1:1 mixture of diastereomers) as a white foam.

$^1$H NMR (400 MHz, $CDCl_3$) for diastereomers: δ 7.97 (m, 1 H, Ph-H), 7.89 (d, 1 H, J=7.1 Hz, H-6), 7.65 (m, 2 H, Ph-H), 7.41 (m, 1 H, Ph-H), 6.19 (m, 1 H, H-1'), 5.91 (m, 1 H, H-5), 5.37 (m, 1 H, Ph-CH), 4.34 (m, 1 H, H-3'), 3.86 (m, 2 H, H-4' and H-5'a), 3.72 (m, 1 H, H-5'b), 2.05 (m, 1 H, H-2'a), 1.83 (m, 1 H, H-2'b), 1.59 (bs, 3 H, $CH_3$), 0.86 (s, 12 H, $(CH_3)_3CSi$), 0.03 (s, 12 H, $(CH_3)_2Si$).

$N^4$-[1-(2-nitrophenyl)ethyl]-2'-deoxycytidine (dC.14)

A solution of n-$Bu_4NF$ (142 mg, 0.54 mmol) in THF (3 mL) was added to a solution of compound dC.13 (130 mg, 0.22 mmol) in THF (2 mL) at 0° C. The reaction mixture was stirred at 0° C. for two hours and then at room temperature for one hour, concentrated in vacuo, and purified by silica gel column chromatography to yield $N^4$-[1-(2-nitrophenyl)ethyl]-2'-deoxycytidine dC.14 (80 mg, 90%, 1:1 mixture of diastereomers) as a white powder.

$^1$H NMR (400 MHz, $CD_3OD$) for diastereomers: δ 7.95 (m, 2 H, Ph-H and H-5), 7.65 (m, 2 H, Ph-H), 7.45 (m, 1 H, Ph-H), 6.22 (m, 1 H, H-1'), 5.97 (m, 1 H, H-5), 5.74 (m, 1 H, Ph-CH), 4.34 (m, 1 H, H-3'), 3.93 (m, 1 H, H-4'), 3.75 (m, 2 H, H-5'), 2.32 (m, 1 H, H-2'a), 2.09 (m, 1 H, H-2'b), 1.59 (m, 3 H, $CH_3$).

$N^4$-[1-(2-nitrophenyl)ethyl]-2'-deoxycytidine-5'-triphosphate (WW2p115)

$POCl_3$ (14 μL, 0.15 mmol) was added to a solution of compound dC.14 (28 mg, 0.08 mmol) and proton sponge (23 mg, 0.11 mmol) in trimethylphosphate (0.5 mL) at 0° C. and stirred for two hours. A solution of bis-tri-n-butylammonium pyrophosphate (180 mg, 0.38 mmol) and tri-n-butylamine (80 μL) in anhydrous DMF (0.8 mL) was added. After five minutes of stirring, triethylammonium bicarbonate buffer (1 M, pH 7.5; 10 mL) was added. The reaction was stirred for one hour at room temperature and then lyophilized to dryness. The residue was dissolved in water (10 mL), filtered, and purified by anion exchange chromatography using a Q Sepharose FF column (2.5×20 cm) with a linear gradient of $NH_4HCO_3$ (50 mM to 500 mM in 300 minutes) at a flow rate of 4.5 mL/min. The fractions containing triphosphate were combined and lyophilized to give the triphosphate WW2p115 (24 mg, 47%, 1:1 mixture of diastereomers) as a white fluffy solid.

$^1$H NMR (400 MHz, $D_2O$) for diastereomers: δ 7.98 (m, 1 H, Ph-H), 7.80 (m, 1 H, H-6), 7.66 (m, 2 H, Ph-H), 7.49 (m, 1 H, Ph-H), 6.24 (m, 1 H, H-1'), 6.11 (m, 1 H, H-5), 5.60 (m, 1 H, Ph-CH), 4.55 (m, 1 H, H-3'), 4.19 (m, 3 H, H-4'and H-5'), 2.35 (m, 1 H, H-2'a), 2.24 (m, 1 H, H-2'b), 1.59 (d, 3 H, J=6.7 Hz, $CH_3$);

$^{31}$P NMR (162 MHz, $D_2O$) for diastereomers: 6-6.00 (d, J=14.1 Hz), −10.82 (d, J=15.6 Hz), −19.36 (t, J=15.9 Hz);

ToF-MS (ESI): For the molecular ion $C_{17}H_{23}N_4O_{15}P_3Na$ $[M+Na]^+$, the calculated mass was 639.0271, and the observed mass was 639.0332.

Synthesis of 1-(2-nitrophenyl)ethylamine (dC.13c)

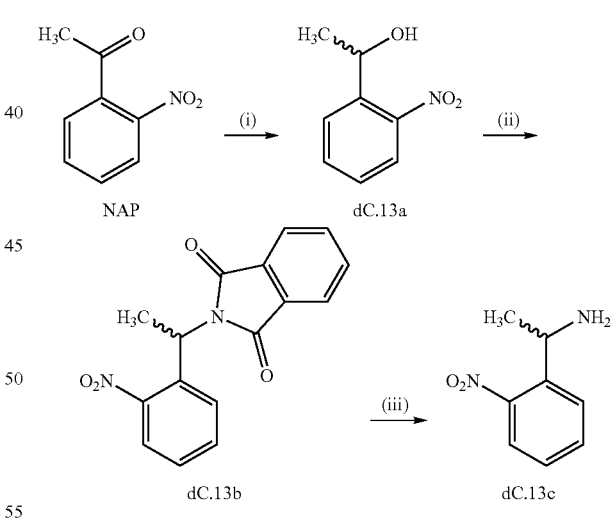

Scheme for dC.13c. Synthesis of 1-(2-nitrophenyl)ethylamine. (i) $NaBH_4$, MeOH, dioxane, room temperature, one hour, 92%; (ii) Phthalimide, DIAD, $Ph_3P$, THF, 0° C., three hours, 99%; (iii) $NH_2NH_2$, $CH_3CH_2OH$, reflux, one hour, 80%.

1-(2-Nitrophenyl)ethanol (dC.13a)

$NaBH_4$ (3.24 g, 85.60 mmol) was slowly added to a solution of 2'-nitroacetophenone NAP (3.74 g, 22.65 mmol) in a mixture of methanol (34 mL) and dioxane (22 mL). The reaction mixture was stirred at room temperature for one hour and then diluted with ethyl acetate (100 mL) and washed with water (25 mL). The organic layer was dried with $Na_2SO_4$, filtered, and concentrated in vacuo to yield 1-(2-nitrophenyl) ethanol dC.13a (3.49 g, 92%) as a white powder.

$^1$H NMR (400 MHz, $CDCl_3$): δ 7.89 (d, 1 H, J=8.1 Hz, Ph-H), 7.83 (d, 1 H, J=7.4 Hz, Ph-H), 7.65 (t, 1 H, J=7.4 Hz, Ph-H), 7.42 (t, 1 H, J=8.1 Hz, Ph-H), 5.41 (q, 1 H, J=6.0 Hz, Ph-CH), 2.48 (s, 1 H, OH), 1.57 (d, 3 H, J=6.4 Hz, $CH_3$).

N-[1-(2-nitrophenyl)ethyl]phthalimide (dC.13b)

Phthalimide (660 mg, 4.5 mmol) was added to a solution of compound dC.13a (750 mg, 4.5 mmol) and $Ph_3P$ (1.41 g, 5.4 mmol) in THF (12 mL). The suspension was cooled to 0° C. and stirred for 10 minutes, and then diisopropyl azodicarboxylate (1.1 mL, 5.4 mmol) was added dropwise. After stirring at 0° C. for three hours, the reaction mixture was concentrated in vacuo and purified by silica gel column chromatography to yield N-[1-(2-nitrophenyl)ethyl]phthalimide dC.13b (1.33 g, 99%) as a brown oil.

$^1$H NMR (400 MHz, $CDCl_3$): δ 7.93 (d, 1 H. J=7.9 Hz, Ph-H), 7.81 (m, 3 H, Ph-H), 7.71 (m, 2 H, Ph-H), 7.61 (t, 1 H, J=7.6 Hz, Ph-H), 7.44 (t, 1 H, J=7.6 Hz, Ph-H), 6.08 (q, 1 H, J=7.2 Hz, Ph-CH), 1.97 (d, 3 H, J=7.2 Hz, $CH_3$).

1-(2-nitrophenyl)ethylamine (dC.13c)

Compound dC.13b (1.33 g, 4.5 mmol) was dissolved in ethanol (21 mL) upon heating to 50° C. and then cooled to room temperature. Hydrazine (0.55 mL, 11.22 mmol) was added, and the reaction mixture was refluxed for one hour and then cooled with ice. Diethyl ether (40 mL) was added to precipitate the compound, which was isolated by filtration and washed two times with diethyl ether (40 mL each). The combined filtrate was washed two times with water (40 mL each) and then with brine (40 mL). The organic layer was dried over $Na_2SO_4$ and concentrated in vacuo to yield 1-(4-iodo-2-nitrophenyl)ethylamine dC.13c (600 mg, 80%) as a brown oil.

$^1$H NMR (400 MHz, $CDCl_3$): δ 7.78 (m, 2 H. Ph-H), 7.61 (t, 1 H, J=7.6 Hz, Ph-H), 7.37 (t, 1 H, J=7.6 Hz, Ph-H), 4.59 (q, 1 H, J=6.4 Hz, Ph-CH), 1.45 (d, 3 H, J=6.4 Hz, $CH_3$).

Synthesis of N4-[1-(2-nitrophenyl)ethyl]-cytidine-5'-triphosphate (WW2p152 and WW3p026)

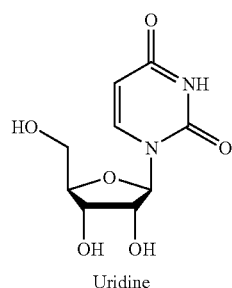
Uridine (i)

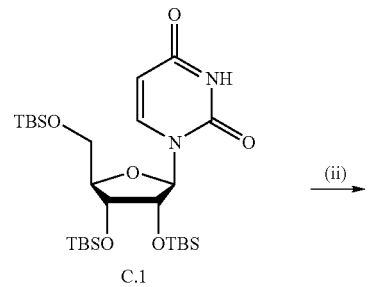
C.1

(ii)

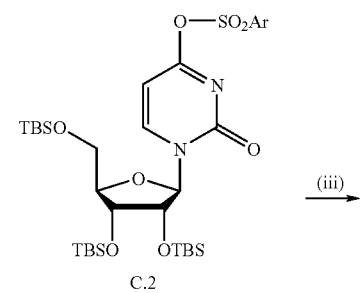
C.2
Ar = 2,4,6-iPr$_3$Ph (iii)

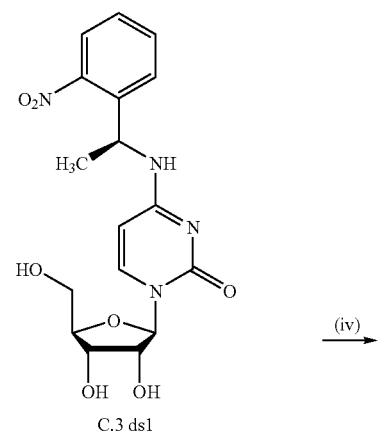
C.3 ds1
fast eluting fraction,
absolute configuration not determined,
drawing is representative (iv)

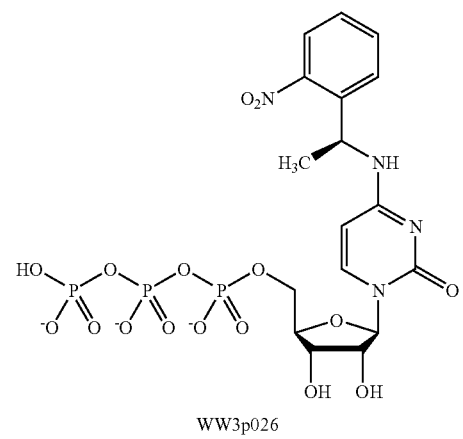
WW3p026

-continued

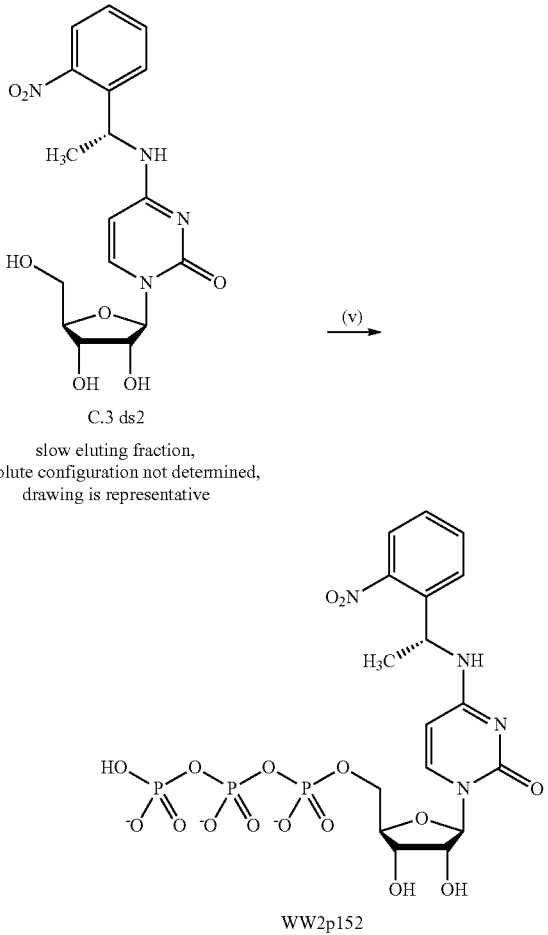

C.3 ds2
slow eluting fraction,
absolute configuration not determined,
drawing is representative WW2p152

Scheme. Synthesis of $N^4$-[1-(2-nitrophenyl)ethyl]-cytidine-5'-triphosphate. (i) TBSCl, imidiazole, DMF, room temperature, 60 hours, 95%; (ii) TPSCl, Et$_3$N, DMAP, CH$_2$Cl$_2$, room temperature, overnight, 80%; (iii) 1-(2-nitrophenyl)ethylamine, DMF, 90° C., 45 minutes; n-Bu$_4$NF, THF, 0° C., then gradually warmed to room temperature, two hours; 60% for two diastereoisomers; (iv) POCl$_3$, proton sponge, (MeO)$_3$PO, 0° C., two hours; (n-Bu$_3$NH)$_2$H$_2$P$_2$O$_7$, n-Bu$_3$N, DMF, five minutes; 1 M HNEt$_3$HCO$_3$, one hour.

2',3',5'-O-Tris-tert-butyldimethylsilyl-uridine (C.1)

TBSCl (995 mg, 6.6 mmol) was added to a solution of uridine (244 mg, 1 mmol) and imidiazole (898 mg, 13.2 mmol) in anhydrous DMF (5 mL) at 0° C. under a nitrogen atmosphere. The mixture was warmed to room temperature and stirred for 60 hours. Ethyl acetate (30 mL) was added, and the mixture was washed two times with saturated NH$_4$Cl solution (20 mL each) and with water (20 mL), dried over Na$_2$SO$_4$, concentrated and purified by silica gel column chromatography to yield 2',3',5'-O-tris-tert-butyldimethylsilyl-uridine C.1 (558 mg, 95%) as a white foam.

$^1$H NMR (400 MHz, CDCl$_3$): δ 8.79 (s, 1 H, NH), 8.03 (d, 1 H, J=8.2 Hz, H-6), 5.87 (d, 1 H, J=3.5 Hz, H-1'), 5.68 (d, 1 H, J=8.2 Hz, H-5), 4.08 (m, 3 H, H-2', H-3' and H-4'), 3.99 (d, 1 H, J=11.6 Hz, H-5'a), 3.77 (d, 1 H, J=11.6 Hz, H-5'b), 0.95 (s, 9 H, (CH$_3$)$_3$CSi), 0.91 and 0.90 (2 s, 18 H, (CH$_3$)$_3$CSi), 0.09 (5 s, 18 H, (CH$_3$)$_2$Si).

$O^4$-(2,4,6-Triisopropylbenzenesulfonyl)-2',3',5'-O-tris-tert-butyldimethylsilyl-uridine (C.2)

2,4,6-Triisopropylbenzenesulfonyl chloride (557 mg, 1.84 mmol) was added to a solution of compound C.1 (540 mg, 0.92 mmol), DMAP (12 mg, catalytic amount) and Et$_3$N (0.5 mL, 3.68 mmol) in anhydrous CH$_2$Cl$_2$ (10 mL) under a nitrogen atmosphere. The mixture was stirred overnight at room temperature, CH$_2$Cl$_2$ (20 mL) was added, washed with saturated NH$_4$Cl solution (15 mL), dried over Na$_2$SO$_4$, concentrated and purified by silica gel column chromatography to yield $O^4$-(2,4,6-triisopropyl-benzenesulfonyl)-2',3',5'-O-tris-tert-butyldimethylsilyl-uridine C.2 (629 mg, 80%) as a white foam.

$^1$H NMR (400 MHz, CDCl$_3$): δ 8.62 (d, 1 H, J=7.3 Hz, H-6), 7.20 (s, 2 H, Ph-H), 5.99 (d, 1 H, J=7.3 Hz, H-5), 5.68 (d, 1 H, J=1.0 Hz, H-1'), 4.23 (m, 2 H, CH), 4.09 (m, 3 H, H-2', H-3' and H-4'), 4.00 (m, 1 H, H-5'a), 3.78 (1 H, d, J=11.8 Hz, H-5'b), 2.90 (m, 1 H, CH), 1.31 (d, 6 H, CH$_3$), 1.26 (dd, 12 H, CH$_3$), 0.94 (s, 9 H, (CH$_3$)$_3$CSi), 0.88 (2 s, 18 H, (CH$_3$)$_3$CSi), 0.17-0.05 (6 s, 18 H, (CH$_3$)$_2$Si).

$N^4$-[1-(2-Nitrophenyl)ethyl]-cytidine (Single Diastereoisomer C.3 ds1 and C.3 ds2)

A solution of compound C.2 (476 mg, 0.56 mmol) and 1-(2-nitrophenyl)ethylamine dC.13c (498 mg, 3 mmol) in anhydrous DMF (4 mL) was heated at 90° C. for 45 minutes. Ethyl acetate (40 mL) was added, the mixture was washed with saturated NH$_4$Cl solution (20 mL) and water (20 mL), and dried with Na$_2$SO$_4$, concentrated. The two diastereoisomers were separated by silica gel column chromatography to yield $N^4$-[1-(2-nitrophenyl)ethyl]-2',3',5'-O-bis-tert-butyldimethylsilyl-cytidine single diastereo-isomer ds1 (fast eluting, 290 mg) and ds2 (slow eluting, 203 mg). Both single diastereoisomers were used in the next step without further purification.

$N^4$-[(R or S)-1-(2-nitrophenyl)ethyl]-cytidine (Single Diastereoisomer C.3 ds1)

A solution of n-Bu$_4$NF (235 mg, 0.9 mmol) in THF (3 mL) was added to a solution of $N^4$-[1-(2-nitrophenyl)ethyl]-2',3',5'-O-bis-tert-butyldimethylsilyl-cytidine single diastereoisomer ds1 (264 mg) in THF (4 mL) at 0° C. The reaction mixture was gradually warmed to room temperature and stirred for two hours. Silica gel 60 (1 g) was added, and the mixture was evaporated in vacuo to dryness. The residue was purified by silica gel column chromatography to yield $N^4$-[(R or S)-1-(2-nitrophenyl)ethyl]-cytidine single diastereoisomer C.3 ds1 (65 mg, ca. 30% for two steps, absolute configuration not determined) as a white foam.

$^1$H NMR (400 MHz, DMSO-d$_6$): δ 8.39 (d, 1 H, D$_2$O exchangeable, NH), 7.92 (dd, 1 H, J=1.1 and 8.1 Hz, Ph-H), 7.82 (d, 1 H, J=7.5 Hz, H-6), 7.70 (dt, 1 H, J=1.1 and 7.5 Hz, Ph-H), 7.64 (dd, 1 H, J=1.2 and 7.5 Hz, Ph-H), 7.49 (dt, 1 H, J=1.3 and 7.5 Hz, Ph-H), 1 H, Ph-H), 5.80 (d, 1 H, J=7.5 Hz, H-5), 5.65 (d, 1 H, J=3.4 Hz, H-1'), 5.50 (m, 1 H, Ph-CH), 5.30 (d, 1 H, D$_2$O exchangeable, 3'-OH), 5.02 (t, 1 H, D$_2$O exchangeable, 5'-OH), 4.96 (d, 1 H, D$_2$O exchangeable, 2'-OH), 3.90 (m, 2 H, H-2' and H-3'), 3.78 (m, 1 H, H-4'), 3.59 (m, 1 H, H-5'a), 3.50 (m, 1 H, H-5'b), 1.48 (d, 3 H, J=6.9 Hz, CH$_3$).

N⁴-[(S or R)-1-(2-nitrophenyl)ethyl]-cytidine (Single Diastereoisomer C.3 ds2)

A solution of n-Bu₄NF (167 mg, 0.64 mmol) in THF (2 mL) was added to a solution of N⁴-[1-(2-nitrophenyl)ethyl]-2',3',5'-O-bis-tert-butyldimethylsilyl-cytidine single diastereo-isomer ds2 (188 mg) in THF (3 mL) at 0° C. The reaction mixture was gradually warmed to room temperature and stirred for one hour. Silica gel 60 (1 g) was added, and the mixture was evaporated in vacuo to dryness. The residue was purified by silica gel column chromatography to yield N⁴-[(S or R)-1-(2-nitrophenyl)ethyl]-cytidine single diastereoisomer C.3 ds2 (67 mg, ca. 30% for two steps, absolute configuration not determined) as a white foam.

¹H NMR (400 MHz, DMSO-d₆): δ 8.38 (d, 1 H, D₂O exchangeable, NH), 7.92 (dd, 1 H, J=1.1 and 8.1 Hz, Ph-H), 7.80 (d, 1 H, J=7.5 Hz, H-6), 7.72 (dt, 1 H, J=1.0 and 7.5 Hz, Ph-H), 7.63 (dd, 1 H, J=1.1 and 7.5 Hz, Ph-H), 7.49 (dt, 1 H, J=1.3 and 7.5 Hz, Ph-H), 5.79 (d, 1 H, J=7.5 Hz, H-5), 5.68 (d, 1 H, J=4.0 Hz, H-1'), 5.51 (m, 1 H, Ph-CH), 5.20 (d, 1 H, D₂O exchangeable, 3'-OH), 5.01 (t, 1 H, D₂O exchangeable, 5'-OH), 4.93 (d, 1 H, D₂O exchangeable, 2'-OH), 3.87 (m, 2 H, H-2' and H-3'), 3.78 (m, 1 H, H-4'), 3.59 (m, 1 H, H-5'a), 3.50 (m, 1 H, H-5'a), 1.49 (d, 3 H, J=6.9 Hz, CH₃).

N⁴-[(R or S)-1-(2-Nitrophenyl)ethyl]-cytidine-5'-triphosphate Single Diastereoisomer (WW3p026)

POCl₃ (14 µL, 0.15 mmol) was added to a solution of compound C.3 ds1 (29 mg, 0.074 mmol) and proton sponge (32 mg, 0.15 mmol) in trimethylphosphate (0.5 mL) at 0° C. and stirred for two hours. A solution of bis-tri-n-butylammonium pyrophosphate (175 mg, 0.37 mmol) and tri-n-butylamine (74 µL) in anhydrous DMF (0.74 mL) was added. After five minutes of stirring, triethylammonium bicarbonate buffer (1 M, pH 7.5; 10 mL) was added. The reaction was stirred for one hour at room temperature and then lyophilized to dryness. The residue was dissolved in water (10 mL), and part of the solution was purified with reverse-phase HPLC using a Perkin Elmer OD-300 C₁₈ column (4.6×250 mm) to yield N⁴-[(R or S)-1-(2-nitrophenyl)ethyl]-cytidine-5'-triphosphate single diastereoisomer WW3p026 (absolute configuration not determined). Mobile phase: A, 100 mM triethylammonium acetate (TEAA) in water (pH 7.0); B, 100 mM TEAA in water/CH₃CN (30:70). HPLC purification was achieved a linear gradient of 5-50% B for 20 minutes and then 50-90% B for 10 minutes.

¹H NMR (400 MHz, D₂O): δ 8.0 (d, 1 H, J=8.1 Hz, Ph-H), 7.92 (d, 1 H, J=7.6 Hz, H-6), 7.70 (m, 2 H, Ph-H), 7.50 (t, 1 H, J=8.0 Hz, Ph-H), 6.14 (d, 1 H, J=7.6 Hz, H-5), 5.92 (d, 1 H, J=4.1 Hz, H-1'), 5.61 (q, 1 H, J=6.8 Hz, Ph-CH), 4.33-4.21 (m, 3 H, H-2', H-3' and H-4'), 4.01 (m, 2 H, H-5'), 1.60 (d, 3 H, J=6.8 Hz, CH₃);

N⁴-[(S or R)-1-(2-nitrophenyl)ethyl]-cytidine-5'-triphosphate Single Diastereoisomer (WW2p152)

POCl₃ (11 µL, 0.12 mmol) was added to a solution of compound C.3 ds2 (31 mg, 0.08 mmol) and proton sponge (26 mg, 0.12 mmol) in trimethylphosphate (0.5 mL) at 0° C. and stirred for two hours. A solution of bis-tri-n-butylammonium pyrophosphate (190 mg, 0.4 mmol) and tri-n-butylamine (80 µL) in anhydrous DMF (0.8 mL) was added. After five minutes of stirring, triethylammonium bicarbonate buffer (1 M, pH 7.5; 10 mL) was added. The reaction was stirred for one hour at room temperature and then lyophilized to dryness. The residue was dissolved in water (10 mL), filtered, and purified by anion exchange chromatography using a Q Sepharose FF column (2.5×20 cm) with a linear gradient of NH₄HCO₃ (50 mM to 500 mM in 240 minutes) at a flow rate of 4.5 mL/min. The fractions containing triphosphate were combined and lyophilized to yield N⁴-[(S or R)-1-(2-nitrophenyl)ethyl]-cytidine-5'-triphosphate single diastereoisomer WW2p152 (26 mg, 47%, absolute configuration not determined) as a white fluffy solid.

¹H NMR (400 MHz, D₂O): δ 7.99 (d, 1 H, J=8.2 Hz, Ph-H), 7.82 (d, 1 H, J=7.6 Hz, H-6), 7.68 (m, 2 H, Ph-H), 7.50 (t, 1 H, J=7.8 Hz, Ph-H), 6.12 (d, 1 H, J=7.5 Hz, H-5), 5.91 (d, 1 H, J=4.4 Hz, H-1'), 5.60 (q, 1 H, J=6.8 Hz, Ph-CH), 4.26 (m, 5 H, H-2', H-3', H-4' and H-5'), 1.60 (d, 3 H, J=6.8 Hz, CH₃);

³¹P NMR (162 MHz, D₂O): 6-5.18(d, J=19.8 Hz), −10.46 (d, J=19.1 Hz), −20.98 (t, J=19.6 Hz);

ToF-MS (ESI): For the molecular ion C₁₇H₂₁N₄O₁₆P₃Na [M-2H+Na]⁻, the calculated mass was 653.0063, and the observed mass was 652.9975.

Synthesis of 5-[1-(2-nitrophenyl)ethyloxymethyl]-2'-deoxycytidine-5'-triphosphate (WW3p###)

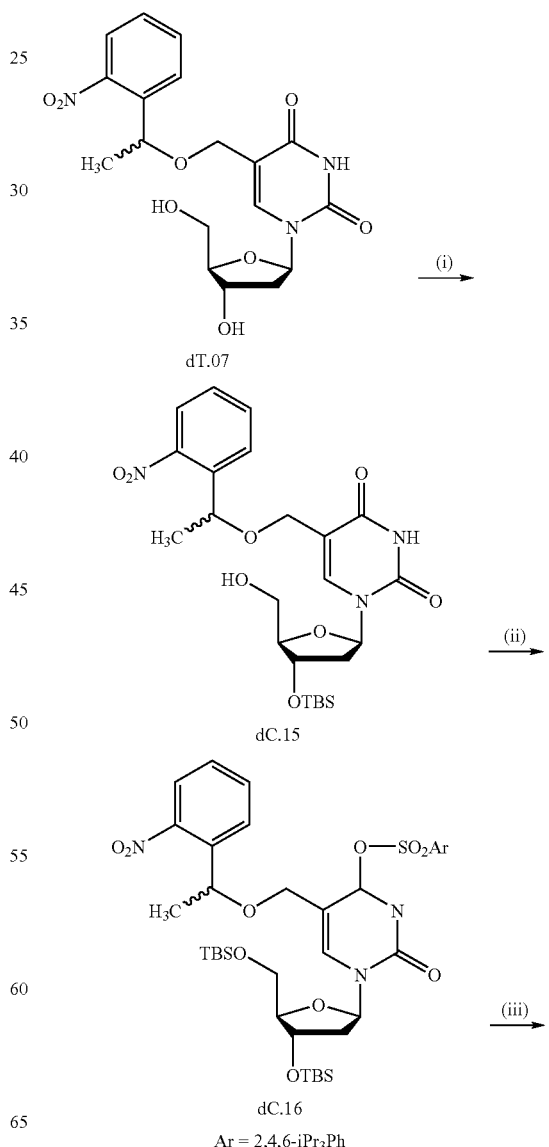

Ar = 2,4,6-iPr₃Ph

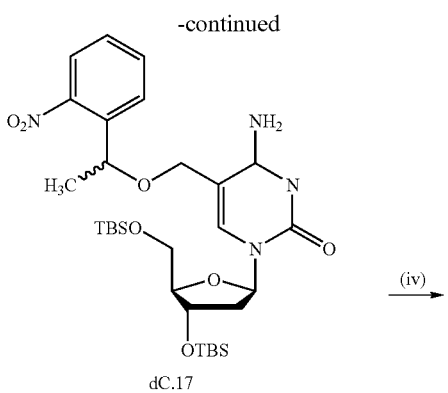

dC.17 dC.18

WW3p###

Scheme. Synthesis of 5-[1-(2-nitrophenyl)ethyloxymethyl]-2'-deoxycytidine-5'-triphosphate. (i) TBSCl, imidazole, DMF, room temperature, 24 hours, 42%; (ii) TPSCl, DMAP, Et$_3$N, CH$_2$Cl$_2$, room temperature, 48 hours, 56%; (iii) NH$_3$, 1,4-dioxane, 80° C., two hours, 56%; (iv) n-Bu$_4$NF, THF, room temperature; (v) POCl$_3$, proton sponge, (MeO)$_3$PO, 0° C.; (n-Bu$_3$NH)$_2$H$_2$P$_2$O$_7$, n-Bu$_3$N, DMF, five minutes; 1 M HNEt$_3$HCO$_3$, one hour.

3',5'-Bis-tert-butyldimethylsilyl-5-[1-(2-nitrophenyl)ethyloxymethyl]-2'-deoxyurdine (dC.15)

A solution of TBSCl (114 mg, 0.76 mmol) in anhydrous DMF (0.5 mL) was added to a solution of compound dT.07 (97 mg, 0.24 mmol) and imidiazole (103 mg, 1.52 mmol) in anhydrous DMF (1 mL). The mixture was stirred at room temperature for 24 hours under a nitrogen atmosphere, then concentrated in vacuo and purified by silica gel column chromatography to yield 3',5'-bis-tert-butyldimethylsilyl-5-[1-(2-nitrophenyl)-ethyloxymethyl]-2'-deoxyurdine dC.15 (64 mg, 42%, 1:1 mixture of diastereomers).

$^1$H NMR (400 MHz, CDCl$_3$) for diastereomers: δ 9.39 and 9.33 (2 br s, 1 H, NH), 7.92 (m, 2 H, Ph-H), 7.70 (m, 2 H, H-6 and Ph-H), 7.42 (m, 1 H, Ph-H), 6.29 (m, 1 H, H-1'), 5.11 (m, 1 H, Ph-CH), 4.41 (m, 1 H, H-3'), 4.04 (m, 2 H, CH$_2$), 3.96 (m, 1 H, H-4'), 3.80 (m, 2 H, H-5'), 2.38 (m, 1 H, H-2'a), 2.04 (m, 1 H, H-2'b), 1.55 (m, 3 H, CH$_3$), 0.91 (s, 18 H, (CH$_3$)$_3$CSi), 0.10 (s, 12 H, (CH$_3$)$_2$Si);

$^{13}$C NMR (100 MHz, CDCl$_3$) for diastereomers: δ 162.89/162.76 (C), 150.15 (C), 148.40 (C), 139.21/139.17 (C), 138.94/138.68 (CH), 133.86/133.76 (CH), 128.22/128.19 (CH), 128.17/128.07 (CH), 124.23 (CH), 111.30/111.22 (C), 87.97/87.94 (CH), 85.43/85.37 (CH), 73.46/73.43 (CH), 72.34/72.28 (CH), 63.92/63.77 (CH$_2$), 63.07 (CH$_2$), 41.27/41.17 (CH$_2$), 25.97/25.93 (CH$_3$), 23.69/23.57 (CH$_3$), 18.43/18.41 (C), −4.64/−4.82 (CH$_3$), −5.37/−5.40 (CH$_3$).

ES+ MS (ESI): 658 [M+Na]$^+$;

O$^4$-(2,4,6-Triisopropylbenzenesulfonyl)-3',5'-bis-tert-butyldimethylsilyl-5-[1-(2-nitro-phenyl)ethyloxymethyl]-2'-deoxyurdine (dC.16)

A solution of 2,4,6-triisopropylbenzenesulfonyl chloride (61 mg, 0.20 mmol) was added to a solution of dC.15 (64 mg, 0.10 mmol) and DMAP (6 mg, 0.05 mmol) in anhydrous CH$_2$Cl$_2$ (3 mL) followed by Et$_3$N (63 µL, 0.45 mmol). The mixture was stirred at room temperature for 48 hours under a nitrogen atmosphere, then concentrated in vacuo and purified by silica gel column chromatography to give O$^4$-(2,4,6-triisopropylbenzenesulfonyl)-3',5'-bis-tert-butyldimethylsilyl-5-[1-(2-nitrophenyl)ethyloxy-methyl]-2'-deoxyurdine dC.16 (50 mg, 56%, 1:1 mixture of diastereomers).

$^1$H NMR (400 MHz, CDCl$_3$) for diastereomers: δ 8.33 and 8.28 (2 s, 1 H, Ph-H), 7.90 (m, 3 H, Ph-H), 7.67 (m, 2 H, H-6 and Ph-H), 7.44 (m, 1 H, Ph-H), 6.27 (m, 1 H, H-1'), 5.11 (m, 1 H, Ph-CH), 4.40 (m, 1 H, H-3'), 4.06 (m, 2 H, CH$_2$), 3.97 (m, 1 H, H-4'), 3.79 (m, 2 H, H-5'), 2.38 (m, 1 H, H-2'a), 2.04 (m, 1 H, H-2'b), 1.54 (m, 3 H, CH$_3$), 1.60 (m, 3 H, CH), 0.91 (s, 18 H, (CH$_3$)$_3$CSi), 0.80 (m, 18 H, CH$_3$), 0.09 (s, 12 H, (CH$_3$)$_2$Si);

3',5'-Bis-tert-butyldimethylsilyl-5-[1-(2-nitrophenyl)ethyloxymethyl]-2'-deoxycytidine (dC.17)

A solution of NH$_3$ (1 mL, 0.5 M in dioxane) was added to a solution of compound dC.16 (48 mg, 0.05 mmol) in anhydrous 1,4-dioxane (1 mL). The mixture was stirred at 80° C. for two hours, then concentrated in vacuo and purified by silica gel column chromatography to give 3',5'-bis-tert-butyldimethylsilyl-5-[1-(2-nitrophenyl)ethyloxy-methyl]-2'-deoxycytidine dC.18 (25 mg, 58%, 1:1 mixture of diastereomers).

Example 4 dG Compounds

Synthesis of $N^2$-(2-nitrobenzyl)-2'-deoxyguanidine-5'-triphosphate (WW2p067)

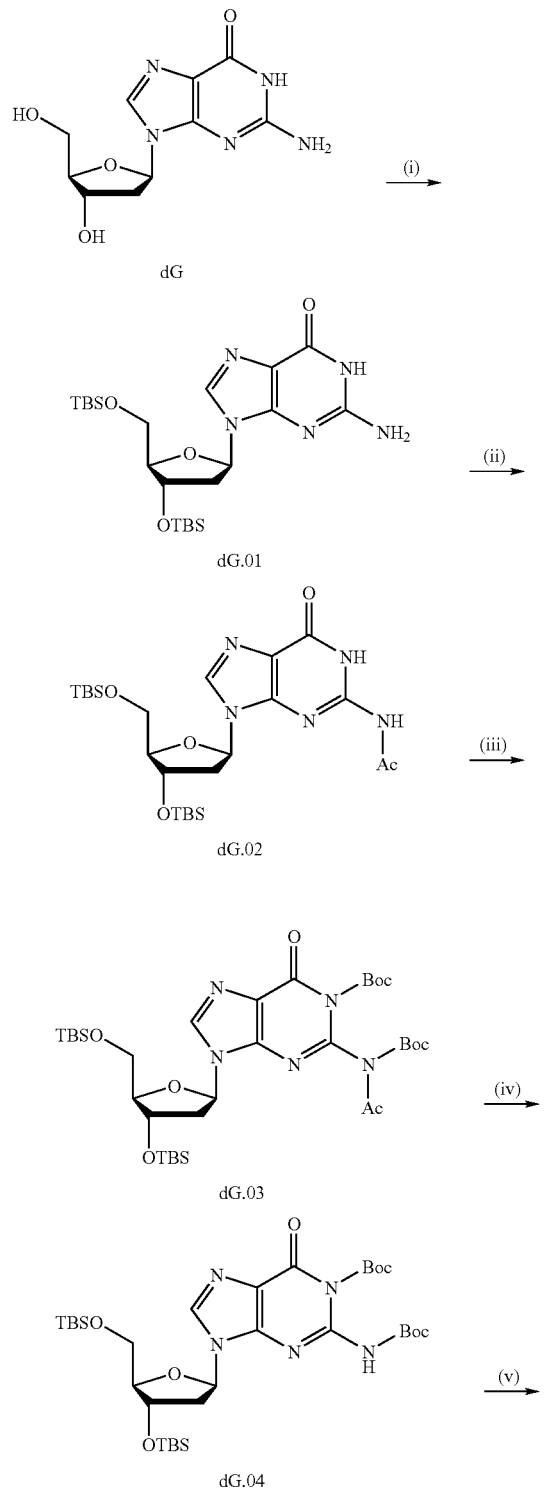

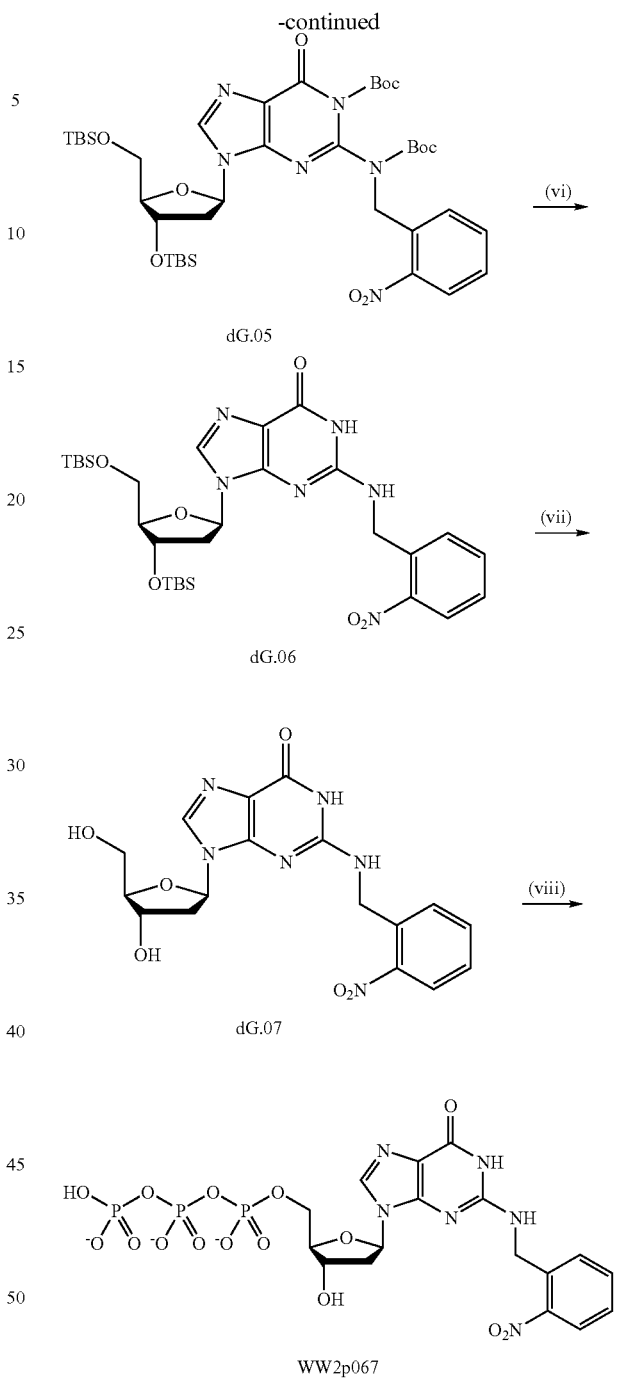

Scheme. Synthesis of $N^2$-(2-nitrobenzyl)-2'-deoxyguanidine-5'-triphosphate. (i) TBSCl, imidazole, anhydrous DMF, 0° C., then gradually warmed to room temperature, overnight, 96%; (ii) Ac$_2$O, anhydrous pyridine, room temperature, 100° C., 72%; (iii) Boc$_2$O, Et$_3$N, DMAP, CH$_2$Cl$_2$, reflux, two hours, 54%; (iv) K$_2$CO$_3$, MeOH, 95%; (v). 2-nitrobenzylbromide, NaH, DMF, 0° C., then gradually warmed to room temperature, one hour, 91%; (vi) SiO$_2$, vacuum, 70-80° C., 48 hours, 97%; (vii) n-Bu$_4$NF, THF, 0° C., one hour, then room temperature, two hours, 83%; (viii) POCl$_3$, (MeO)$_3$PO, minus 20-30° C., two hours; (n-Bu$_3$NH)$_2$H$_2$P$_2$O$_7$, n-Bu$_3$N, DMF, five minutes; 1 M HNEt$_3$HCO$_3$, one hour, 62%.

3',5'-O-Bis-tert-butyldimethylsilyl-2'-deoxyguanosine (dG.01)

2'-deoxyguanosine dG (0.89 g, 3.30 mmol), imidiazole (2.0 g, 29.32 mmol), and TBSCl (2.34 g, 15.55 mmol) were added to anhydrous DMF (8 mL) at 0° C. under a $N_2$ atmosphere. The reaction mixture was gradually warmed to room temperature and stirred overnight. The mixture was then concentrated in vacuo, treated with a mixture of $CHCl_3$ (8 mL) and MeOH (8 mL), concentrated in vacuo, and purified by silica gel chromatography to yield 3',5'-O-bis-tert-butyldimethylsilyl-2'-deoxyguanosine dG.01 (1.57 g, 96%) as a white powder.

$^1$H NMR (400 MHz, DMSO-$d_6$): δ 10.60 (br s, 1 H, H-1), 7.88 (s, 1 H, H-8), 6.47 (br s, 2 H, $NH_2$), 6.10 (t, 1 H, J=6.8 Hz, H-1'), 4.48 (m, 1 H, H-3'), 3.80 (m, 1 H, H-4'), 3.70 (m, 2 H, H-5'a and H-5'b), 2.64 (m, 1 H, H-2'a), 2.18 (m, 1 H, H-2'b), 0.89 (s, 9 H, $(CH_3)_3CSi$), 0.86 (s, 9 H, $(CH_3)_3CSi$), 0.11 (s, 6 H, $(CH_3)_2Si$), 0.03 (s, 6 H, $(CH_3)_2Si$).

$N^2$-Acetyl-3',5'-O-bis-tert-butyldimethylsilyl-2'-deoxyguanosine (dG.02)

Acetic anhydride (1.22 mL, 12.92 mmol) was slowly added to a solution of compound dG.01 (0.51 g, 1.03 mmol) in anhydrous pyridine (10 mL) at room temperature and stirred at 100° C. for three hour. The reaction was concentrated in vacuo, co-evaporated three times with anhydrous ethanol (15 mL), and purified by silica gel chromatography to yield $N^2$-acetyl-3',5'-O-bis-tert-butyldimethylsilyl-2'-deoxyguanosine dG.02 (0.34 g, 56%) as a white foam.

$^1$H NMR (400 MHz, DMSO-$d_6$): δ 12.03 (s, 1 H, NH), 11.70 (s. 1 H, NH), 8.20 (s, 1 H, H-8), 6.19 (t, 1 H, J=6.2 Hz, H-1'), 4.51 (m, 1 H, H-3'), 3.84 (m, 1 H, H-4'), 3.68 (m, 2 H, H-5'a and H-5'b), 2.71 (m, 1 H, H-2'a), 2.17 (m, 1 H, H-2'b), 0.89 (s, 9 H, $(CH_3)_3CSi$), 0.86 (s, 9 H, $(CH_3)_3CSi$), 0.11 (s, 6 H, $(CH_3)_2Si$), 0.04 (s, 6 H, $(CH_3)_2Si$).

$N^1,N^2$-Bis-tert-butyloxycarbonyl-$N^2$-acetyl-3',5'-O-bis-tert-butyldimethylsilyl-2'-deoxyguanidine (dG.03)

A solution of di-tert-butyldicarbonate (8.75 g, 40 mmol) in anhydrous $CH_2Cl_2$ (27 mL) was added to a solution of compound dG.02 (1.85 g, 3.44 mmol), $Et_3N$ (12.17 mL, 15.48 mmol), and DMAP (1.72 g, 14.10 mmol) in anhydrous $CH_2Cl_2$ (20 mL) under a $N_2$ atmosphere. The reaction mixture was refluxed for two hours, concentrated in vacuo, and purified by silica gel chromatography to yield $N^1,N^2$-bis-tert-butyloxy-carbonyl-$N^2$-acetyl-3',5'-O-bis-tert-butyldimethylsilyl-2'-deoxyguanidine dG.03 (1.37 g, 54%) as a white foam.

$^1$H NMR (400 MHz, $CDCl_3$): δ 8.25 (s, 1 H, H-8), 6.43 (t, 1 H, J=6.4 Hz, H-1'), 4.59 (m, 1 H, H-3'), 3.99 (m, 1 H, H-4'), 3.87 (m, 1 H, H-5'a), 3.87 (m, 1 H, H-5'b), 2.60 (a, 3 H, $CH_3CO$), 2.52 (m, 1 H, H-2'a), 2.41 (m, 1 H, H-2'b), 1.71 (s, 9 H, $(CH_3)_3CO$), 1.36 (s, 9H, $(CH_3)_3CO$), 0.92 (s, 9 H, $(CH_3)_3CSi$), 0.91 (s, 9 H, $(CH_3)_3CSi$), 0.10 (s, 6 H, $(CH_3)_2Si$), 0.09 (s, 6 H, $(CH_3)_2Si$).

$N^1,N^2$-Bis-tert-butyloxycarbonyl-3',5'-O-bis-tert-butyldimethylsilyl-2'-deoxyguanidine (dG.04)

Compound dG.03 (1.31 g, 1.78 mmol) was treated with $K_2CO_3$ (1.23 g, 8.90 mmol) in MeOH (20.5 mL) at room temperature for 30 minutes. The reaction was concentrated in vacuo, dissolved in ethyl acetate (50 mL), and washed twice with water (10 mL). The organic layer was dried with $Na_2SO_4$ and concentrated in vacuo to give $N^1,N^2$-bis-tert-butyloxycarbonyl-3',5'-O-bis-tert-butyldimethylsilyl-2'-deoxyguanidine dG.04 (1.18 g, 95%) as a white foam.

$^1$H NMR (400 MHz, DMSO-$d_6$): δ 9.82 (bs, 1 H, N—H), 8.24 (s, 1 H, H-8), 6.27 (t, 1 H, J=6.6 Hz, H-1'), 4.71 (m, 1H, H-3'), 3.82 (m, 1 H, H-4'), 3.79 (m, 1 H, H-5'a), 3.73 (m, 1 H, H-5'b), 2.95 (m, 1 H, H-2'a), 2.30 (m, 1 H, H-2'b), 1.66 (s, 9 H, $(CH_3)_3CO$), 1.48 (s, 9 H, $(CH_3)_3CO$), 0.89 (s, 9 H, $(CH_3)_3CSi$), 0.83 (s, 9 H, $(CH_3)_3CSi$), 0.11 (2 s, 6 H, $(CH_3)_2Si$), −0.01 (2 s, 6 H, $(CH_3)_2Si$).

$N^1,N^2$-Bis-tert-butyloxycarbonyl-$N^2$-(2-nitrobenzyl)-3',5'-O-bis-tert-butyldimethylsilyl-2'-deoxyguanidine (dG.05)

NaH (22 mg, 0.93 mmol, dry) was added to a solution of compound dG.04 (500 mg, 0.72 mmol) in anhydrous DMF (6 mL) at 0° C. and stirred for 30 minutes under a $N_2$ atmosphere. A solution of 2-nitrobenzyl bromide (202 mg, 0.94 mmol) in anhydrous DMF (3 mL) was added dropwise. The reaction was stirred at 0° C. for one hour and then concentrated in vacuo. Ethyl acetate (50 mL) was added, and the mixture was washed twice with saturated $NH_4Cl$ solution (20 mL). The combined aqueous layer was extracted with ethyl acetate (20 mL), and the combined organic layer was dried with $Na_2SO_4$, concentrated in vacuo, and purified by silica gel chromatography to yield $N^1,N^2$-bis-tert-butyloxycarbonyl-$N^2$-(2-nitrobenzyl)-3',5'-O-bis-tert-butyldimethylsilyl-2'-deoxyguanidine dG.05 (543 mg, 91%) as a white foam.

$^1$H NMR (400 MHz, $CDCl_3$): δ 8.12 (s, 1 H, H-8), 8.06 (m, 1 H, Ph-H), 7.68 (m, 1 H, Ph-H), 7.56 (m, 1 H, Ph-H), 7.38 (m, 1 H, Ph-H), 6.41 (6, J=6.2 Hz, 1 H, H-2'), 5.49 (s, 2 H, Ph-$CH_2$), 4.56 (m, 1 H, H-3'), 4.00 (m, 1 H, H-4'), 3.80 (m, 2 H, H-5'), 2.52 (m, 1 H, H-2'a), 2.39 (m, 1 H, H-2'b), 1.54 (s, 9 H, $(CH_3)_3CO$), 1.45 (s, 9 H, $(CH_3)_3CO$), 0.92 (s, 18 H, $(CH_3)_3CSi$), 0.10 (s, 12 H, $(CH_3)_2Si$).

$N^2$-(2-Nitrobenzyl)-3',5'-O-bis-tert-butyldimethylsilyl-2'-deoxyguanidine (dG.06)

Silica gel 60 (4.5 g, 100-200 mesh, activated by heating to 50-60° C. under reduced pressure for 24 hours) was added to a solution of compound dG.05 (450 mg, 0.54 mmol) in $CH_2Cl_2$ (5 mL), and the mixture was evaporated in vacuo to dryness. The residue was heated to 60-70° C. under reduced pressure for 48 hours, washed three times with MeOH (50 mL), and filtered using a buchi funnel. The combined filtrate was concentrated in vacuo and purified by silica gel chromatography to yield N2-(2-nitrobenzyl)-3',5'-O-bis-tert-butyldimethylsilyl-2'-deoxyguanidine dG.06 (333 mg, 97%) as a white foam.

$^1$H NMR (400 MHz, DMSO-$d_6$): δ 10.85 (s, 1 H, N—H), 8.05 (m, 1 H, Ph-H), 7.85 (s, 1 H, H-8), 7.69 (m, 1 H, Ph-H), 7.62 (m, 1 H, Ph-H), 7.54 (m, 1 H, Ph-H), 7.10 (t, 1 H, N—H), 6.07 (t, 1 H, J=, H-1'), 4.78 (m, 2 H, Ph-$CH_2$), 4.40 (m, 1 H, H-3'), 3.79 (m, 1 H, H-4'), 3.62 (m, 2 H, H-5'), 2.60 (m, 1 H, H-2'a), 2.15 (m, 1 H, H-2'b), 0.86 (s, 9H, $(CH_3)_3CSi$), 0.85 (s, 9H, $(CH_3)_3CSi$), 0.06 (s, 6 H, $(CH_3)_2Si$), 0.01 (s, 6 H, $(CH_3)_2Si$).

$N^2$-(2-Nitrobenzyl)-2'-deoxyguanidine (dG.07)

A solution of n-$Bu_4NF$ (393 mg, 1.5 mmol) in THF (6 mL) was added dropwise to a solution of compound dG.06 (313 mg, 0.5 mmol) in THF (12 mL) at 0° C. The reaction mixture was stirred at 0° C. for one hour and then at room temperature for two hours. The reaction was concentrated in vacuo and purified by silica gel chromatography to yield N²-(2-nitrobenzyl)-2'-deoxyguanidine dG.07 (165 mg, 83%) as a yellow foam.

¹H NMR (400 MHz, DMSO-d₆): δ 10.82 (s, 1 H, D₂O exchangeable, N—H), 8.06 (m, 1 H, Ph-H), 7.90 (s, 1 H, H-8), 7.72 (m, 1 H, Ph-H), 7.64 (m, 1 H, Ph-H), 7.55 (m, 1 H, Ph-H), 7.06 (t, 1 H, D₂O exchangeable, N—H), 6.08 (t, 1 H, J=6.4 Hz, H-1'), 5.23 (d, 1 H, D₂O exchangeable, 3'-OH), 4.80 (t, 3 H, among them 1H D₂O exchangeable, 5'-OH and Ph-CH₂), 4.25 (m, 1 H, H-3'), 3.77 (m, 1 H, H-4'), 3.42 (m, 2 H, H-5'), 2.45 (m, 1 H, H-2'a), 2.12 (m, 1 H, H-2'b).

N²-(2-Nitrobenzyl)-2'-deoxyguanidine-5'-triphosphate (WW2p067)

POCl₃ (17 µL, 0.18 mmol) was added dropwise to a solution of compound dG.07 (50 mg, 0.12 mmol) in trimethylphosphate (0.5 mL) and maintained at minus 20-30° C. for two hours. A solution of bis-tri-n-butylammonium pyrophosphate (205 mg, 0.6 mmol) and tri-n-butylamine (120 µL) in anhydrous DMF (1.2 mL) was added. After five minutes of stirring, triethylammonium bicarbonate buffer (1 M, pH 7.5; 10 mL) was added. The reaction was stirred for one hour at room temperature and then lyophilized to dryness. The residue was dissolved in water (10 mL), filtered, and purified by anion exchange chromatography using a Q Sepharose FF column (2.5×20 cm) with a linear gradient of NH₄HCO₃ (50 mM to 500 mM in 300 minutes) at a flow rate of 4.5 mL/min. The fractions containing triphosphate were combined and lyophilized to give N²-(2-nitrobenzyl)-2'-deoxyguanidine-5'-triphosphate WW2p067 (52 mg, 62%) as a white fluffy solid.

¹H NMR (400 MHz, D₂O): δ 8.08 (d, 1 H, Ph-H), 8.04 (s, 1 H, H-8), 7.68 (m, 2 H, Ph-H), 7.51 (t, 1 H, Ph-H), 6.27 (t, 1 H, J=6.8 Hz, H-1'), 4.63 (m, 1 H, H-3'), 4.21 (m, 1 H, H-4'), 4.10 (m, 2 H, H-5'), 2.66 (m, 1 H, H-2'a), 2.41 (m, 1 H, H-2'b);

³¹P NMR (162 MHz, D₂O): 6-6.48 (d, J=15.7 Hz), −11.40 (d, J=15.2 Hz), −19.94 (br);

ToF-MS (ESI): For the molecular ion C₁₇H₁₉N₆O₁₅P₃Na [M-2H+Na]⁻, the calculated mass was 663.0019, and the observed mass was 663.0143.

Synthesis of O⁶-(2-nitrobenzyl)-2'-deoxyguanosine-5'-triphosphate (WW2p077)

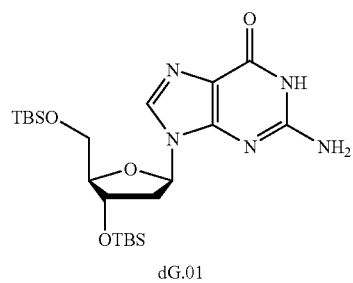
dG.01

(i)

-continued

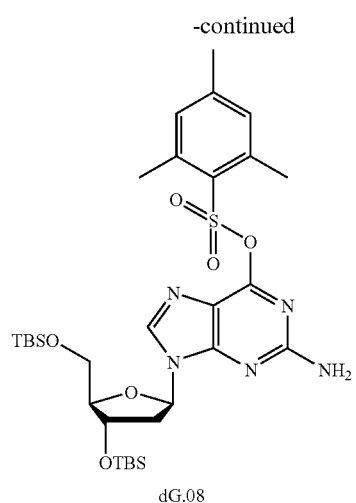
dG.08

(ii)

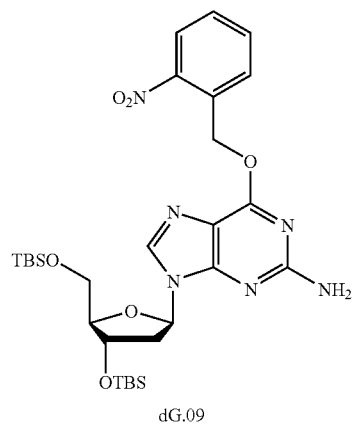
dG.09

(iii)

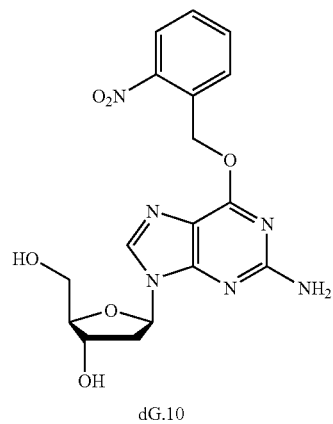
dG.10

(iv)

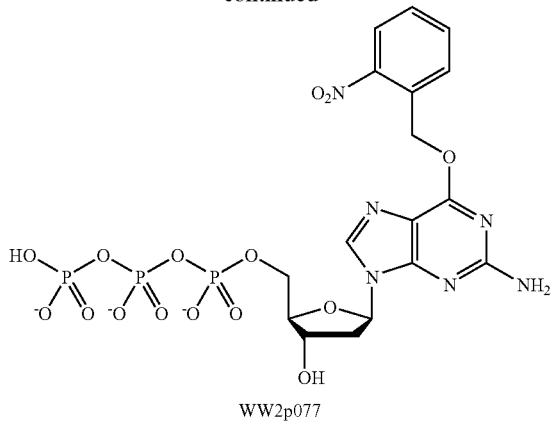

WW2p077

Scheme. Synthesis of O⁶-(2-nitrobenzyl)-2'-deoxyguanosine-5'-triphosphate. (i) 2-mesitylene-sulfonyl chloride, Et₃N, DMAP, anhydrous CH₂Cl₂, HMPA, room temperature, overnight, 98%; (ii) 2-nitrobenzyl alcohol, DABCO, DBU, molecular sieves, anhydrous 1,2-DME, 0° C., then gradually warmed to room temperature, 24 hours, 77%; (iii) n-Bu₄NF, THF, room temperature, 1.5 hours, 94%; (iv) POCl₃, (MeO)₃PO, minus 20-30° C., two hours; (n-Bu₃NH)₂H₂P₂O₇, n-Bu₃N, DMF, five minutes; 1 M HNEt₃HCO₃, one hour, 35%.

O⁶-(2-Mesitylenesulfonyl)-3',5'-bis-O-(tert-butyldimethylsilyl)-2-deoxyguanosine (dG.08)

2-Mesitylenesulfonyl chloride (510 mg, 2.34 mmol), Et₃N (0.56 mL, 4.0 mmol), and DMAP (27 mg, 0.197 mmol) were added to a solution of compound dG.01 (500 mg, 1.0 mmol) in a mixture of hexmethylphosphoramide (1.5 mL) and anhydrous CH₂Cl₂ (7 mL). The reaction was stirred at room temperature overnight and then diluted with ethyl ether (25 mL). The ether solution was washed twice with a saturated solution of NaHCO₃ (10 mL each) and then with brine (10 mL). The organic layer was dried over Na₂SO₄ and concentrated in vacuo to give a semi-solid, which was dissolved in ethyl ether (2 mL) and gradually diluted with hexane (40 mL). The precipitate was collected by filtration to yield O⁶-(2-mesitylenesulfonyl)-3',5'-bis-O-(tert-butyldimethylsilyl)-2'-deoxyguanosine dG.08 (737 mg, 98%).

¹H NMR (400 MHz, CDCl₃): δ 7.98 (s, 1 H, H-8), 6.98 (s, 2 H, Ph-H), 6.28 (t, 1 H, J=6.5 Hz, H-1'), 4.84 (br s, 2 H, NH₂), 4.57 (m, 1 H, H-3'), 3.97 (m, 1 H, H-4'), 3.78 (dd, 1 H, J=2.9 and 11.0 Hz, H-5'a), 3.75 (dd, 1 H, J=2.9 and 11.0 Hz, H-5'b), 2.75 (s, 6 H, CH₃), 2.53 (m, 1 H, H-2'a), 2.34 (m, 1 H, H-2'b), 2.31 (s, 3 H, CH₃), 0.91 (s, 9 H, (CH₃)₃CSi), 0.90 (s, 9 H, (CH₃)₃CSi), 0.09 (s, 6 H, (CH₃)₂Si), 0.06 (s, 6 H, (CH₃)₂Si).

O⁶-(2-Nitrobenzyl)-3',5'-bis-O-(tert-butyldimethylsilyl)-2'-deoxyguanosine (dG.09)

DABCO (139 mg, 1.24 mmol) and 2-nitrobenzyl alcohol (474 mg, 3.10 mmol) were added to a solution of compound dG.08 (420 mg, 0.62 mmol) and 4 Å molecular sieves (200 mg) in anhydrous 1,2-DME (6.2 mL) at 0° C. The mixture was warmed to room temperature and stirred for 30 minutes. DBU (139 μL, 0.93 mmol) was added, and the reaction was stirred at room temperature for 24 hours. Ethyl acetate (100 mL) was added, and the organic layer was washed with water (20 mL) and brine (20 mL), dried over Na₂SO₄, concentrated in vacuo, and purified by silica gel chromatography to yield O⁶-(2-nitrobenzyl)-3',5'-bis-O-(tert-butyldimethylsilyl)-2'-deoxyguanosine dG.09 (300 mg, 77%).

¹H NMR (400 MHz, CDCl₃): δ 8.09 (dd, 1 H, J=1.1 and 8.2 Hz, Ph-H), 7.94 (s, 1 H, H-8), 7.86 (d, 1 H, J=7.7 Hz, Ph-H), 7.60 (dt, 1 H, J=1.1 and 7.7 Hz, Ph-H), 7.45 (dt, 1 H, J=1.0 and 8.2 Hz, Ph-H), 6.32 (t, 1 H, J=6.5 Hz, H-1'), 5.94 (s, 2H, NH₂), 4.89 (s, 2 H, PhCH₂), 4.59 (m, 1 H, H-3'), 3.98 (m, 1 H, H-4'), 3.81 (dd, 1 H, J=2.9 and 11.0 Hz, H-5'a), 3.75 (dd, 1 H, J=2.9 and 11.0 Hz, H-5'b), 2.58 (m, 1 H, H-2'a), 2.37 (m, 1 H, H-2'b), 0.91 (s, 18 H, (CH₃)₃CSi), 0.10 (s, 6 H, (CH₃)₂Si), 0.08 (s, 6 H, (CH₃)₂Si).

O⁶-(2-Nitrobenzyl)-2'-deoxyguanosine (dG.10)

A solution of n-Bu₄NF (252 mg, 0.80 mmol) in THF (4 mL) was added to a solution of compound dG.09 (200 mg, 0.32 mmol) in THF (4 mL) at room temperature. The mixture was stirred for 1.5 hours, concentrated in vacuo, and purified by silica gel chromatography to yield O⁶-(2-nitrobenzyl)-2'-deoxyguanosine dG.10 (119 mg, 94%).

¹H NMR (400 MHz, DMSO-d₆): δ 8.16 (dd, 1 H, J=1.0 and 8.2, Hz, Ph-H), 8.13 (s, 1 H, H-8), 7.79 (m, 2 H, Ph-H), 7.63 (m, 1 H, Ph-H), 6.49 (br s, 2 H, D₂O exchangeable, NH₂), 6.22 (dd, 1 H, J=6.1 and 7.7 Hz, H-1'), 5.87 (s, 2 H, PhCH₂), 5.28 (br, 1 H, D₂O exchangeable, 5'-OH), 4.99 (br, 1 H, D₂O exchangeable, 3'-OH), 4.35 (m, 1 H, H-3'), 3.82 (m, 1 H, H-4'), 3.55 (m, 1 H, H-5'b), 3.52 (m, 1 H, H-5'a), 2.58 (m, 1 H, H-2'a), 2.23 (m, 1 H, H-2'b).

O⁶-(2-Nitrobenzyl)-2'-deoxyguanosine-5'-triphosphate (WW2p077)

POCl₃ (14 μL, 0.1 mmol) was added dropwise to a solution of compound dG.10 (43 mg, 0.1 mmol) in trimethylphosphate (0.5 mL) and maintained at minus 20-30° C. for two hours. A solution of bis-tri-n-butylammonium pyrophosphate (237 mg, 0.5 mmol) and tri-n-butylamine (100 μL) in anhydrous DMF (1.0 mL) was added. After five minutes of stirring, triethylammonium bicarbonate buffer (1 M, pH 7.5; 10 mL) was added. The reaction was stirred for one hour at room temperature and then lyophilized to dryness. The residue was dissolved in water (10 mL), filtered, and purified by anion exchange chromatography using a Q Sepharose FF column (2.5×20 cm) with a linear gradient of NH₄HCO₃ (50 mM to 500 mM in 300 minutes) at a flow rate of 4.5 mL/min. The fractions containing triphosphate were combined and lyophilized to give O⁶-(2-nitrobenzyl)-2'-deoxyguanosine-5'-triphosphate WW2p077 (24 mg, 35%) as a white fluffy solid.

¹H NMR (400 MHz, D₂O): δ 8.21 (s, 1 H, H-8), 8.13 (d, J=8.2 Hz, 1 H, Ph-H), 7.83 (d, 1 H, J=7.8 Hz, Ph-H), 7.74 (t, 1 H, J=7.8 Hz, Ph-H), 7.51 (t, J=7.8 Hz, 1 H, Ph-H), 6.35 (t, 1 H, J=6.8 Hz, H-1'), 5.86 (s, 2 H, Ph-CH₂), 4.28 (m, 1 H, H-4'), 4.23 (m, 2 H, H-5'), 2.82 (m, 1 H, H-2'a), 2.57 (m, 1 H, H-2'b);

³¹P NMR (162 MHz, D₂O): δ −6.48 (br), −10.96 (br), −21.83 (br);

ToF-MS (ESI): For the molecular ion C₁₇H₁₉N₆O₁₅P₃Na [M-2H+Na]⁻, the calculated mass was 663.0019, and the observed mass was 663.0228.

Synthesis of 6-ROX labeled O$^6$-[4-(3-amino-1-propynyl)-2-nitrobenzyl]-2'-deoxyguanosine-5'-triphosphate (WW2p121)
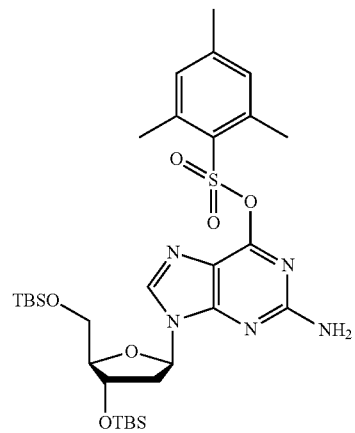
dG.08
(i)
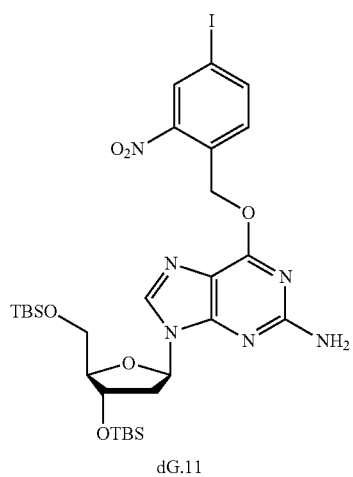
dG.11
(ii)
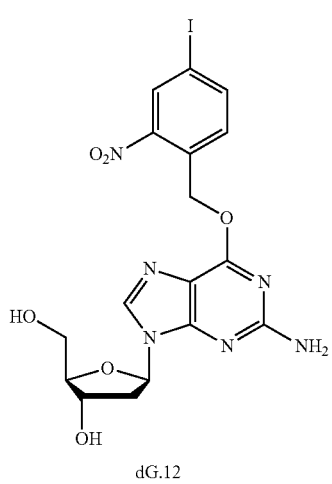
dG.12
(iii)
-continued
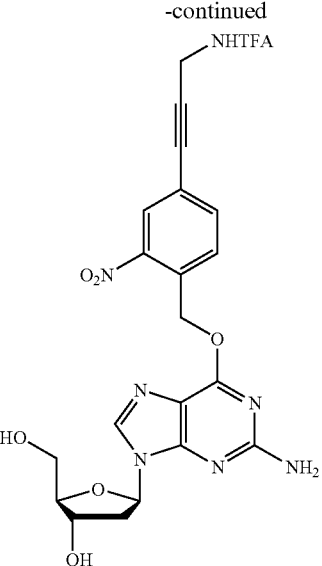
dG.13
(iv)
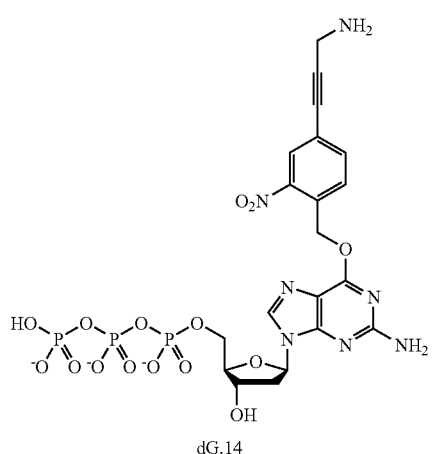
dG.14
(v)
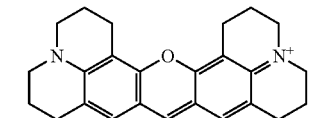
WW2p121

Scheme. Synthesis of 6-ROX labeled $O^6$-[4-(3-amino-1-propynyl)-2-nitrobenzyl]-2'-deoxyguanosine-5'-triphosphate. (i) 4-iodo-2-nitrobenzyl alcohol, DABCO, DBU, 4 Å molecular sieves, anhydrous 1,2-DME, 0° C., then gradually warmed to room temperature, 24 hours, 77%; (ii) n-Bu$_4$NF, THF, room temperature, 1.5 hours, 62%; (iii) N-propargyltrifluoroacetamide, Pd(PPh$_3$)$_4$, CuI, Et$_3$N, anhydrous DMF, four hours, 42%; (iv) POCl$_3$, proton sponge, (MeO)$_3$PO, 0° C., one hour; (n-Bu$_3$NH)$_2$H$_2$P$_2$O$_7$, n-Bu$_3$N, DMF, five minutes; 1 M HNEt$_3$HCO$_3$, one hour; NH$_4$OH, one hour; (v) 6-ROX-SE, 0.1 M Na$_2$CO$_3$/NaHCO$_3$ buffer (pH 9.2), one hour.

$O^6$-(4-Iodo-2-nitrobenzyl)-3',5'-bis-O-(tert-butyldimethylsilyl)-2-deoxyguanosine (dG.11)

DABCO (90 mg, 0.80 mmol) and 4-iodo-2-nitrobenzyl alcohol (555 mg, 2.00 mmol) were added to a solution of compound dG.08 (270 mg, 0.40 mmol) and 4 Å molecular sieves (129 mg) in anhydrous 1,2-DME (4 mL) at 0° C. The mixture was warmed to room temperature and stirred for 30 minutes. DBU (91 µL, 0.60 mmol) was added, and the reaction was stirred at room temperature for 24 hours. Ethyl acetate (70 mL) was added, and the organic solution was washed with water (10 mL) and brine (10 mL), dried over Na$_2$SO$_4$, concentrated in vacuo, and purified by silica gel chromatography to give $O^6$-(4-iodo-2-nitrobenzyl)-3',5'-bis-O-(tert-butyldimethylsilyl)-2-deoxyguanosine dG.11 (233 mg, 77%).

$^1$H NMR (400 MHz, CDCl$_3$): δ 8.40 (d, 1 H, J=1.7 Hz, Ph-H), 7.94 (s, 1 H, H-8), 7.86 (dd, 1 H, J=1.7 and 8.3 Hz, Ph-H), 7.60 (d, 1 H, J=8.3 Hz, Ph-H), 6.31 (t, 1 H, J=6.5 Hz, H-1'), 5.86 (s, 2 H, NH$_2$), 4.87 (s, 2 H, PhCH$_2$), 4.59 (m, 1 H, H-3'), 3.98 (m, 2 H, H-4'), 3.82 (dd, AB, 1 H, J=4.2 and 11.2 Hz, H-5'a), 3.75 (dd, 1 H, J=4.2 and 11.2 Hz, H-5'b), 2.57 (m, 1 H, H-2'a), 2.37 (m, 1 H, H-2'b), 0.91 (s, 18 H, (CH$_3$)$_3$CSi), 0.10 (s, 6 H, (CH$_3$)$_2$Si), 0.08 (s, 6 H, (CH$_3$)$_2$Si).

$O^6$-(4-Iodo-2-nitrobenzyl)-2-deoxyguanosine (dG.12)

A solution of n-Bu$_4$NF (291 mg, 0.924 mmol) in THF (2 mL) was added to a solution of compound dG.11 (233 mg, 0.31 mmol) in THF (4 mL) at room temperature. The mixture was stirred for 1.5 hours, concentrated in vacuo, and purified by silica gel chromatography to give $O^6$-(4-iodo-2-nitrobenzyl)-2-deoxyguanosine dG.12 (101 mg, 62%).

$^1$H NMR (400 MHz, DMSO-d$_6$): δ 8.43 (d, 1 H, J=1.8 Hz, Ph-H), 8.16 (dd, 1 H, J=1.8 and 8.2 Hz, Ph-H), 8.13 (s, 1 H, H-8), 7.52 (d, 1 H, J=8.2 Hz, Ph-H), 6.48 (br s, 2 H, D$_2$O exchangeable, NH$_2$), 6.22 (dd, 1 H, J=6.2 and 7.7 Hz, H-1'), 5.79 (s, 2 H, PhCH$_2$), 5.27 (d, 1 H, D$_2$O exchangeable, 5'-OH), 4.97 (t, 1 H, D$_2$O exchangeable, 3'-OH), 4.35 (m, 1 H, H-3'), 3.82 (m, 1 H, H-4'), 3.52 (m, 2 H, H-5'a and H-5'b), 2.58 (m, 1 H, H-2'a), 2.22 (m, 1 H, H-2'b).

$O^6$-[4-(3-Trifluoroacetamido-1-propynyl)-2-nitrobenzyl]-2'-deoxyguanosine (dG.13)

A solution of compound dG.12 (95 mg, 0.18 mmol), N-propargyltrifluoroacetylamide (82 mg, 0.53 mmol), tetrakis(triphenylphosphine)-palladium(0) (21 mg, 0.018 mmol), CuI (7 mg, 0.036 mmol) and Et$_3$N (51 µL, 0.36 mmol) in anhydrous DMF (1.4 mL) was stirred at room temperature for four hours. CH$_2$Cl$_2$ (1 mL), methanol (1 mL), and NaHCO$_3$ (84 mg, 1 mmol) were added, and the mixture was stirred for 20 minutes, concentrated in vacuo, and purified by silica gel column chromatography and preparative HPLC to give $O^6$-[4-(3-trifluoroacetamido-1-propynyl)-2-nitrobenzyl]-2'-deoxyguanosine dG.13 (42 mg, 42%).

$^1$H NMR (400 MHz, DMSO-d$_6$): δ 10.11 (br 1 H, NH), 8.16 (d, 1 H, J=1.7 Hz, Ph-H), 8.13 (s, 1 H, H-8), 7.86 (dd, 1 H, J=1.7 and 8.2 Hz, Ph-H), 7.75 (d, 1 H, J=8.2 Hz, Ph-H), 6.50 (br s, 2 H, D$_2$O exchangeable, NH$_2$), 6.22 (t, 1 H, J=6.4 Hz, H-1'), 5.87 (s, 2 H, PhCH$_2$), 5.27 (d, 1 H, D$_2$O exchangeable, 5'-OH), 4.97 (t, 1 H, D$_2$O exchangeable, 3'-OH), 4.35 (m, 1 H, H-3'), 4.33 (s, 2 H, CH$_2$), 3.82 (m, 2 H, H-4'), 3.55 (m, 1 H, H-5'b), 3.51 (m, 1 H, H-5'a), 2.58 (m, 1 H, H-2'a), 2.23 (m, 1 H, H-2'b).

$O^6$-[4-(3-Amino-1-propynyl)-2-nitrobenzyl]-2'-deoxyguanosine-5'-triphosphate (dG.14)

Compound dG.13 (33 mg, 0.06 mmol) and proton sponge (26 mg, 0.12 mmol) were evaporated three times from anhydrous pyridine (3 mL) and dissolved in trimethylphosphate (0.3 mL). POCl$_3$ (8 µL, 0.09 mmol) was added, and the mixture was stirred for one hour at 0° C. A solution of bis-tri-n-butylammonium pyrophosphate (142 mg, 0.3 mmol) and tri-n-butylamine (60 µL) in anhydrous DMF (0.6 mL) was added. After five minutes of stirring, triethylammonium bicarbonate buffer (1 M, pH 7.5; 10 mL) was added. The reaction was stirred for one hour at room temperature, followed by the dropwise addition of concentrated ammonium hydroxide (5 mL, 27%) at 0° C. The mixture was stirred for one additional hour at room temperature and then lyophilized to dryness. The residue was dissolved in water (10 mL), filtered, and purified with reverse-phase HPLC using a Perkin Elmer OD-300 C$_{18}$ column (4.6×250 mm) to yield $O^6$-[4-(3-amino-1-propynyl)-2-nitrobenzyl]-2'-deoxyguanosine-5'-triphosphate dG.14. Mobile phase: A, 100 mM triethylammonium acetate (TEAA) in water (pH 7.0); B, 100 mM TEAA in water/CH$_3$CN (30:70). HPLC purification was achieved using a linear gradient of 5-50% B for 20 minutes and then 50-90% B for 10 minutes.

$^1$H NMR (400 MHz, D$_2$O): δ 8.28 (s, H-8), 8.26 (s, 1 H, Ph-H), 7.80 (d, 1 H, J=8.0 Hz, Ph-H), 7.63 (d, 1 H, J=8.0 Hz, Ph-H), 6.38 (t, 1 H, J=6.4 Hz, H-1'), 5.88 (br s, 2 H, Ph-CH$_2$), 4.29 (m, 3 H, H-4', H-5'), 3.67 (s, 2 H, CH$_2$), 2.80 (m, 1 H, H-2'a), 2.56 (m, 1 H, H-2'b);

$^{31}$P NMR (162 MHz, D$_2$O): 6-5.85 (d, J=19.4 Hz), −10.98 (d, J=19.4 Hz), −21.78 (t, J=19.4 Hz);

ToF-MS (ESI): For the molecular ion C$_{20}$H$_{24}$N$_7$O$_{15}$P$_3$Na [M+Na]$^+$, the calculated mass was 718.0441, and the observed mass was 718.0600.

6-ROX Lableled $O^6$-[4-(3-Amino-1-propynyl)-2-nitrobenzyl]-2'-deoxyguanosine-5'-triphosphate (WW2p121)

A solution of 6-ROX-SE (0.3 mg, 0.47 µmol) in anhydrous DMSO (12 µL) was added to a solution of triphosphate dG.14 (0.36 µmol) in Na$_2$CO$_3$/NaHCO$_3$ buffer (0.1 M, pH 9.2; 0.6 mL) and incubated at room temperature for one hour. The reaction was purified with reverse-phase HPLC using a Perkin Elmer OD-300 C$_{18}$ column (4.6×250 mm) to yield the 6-ROX labeled triphosphate WW2p121. Mobile phase: A, 100 mM TEAA in water (pH 7.0); B, 100 mM TEAA in water/CH$_3$CN (30:70). HPLC purification was achieved using a linear gradient of 5-50% B for 20 minutes and then 50-90% B for 10 minutes. The concentration of WW2p121 was estimated by adsorption spectroscopy using the extinction coefficient of the 6-ROX dye (i.e., 82,000 at 575 nm).

Synthesis of O⁶-[1-(2-nitrophenyl)ethyl]-2'-deoxyguanosine-5'-triphosphate (WW2p143)

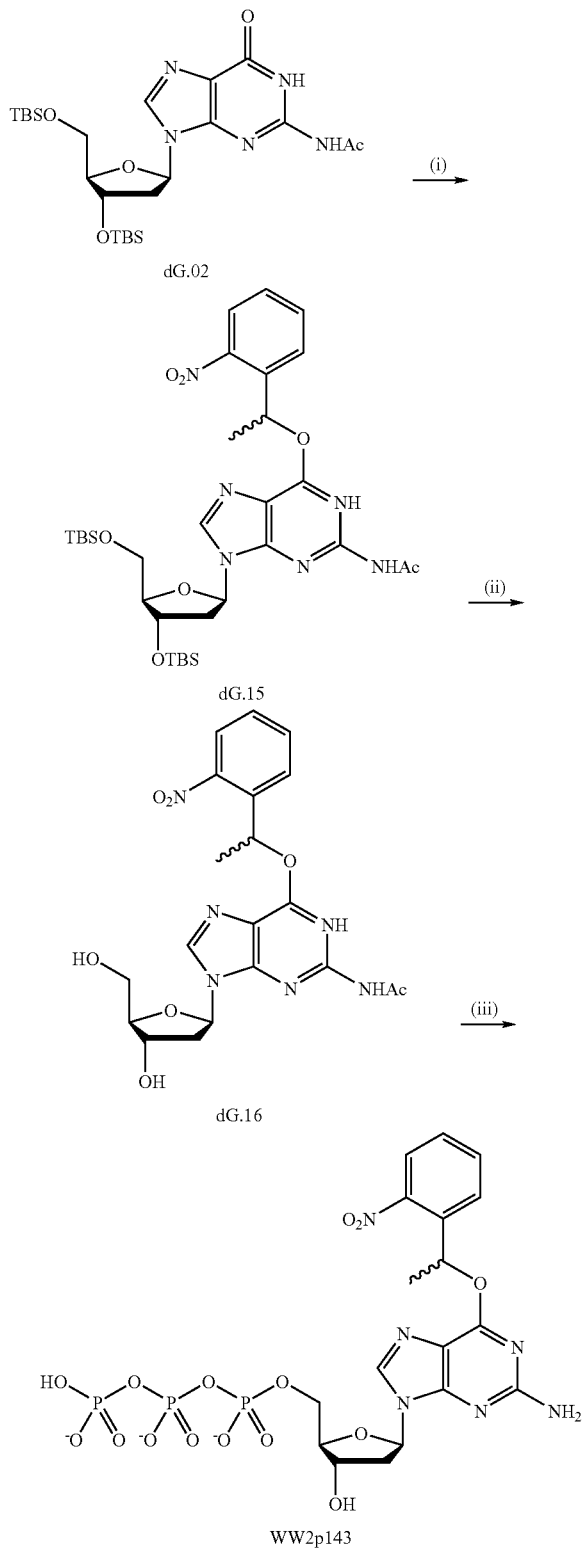

dG.02 dG.15 dG.16

WW2p143

Scheme. Synthesis of O⁶-[1-(2-nitrophenyl)ethyl]-2'-deoxyguanosine-5'-triphosphate. (i) 1-(2-nitrophenyl)etha-nol, PPh₃, DIAD, anhydrous THF, room temperature, six hours, 74%; (ii) n-Bu₄NF, THF, 0° C., then gradually warmed to room temperature, four hours, 64%; (iii) POCl₃, proton sponge, (MeO)₃PO, 0° C., two hours; (n-Bu₃NH)₂H₂P₂O₇, n-Bu₃N, DMF, five minutes; 1 M HNEt₃HCO₃, one hour; NH₄OH, 60° C., three hours.

O⁶-[1-(2-Nitrophenyl)ethyl]-N²-acetyl-3',5'-bis-O-(tert-butyldimethylsilyl)-2'-deoxyguanosine (dG.15)

A solution of compound dG.02 (108 mg, 0.2 mmol), 1-(2-nitrophenyl)ethanol (33 mg, 0.23 mmol) and PPh₃ (79 mg, 0.3 mmol) in anhydrous THF (2 mL) was treated with diisopropyl azodicarboxylate (DIAD, 59 μL, 0.3 mmol) and stirred for six hours at room temperature. The mixture was diluted with CH₂Cl₂ (20 mL), washed once with saturated NH₄Cl solution (10 mL), dried over Na₂SO₄, concentrated, and purified by silica gel chromatography to yield O⁶-[1-(2-nitrophenyl)ethyl]-N²-acetyl-3',5'-bis-O-(tert-butyldimethylsilyl)-2'-deoxyguanosine dG.15 (102 mg, 74%, 1:1 mixture of diastereomers) as a yellow foam.

¹H NMR (400 MHz, CDCl₃) for diastereomers: 68.13 and 8.12 (2 s, 1 H, H-8). 7.89 (d, 1 H, J=8.0 Hz, Ph-H), 7.83 (m, 1 H, Ph-H), 7.74 (br s., 1 H, NH), 7.57 (t, 1 H, J=7.2 Hz, Ph-H), 7.40 (t, 1 H, J=8.0 Hz, Ph-H), 6.69 (m, 1 H, PhCH), 6.36 (t, 1 H, J=6.3 Hz, H-1'), 4.56 (m, 1 H, H-3'), 3.98 (m, 1 H, H-4'), 3.82 (m, 1 H, H-5'a), 3.76 (m, 1 H, H-5'b), 2.50 (m, 1 H, H-2'a), 2.41 (m, 4 H, H-2'b and CH₃CO), 1.88 (2 d, J=6.5 Hz, CH₃), 0.91 (s, 18 H, (CH₃)₃CSi), 0.10 (s, 6 H, (CH₃)₂Si), 0.09 (s, 6 H, (CH₃)₂Si).

O⁶-[1-(2-Nitrophenyl)ethyl]-N²-acetyl-2'-deoxyguanosine (dG.16)

A solution of n-Bu₄NF (95 mg, 0.36 mmol) in THF (2 mL) was added to a solution of compound dG.15 (100 mg, 0.15 mmol) in THF (5 mL) at 0° C. The mixture was gradually warmed to room temperature and stirred for four hours. Silica gel (500 mg, 60-200 mesh) was added, and the mixture was evaporated in vacuo. The residue was purified by silica gel chromatography to yield O⁶-[1-(2-nitrophenyl)ethyl]-N²-acetyl-2'-deoxyguanosine dG.16 (43 mg, 64%, 1:1 mixture of diastereomers).

¹H NMR (400 MHz, DMSO-d₆) for diastereomers: δ 10.19 and 10.18 (2 s, 1 H, D₂O exchangeable, NH), 8.43 (2 s, 1 H, H-8), 8.04 (d, J=8.2 Hz, Ph-H), 7.79-7.74 (m, 2 H, Ph-H), 7.56 (t, 1 H, J=8.1 Hz, Ph-H), 6.84 (m, 1 H, PhCH), 6.26 (t, 1 H, J=6.8 Hz, H-1'), 5.29 (2 d, 1 H, D₂O exchangeable, 5'-OH), 4.88 (m, 1 H, D₂O exchangeable, 3'-OH), 4.39 (m, 1 H, H-3'), 3.82 (m, 1 H, H-4'), 3.56 (m, 1 H, H-5'b), 3.51 (m, 1 H, H-5'a), 2.56 (m, 1 H, H-2'a), 2.23 (m, 1 H, H-2'b), 2.12 (s, 3 H, CH₃CO), 1.79 (2 d, J=6.4 Hz, CH₃);

ToF-MS (ESI): For the molecular ion C₂₀H₂₁N₆O₇ [M-H]⁻, the calculated mass was 457.1472, and the observed mass was 457.1392.

O⁶-[1-(2-Nitrophenyl)ethyl]-2'-deoxyguanosine-5'-triphosphate (WW2p143)

Compound dG.16 (25 mg, 0.055 mmol) and proton sponge (23 mg, 0.11 mmol) were evaporated three times from anhydrous pyridine (2 mL) and dissolved in trimethylphosphate (0.3 mL). POCl₃ (8 μL, 0.08 mmol) was added, and the mixture was stirred for two hours at 0° C. A solution of bis-tri-n-butylammonium pyrophosphate (130 mg, 0.28 mmol) and tri-n-butylamine (55 μL) in anhydrous DMF (0.55 mL) was added. After five minutes of stirring, triethylammonium bicarbonate buffer (1 M, pH 7.5; 10 mL) was added. The reaction was stirred for one hour at room temperature and then lyophilized to dryness. The residue was dissolved in water (10 mL), filtered, and part of the solution was purified with reverse-phase HPLC using a Perkin Elmer OD-300 $C_{18}$ column (4.6×250 mm) to yield $O^6$-[1-(2-nitrophenyl)ethyl]-$N^2$-acetyl-2'-deoxyguanosine-5'-triphosphate. Mobile phase: A, 100 mM triethylammonium acetate (TEAA) in water (pH 7.0); B, 100 mM TEAA in water/$CH_3CN$ (30:70). HPLC purification was achieved using a linear gradient of 5-50% B for 40 minutes and then 50-90% B for 10 minutes. The purified triphosphate was then treated with concentrated ammonium hydroxide (2 mL, 27%) at 60° C. for three hours. Purification using reverse-phase HPLC was performed as described above to yield $O^6$-[1-(2-nitrophenyl)ethyl]-2'-deoxyguanosine-5'-triphosphate WW2p143 (1:1 mixture of diastereomers).

$^1$H NMR (400 MHz, $D_2O$) for diastereomers: 8.26 and 8.25 (2 s, 1 H, H-8), 8.02 (d, J=8.2 Hz, Ph-H), 7.88 (d, 1 H, J=7.8 Hz, Ph-H), 7.72 (t, 1 H, J=7.6 Hz, Ph-H), 7.53 (t, 1 H, J=8.2 Hz, Ph-H), 6.71 (m, 1 H, PhCH), 6.34 (t, 1 H, J=6.8 Hz, H-1'), 4.25-4.16 (m, 3 H, H-4' and H-5'), 2.80 (m, 1 H, H-2'a), 2.51 (m, 1 H, H-2'b), 1.86 (d, 1 H, J=6.4 Hz, $CH_3$);

$^{31}$P NMR (162 MHz, $D_2O$) for diastereomers: 6-5.18 (d, J=20.4 Hz), −10.25 (d, J=19.3 Hz), −21.07 (t, J=19.8 Hz);

ToF-MS (ESI): For the molecular ion $C_{18}H_{22}N_6O_{15}P_3$ [M-H]$^-$, the calculated mass was 655.0356, and the observed mass was 655.0430.

Synthesis of 6-ROX Labeled $O^6$-{1-[4-(3-amino-1-propynyl)-2-nitrophenyl]ethyl}-2'-deoxyguanosine-5'-triphosphate (WW3p008)

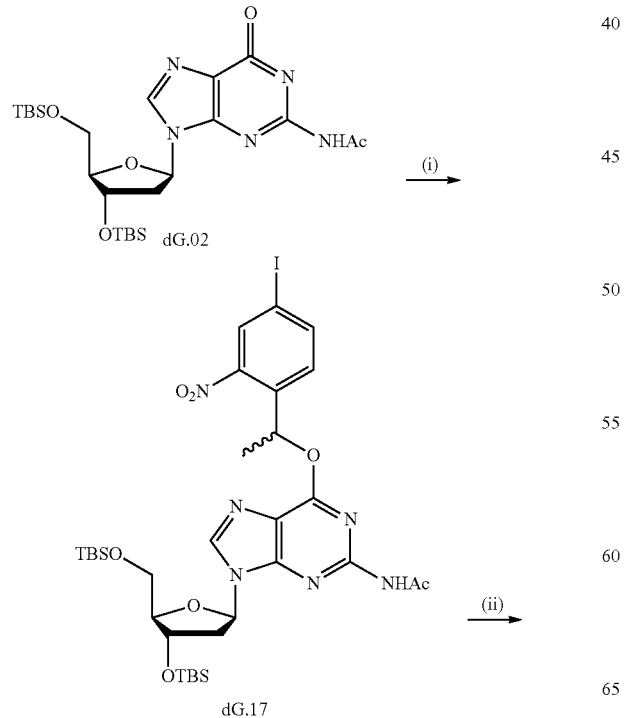

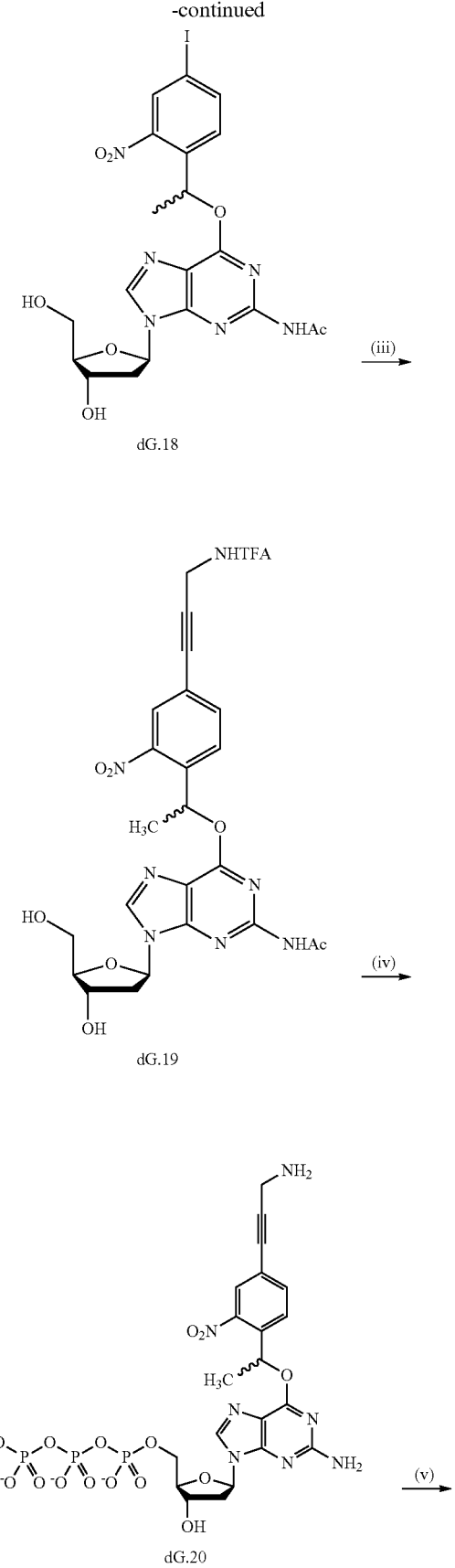

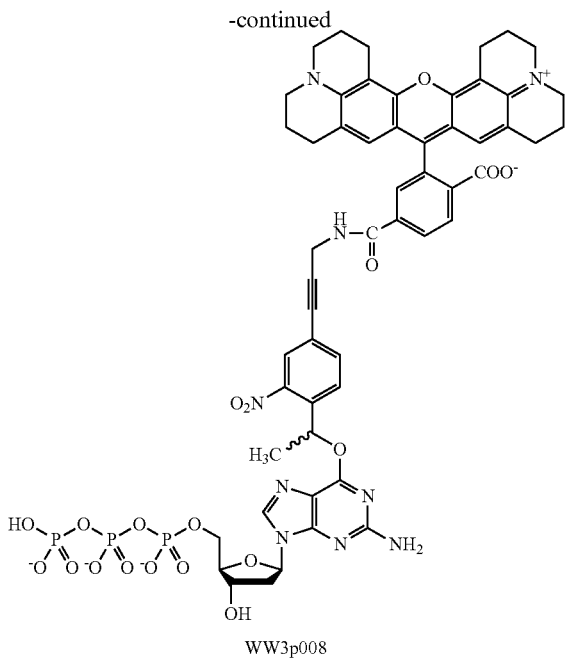

WW3p008

Scheme. Synthesis of 6-ROX labeled O$^6$-{1-[4-(3-amino-1-propynyl)-2-nitrophenyl]ethyl}-2'-deoxyguanosine-5'-triphosphate. (i) 1-(4-iodo-2-nitrophenyl)ethanol, PPh$_3$, DIAD, anhydrous THF, room temperature, overnight, 76%; (ii) n-Bu$_4$NF, THF, 0° C., then gradually warmed to room temperature, TWO hours, 52%; (iii) N-propargyltrifluoroacetamide, Pd(PPh$_3$)$_4$, CuI, Et$_3$N, anhydrous DMF, four hours, 96%; (iv) POCl$_3$, proton sponge, (MeO)$_3$PO, 0° C., two hours; (n-Bu$_3$NH)$_2$H$_2$P$_2$O$_7$, n-Bu$_3$N, DMF, five minutes; 1 M HNEt$_3$HCO$_3$, one hour; NH$_4$OH, 60° C., six hours; (v) 6-ROX-SE, 0.1 M Na$_2$CO$_3$/NaHCO$_3$ buffer (pH 9.2), one hour.

O$^6$-[1-(4-Iodo-2-nitrophenyl)ethyl]-N$^2$-acetyl-3',5'-bis-O-(tert-butyldimethylsilyl)-2'-deoxyguanosine (dG.17)

A solution of compound dG.02 (146 mg, 0.27 mmol), 1-(4-iodo-2-nitrophenyl)ethanol (79 mg, 0.27 mmol) and PPh$_3$ (106 mg, 0.4 mmol) in anhydrous THF (2 mL) was treated with diisopropyl azodicarboxylate (DIAD, 79 μL, 0.4 mmol) and stirred overnight at room temperature. The mixture was diluted with CH$_2$Cl$_2$ (20 mL), washed once with saturated NH$_4$Cl solution (10 mL), dried over Na$_2$SO$_4$, concentrated, and purified by silica gel chromatography to yield O$^6$-[1-(4-iodo-2-nitrophenyl)ethyl]-N$^2$-acetyl-3',5'-bis-O-(tert-butyldimethylsilyl)-2'-deoxyguanosine dG.17 (168 mg, 76%, 1:1 mixture of diastereomers) as a yellow foam.

$^1$H NMR (400 MHz, CDCl$_3$) for diastereomers: δ 8.20 (s, 1 H, Ph-H), 8.13 and 8.12 (2 s, 1 H, H-8), 7.87 (d, 1 H, J=8.0 Hz, Ph-H), 7.73 (br s, 1 H, NH), 7.55 (d, 1 H, J=8.0 Hz, Ph-H), 6.62 (m, 1 H, PhCH), 6.35 (t, 1 H, J=6.5 Hz, H-1'), 4.56 (m, 1 H, H-3'), 3.98 (m, 1 H, H-4'), 3.82 (m, 1 H, H-5'a), 3.77 (m, 1 H, H-5'b), 2.50 (m, 1 H, H-2'a), 2.41 (m, 4 H, H-2'b and CH$_3$CO), 1.85 (d, J=6.4 Hz, CH$_3$), 0.91 (s, 18 H, (CH$_3$)$_3$CSi), 0.09 (2 s, 12 H, (CH$_3$)$_2$Si).

O$^6$-[1-(4-Iodo-2-nitrophenyl)ethyl]-N$^2$-acetyl-2'-deoxyguanosine (dG.18)

A solution of n-Bu$_4$NF (125 mg, 0.48 mmol) in THF (1.5 mL) was added to a solution of compound dG.17 (155 mg, 0.19 mmol) in THF (2 mL) at 0° C. The reaction mixture was gradually warmed to room temperature and stirred for two hours. Silica gel 60 (1 g, 60-200 mesh) was added, and the mixture was evaporated in vacuo to dryness. The residue was purified by silica gel column chromatography to yield O$^6$-[1-(4-iodo-2-nitrophenyl)ethyl]-N$^2$-acetyl-2'-deoxyguanosine dG.18 (58 mg, 52%, 1:1 mixture of diastereomers) as a white foam.

$^1$H NMR (400 MHz, DMSO-d$_6$) for diastereomers: δ 10.21 and 10.20 (2 s, 1 H, D$_2$O exchangeable, NH), 8.43 (2 s, 1 H, H-8), 8.34 (2 s, Ph-H), 8.08 (2 d, 1 H, J=8.3 Hz, Ph-H), 7.54 (2 d, 1 H, J=8.3 Hz, Ph-H), 6.75 (m, 1 H, PhCH), 6.27 (t, 1 H, J=6.4 Hz, H-1'), 5.30 (m, 1 H, D$_2$O exchangeable, 5'-OH), 4.89 (m, 1 H, D$_2$O exchangeable, 3'-OH), 4.39 (m, 1 H, H-3'), 3.82 (m, 1 H, H-4'), 3.56 (m, 1 H, H-5'b), 3.50 (m, 1 H, H-5'a), 2.60 (m, 1 H, H-2'a), 2.22 (m, 1 H, H-2'b), 2.12 (s, 3 H, CH$_3$CO), 1.75 (2 d, J=6.4 Hz, CH$_3$).

O$^6$-{1-[4-(3-Trifluoroacetamido-1-propynyl)-2-nitrophenyl]ethyl}-N$^2$-acetyl-2'-deoxyguanosine (dG.19)

A solution of compound dG.18 (58 mg, 0.1 mmol), N-propargyl trifluoroacetylamide (45 mg, 0.3 mmol), tetrakis(triphenylphosphine)-palladium(0) (11.5 mg, 0.01 mmol), copper(I) iodide (3.8 mg, 0.02 mmol) and triethylamine (27 μL, 0.19 mmol) was stirred at room temperature for four hours. Methanol (1 mL), CH$_2$Cl$_2$ (1 mL), and sodium bicarbonate (80 mg, 0.95 mmol) were added, and the mixture was stirred for an additional half hour, then concentrated in vacuo and purified by column chromatography on silica gel to yield O$^6$-{1-[4-(3-trifluoroacetamido-1-propynyl)-2-nitrophenyl]ethyl}-N$^2$-acetyl-2'-deoxyguanosine dG.19 (58 mg, 96%, 1:1 mixture of diastereomers).

$^1$H NMR (400 MHz, DMSO-d$_6$) for diastereomers: δ 10.21 and 10.20 (2 s. 1 H, D$_2$O exchangeable, NH), 10.08 (br, 1 H, NHCOCF$_3$), 8.43 (2 s, 1 H, H-8), 8.06 (s, 1 H, Ph-H), 7.77 (m, 2 H, Ph-H), 6.78 (m, 1 H, PhCH), 6.28 (t, 1 H, J=6.4 Hz, H-1'), 5.29 (2 d, 1 H, D$_2$O exchangeable, 5'-OH), 4.89 (t, 1 H, D$_2$O exchangeable, 3'-OH), 4.39 (m, 1 H, H-3'), 4.29 (d, 2 H, CH$_2$), 3.82 (m, 2 H, H-4'), 3.50 (m, 1 H, H-5'a), 3.44 (m, 1 H, H-5'b), 2.67 (m, 1 H, H-2'a), 2.23 (m, 1 H, H-2'b), 2.11 (s, 3 H, CH$_3$), 1.78 (d, 3 H, J=6.4 Hz, CH$_3$);

O$^6$-{1-[4-(3-Amido-1-propynyl)-2-nitrophenyl]ethyl}-2'-deoxyguanosine-5'-triphosphate (dG.20)

Compound dG.19 (44 mg, 0.07 mmol) and proton sponge (30 mg, 0.14 mmol) were evaporated three times from anhydrous pyridine (3 mL) and dissolved in trimethylphosphate (0.5 mL). POCl$_3$ (10 μL, 0.11 mmol) was added, and the mixture was stirred for three hours at 0° C. A solution of bis-tri-n-butylammonium pyrophosphate (166 mg, 0.35 mmol) and tri-n-butylamine (70 μL) in anhydrous DMF (0.7 mL) was added. After five minutes of stirring, triethylammonium bicarbonate buffer (1 M, pH 7.5; 10 mL) was added. The reaction was stirred for one hour at room temperature and then lyophilized to dryness. The residue was dissolved in water (10 mL), filtered, and part of the solution was purified with reverse-phase HPLC using a Perkin Elmer OD-300 C$_{18}$ column (4.6×250 mm) to yield O$^6$-{1-[4-(3-trifluoroacetamido-1-propynyl)-2-nitrophenyl]ethyl}-N$^2$-acetyl-2'-deoxyguanosine-5'-triphosphate. Mobile phase: A, 100 mM triethylammonium acetate (TEAA) in water (pH 7.0); B, 100 mM TEAA in water/CH₃CN (30:70). HPLC purification was achieved using a linear gradient of 5-50% B for 20 minutes and then 50-90% B for 10 minutes. The purified triphosphate was then treated with concentrated ammonium hydroxide (2 mL, 27%) at 60° C. for six hours to yield $O^6$-{1-[4-(3-amido-1-propynyl)-2-nitrophenyl]ethyl}-2'-deoxyguanosine-5'-triphosphate dG.20 (1:1 mixture of diastereomers).

$^1$H NMR (400 MHz, $D_2O$) for diastereomers: 8.21 and 8.20 (2 s, 1 H, H-8), 7.85 and 7.75 (2 s, 1 H, Ph-H), 7.64 (m, 1 H, Ph-H), 7.45 (m, 1 H, Ph-H), 6.53 (m, 1 H, PhCH), 6.28 (m, 1 H, H-1'), 4.23-4.12 (m, 3 H, H-4' and H-5'), 3.97 (s, 2 H, $CH_2$), 2.70 (m, 1 H, H-2'a), 2.50 (m, 1 H, H-2'b), 1.74 (m, 1 H, $CH_3$);

$^{31}$P NMR (162 MHz, $D_2O$) for diastereomers: 6-5.53 (d, J=20.1 Hz), −10.50 (d, J=19.3 Hz), −21.29 (t, J=19.8 Hz);

ToF-MS (ESI): For the molecular ion $C_{21}H_{25}N_7O_{15}P_3$ [M-H]⁻, the calculated mass was 708.0622, and the observed mass was 708.0609.

6-ROX Labeled $O^6$-{1-[4-(3-Amido-1-propynyl)-2-nitrophenyl]ethyl}-2'-deoxyguanosine-5'-triphosphate (WW3p008)

A solution of 6-ROX-SE (3 mg, 4.7 µmol) in anhydrous DMSO (120 µL) was added to a solution of triphosphate dG.20 (1.45 µmol) in $Na_2CO_3/NaHCO_3$ buffer (0.1 M, pH 9.2; 0.3 mL) and incubated at room temperature for one hour. The reaction was purified with reverse-phase HPLC using a Perkin Elmer OD-300 $C_{18}$ column (4.6×250 mm) to yield the 6-ROX labeled triphosphate WW3p008. Mobile phase: A, 100 mM TEAA in water (pH 7.0); B, 100 mM TEAA in water/CH₃CN (30:70). HPLC purification was achieved using a linear gradient of 5-50% B for 20 minutes and then 50-90% B for 10 minutes. The concentration of WW3p008 was estimated by adsorption spectroscopy using the extinction coefficient of the 6-ROX dye (i.e., 82,000 at 575 nm).

Separation of the Two Diastereoisomers of $O^6$-{1-[4-(3-amino-1-propynyl)-2-nitro-phenyl]ethyl}-2'-deoxyguanosine-5'-triphosphate (dG.20 ds1 and dG.20 ds2)

Separation of the two diastereoisomers of dG.20 was performed by reverse-phase HPLC using a Perkin Elmer OD-300 $C_{18}$ column (4.6×250 mm) to yield $O^6$-{(R or S)-1-[4-(3-amino-1-propynyl)-2-nitrophenyl]ethyl}-2'-deoxyguanosine triphosphate dG.20 ds1 (single diastereoisomer, absolute configuration not determined) and $O^6$-{(S or R)-1-[4-(3-amino-1-propynyl)-2-nitrophenyl]ethyl}-2'-deoxyguanosine triphosphate dG.20 ds2 (single diastereoisomer, absolute configuration not determined). Mobile phase: A, 100 mM triethylammonium acetate (TEAA) in water (pH 7.0); B, 100 mM TEAA in water/CH₃CN (30:70). HPLC purification was achieved using a linear gradient of 5-25% B for 70 minutes and then 25-50% B for 30 minutes.

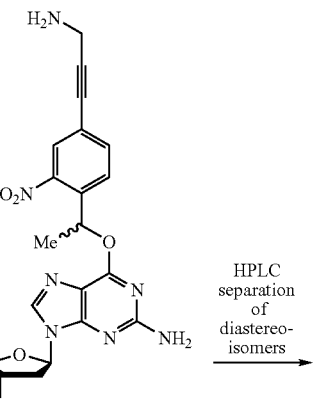

dG.20
1.1 mixture of diastereoisomers

HPLC separation of diastereoisomers →

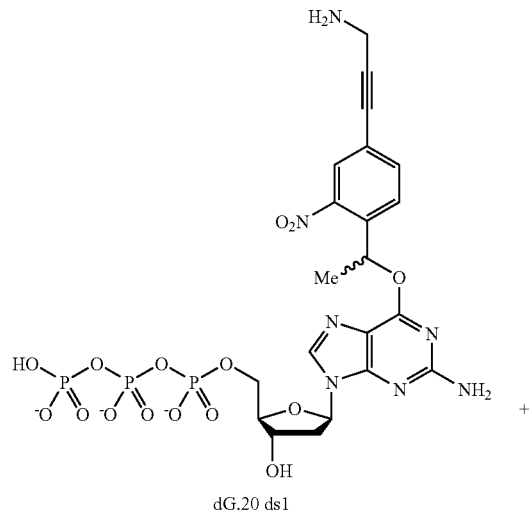

dG.20 ds1
Fast eluting single diastereoisomer, absolute configuration not determined, drawing is representative

+

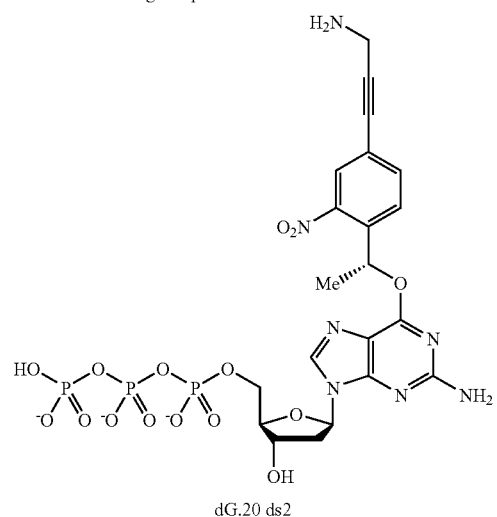

dG.20 ds2
Slow eluting single diastereoisomer, absolute configuration not determined, drawing is representative

Synthesis of 6-ROX labeled Single Diastereoisomer O⁶-{(R or S)-1-[4-(3-amino-1-propynyl)-2-nitrophenyl]ethyl}-2'-deoxyguanosine-5'-triphosphate (WW3p037)

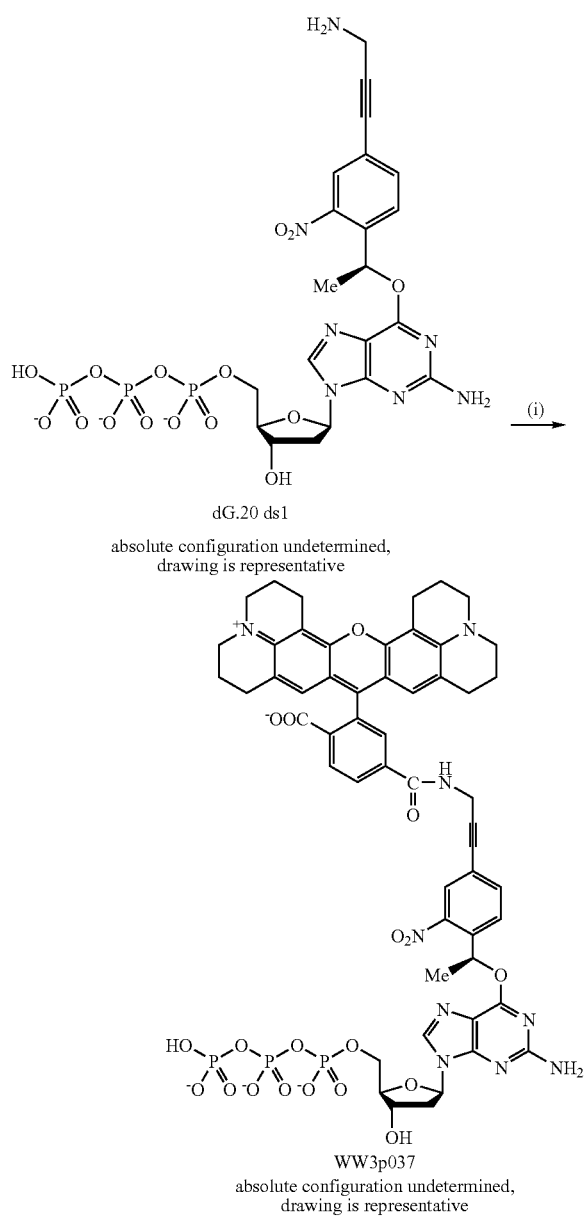

Scheme. Synthesis of 6-ROX labeled single diastereoisomer O⁶-{(R or S)-1-[4-(3-amino-1-propynyl)-2-nitrophenyl]ethyl}-2'-deoxyguanosine-5'-triphosphate. (i) 6-ROX-SE, 0.1 M NaHCO₃/Na₂CO₃, pH 9.2, one hour.

6-ROX Labeled Single Diastereoisomer O⁶-{(R or S)-1-[4-(3-amino-1-propynyl)-2-nitrophenyl]ethyl}-2'-deoxyguanosine-5'-triphosphate (WW3p037)

A solution of 6-ROX-SE (1.5 mg, 2.38 μmol) in anhydrous DMSO (120 μL) was added to a solution of triphosphate dG.20 ds1 (0.67 μmol, single diastereoisomer, absolute configuration not determined) in Na₂CO₃/NaHCO₃ buffer (0.1 M, pH 9.2; 150 μL) and incubated at room temperature for one hour. The reaction was purified by reverse-phase HPLC using a Perkin Elmer OD-300 C₁₈ column (4.6×250 mm) to yield the 6-ROX labeled single diastereoisomer triphosphate WW3p037. Mobile phase: A, 100 mM triethylammonium acetate (TEAA) in water (pH 7.0); B, 100 mM TEAA in water/CH₃CN (30:70). HPLC purification was achieved using a linear gradient of 5-50% B for 20 minutes and then 50-90% B for 20 minutes. The concentration of WW3p037 was estimated by absorption spectroscopy using the extinction coefficient of the 6-ROX dye (i.e., 82,000 at 575 nm).

Synthesis of 6-ROX Labeled Single Diastereoisomer O⁶-{(S or R)-1-[4-(3-amino-1-propynyl)-2-nitrophenyl]ethyl}-2'-deoxyguanosine-5'-triphosphate (WW3p039)

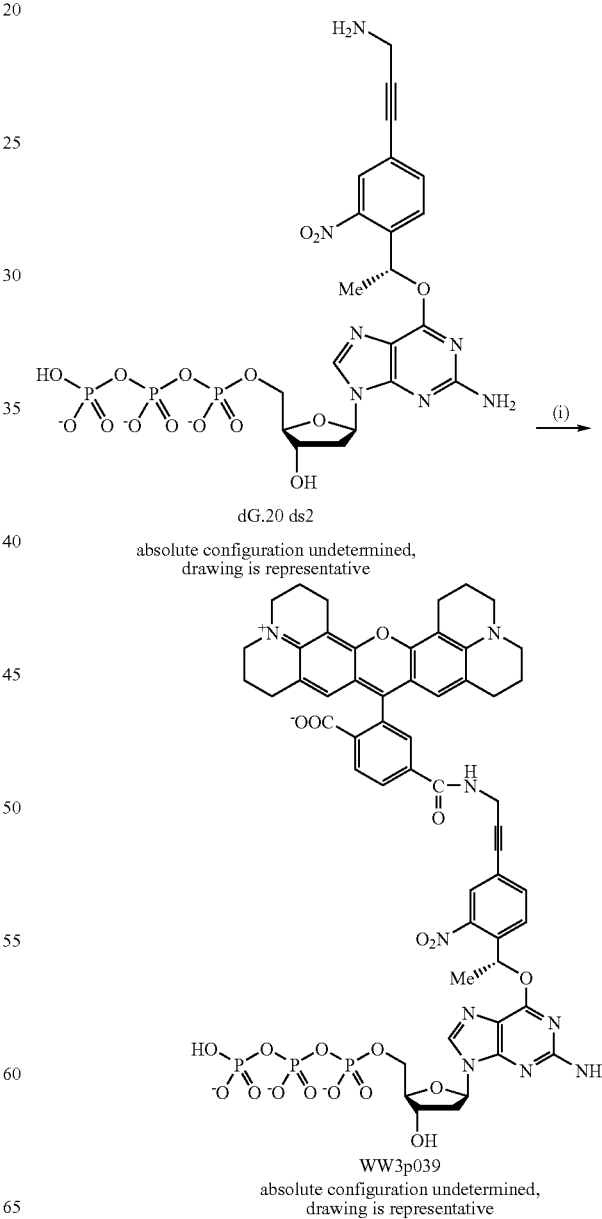

Scheme. Synthesis of 6-ROX labeled single diastereoisomer $O^6$-{(S or R)-1-[4-(3-amino-1-propynyl)-2-nitrophenyl]ethyl}-2'-deoxyguanosine-5'-triphosphate. (i) 6-ROX-SE, 0.1 M $NaHCO_3/Na_2CO_3$, pH 9.2, one hour.

6-ROX Labeled Single Diastereoisomer $O^6$-{(S or R)-1-[4-(3-amino-1-propynyl)-2-nitrophenyl]ethyl}-2'-deoxyguanosine-5'-triphosphate (WW3p039)

A solution of 6-ROX-SE (2.5 mg, 3.96 μmol) in anhydrous DMSO (200 μL) was added to a solution of triphosphate dG.20 ds2 (0.97 μmol, single diastereoisomer, absolute configuration not determined) in $Na_2CO_3/NaHCO_3$ buffer (0.1 M, pH 9.2; 150 μL) and incubated at room temperature for one hour. The reaction was purified by reverse-phase HPLC using a Perkin Elmer OD-300 $C_{18}$ column (4.6×250 mm) to yield the 6-ROX labeled single diastereoisomer triphosphate WW3p039. Mobile phase: A, 100 mM triethylammonium acetate (TEAA) in water (pH 7.0); B, 100 mM TEAA in water/$CH_3CN$ (30:70). HPLC purification was achieved using a linear gradient of 5-50% B for 20 minutes and then 50-90% B for 20 minutes. The concentration of WW3p039 was estimated by adsorption spectroscopy using the extinction coefficient of the 6-ROX dye (i.e., 82,000 at 575 nm).

Synthesis of 6-ROX Labeled Single Diastereoisomer $O^6$-{(R or S)-1-{4-[3-(6-amino-caproyl)amino-1-propynyl]-2-nitrophenyl}ethyl}-2'-deoxyguanosine-5'-triphosphate (WW3p041)

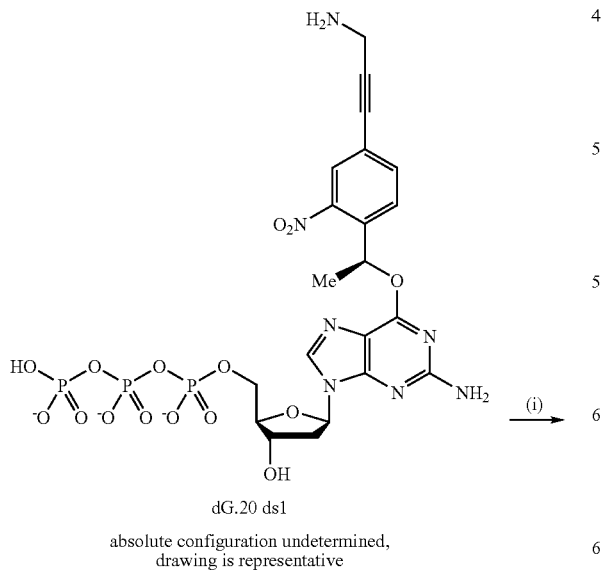

dG.20 ds1
absolute configuration undetermined, drawing is representative dG.21 ds1
absolute configuration undetermined, drawing is representative WW3p041
absolute configuration undetermined, drawing is representative Scheme. Synthesis of 6-ROX labeled single diastereoisomer $O^6$-{(R or S)-1-{4-[3-(6-aminocaproyl)amino-1-propynyl]-2-nitrophenyl}ethyl}-2'-deoxyguanosine triphosphate. (i) 6-N-(trifluoroacetyl)aminocaproic acid N-succinimidyl ester, 0.1 M $NaHCO_3/Na_2CO_3$, pH 9.2, one hour; $NH_4OH$, one hour; (ii) 6-ROX-SE, 0.1 M $NaHCO_3/Na_2CO_3$, pH 9.2, one hour.

$O^6$-{(R or S)-1-{4-[3-(6-Aminocaproyl)amino-1-propynyl]-2-nitrophenyl}ethyl}-2'-deoxyguanosine-5'-triphosphate (Single Diastereoisomer dG.21 ds1)

A solution of 6-N-(trifluoroacetyl)aminocaproic acid N-succinimidyl ester (1.0 mg, 3.08 μmol) in anhydrous DMSO (20 μL) was added to a solution of triphosphate dG.20 ds1 (0.89 μmol, single diastereoisomer, absolute configuration not determined) in $Na_2CO_3/NaHCO_3$ buffer (0.1 M, pH 9.2; 200 μL) and incubated at room temperature for one hour. Concentrated ammonium hydroxide (25% aq., 0.5 mL) was added, and the mixture was incubated at room temperature for another hour. The reaction was purified by reverse-phase HPLC using a Perkin Elmer OD-300 $C_{18}$ column (4.6×250 mm) to yield the triphosphate dG.21 ds1 (single diastereoisomer, absolute configuration not determined). Mobile phase: A, 100 mM triethylammonium acetate (TEAA) in water (pH 7.0); B, 100 mM TEAA in water/$CH_3CN$ (30:70). HPLC purification was achieved using a linear gradient of 5-50% B for 20 minutes and then 50-90% B for 10 minutes.

Synthesis of 6-ROX Labeled Single Diastereoisomer
$O^6$-{(R or S)-1-{4-[3-(6-amino-caproyl)amino-1-propynyl]-2-nitrophenyl}ethyl}-2'-deoxyguanosine-5'-triphosphate (WW3p041)

A solution of 6-ROX-SE (1.5 mg, 2.34 µmol) in anhydrous DMSO (120 µL) was added to a solution of triphosphate dG.21 ds1 (0.59 µmol, single diastereoisomer, absolute configuration not determined) in $Na_2CO_3$/$NaHCO_3$ buffer (0.1 M, pH 9.2; 200 µL) and incubated at room temperature for one hour. The reaction was purified by reverse-phase HPLC using a Perkin Elmer OD-300 $C_{18}$ column (4.6×250 mm) to yield the 6-ROX labeled single diastereoisomer triphosphate WW3p041. Mobile phase: A, 100 mM triethylammonium acetate (TEAA) in water (pH 7.0); B, 100 mM TEAA in water/$CH_3CN$ (30:70). HPLC purification was achieved using a linear gradient of 5-50% B for 20 minutes and then 50-90% B for 20 minutes. The concentration of WW3p041 was estimated by adsorption spectroscopy using the extinction coefficient of the 6-ROX dye (i.e., 82,000 at 575 nm).

Example 5

Polymerase End-Point (PEP) Assays

Numerous groups have employed qualitative, Sanger-based assays to estimate relative incorporation efficiencies of terminating nucleotide analogs compared to their natural nucleotide counterparts. Although useful, the ability to assay modified nucleotide analogs in the absence of natural nucleotides is not feasible using these assays. These two limitations led to a quantitative, polymerase end-point (PEP) assay, which is utilized in a high-throughput manner for screening numerous modified nucleotides against a number of well-characterized, commercially available polymerases. Identification of lead compounds with a specific DNA polymerase could then be prioritized for further kinetic studies. The PEP assay is designed with the polymerase concentration in excess of the primer/template complex (i.e., this complex is fully bounded with polymerase at the start of the titration), thereby limiting reaction to nucleotide binding and nucleotyl coupling steps. Limiting amounts of the desired nucleotide are then titrated across the appropriate concentration range (generally three orders of magnitude) to observe extension of a dye-labeled primer by gel electrophoresis. The end-point concentration is determined from a semi-log plot where the number of moles of substrate and product are equal, called the $IC_{50}$ (i.e., incorporation concentration at 50%) value.

For all polymerases evaluated in this study, 40 nM of oligo-template (5'-TACGGAGCA-GTACTGGCCGTCGTTTTACA (SEQ ID NO: 1), interrogation base is underlined and bolded) was annealed to 5 nM BODIPY-FL labeled primer (5'-TTGTAAAACGACGGC-CAGT (SEQ ID NO: 2)) in 1×ThermoPol buffer (20 mM Tris-HCl, pH 8.8; 10 mM $(NH_4)_2SO_4$; 10 mM KCl; 2 mM $MgSO_4$; 0.1% Triton X-100, New England BioLabs) at 80° C. for 30 seconds, 57° C. for 30 seconds, and then cooled to 4° C. The primer/template complex is then diluted by one-half (i.e., its final concentration is 2.5 nM in a volume of 10 µL) by the addition of DNA polymerase, nucleotide analog, and Ther-moPol buffer. This defines the lower limit of the $IC_{50}$ value for nucleotide titrations to 1.25 nM (i.e., [primer]=[primer+1]). Polymerase reactions were incubated at their appropriate temperature for 10 minutes, then cooled to 4° C. and quenched with 10 µL of stop solution (98% deionized formamide; 10 mM $Na_2EDTA$, pH 8.0; 25 mg/mL Blue Dextran, MW 2,000,000). Stopped reactions were heated to 90° C. for 30 seconds, and then placed on ice. The extension products were analyzed on a 10% Long Ranger (Cambrex) polyacrylamide gel using an AB model 377 DNA sequencer, and the quantitative data are displayed as a linear-log plot of product formation versus compound concentration. The PEP assays were performed in triplicate for each DNA polymerase/nucleotide analog combination to calculate its $IC_{50}$ values±one standard deviation.

The number of activity units for eight commercially available, 3'-exonuclease deficient (3'-exo-) DNA polymerases was first determined by titration with 2'-deoxyadenosine triphosphate (dATP, concentration range from 0.1 nM to 100 nM) with the goal of reaching the PEP $IC_{50}$ limit of 1.25 nM (data not shown). In general, increasing the number of units reduced the $IC_{50}$ values for dATP towards this limit, with exception with Taq, THERMINATOR™, and THERMINA-TOR™ II. For these enzymes, there was an increase in $IC_{50}$ values for dATP with increasing enzyme concentration, which was not investigated further and presumed to be due to a direct relationship with increasing enzyme concentration and phosphorolysis. For these cases, the number of units used for subsequent PEP assays were those activity units that gave the lowest $IC_{50}$ values for dATP.

Modified Nucleotide Titrations:

WW1p129 and ddATP were then titrated using the PEP assay with the eight DNA polymerases (unit activities previously defined) in the concentration range of either 0.1 nM to 100 nM, 1 nM to 1 µM, 10 nM to 10 µM, or 100 nM to 100 µM (see Table 1). UV-light sensitive compounds were handled at all times in low light conditions to minimize conversion to dATP. These data show in all cases, except that for AMPLI-TAQ® DNA polymerase, FS, that WW1p129 is incorporated more efficiently (i.e., lower $IC_{50}$ value) than ddATP.

TABLE 1

Summary of PEP assay result for WW1p129 using eight different DNA polymerases

| DNA polymerase | $IC_{50}$ values | | |
|---|---|---|---|
| | dATP | WW1p129 | ddATP |
| Bst: 65° C. | 1.2 ± 0.1 nM | 21 ± 3 nM | 0.37 ± 0.03 µM |
| Klenow(3'-exo-): 37° C. | 1.6 ± 0.1 nM | 4.3 ± 0.2 nM | 29 ± 5 nM |
| Taq: 68° C. | 5.5 ± 0.5 nM | 2.1 ± 0.2 µm | 12.6 ± 0.9 µm |
| Taq FS: 68° C. | 5.3 ± 0.2 nM | 0.89 ± 0.06 µm | 3.3 ± 0.1 nm |

TABLE 1-continued

Summary of PEP assay result for WW1p129 using eight different DNA polymerases

| DNA polymerase | IC$_{50}$ values | | |
|---|---|---|---|
| | dATP | WW1p129 | ddATP |
| Therminator: 75° C. | 2.3 ± 0.3 nM | 3.1 ± 0.4 nM | 9.7 ± 1.1 nM |
| Therminator II: 75° C. | 4.4 ± 0.6 nM | 7.8 ± 0.7 nM | 0.23 ± 0.03 µM |
| Vent(3'-exo-): 72° C. | 1.6 ± 0.2 nM | 2.1 ± 0.2 nM | 0.55 ± 0.04 µM |
| DeepVent(3'-exo-): 72° C. | 2.8 ± 0.2 nM | 11.0 ± 0.6 nM | 3.4 ± 0.4 µM |

PEP assays have also been performed using a number of photocleavable terminating nucleotides using Bst polymerase and Therminator DNA polymerase (Table 2), which shows the compounds are effectively incorporated. The data in the Table 2 suggests that the compounds according to the invention are excellent substrates.

TABLE 2

Comparison of IC50 values with Bst and Therminator polymerases

| compound | Bst | Therminator |
|---|---|---|
| WW1p129 | 39 ± 9 nm | 2.5 ± 0.4 nm |
| VL3p03085 | 138 ± 35 nm | 1.1 ± 0.1 nm |
| WW2p044 | 57 ± 11 nm | 1.8 ± 0.2 nm |
| WW2p077 | 3.8 ± 0.2 micromolar | 6.9 ± 0.5 nm |
| WW2p050 | n/a | 4.4 ± 0.6 nm |
| WW2p075 | n/a | 3.8 ± 1.1 nm |
| WW2p080 | n/a | 3.0 ± 0.6 nm |
| WW2p121 | n/a | 6.3 ± 0.4 nm |

All patents and patent publications referred to herein are hereby incorporated by reference. Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:
1. A compound selected from the group consisting of:
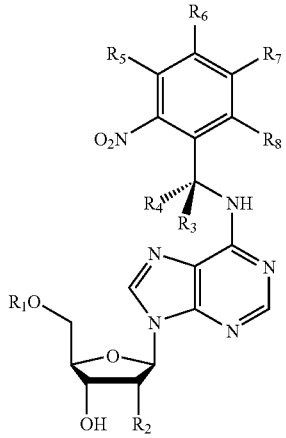
formula I
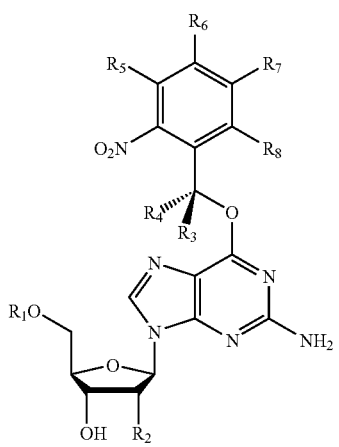
formula II
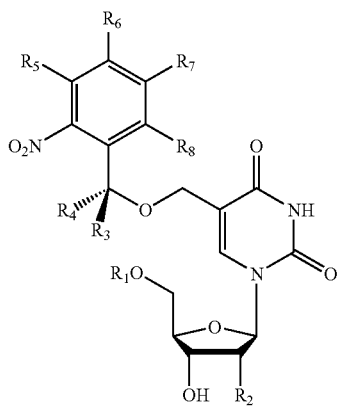
formula III
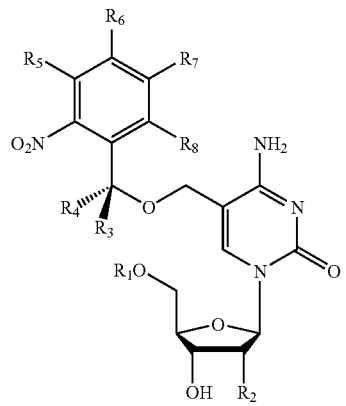
formula IV
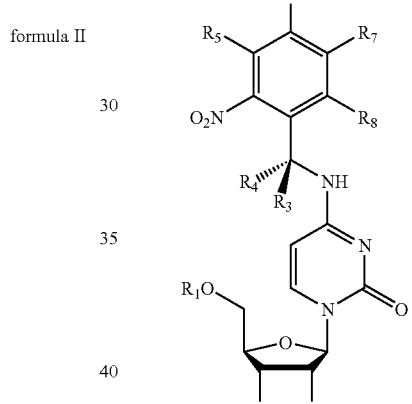
formula V
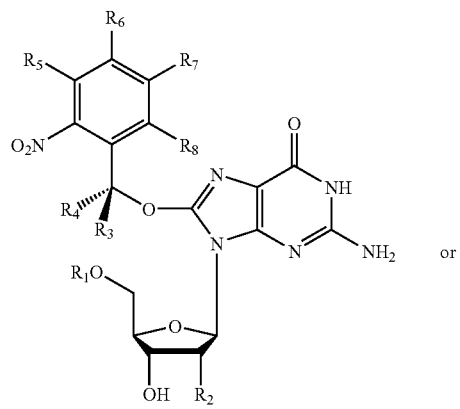
formula VI or

-continued formula VII

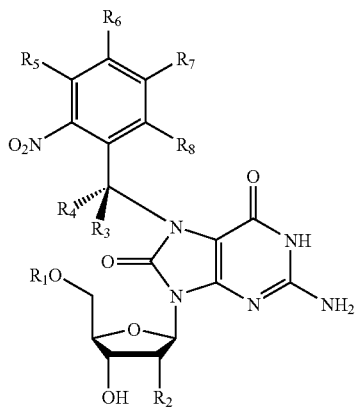

wherein $R_1$=H, monophosphate, diphosphate or triphosphate, $R_2$=H or OH, $R_3$ and $R_4$ are each independently selected from the group consisting of H, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, with the proviso that at least one of $R_3$ and $R_4$ is H, $R_5$, $R_6$, $R_7$, and $R_8$ are each independently selected from the group consisting of H, $OCH_3$, $NO_2$, CN, a halide, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, with the proviso that one of $R_5$, $R_6$, $R_7$, and $R_8$ is a linker group of the structure —C≡CCH$_2$NH$_2$, —C≡CCH$_2$NHC(O)(CH$_2$)$_5$NH$_2$,

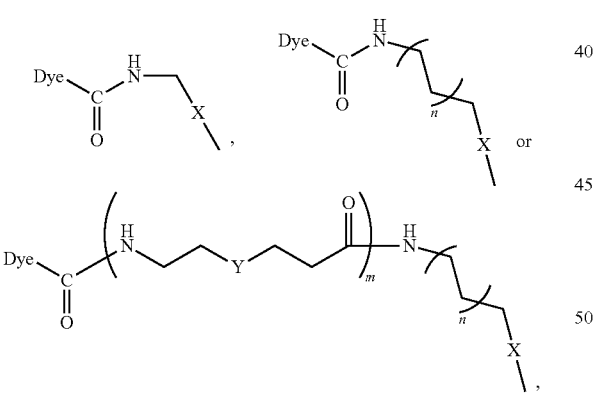

wherein X=CH$_2$, CH=CH, C≡C, O, S, or NH,
Y=CH$_2$, O, or NH,
n=an integer from 0-12;
m=an integer from 0-12, and
Dye=a fluorophore.

2. A compound according to claim 1, wherein $R_3$ and $R_4$ are each independently selected from the group consisting of H, —CH$_3$, —CH$_2$CH$_3$, —CH$_2$CH$_2$CH$_3$, isopropyl, tert-butyl, phenyl, 2-nitrophenyl, and 2,6-dinitrophenyl, with the proviso that at least one of $R_3$ and $R_4$ is H.

3. A compound according to claim 1, wherein $R_3$ or $R_4$ are each independently selected from the group consisting of H, alkyl and aromatic groups optionally containing at least one heteroatom in the alkyl or aromatic groups, and further wherein the aromatic group may optionally be an aryl or polycyclic group, with the proviso that at least one of $R_3$ and $R_4$ is H.

4. The compound of claim 2, wherein $R_3$ or $R_4$ is —CH$_3$ or isopropyl.

5. The compound of claim 1, further defined as:

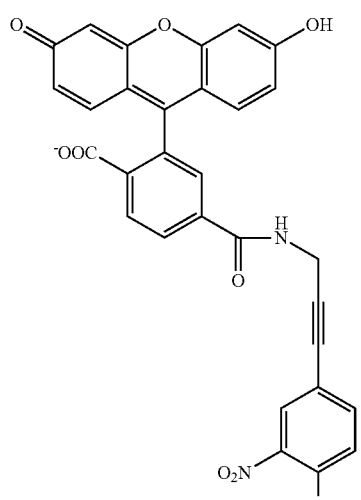

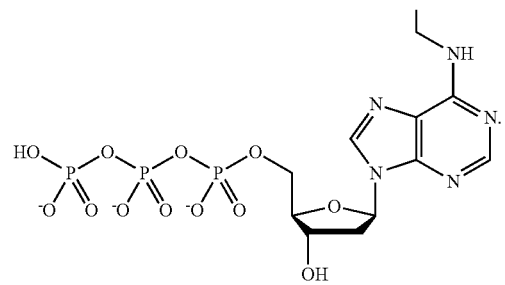

6. The compound of claim 5, further defined as:

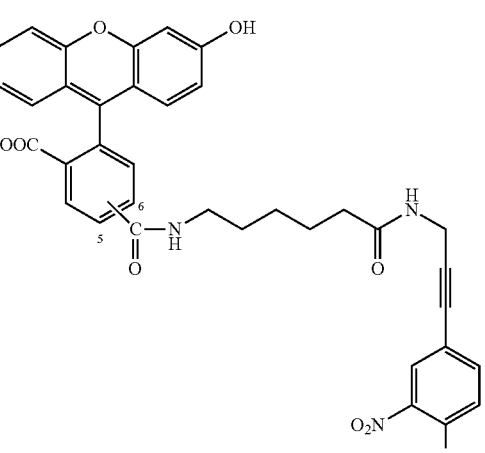

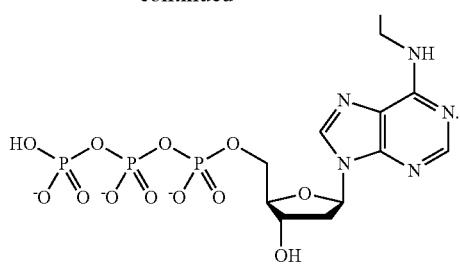
7. The compound of claim 1, further defined as:
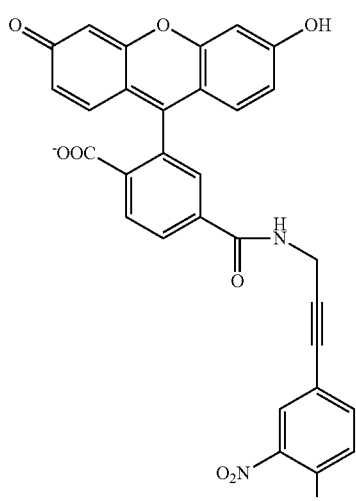
or a stereoisomer thereof.
8. The compound of claim 1, further defined as:
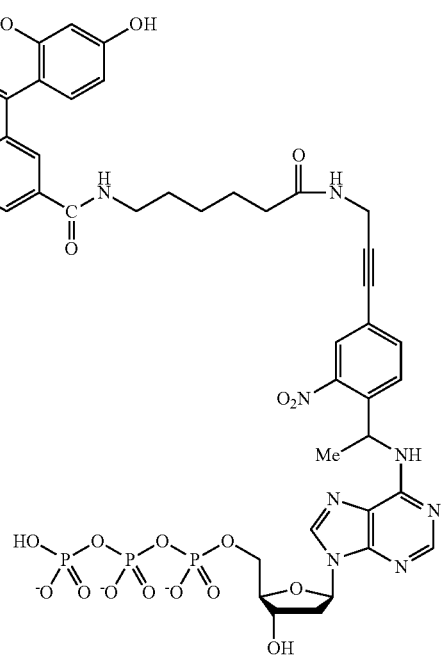
or a stereoisomer thereof.
9. The compound of claim 1, further defined as:
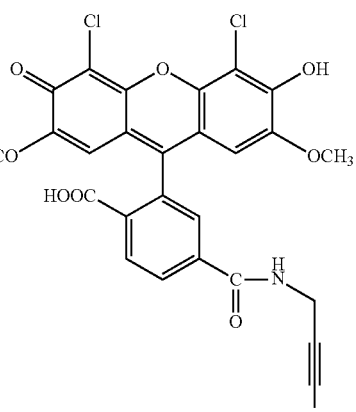
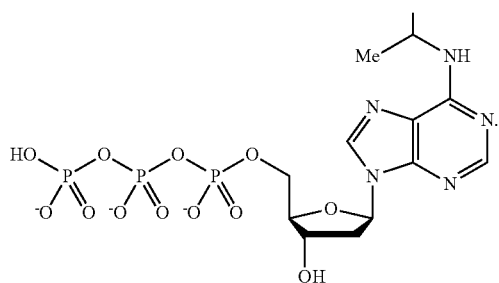
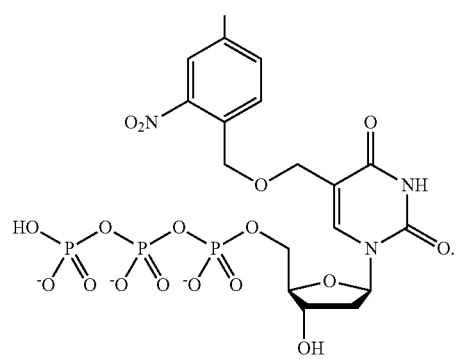

10. The compound of claim 1, further defined as:
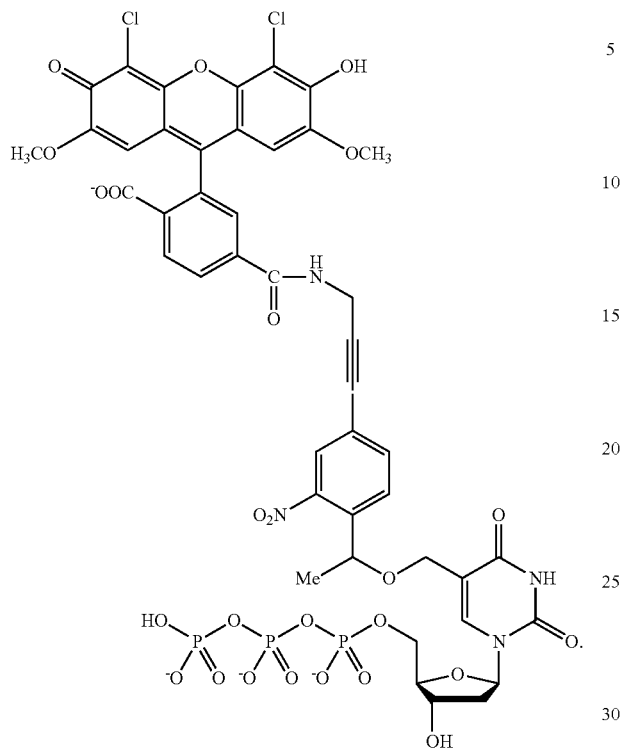
or a stereoisomer thereof.
11. The compound of claim 1, further defined as:
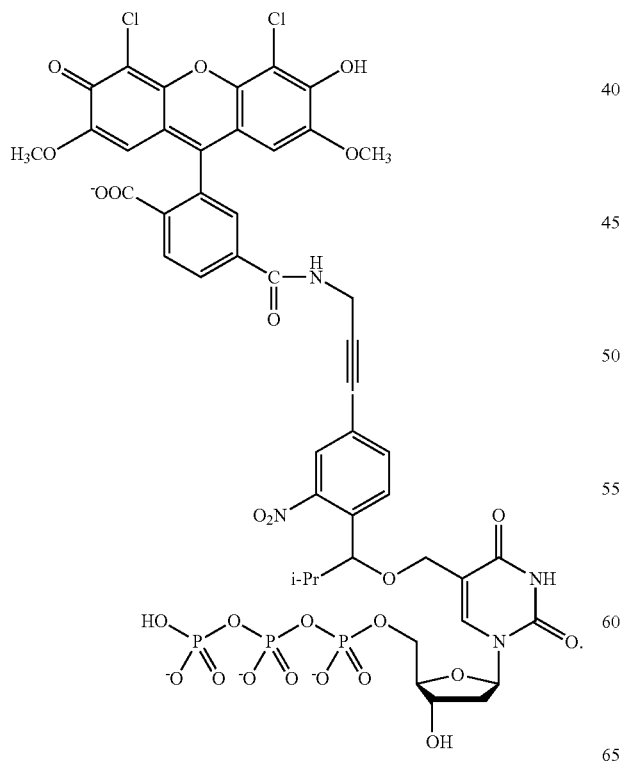
or a stereoisomer thereof.
12. The compound of claim 1, further defined as:
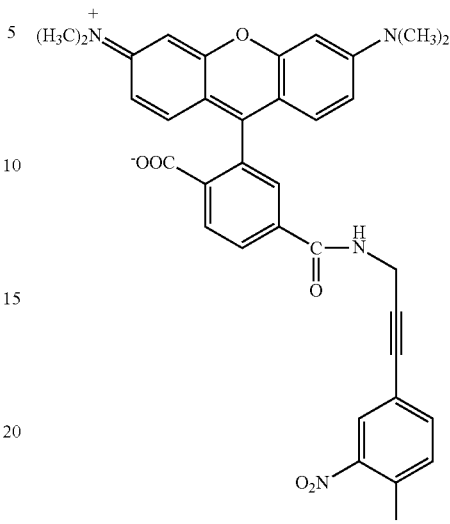
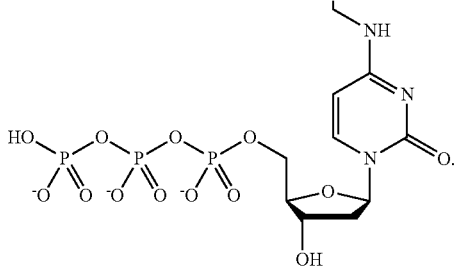
13. The compound of claim 1, further defined as:
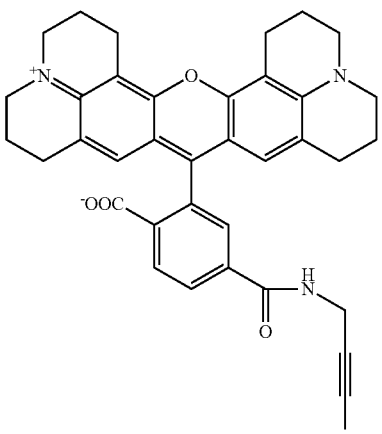

-continued
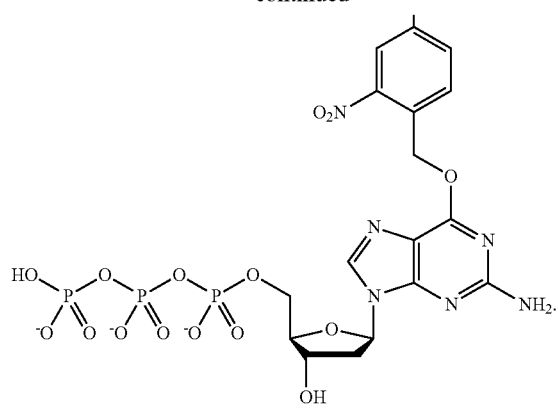
14. The compound of claim 1, further defined as:
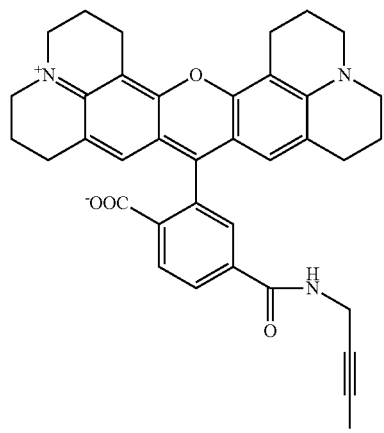
15. The compound of claim 1, further defined as:
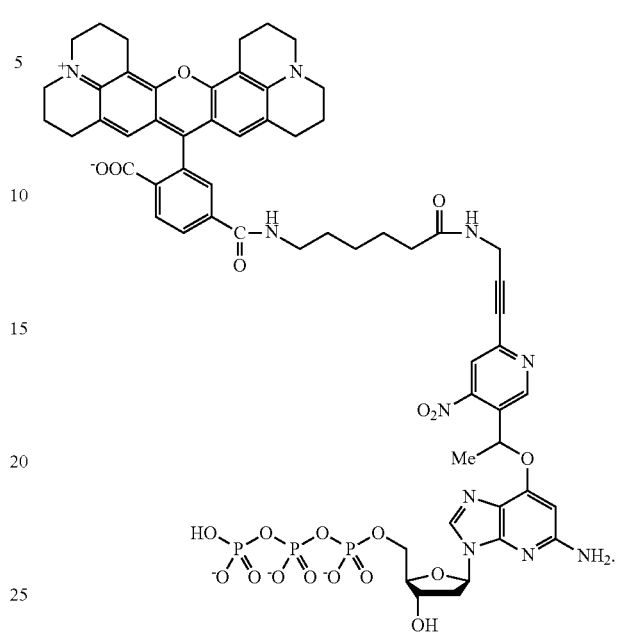
or a stereoisomer thereof.
16. The compound of claim 1, further defined as:
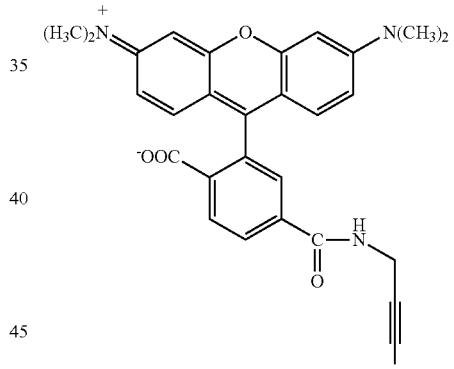
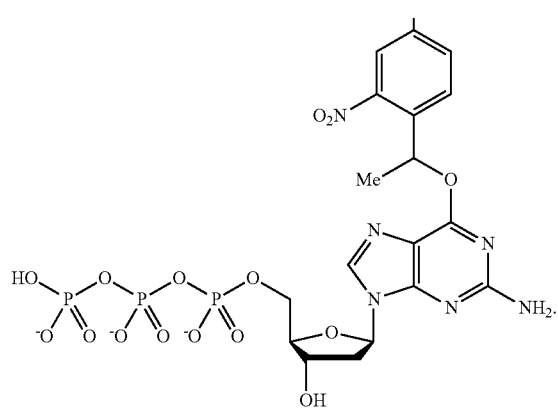
or a stereoisomer thereof.
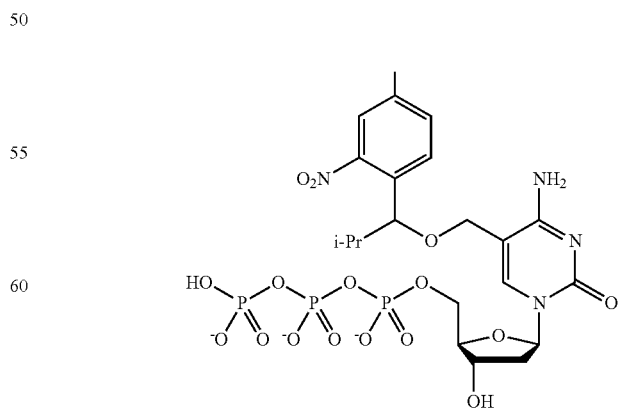
or a stereoisomer thereof.

17. The compound of claim 1, further defined as:

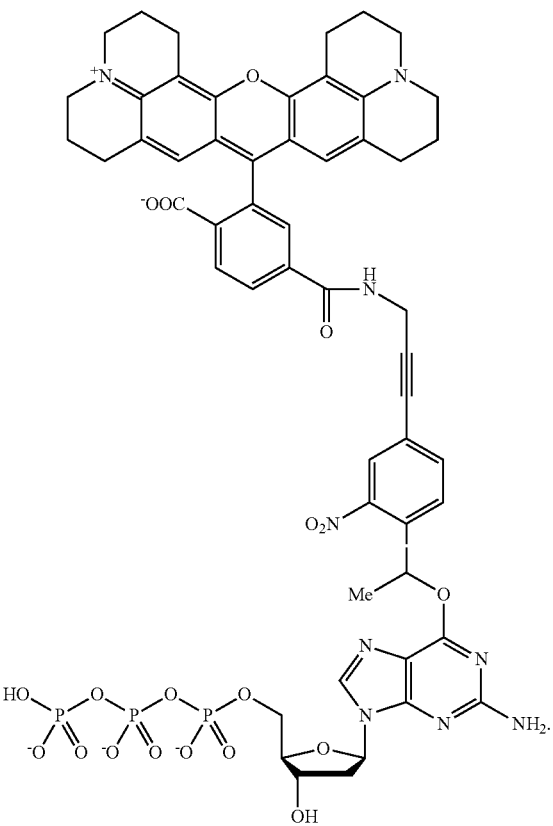

18. The compound of claim 1, further defined as:

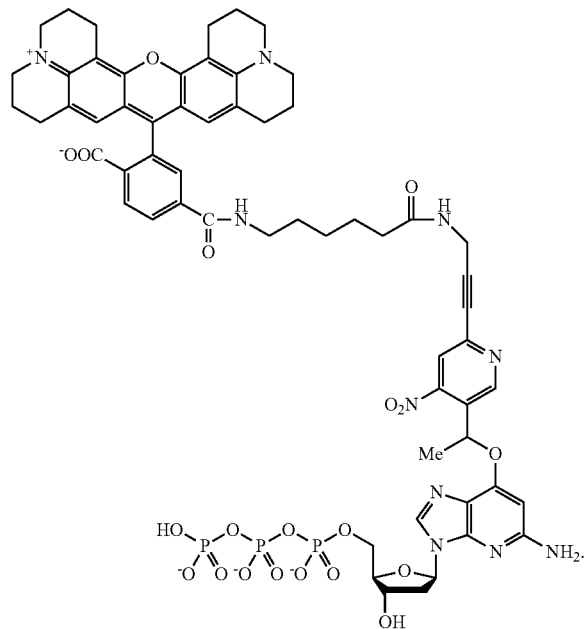

19. The compound of claim 1, further defined as a compound of formula (I).

20. The compound of claim 1, further defined as a compound of formula (II).

21. The compound of claim 1, further defined as a compound of formula (III).

22. The compound of claim 1, further defined as a compound of formula (IV).

23. The compound of claim 1, further defined as a compound of formula (V).

24. The compound of claim 1, further defined as a compound of formula (VI).

25. The compound of claim 1, further defined as a compound of formula (VII).

26. A compound according to any one of claims 19-25, wherein $R_3$ and $R_4$ are each independently selected from the group consisting of H, —$CH_3$, —$CH_2CH_3$, —$CH_2CH_2CH_3$, isopropyl, tert-butyl, phenyl, 2-nitrophenyl, and 2,6-dinitrophenyl, with the proviso that at least one of $R_3$ and $R_4$ is H.

27. A compound according to any one of claims 19-25, wherein $R_3$ or $R_4$ are each independently selected from the group consisting of H, alkyl and aromatic groups optionally containing at least one heteroatom in the alkyl or aromatic groups, and further wherein the aromatic group may optionally be an aryl or polycyclic group, with the proviso that at least one of $R_3$ and $R_4$ is H.

28. A compound according to any one of claims 19-25, wherein $R_3$ or $R_4$ is —$CH_3$ or isopropyl.

* * * * *

UNITED STATES PATENT AND TRADEMARK OFFICE
CERTIFICATE OF CORRECTION

PATENT NO.        : 7,897,737 B2           Page 1 of 10
APPLICATION NO.   : 11/567189
DATED             : March 1, 2011
INVENTOR(S)       : Weidong Wu et al.

It is certified that error appears in the above-identified patent and that said Letters Patent is hereby corrected as shown below:

In column 12, line 57 to column 13, line 18, delete chemical drawings and insert

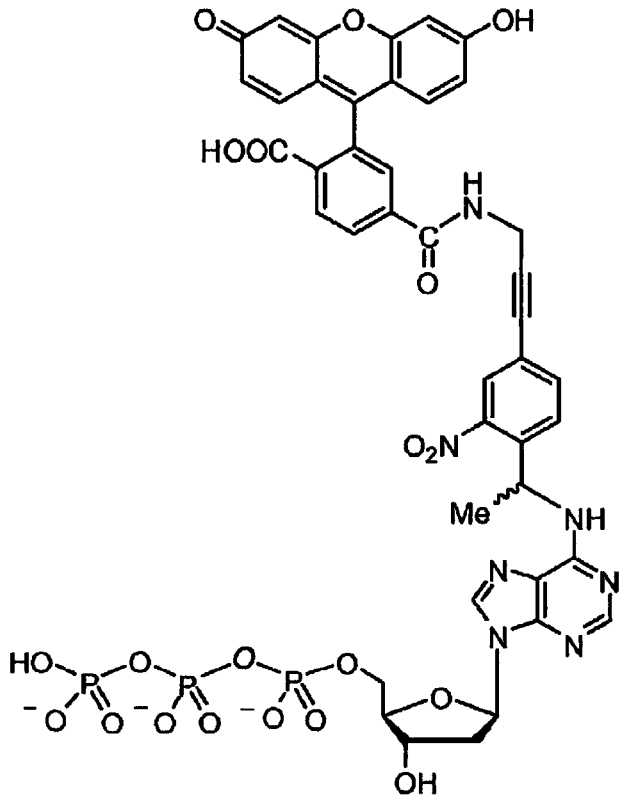

-- therefor.

Signed and Sealed this
Twentieth Day of March, 2012

David J. Kappos
*Director of the United States Patent and Trademark Office*

CERTIFICATE OF CORRECTION (continued)
U.S. Pat. No. 7,897,737 B2

In column 13, lines 18-49, delete chemical drawings and insert

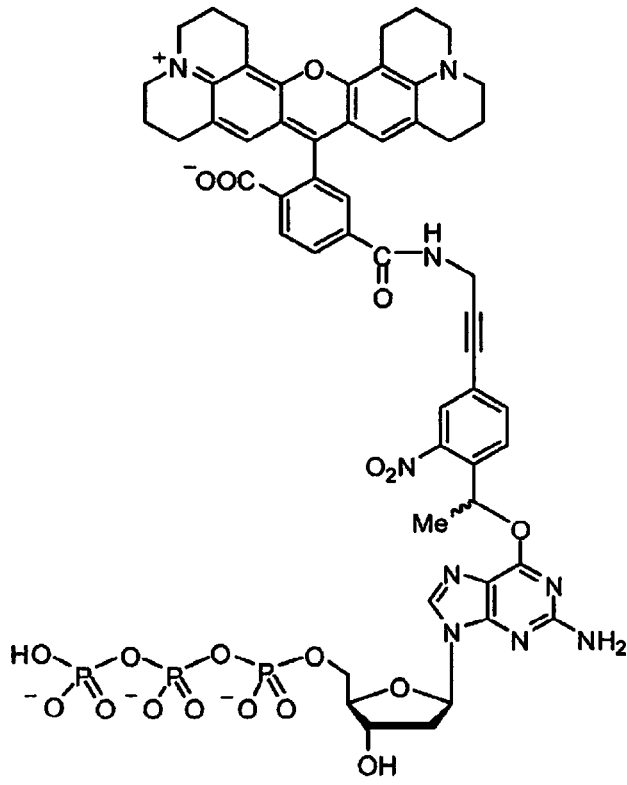

-- , -- therefor.

In column 13, line 50 to column 14, line 15, delete chemical drawings and insert

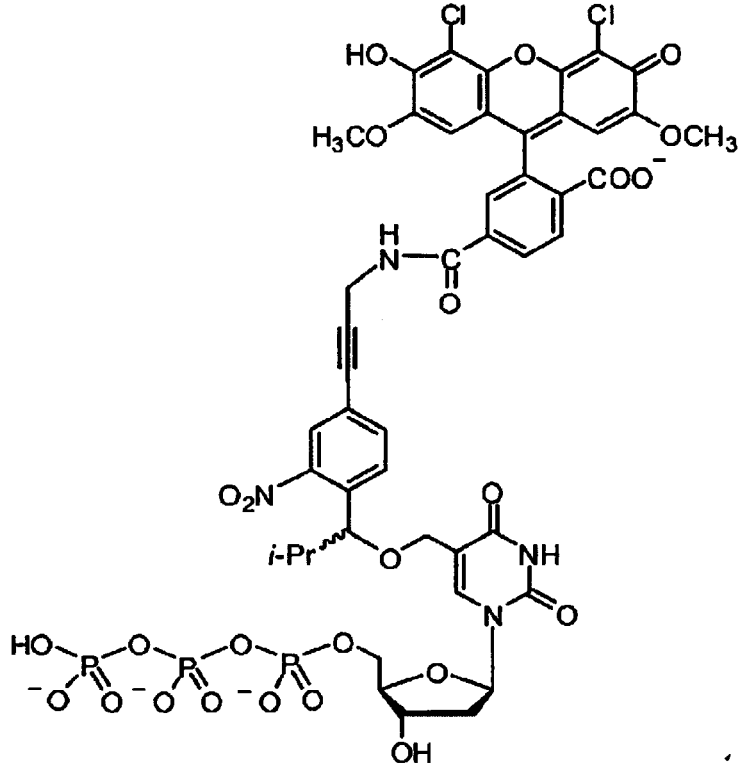

-- , -- therefor.

CERTIFICATE OF CORRECTION (continued)
U.S. Pat. No. 7,897,737 B2

In column 14, lines 16-44, delete chemical drawings and insert

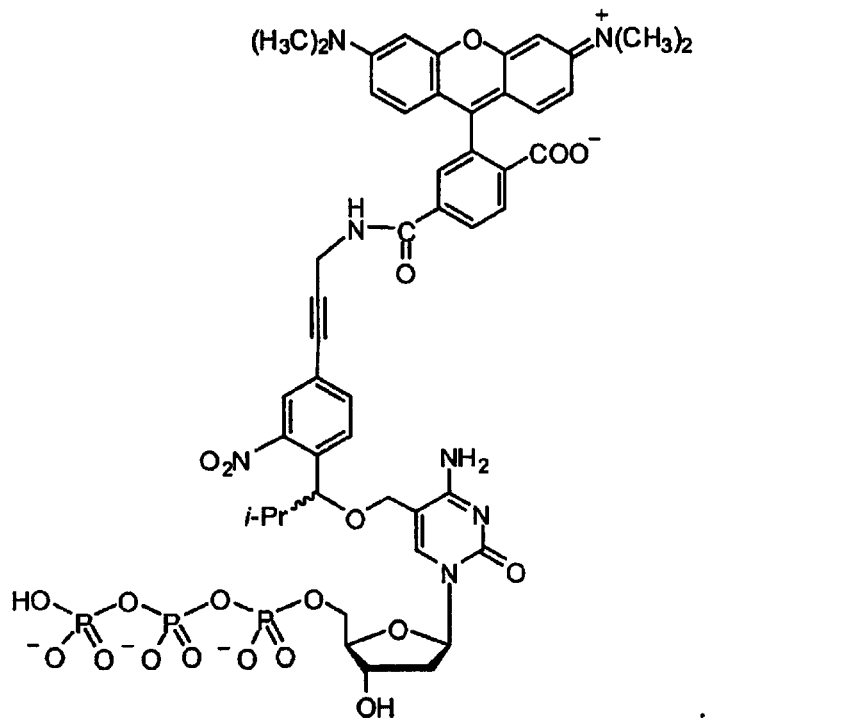

-- -- therefor.

In column 38, lines 48-66, delete chemical drawing and insert

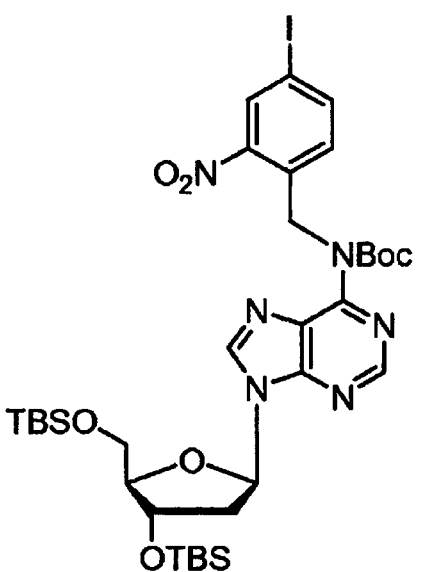

-- -- therefor.

In column 55, lines 3-27, delete chemical drawing and insert

CERTIFICATE OF CORRECTION (continued)
U.S. Pat. No. 7,897,737 B2

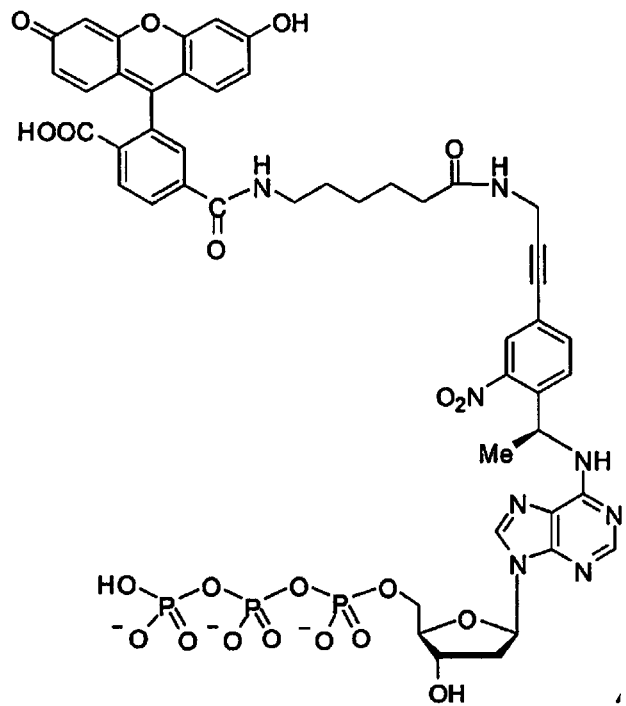

-- -- therefor.

In claim 1, column 132, line 60, delete "or" and insert --and-- therefor.

In claim 5, column 134, lines 10-46, delete the chemical drawing and the dot near one of the nitrogen atoms. Insert

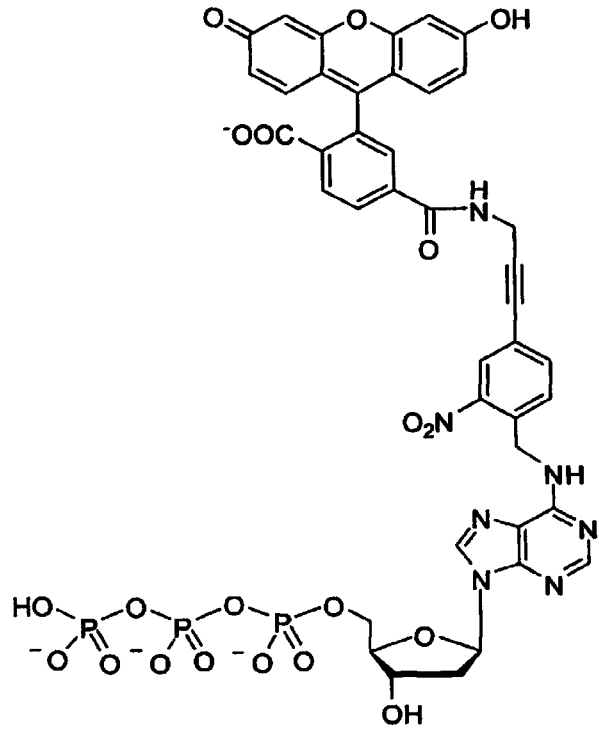

-- -- therefor.

In claim 7, column 135, lines 20-63, delete the chemical drawing and the dot near one

CERTIFICATE OF CORRECTION (continued)
U.S. Pat. No. 7,897,737 B2 of the nitrogen atoms. Insert

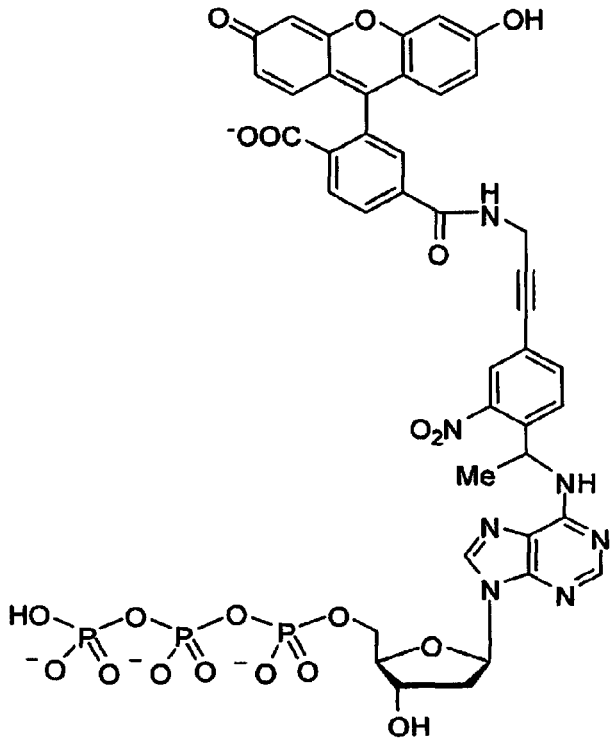

-- -- therefor.

In claim 9, column 136, lines 33-65, delete the chemical drawing and the dot near one of the oxygen atoms. Insert

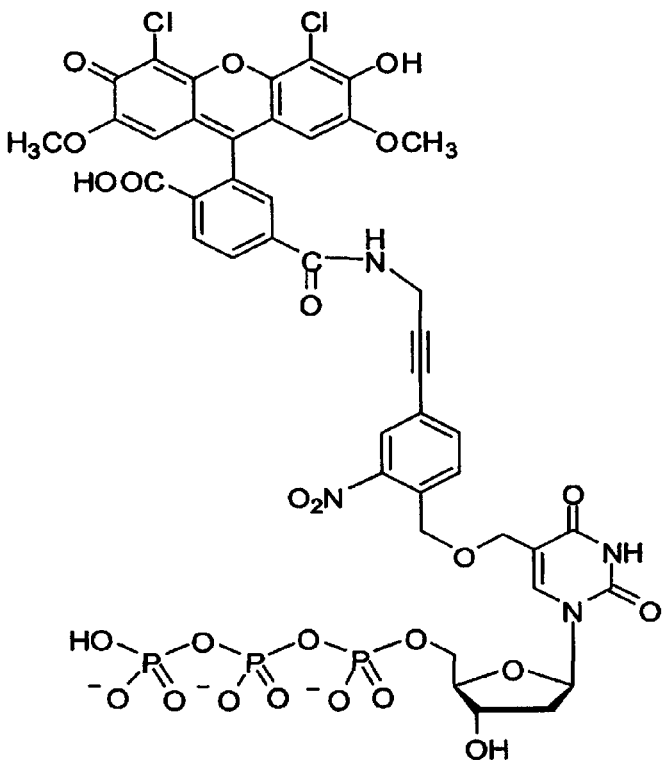

-- -- therefor.

In claim 10, column 137, lines 3-33, delete chemical drawings and insert

CERTIFICATE OF CORRECTION (continued)
U.S. Pat. No. 7,897,737 B2

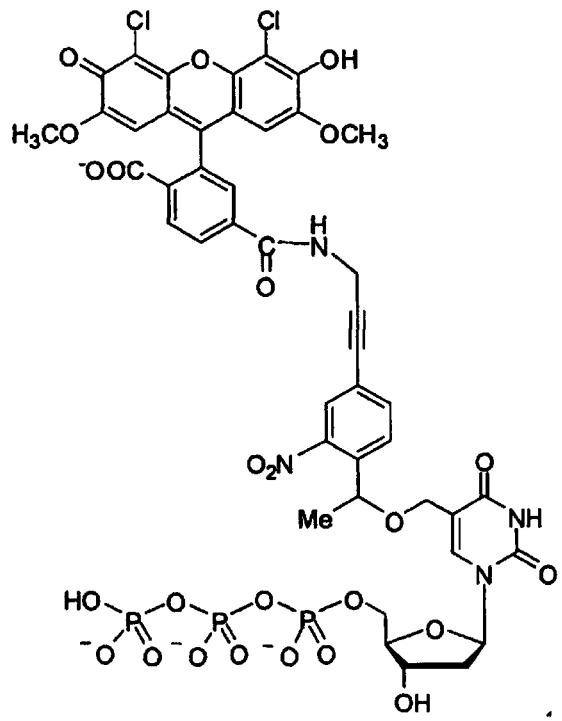

-- ‘ -- therefor.

In claim 11, column 137, lines 36-65, delete chemical drawings and insert

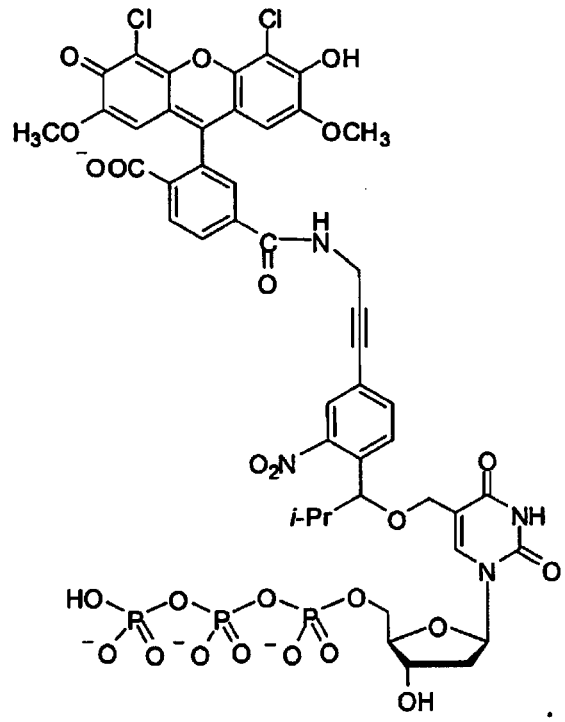

-- ‘ -- therefor.

In claim 12, column 138, lines 3-45, delete the chemical drawing and the dot near one of the oxygen atoms. Insert
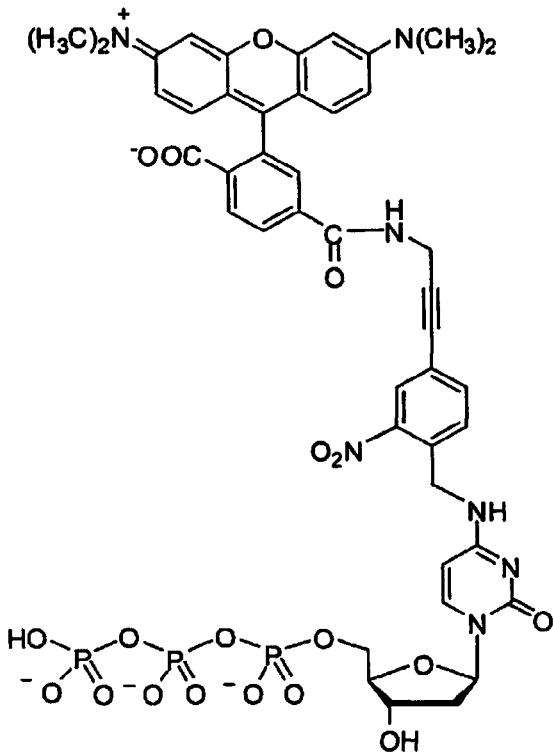
-- -- therefor.
In claim 13, column 138, line 49 to column 139, line 18, delete the chemical drawing and the dot near the NH₂ group. Insert
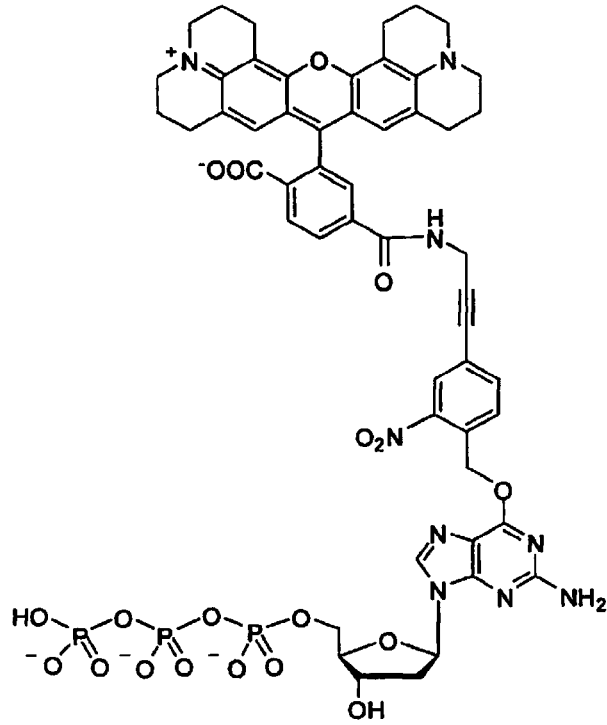
-- -- therefor.
In claim 14, column 139, lines 22-65, delete chemical drawings and insert

CERTIFICATE OF CORRECTION (continued)
U.S. Pat. No. 7,897,737 B2

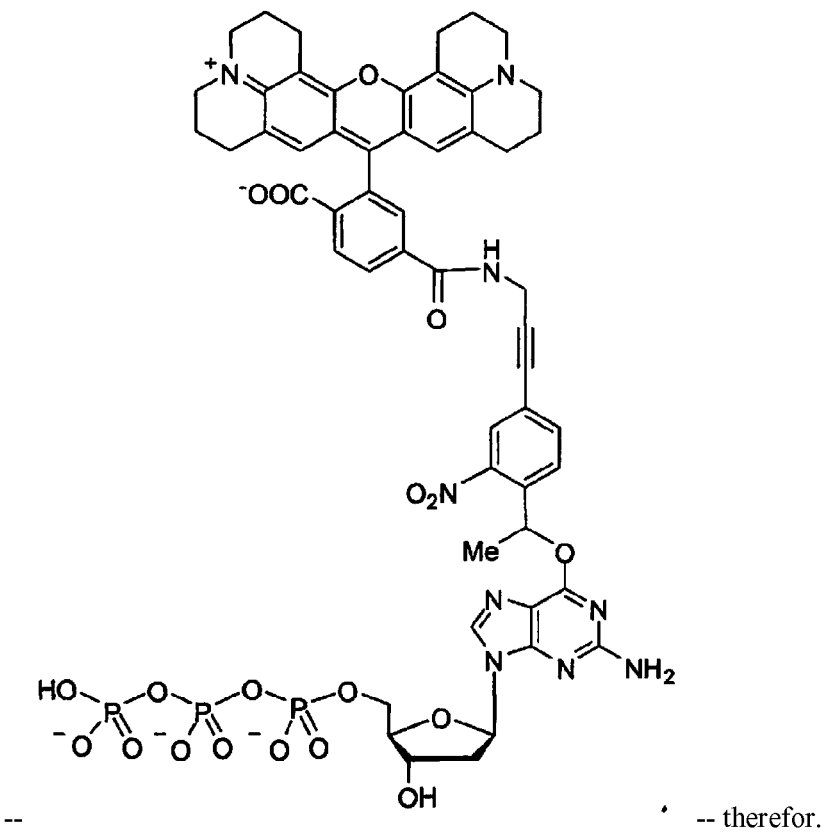

--      ' -- therefor.

In claim 15, column 140, lines 3-28, delete chemical drawing and insert

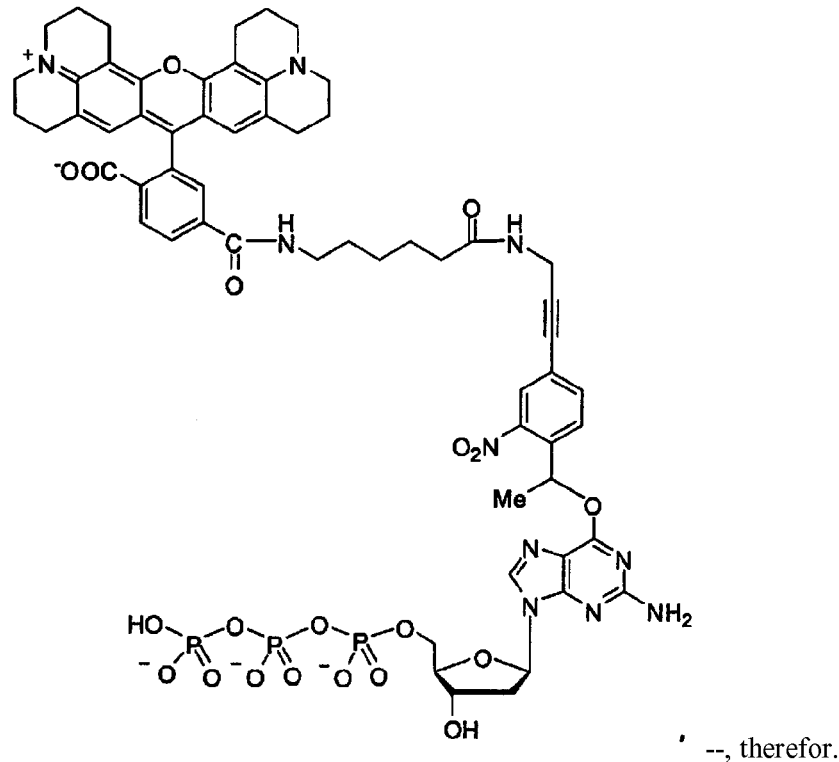

--      ' --, therefor.

In claim 16, column 140, lines 32-65, delete chemical drawings and insert

CERTIFICATE OF CORRECTION (continued)
U.S. Pat. No. 7,897,737 B2

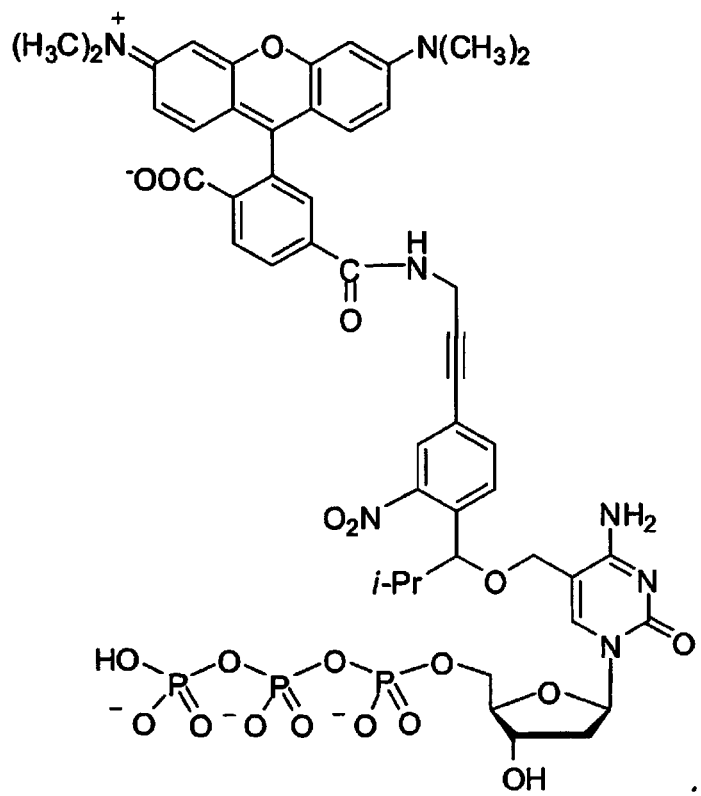

-- -- therefor.

In claim 17, column 141, lines 2-35, delete the chemical drawing and the dot near the NH₂ group. Insert

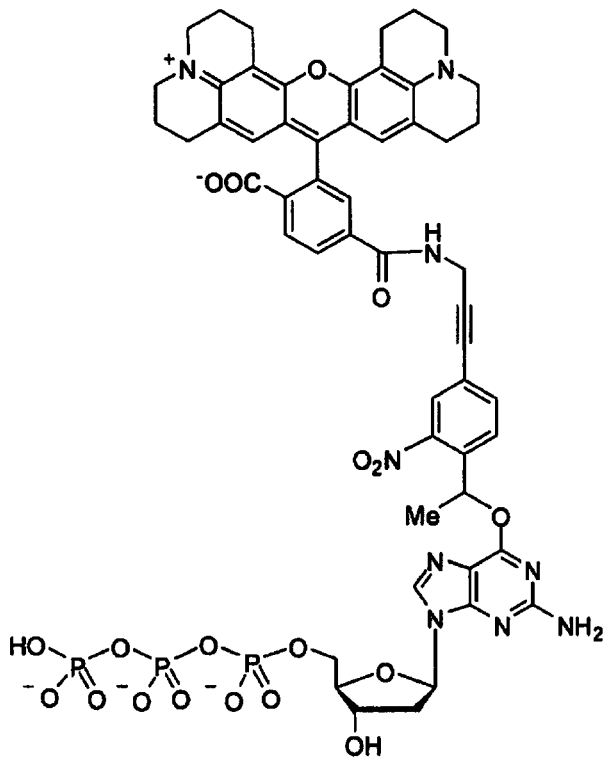

-- -- therefor.

In claim 18, column 141, lines 38-63, delete the chemical drawing and the dot near the

CERTIFICATE OF CORRECTION (continued)
U.S. Pat. No. 7,897,737 B2

NH₂ group. Insert

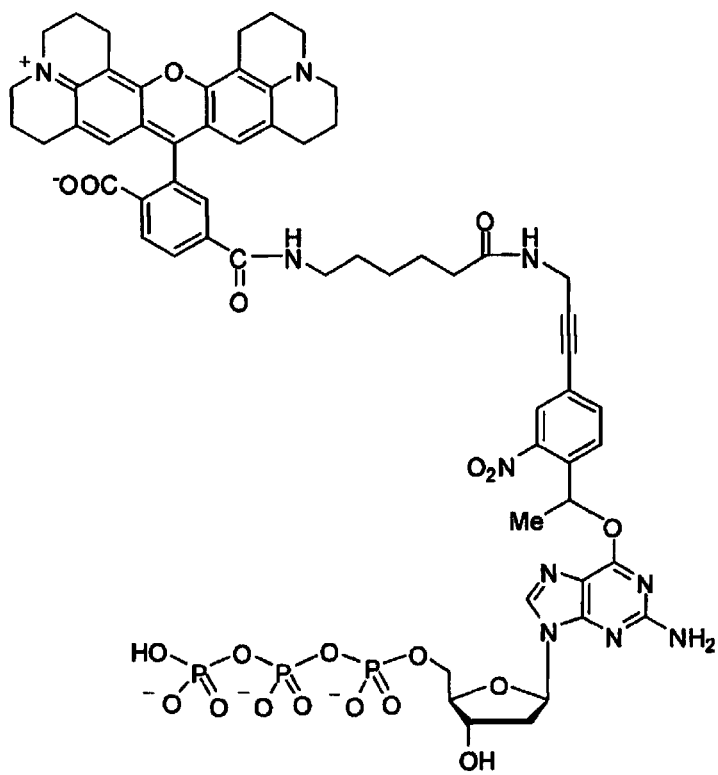

--                          -- therefor.

UNITED STATES PATENT AND TRADEMARK OFFICE
CERTIFICATE OF CORRECTION

| | | |
|---|---|---|
| PATENT NO. | : 7,897,737 B2 | |
| APPLICATION NO. | : 11/567189 | |
| DATED | : March 1, 2011 | |
| INVENTOR(S) | : Weidong Wu et al. | |

It is certified that error appears in the above-identified patent and that said Letters Patent is hereby corrected as shown below:

In title page, item (56) References Cited - OTHER PUBLICATIONS, insert
--International Preliminary Report on Patentability, issued in International Application
No. PCT/US2007/086559, mailed June 18, 2009.--.

In the Specification

In column 12, line 57 to column 13, line 18, delete chemical drawings and insert

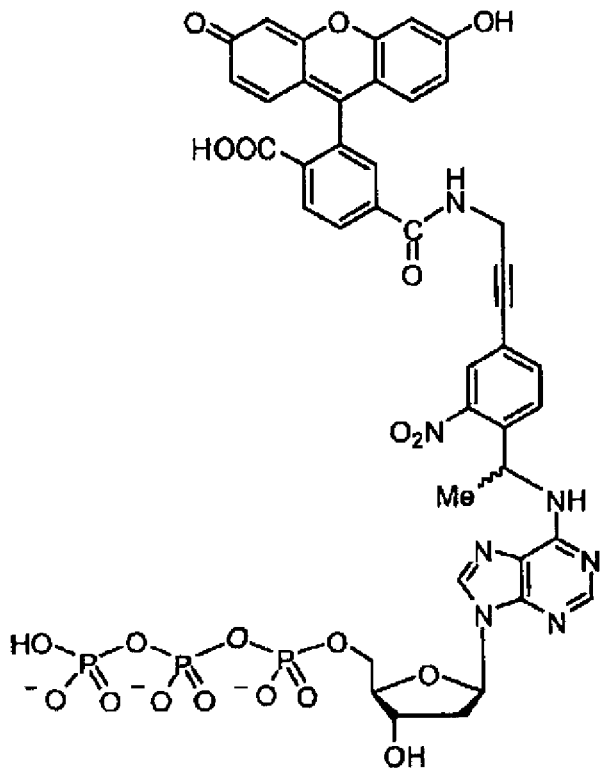

-- therefor.

This certificate supersedes the Certificate of Correction issued March 20, 2012.

Signed and Sealed this
Twenty-second Day of October, 2013

Teresa Stanek Rea
*Deputy Director of the United States Patent and Trademark Office*

CERTIFICATE OF CORRECTION (continued)
U.S. Pat. No. 7,897,737 B2

In column 13, lines 18-49, delete chemical drawings and insert

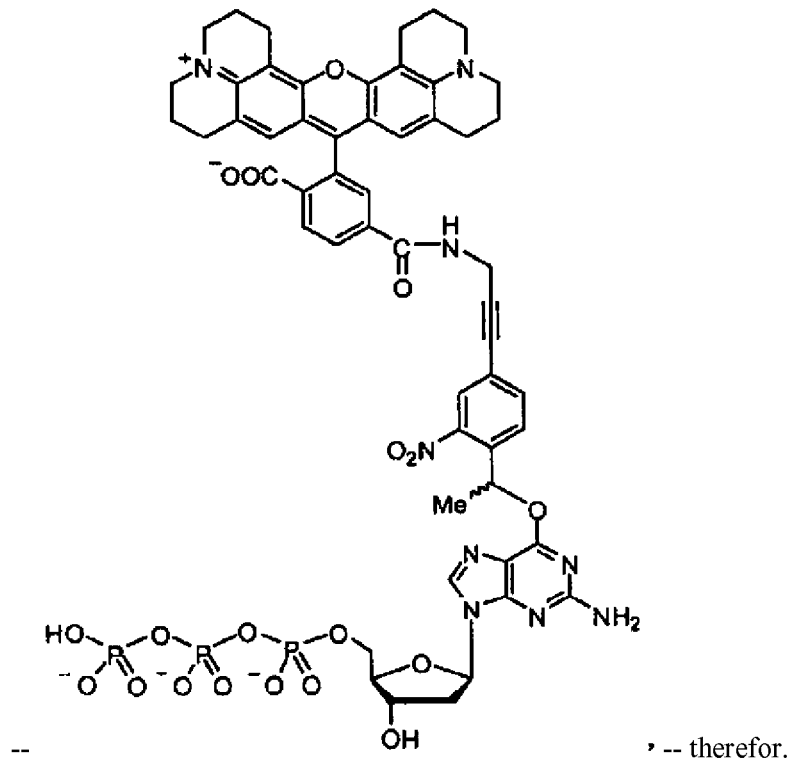

-- , -- therefor.

In column 13, line 50 to column 14, line 15, delete chemical drawings and insert

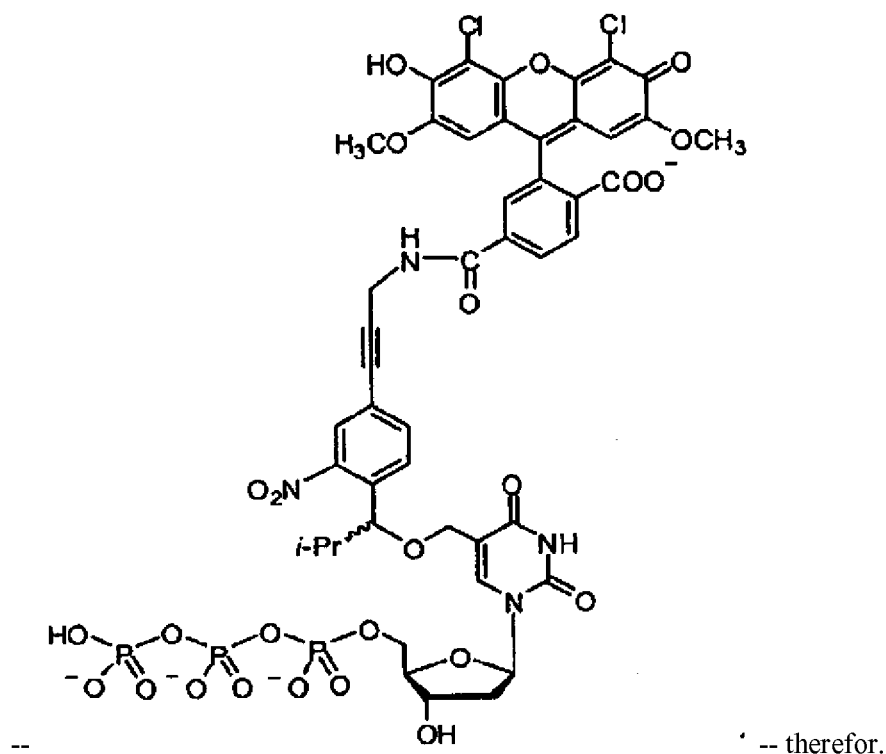

-- ' -- therefor.

CERTIFICATE OF CORRECTION (continued)
U.S. Pat. No. 7,897,737 B2

Page 3 of 10

In column 14, lines 16-44, delete chemical drawings and insert

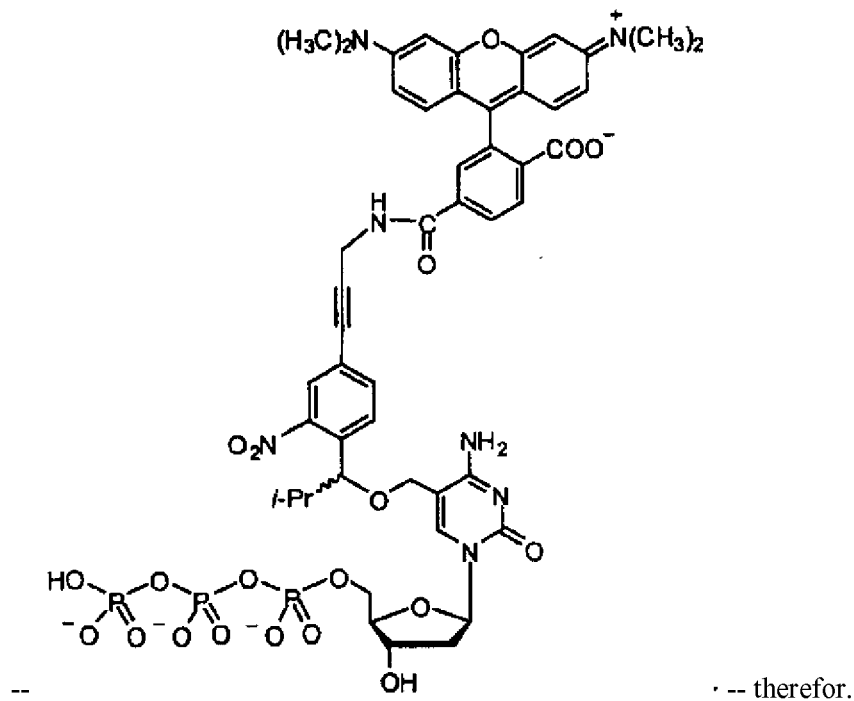

-- · -- therefor.

In column 38, lines 48-66, delete chemical drawing and insert

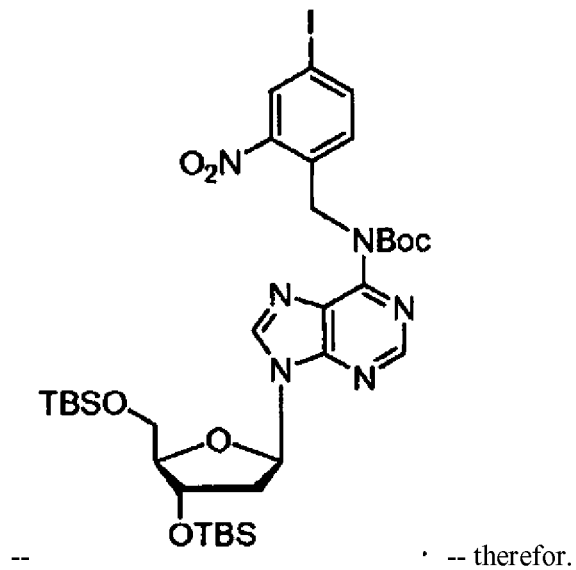

-- · -- therefor.

CERTIFICATE OF CORRECTION (continued)
U.S. Pat. No. 7,897,737 B2

In column 55, lines 3-27, delete chemical drawing and insert

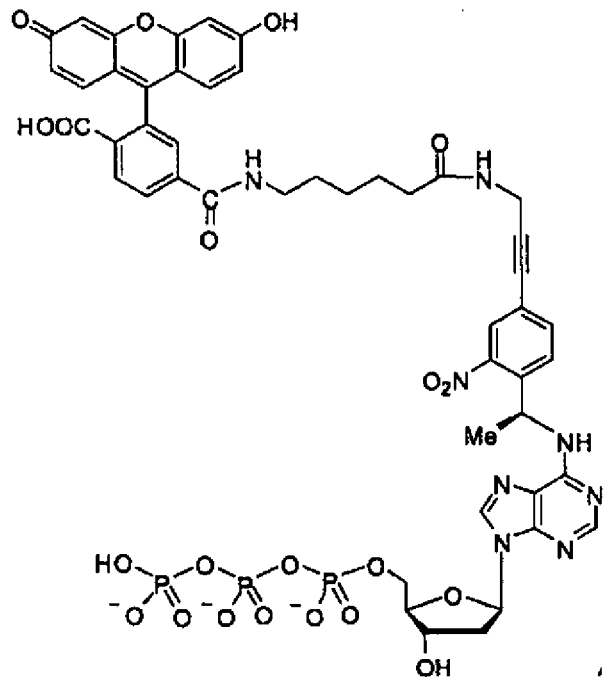

-- ' -- therefor.

In the Claims

In claim 1, column 132, line 60, delete "or" and insert --and-- therefor.

In claim 5, column 134, lines 10-46, delete the chemical drawing and the dot near one of the nitrogen atoms. Insert

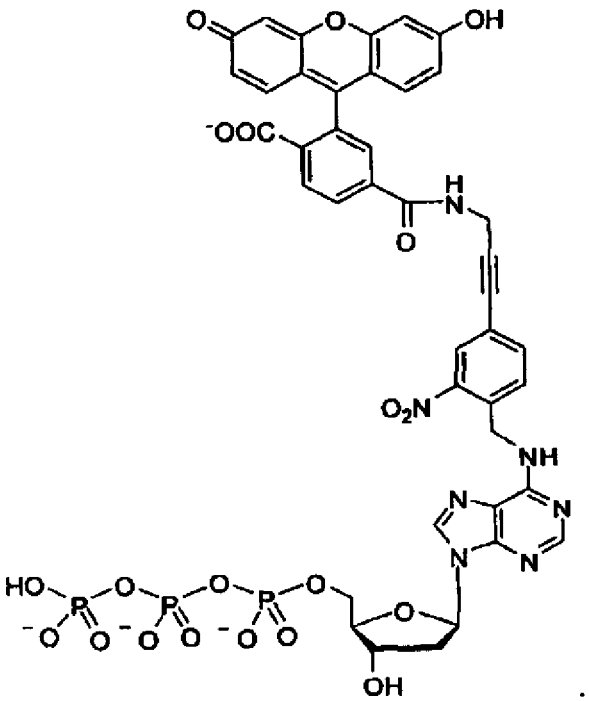

-- · -- therefor.

In claim 7, column 135, lines 20-63, delete the chemical drawing and the dot near one of the nitrogen atoms. Insert
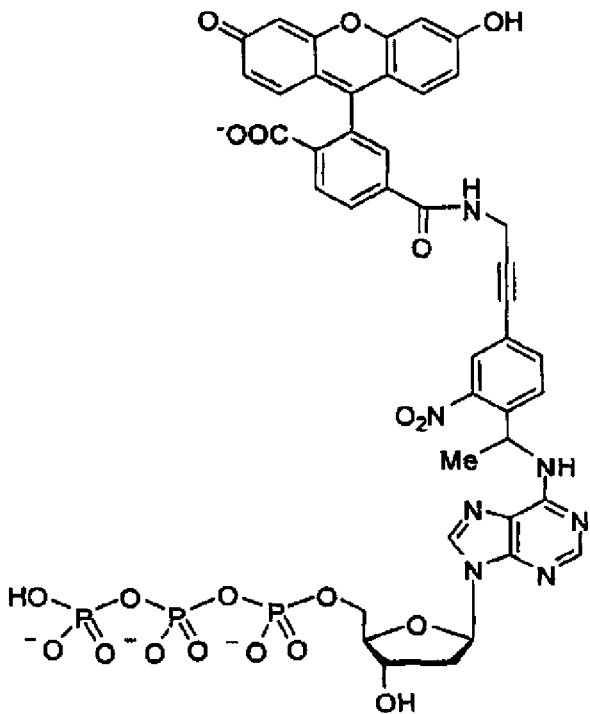
-- ● -- therefor.
In claim 9, column 136, lines 33-65, delete the chemical drawing and the dot near one of the oxygen atoms. Insert
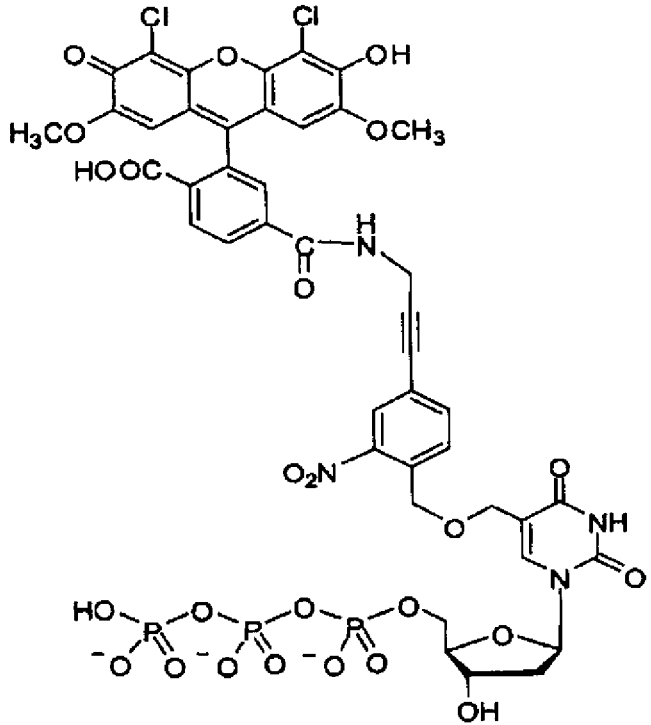
-- ● -- therefor.

CERTIFICATE OF CORRECTION (continued)

In claim 10, column 137, lines 3-33, delete chemical drawings and insert

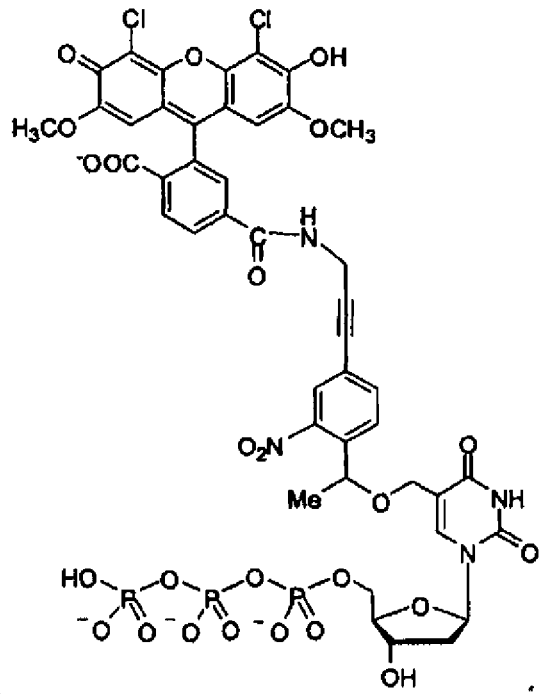

-- ` -- therefor.

In claim 11, column 137, lines 36-65, delete chemical drawings and insert

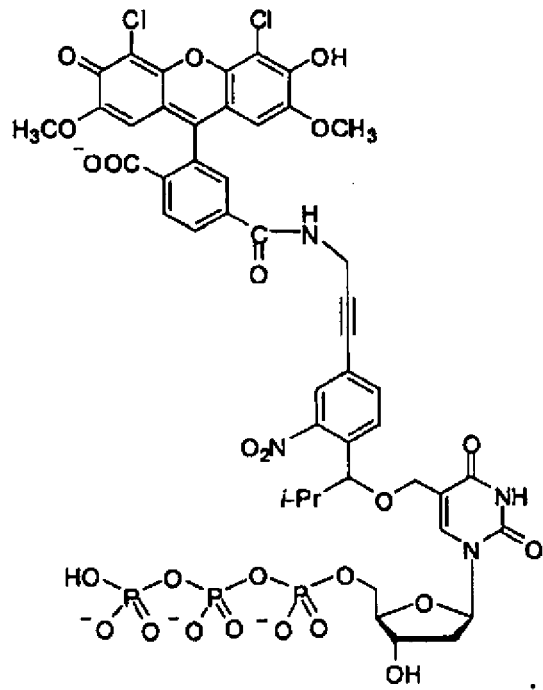

-- ` -- therefor.

In claim 12, column 138, lines 3-45, delete the chemical drawing and the dot near one of the oxygen atoms. Insert
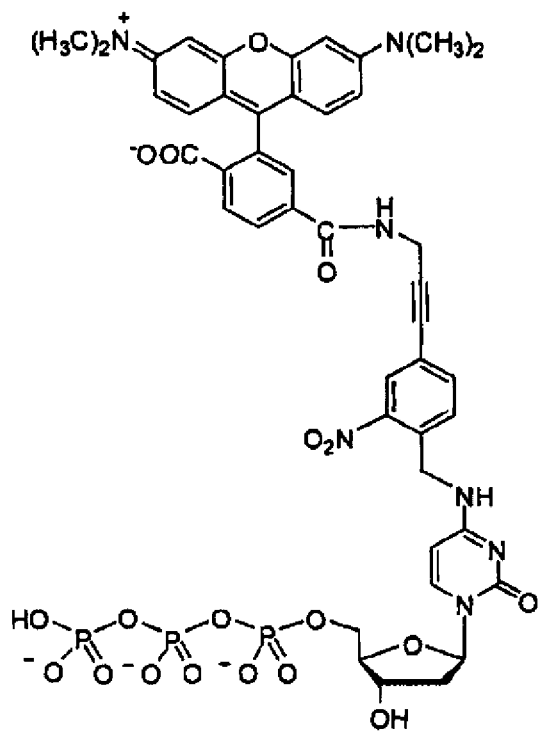
-- ` -- therefor.
In claim 13, column 138, line 49 to column 139, line 18, delete the chemical drawing and the dot near the NH₂ group. Insert
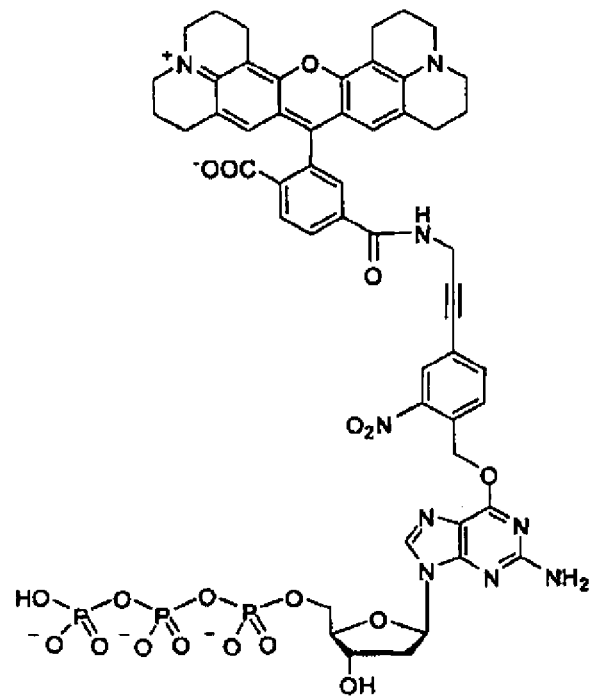
-- ` -- therefor.

CERTIFICATE OF CORRECTION (continued)  
U.S. Pat. No. 7,897,737 B2

Page 8 of 10

In claim 14, column 139, lines 22-65, delete chemical drawings and insert

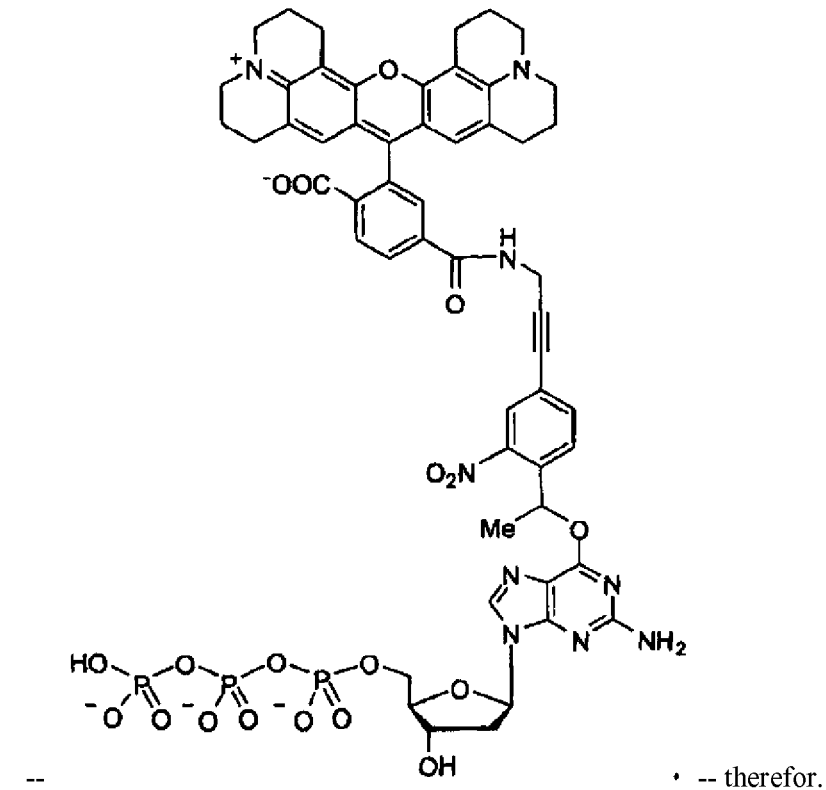

-- therefor.

In claim 15, column 140, lines 3-28, delete chemical drawing and insert

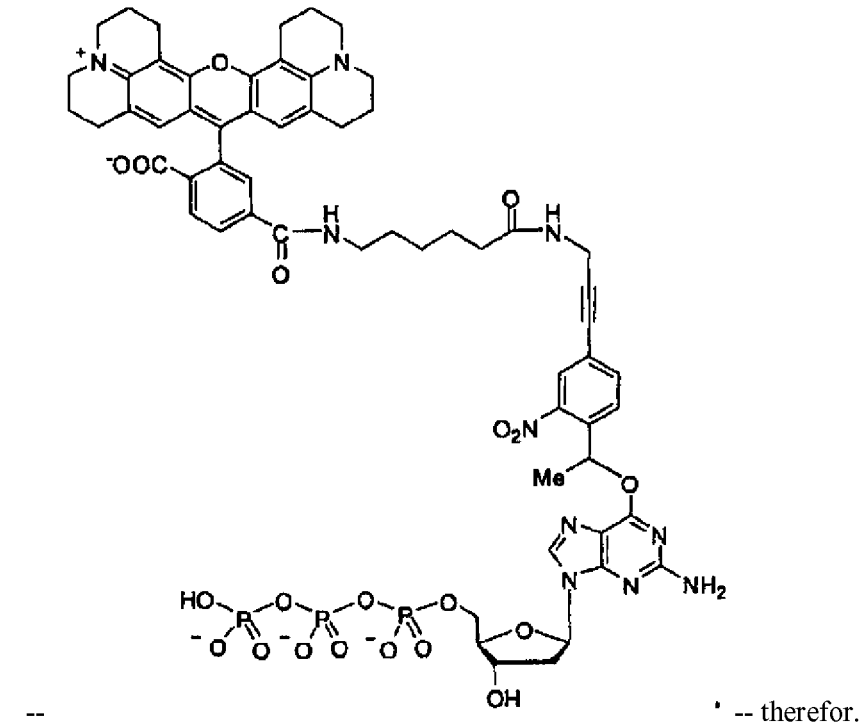

-- therefor.

In claim 16, column 140, lines 32-65, delete chemical drawings and insert
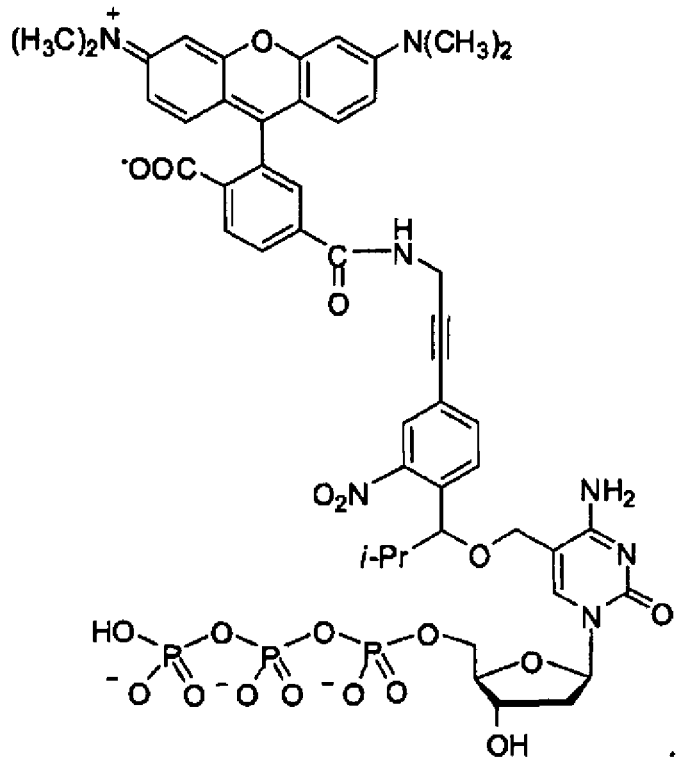
-- • -- therefor.
In claim 17, column 141, lines 2-35, delete the chemical drawing and the dot near the NH₂ group. Insert
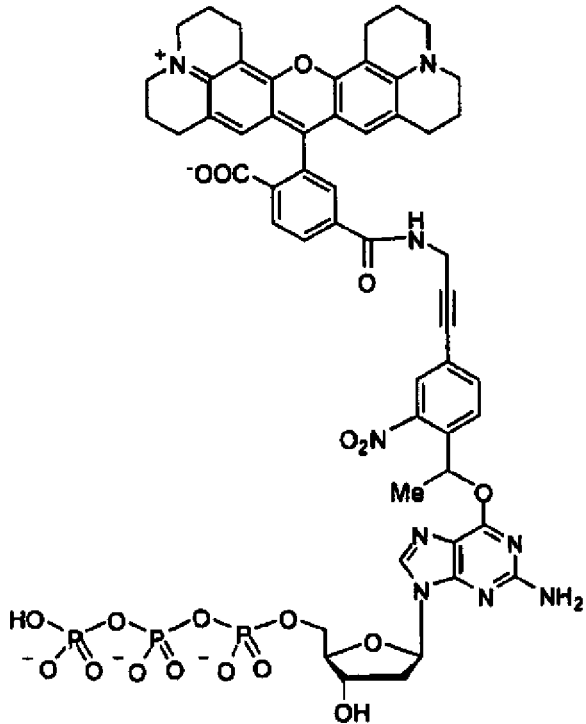
-- • -- therefor.

CERTIFICATE OF CORRECTION (continued)
U.S. Pat. No. 7,897,737 B2

Page 10 of 10

In claim 18, column 141, lines 38-63, delete the chemical drawing and the dot near the NH₂ group. Insert

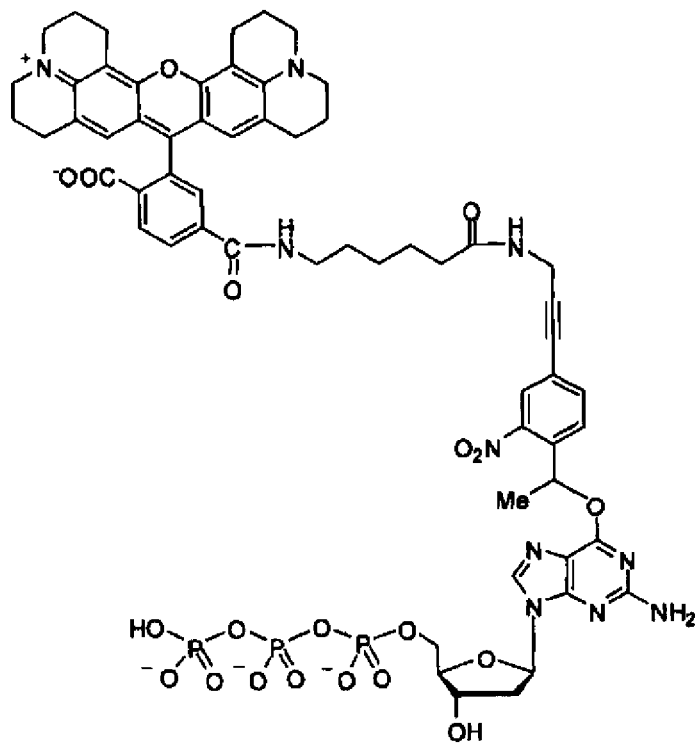

-- therefor.

UNITED STATES PATENT AND TRADEMARK OFFICE
CERTIFICATE OF CORRECTION

PATENT NO. : 7,897,737 B2  Page 1 of 10
APPLICATION NO. : 11/567189
DATED : March 1, 2011
INVENTOR(S) : Weidong Wu et al.

It is certified that error appears in the above-identified patent and that said Letters Patent is hereby corrected as shown below:

In title page, item (56) References Cited - OTHER PUBLICATIONS, insert
--International Preliminary Report on Patentability, issued in International Application
No. PCT/US2007/086559, mailed June 18, 2009.--.

In the Specification

In column 12, line 57 to column 13, line 18, delete chemical drawings and insert

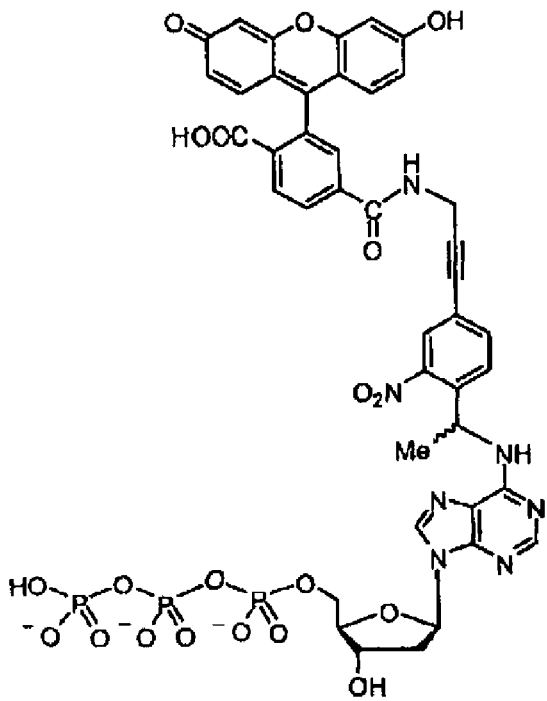

--                                                   -- therefor.

This certificate supersedes the Certificates of Correction issued March 20, 2012 and October 22, 2013.

Signed and Sealed this
Twenty-fourth Day of December, 2013

Margaret A. Focarino
*Commissioner for Patents of the United States Patent and Trademark Office*

CERTIFICATE OF CORRECTION (continued)
U.S. Pat. No. 7,897,737 B2

In column 13, lines 18-49, delete chemical drawings and insert

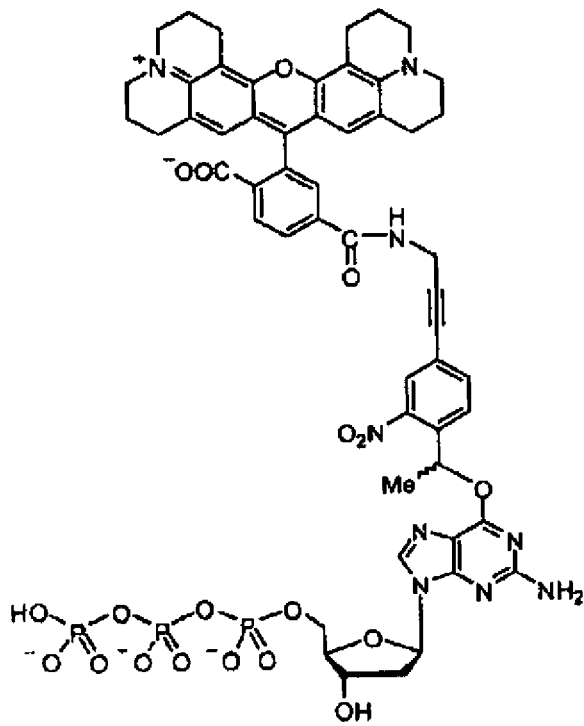

-- '-- therefor.

In column 13, line 50 to column 14, line 15, delete chemical drawings and insert

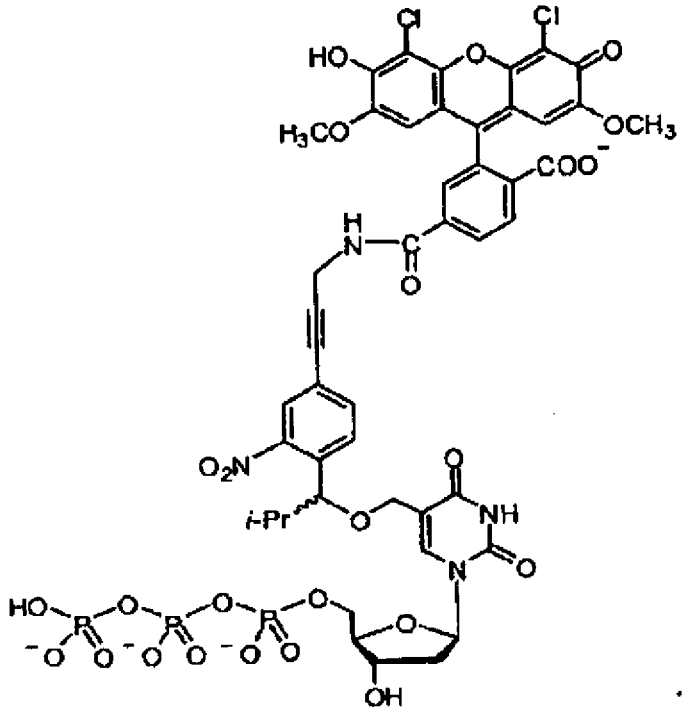

-- '-- therefor.

CERTIFICATE OF CORRECTION (continued)

U.S. Pat. No. 7,897,737 B2

In column 14, lines 16-44, delete chemical drawings and insert

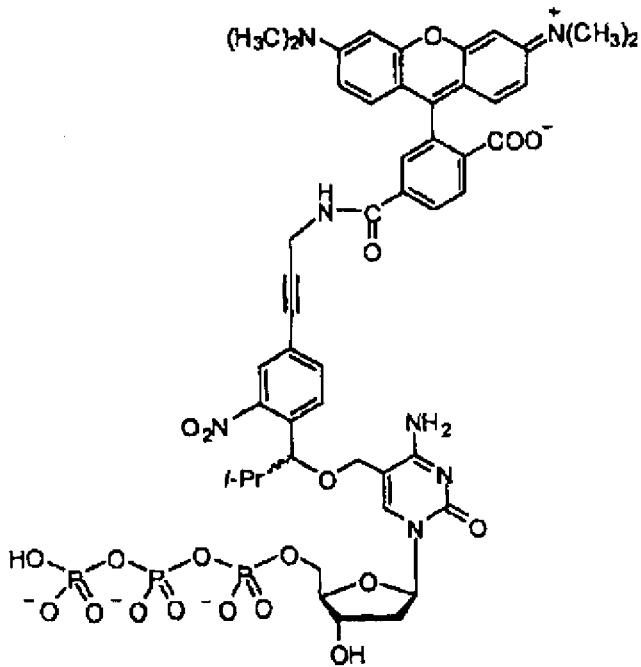

-- -- therefor.

In column 38, lines 48-66, delete chemical drawing and insert

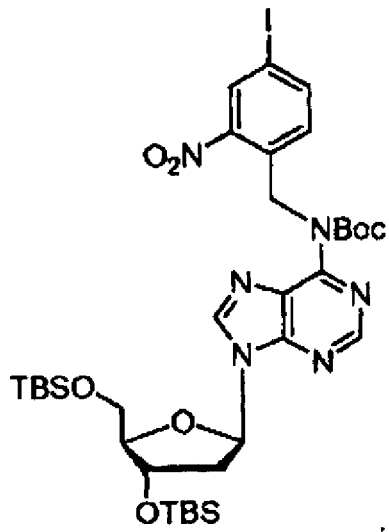

-- -- therefor.

CERTIFICATE OF CORRECTION (continued)
U.S. Pat. No. 7,897,737 B2

In column 55, lines 3-27, delete chemical drawing and insert

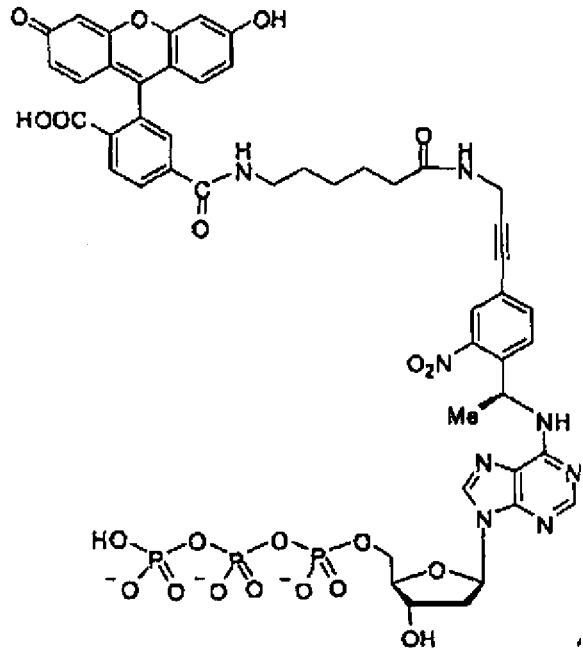

-- ' -- therefor.

In the Claims

In claim 1, column 132, line 60, delete "or" and insert --and-- therefor.

In claim 5, column 134, lines 10-46, delete the chemical drawing and the dot near one of the nitrogen atoms. Insert

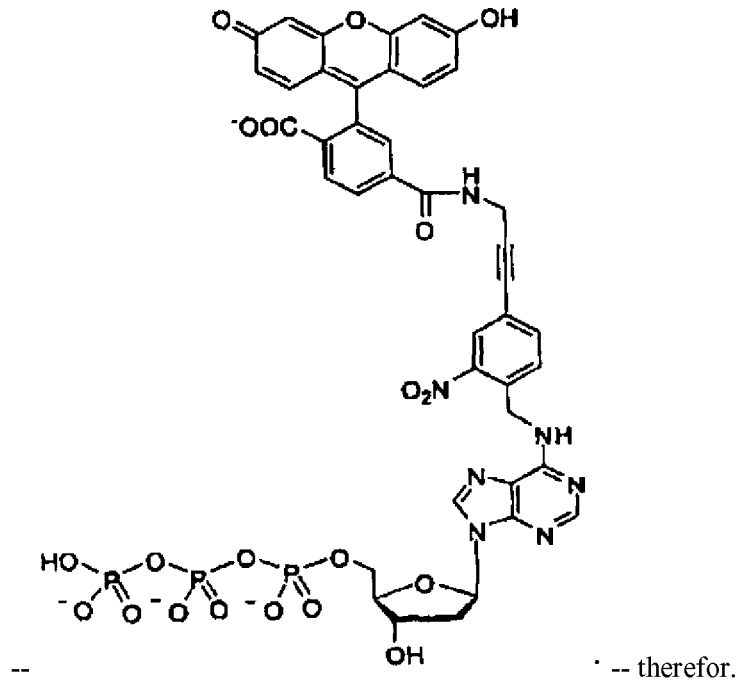

-- · -- therefor.

In claim 6, column 134, line 50 to column 135, line 13, delete the chemical drawing and the dot near one of the nitrogen atoms. Insert
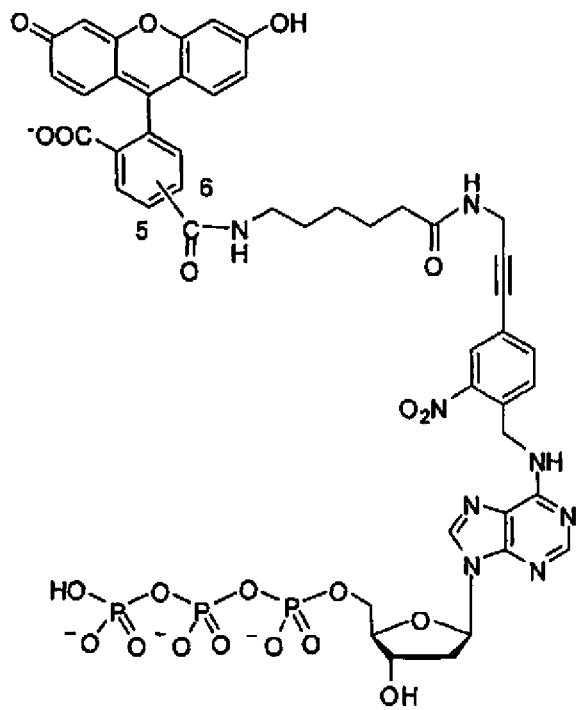
-- ⋅--- therefor.
In claim 7, column 135, lines 20-63, delete the chemical drawing and the dot near one of the nitrogen atoms. Insert
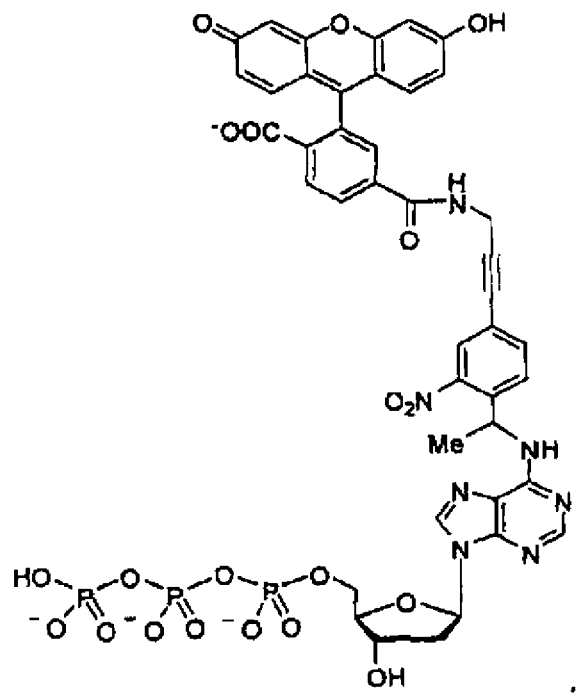
-- ⋅ -- therefor.

CERTIFICATE OF CORRECTION (continued)

In claim 9, column 136, lines 33-65, delete the chemical drawing and the dot near one of the oxygen atoms. Insert

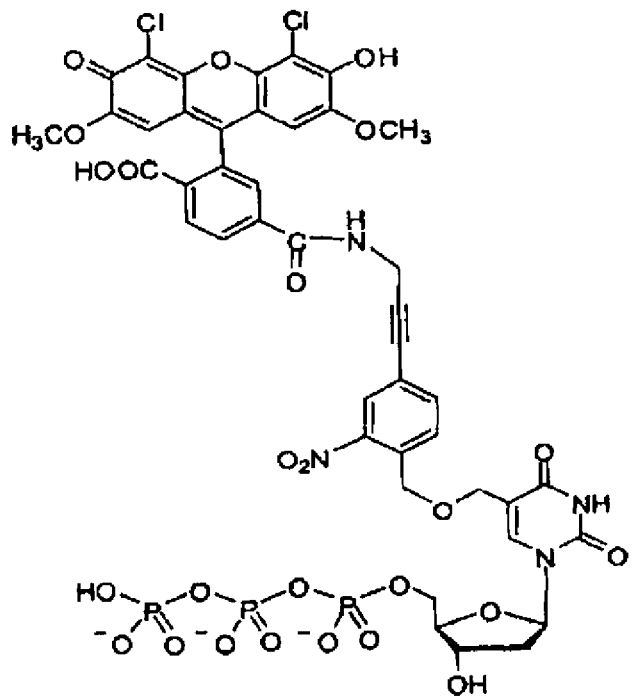

-- therefor.

In claim 10, column 137, lines 3-33, delete chemical drawings and insert

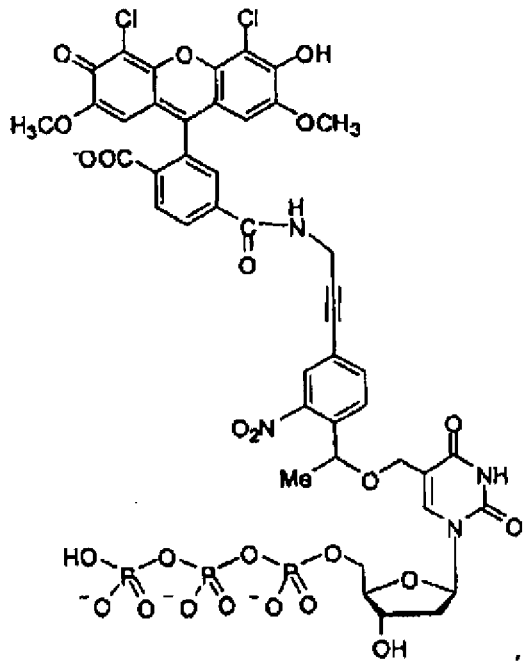

-- therefor.

CERTIFICATE OF CORRECTION (continued)
U.S. Pat. No. 7,897,737 B2

In claim 11, column 137, lines 36-65, delete chemical drawings and insert

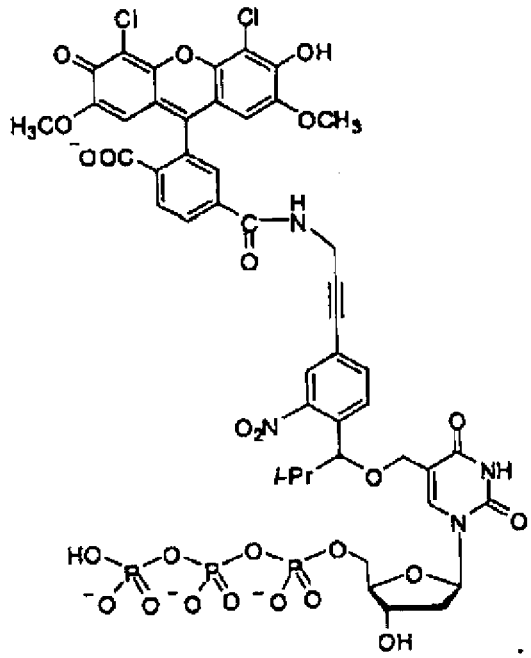

-- -- therefor.

In claim 12, column 138, lines 3-45, delete the chemical drawing and the dot near one of the oxygen atoms. Insert

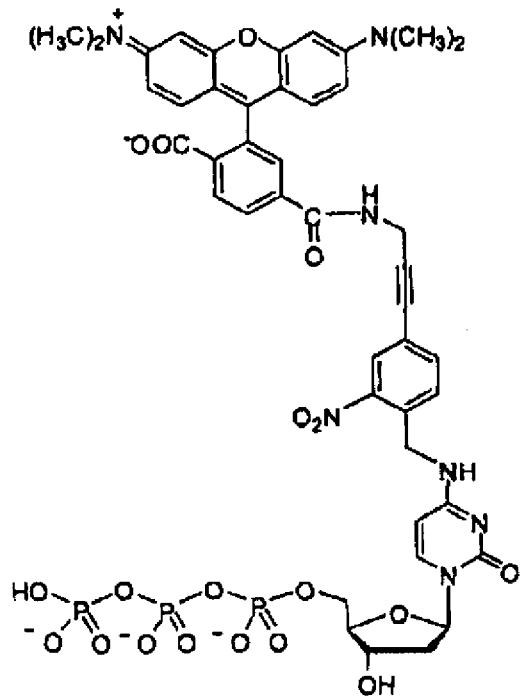

-- ' -- therefor.

CERTIFICATE OF CORRECTION (continued)
U.S. Pat. No. 7,897,737 B2

In claim 13, column 138, line 49 to column 139, line 18, delete the chemical drawing and the dot near the NH₂ group. Insert

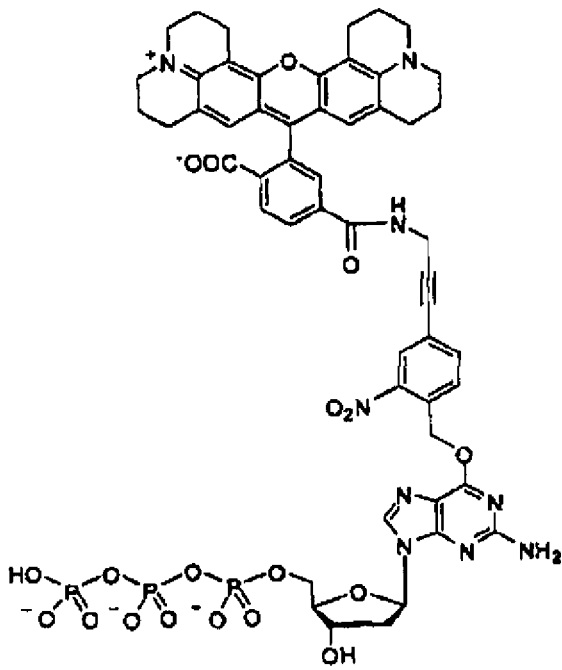

-- -- therefor.

In claim 14, column 139, lines 22-65, delete chemical drawings and insert

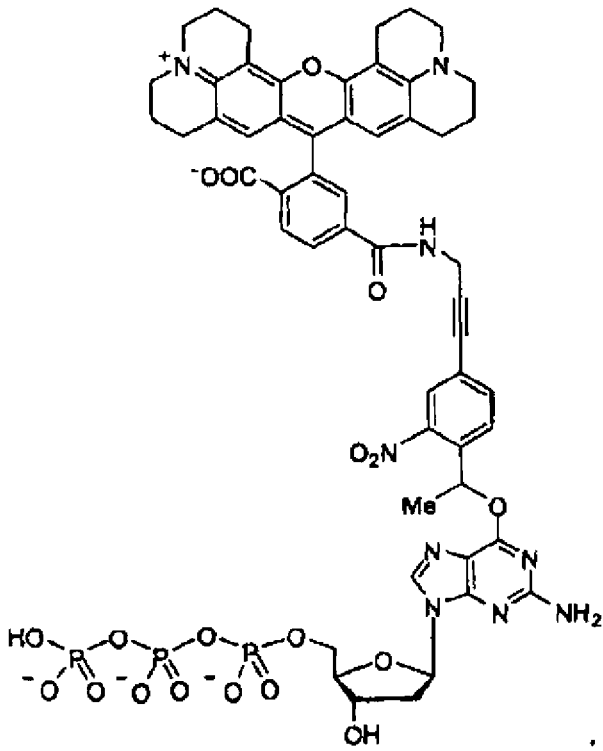

-- · -- therefor.

In claim 15, column 140, lines 3-28, delete chemical drawing and insert

CERTIFICATE OF CORRECTION (continued)

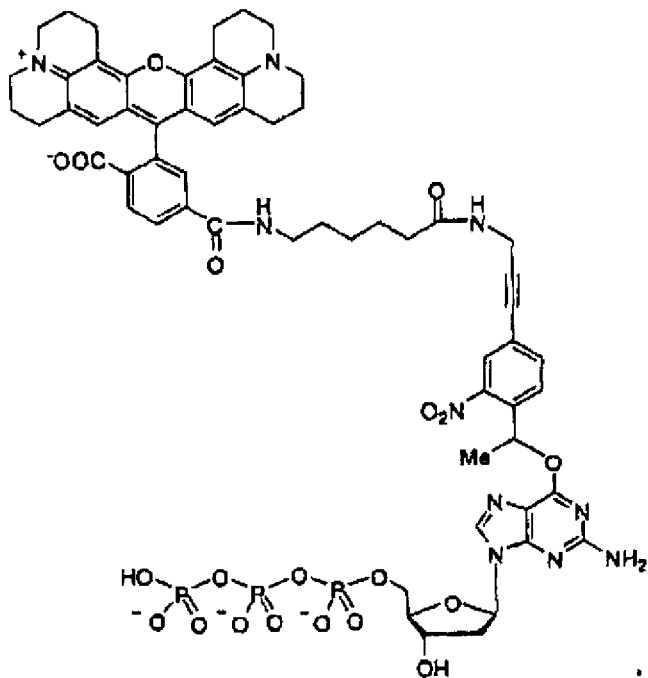

-- * -- therefor.

In claim 16, column 140, lines 32-65, delete chemical drawings and insert

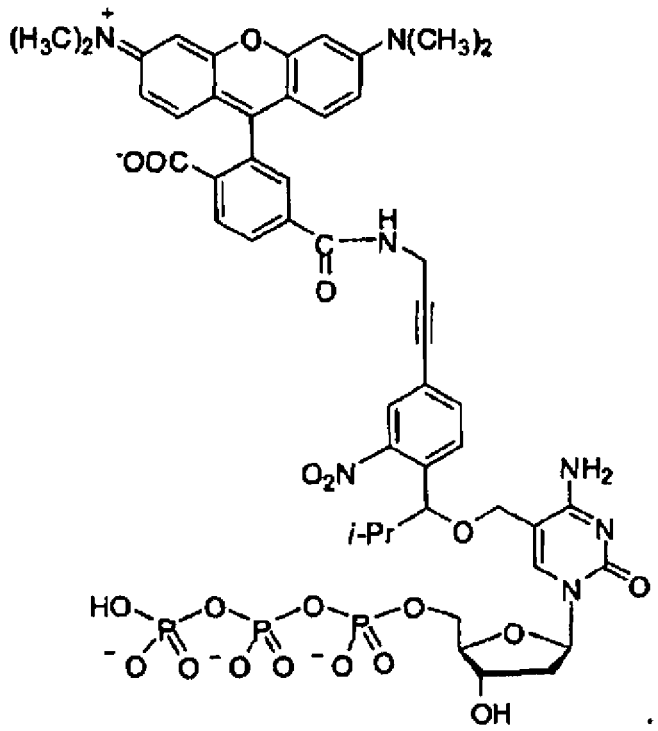

-- * -- therefor.

In claim 17, column 141, lines 2-35, delete the chemical drawing and the dot near the $NH_2$ group.

Insert
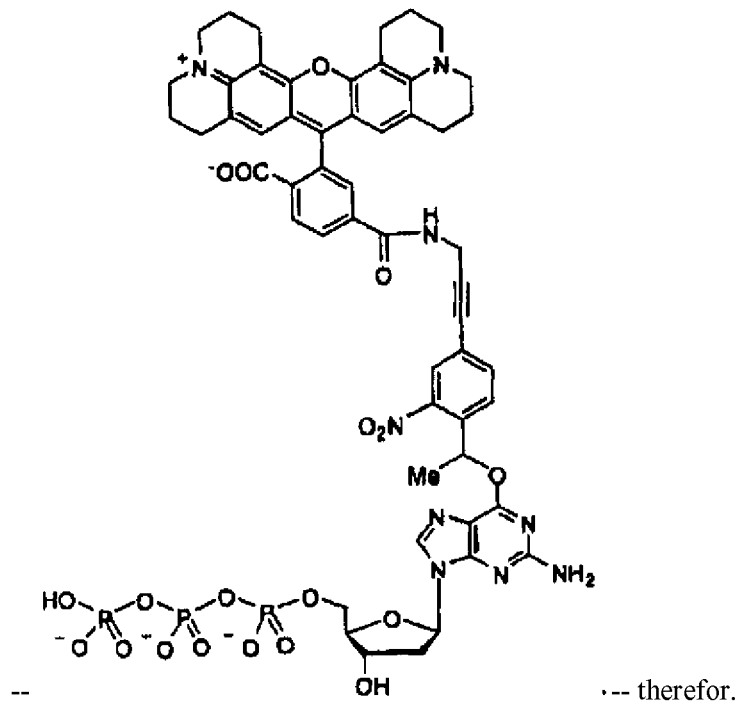
-- ·--- therefor.
In claim 18, column 141, lines 38-63, delete the chemical drawing and the dot near the NH$_2$ group.
Insert
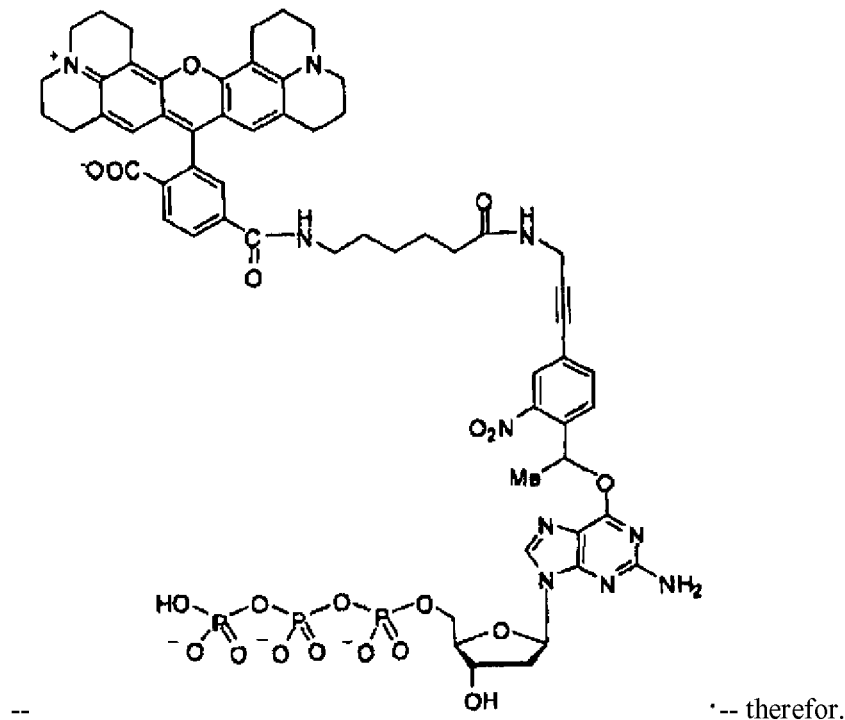
-- ·-- therefor.

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tacggagcag tactggccgt cgttttaca                                     29

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttgtaaaacg acggccagt                                                19
```